US012098169B2

United States Patent
Dong et al.

(10) Patent No.: US 12,098,169 B2
(45) Date of Patent: Sep. 24, 2024

(54) ***ENTEROCOCCUS FAECIUM* NEUROTOXIN (BONT/EN) AND DERIVATIVES THEREOF**

(71) Applicants: Children's Medical Center Corporation, Boston, MA (US); Paul Stenmark, Stockholm (SE)

(72) Inventors: Min Dong, Weatogue, CT (US); Paul Stenmark, Stockholm (SE); Sicai Zhang, Boston, MA (US); Andrew Doxey, Waterloo (CA)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/651,720

(22) PCT Filed: Sep. 28, 2018

(86) PCT No.: PCT/US2018/053262
§ 371 (c)(1),
(2) Date: Mar. 27, 2020

(87) PCT Pub. No.: WO2019/067815
PCT Pub. Date: Apr. 4, 2019

(65) Prior Publication Data
US 2020/0255481 A1    Aug. 13, 2020

Related U.S. Application Data

(60) Provisional application No. 62/566,171, filed on Sep. 29, 2017.

(51) Int. Cl.
| | | |
|---|---|---|
| *C07K 14/315* | (2006.01) | |
| *A61K 38/00* | (2006.01) | |
| *C07K 14/00* | (2006.01) | |
| *C07K 14/195* | (2006.01) | |
| *C07K 14/33* | (2006.01) | |

(52) U.S. Cl.
CPC ............ *C07K 14/315* (2013.01); *C07K 14/33* (2013.01); *A61K 38/00* (2013.01); *C07K 2319/50* (2013.01)

(58) Field of Classification Search
CPC .... A61K 38/00; A61K 38/4893; C07K 14/33; C07K 14/315; C07K 2317/24; C07K 2319/55; C07K 2319/50; A61P 25/02; C12R 1/46
See application file for complete search history.

(56) References Cited

U.S. PATENT DOCUMENTS

| | | | |
|---|---|---|---|
| 10,883,096 B2 | 1/2021 | Rummel et al. | |
| 11,104,891 B2 | 8/2021 | Dong et al. | |
| 2009/0087478 A1 | 4/2009 | Hansen et al. | |
| 2011/0070621 A1 | 3/2011 | Steward et al. | |
| 2018/0244731 A1* | 8/2018 | Collier .................. | C07K 14/32 |
| 2019/0127427 A1 | 5/2019 | Liu | |
| 2019/0300869 A1 | 10/2019 | Dong et al. | |
| 2021/0040467 A1* | 2/2021 | Dong ..................... | C12N 15/75 |

FOREIGN PATENT DOCUMENTS

| | | | |
|---|---|---|---|
| CN | 104736166 A | | 6/2015 |
| EP | 1700918 | * | 9/2006 |
| JP | 2008-538902 | | 11/2008 |
| JP | 2009-523420 | | 6/2009 |
| WO | WO 2007/084342 A2 | | 7/2007 |
| WO | WO 2013/180799 A1 | | 12/2013 |
| WO | WO 2016/149404 A1 | | 9/2016 |
| WO | WO 2017/214447 A1 | | 12/2017 |
| WO | WO2018009903 | * | 1/2018 |

OTHER PUBLICATIONS

Botulinum-like toxin in animal gut bacteria frome the Sci News website: www.sci-news.com/biology/botulinum-like-toxin-enterococcus-faecium-05673.html, retrieved on Feb. 4, 2021.*
A0A242DI27 (BXJ_ENTS3) from UniProtKB website: www.uniprot.org/uniprot/A0A242DI27, retrieved on Mar. 24, 2021.*
GenBank NGLI01000004.1 from the NCBI website: www.ncbi.nlm.nih.gov/nuccore/NGLI01000004.1, retrieved on Mar. 24, 2021.*
PRJNA313452 from the NCBI website: www.ncbi.nlm.nih.gov/bioproject/PRJNA313452, retrieved on Mar. 24, 2021.*
Gardner et al., Toxin, 2018; 10.268; doi:10.3390/toxins10070268.*
GenBank: OTO22244.1 from the NCBI website: www.ncbi.nlm.nih.gov/protein/OTO22244.1/ retrieved on Mar. 24, 2021.*
Mansfield et al. Sci. Reports; 2019; 9:1634. doi.org/10.1038/s41598-018-37647-8.*
Lebreton et al., Cell 2017; 169:849-861.*
Lebreton et al. mBio 2013;4:e00534-13.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
The alignment between OTO22244.1 and SEQ ID No. 1 from Blast website performed on Mar. 24, 2021.*
The alignment between OTO22244.1 and SEQ ID No. 5 from Blast website performed on Mar. 24, 2021.*
U.S. Appl. No. 17/555,570, filed Dec. 2021, Stenmark et al.*

(Continued)

*Primary Examiner* — Chang-Yu Wang
(74) *Attorney, Agent, or Firm* — Wolf, Greenfield & Sacks, P.C.

(57) ABSTRACT

Provided herein is a novel homolog of *Clostridial botulinum* neurotoxin (BoNT) identified in the bacterial species *Enterococcus faecium* (BoNT/EN). BoNT/EN variants and chimeric toxins comprising domains from BoNT/EN and other BoNTs are also provided. Further provided herein are methods of producing BoNT/EN and its use, e.g., in therapeutic applications.

11 Claims, 16 Drawing Sheets

Specification includes a Sequence Listing.

(56) References Cited

OTHER PUBLICATIONS

The factsheet of Accession No. OTO22244 from the NCBI website, published May 5, 2017.*
U.S. Appl. No. 16/308,149, filed Dec. 7, 2018, Dong et al.
EP 17733667.4, Mar. 30, 2020, European Exam Report.
PCT/US2017/036628, Oct. 2, 2017, International Search Report and Written Opinion.
PCT/US2017/036628, Dec. 20, 2018, International Preliminary Report on Patentability.
PCT/US2018/053262, Apr. 23, 2019, Invitation to Pay Additional Fees.
PCT/US2018/053262, Jun. 19, 2019, International Search Report and Written Opinion.
PCT/US2018/053262, Apr. 9, 2020, International Preliminary Report on Patentability.
[No Author Listed] UniProt Database. Neurotoxin B8. Retrieved from EBI Accession No. UniProt: 16Z869. Oct. 3, 2012. 5 pgs.
[No Author Listed] UniProt Database. A5816_002916_Botulinum-like toxin eBoNT/J. Enterococcus sp. (strain 3G-1_DIV0629). Retrieved from EBI Accession No. UniProtKB:A0A242DI27. Oct. 3, 2012. 5 pgs.
Berntsson et al., Crystal structures of botulinum neurotoxin DC in complex with its protein receptors synaptotagmin I and II. Cell Structure. Sep. 3, 2013: 21(9) 1602-1611.
Earl et al., *Enterococcus* sp. 3G1_DIV0629 hypothetical protein. Coding ID: OTO22244.1. ENA Database. Submitted on May 8, 2017. Retrieved on Jan. 21, 2019 from https://www.ebi.ac.uk/ena/data/view/OTO22244.
Pirazzini et al., Botulinum Neurotoxins: Biology, Pharmacology, and Toxicology. Pharmacol Rev. Apr. 2017;69(2):200-235.
Rummel et al., Identification of the protein receptor binding site of botulinum neurotoxins B and G proved the double-receptor concept. PNAS. Jan. 2, 2007:4(1) 359-364.
Zhang et al., Identification of a Botulinum Neurotoxin-like Toxin in a Commensal Strain of Enterococcus faecium. Cell Host Microbe. Feb. 14, 2018;23(2):169-176.e6.
[No Author Listed] AFN61309. Clostridium Botulinum Neurotoxin B8. Submitted Apr. 24, 2012 to INSDC.
[No Author Listed], NCBI hypothetical protein *Enterococcus* sp. 3G1_DIV0629. Accession No. WP_086311652.1. May 23, 2017.

* cited by examiner

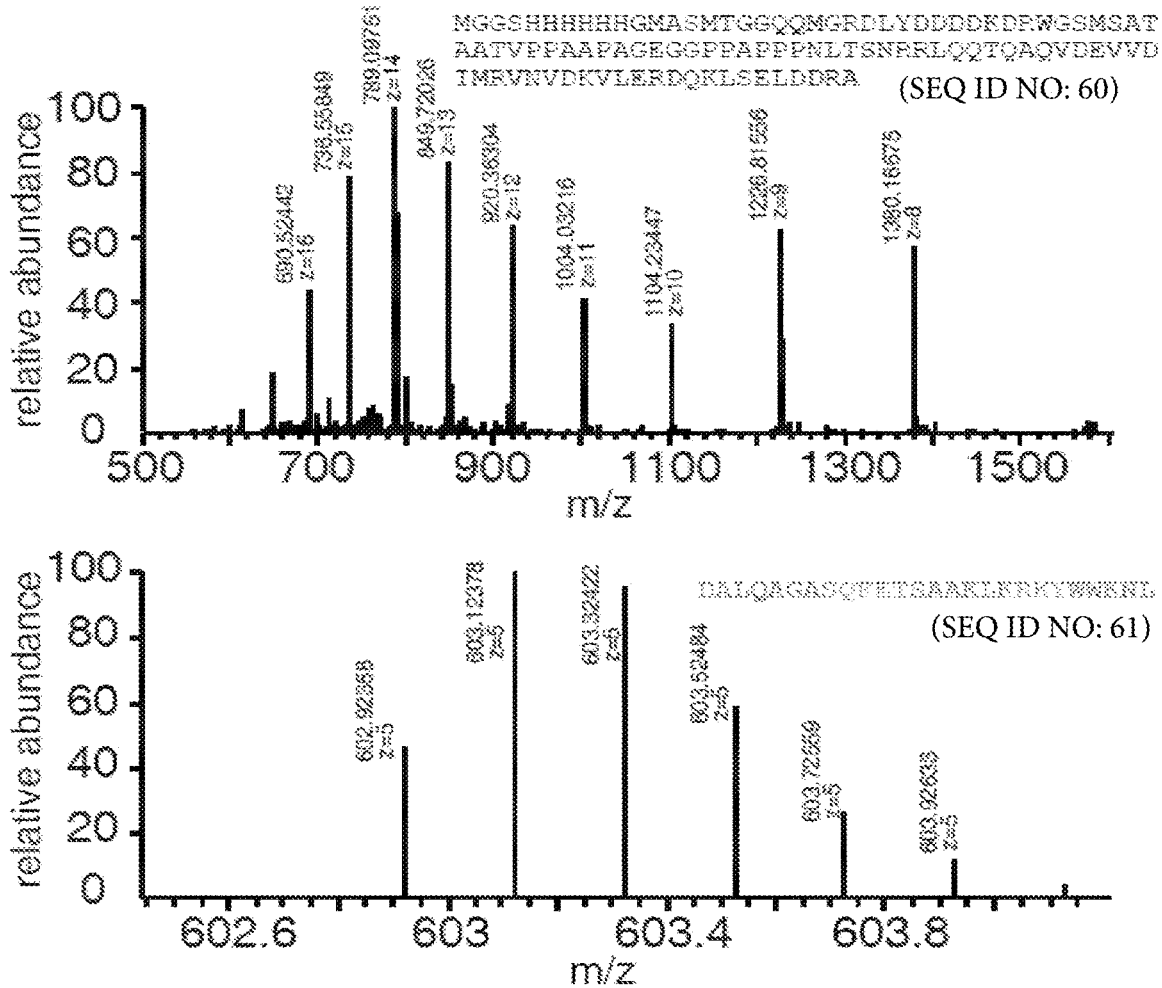
FIG. 2C
FIG. 2D

```
                            thrombin
          LC                   ↓        H_N
En-LC-H_N ▓▓▓▓▓▓▓▓-CPNPHFSSQLVPRGSLSSC-▓▓▓▓▓▓▓
                     (SEQ ID NO: 70)

BoNT/A   -CVRGIITSKTKS--------------------LDKGYNKALNDLC-
BoNT/B   -CK--SVKAPG-------------------------------IC-
BoNT/C   -CHKAIDGRSL---------------------------YNKTLDC-
BoNT/D   -CLRLTK-------------------------------NSRDDSTC-
BoNT/E   -CKN-IVSVKG---------------------------IRKS--IC-
BoNT/F   -CKS-VIPRKG--------------------------TKAPPRLC-
BoNT/G   -CKPVMYKNTG-------------------------------KSEQC-
BoNT/X   -CPRNGLLYNAIYRNSKNYLNNIDLEDKKTTSKTNVSYPCSLLNGC-
BoNT/En  -CPNPHFSSQRGLSS---------------------------C-
                                        (SEQ ID NOs: 48-56)
```

DALQAGASQFETSAAKLKR
(SEQ ID NO: 74)

(SEQ ID NO: 75)

```
Syx1A  174. PAIFASGIIMDSSISKQALSEI.195...250.DTKEAVKYQSKARRKK.265
Syx1B  173. LAIFTDDIKMDSQMTKQALNEI.194...249.DTKEAVKYQSKARRKK.264
Syx4   182. SEVFVSNILKDTQVTRQALNEI.203...258.HVKIALENQKKARRKK.273
              (SEQ ID NOs: 83, 85, 87)           (SEQ ID NOs: 84, 86, 88)
```

ENTEROCOCCUS FAECIUM NEUROTOXIN (BONT/EN) AND DERIVATIVES THEREOF

RELATED APPLICATION

This application is a National Stage Filing under 35 U.S.C. § 371 of International Application No. PCT/US2018/053262, filed Sep. 28, 2018, which claims the benefit under 35 U.S.C. § 119(e) to U.S. Provisional Application No. 62/566,171, filed Sep. 29, 2017, and entitled "A NEUROTOXIN-LIKE TOXIN AND USES THEREOF," the entire contents of each of which are incorporated herein by reference.

GOVERNMENT SUPPORT

This disclosure was made with government support under R01NS080833, R01A1132387 awarded by the National Institutes of Health. The government has certain rights in this invention.

INCORPORATION BY REFERENCE

This application contains a Sequence Listing which has been filed electronically in ASCII and is hereby incorporated by reference in its entirety. This ASCII copy, created on Jun. 29, 2021, is named C123370127US01-SUBSEQ-RE and is 318,612 bytes in size.

BACKGROUND

*Botulinum* neurotoxins (BoNTs) are a family of the most potent bacterial toxins and potential bioterrorism agents. BoNTs have also been used to treat a growing list of medical conditions ranging from muscle spasms to chronic pain, as well as for cosmetic applications. As the application of BoNTs grows, limitations and adverse effects have been reported. The major limitation is the generation of neutralizing antibodies in patients, which renders future treatment ineffective. Termination of BoNT usage often leaves patients with no other effective ways to treat/relieve their disorders. Adverse effects associated with BoNT use range from transient non-serious events such as ptosis and diplopia to life-threatening events even death. The limitations and adverse effects of BoNTs are largely correlated with dose. There are considerable interests in developing novel BoNT types as therapeutic toxins. No BoNT gene clusters have been identified in a bacterial species outside of *Clostridium*.

SUMMARY

Provided herein, in some aspects, is a novel member of the BoNT family, encoded on a plasmid in the *Enterococcus faecium* strain (designated as BoNT/EN). The BoNT/EN cleaves VAMP1/2/3 and several other SNARE proteins including SNAP-25, SNAP-23, syntaxin 1B and syntaxin 4. BoNT/EN variants with a modified linker region are provided. Further provided herein are chimeric toxins comprising the protease domain and translocation domain of BoNT/EN and the receptor binding domain from another BoNT (e.g., BoNT/A, BoNT/B, BoNT/C. BoNT/D, BoNT/E, BoNT/F, or BoNT/G). In some aspects, compositions and methods for treating diseases using the novel BoNT/EN are provided. In other aspects, methods of generating full length BoNT/EN or a chimeric toxin are provided.

Some aspects of the present disclosure relate to isolated *Enterococcus faecium* neurotoxin (BoNT/EN) polypeptides, comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to any one of SEQ ID NOs: 1-3.

In some embodiments, the isolated BoNT/EN polypeptide comprises the amino acid sequence of any one of SEQ ID NOs: 1-3. In some embodiments, the isolated BoNT/EN polypeptide consists of the amino acid sequence of any one of SEQ ID NOs: 1-3.

In some embodiments, the isolated BoNT/EN polypeptide enters a cell. In some embodiments, the isolated BoNT/EN polypeptide cleaves a SNARE protein in the cell. In some embodiments, the SNARE protein is selected from the group consisting of: VAMP1, VAMP2, VAMP3, SNAP-25, SNAP-23, syntaxin 1, and syntaxin 4. In some embodiments, the SNARE protein is VAMP1. In some embodiments, the isolated BoNT/EN cleaves between amino acid residues corresponding to A69 and D70 in SEQ ID NO: 31. In some embodiments, the SNARE protein is VAMP2. In some embodiments, the isolated BoNT/EN cleaves between amino acid residues corresponding to A67 and D68 in SEQ ID NO: 32. In some embodiments, the SNARE protein is VAMP3. In some embodiments, the isolated BoNT/EN cleaves between amino acid residues corresponding to A54 and D55 in SEQ ID NO: 33. In some embodiments, the SNARE protein is SNAP-23. In some embodiments, the SNARE protein is SNAP-25. In some embodiments, the SNARE protein is syntaxin 1. In some embodiments, the isolated BoNT/EN cleaves between amino acid residues corresponding to M182 and D183 in SEQ ID NO: 37. In some embodiments, the SNARE protein is syntaxin 4. In some embodiments, the isolated BoNT/EN cleaves between amino acid residues corresponding to K191 and D192 in SEQ ID NO: 38.

In some embodiments, the cell is a secretory cell. In some embodiments, the cell is a neuronal cell. In some embodiments, the isolated BoNT/EN polypeptide suppresses neuronal activity. In some embodiments, the isolated BoNT/EN polypeptide induces flaccid paralysis. In some embodiments, the cell is an immune cell. In some embodiments, the cell is a cultured cell. In some embodiments, the cell is in vivo. In some embodiments, the cell is from a mammal. In some embodiments, the mammal is a human. In some embodiments, the mammal is a rodent. In some embodiments, the rodent is a mouse. In some embodiments, the rodent is a rat. In some embodiments, the cell is an insect cell.

In some embodiments, the isolated BoNT/EN polypeptide does not cross react with an antibody against BoNT serotype A, B, C, D, E, F, G, or X.

Other aspects of the present disclosure provide isolated *Enterococcus faecium* neurotoxin (BoNT/EN) polypeptide, comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to SEQ ID NOs: 4.

In some embodiments, the isolated BoNT/EN polypeptide comprises the amino acid sequence of SEQ ID NO: 4. In some embodiments, the isolated BoNT/EN polypeptide consists of the amino acid sequence of SEQ ID NO: 4.

Other aspects of the present disclosure provide modified *Enterococcus faecium* neurotoxin (BoNT/EN) polypeptides comprising: (a) a protease domain; (b) a modified linker region; and (c) a translocation domain; wherein the modified linker region comprises a protease cleavage site.

In some embodiments, the protease is selected from the group consisting of: thrombin, TEV, PreScission® (3C protease), Sortase, MMP-12, MMP-13, MMP-17, MMP-20, Granzyme-B, Enterokinase, SUMO protease, LysC, and trypsin. In some embodiments, the modified linker region comprises the amino acid sequence of any one of SEQ ID NOs: 41-47.

In some embodiments, the modified linker is from a *Clostridium botulinum* neurotoxin. In some embodiments, the modified linker region comprises the amino acid sequence of SEQ ID NO: 48-55.

In some embodiments, the modified BoNT/EN polypeptide further comprises a receptor binding domain.

In some embodiments, the modified BoNT/EN polypeptide comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to any one of SEQ ID NOs: 5-22.

In some embodiments, the modified BoNT/EN polypeptide comprises the amino acid sequence of any one of SEQ ID NOs: 5-22. In some embodiments, the modified BoNT/EN polypeptide consists of the amino acid sequence of any one of SEQ ID NOs: 5-22.

In some embodiments, the modified BoNT/EN polypeptide enters a cell. In some embodiments, the modified BoNT/EN polypeptide cleaves a SNARE protein in the cell. In some embodiments, the SNARE protein is selected from the group consisting of: VAMP1, VAMP2, VAMP3, SNAP-25, SNAP-23, syntaxin 1, and syntaxin 4. In some embodiments, the SNARE protein is VAMP1. In some embodiments, the modified BoNT/EN cleaves between amino acid residues corresponding to A69 and D70 in SEQ ID NO: 31. In some embodiments, the SNARE protein is VAMP2. In some embodiments, the modified BoNT/EN cleaves between amino acid residues corresponding to A67 and D68 in SEQ ID NO: 32. In some embodiments, the SNARE protein is VAMP3. In some embodiments, the modified BoNT/EN cleaves between amino acid residues corresponding to A54 and D55 in SEQ ID NO: 33. In some embodiments, the SNARE protein is SNAP-23. In some embodiments, the SNARE protein is SNAP-25. In some embodiments, the SNARE protein is syntaxin 1B. In some embodiments, the modified BoNT/EN cleaves between amino acid residues corresponding to M182 and D183 in SEQ ID NO: 37. In some embodiments, the SNARE protein is syntaxin 4. In some embodiments, the modified BoNT/EN cleaves between amino acid residues corresponding to K191 and D192 in SEQ ID NO: 37.

In some embodiments, the cell is a secretory cell. In some embodiments, the cell is a neuronal cell. In some embodiments, the modified BoNT/EN polypeptide suppresses neuronal activity. In some embodiments, the modified BoNT/EN polypeptide induces flaccid paralysis. In some embodiments, the cell is an immune cell. In some embodiments, the cell is a cultured cell. In some embodiments, the cell is in vivo. In some embodiments, the cell is from a mammal. In some embodiments, the mammal is a human. In some embodiments, the mammal is a rodent. In some embodiments, the rodent is a mouse. In some embodiments, the rodent is a rat. In some embodiments, the cell is an insect cell.

In some embodiments, the modified BoNT/EN polypeptide does not cross react with an antibody against BoNT serotype A, B, C, D, E, F, G, or X.

Further provided herein are chimeric neurotoxin polypeptides comprising: (a) a protease domain; (b) a translocation domain; and (c) a receptor binding domain; wherein the protease domain and the translocation domain are from a *Enterococcus faecium* neurotoxin (BoNT/EN), and wherein the receptor binding domain is from a *Clostridial botulinum* neurotoxin (BoNT).

In some embodiments, the protease domain and the translocation are linked via a linker region. In some embodiments, the linker region comprises the amino acid sequence of CPNPHFSSQRGLSSC (SEQ ID NO: 56). In some embodiments, the linker region comprises a protease cleavage site. In some embodiments, the protease is selected from the group consisting of: thrombin, TEV, PreScission® (3C protease), Sortase, MMP-12, MMP-13, MMP-17, MMP-20, Granzyme-B, Enterokinase, SUMO protease, LysC, and trypsin. In some embodiments, the linker region comprises the amino acid sequence of SEQ ID NOs: 41-47. In some embodiments, the linker region is from a *Clostridium botulinum* neurotoxin. In some embodiments, the linker region comprises the amino acid sequence of SEQ ID NO: 48-55. In some embodiments, the receptor binding domain is from BoNT serotype A, B, C, D, E, F, G, or X. In some embodiments, the receptor binding domain is from BoNT/A1, BoNT/A2, BoNT/C, BoNT/D, BoNT/E, BoNT/F, BoNT/G, or BoNT/X.

In some embodiments, the chimeric neurotoxin polypeptide comprises an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to any one of SEQ ID NOs: 23-30. In some embodiments, the chimeric neurotoxin polypeptide comprises the amino acid sequence of any one of SEQ ID NOs: 23-30. In some embodiments, the chimeric neurotoxin polypeptide consists of the amino acid sequence of any one of SEQ ID NOs: 23-30.

In some embodiments, the chimeric neurotoxin polypeptide enters a cell. In some embodiments, the chimeric neurotoxin polypeptide cleaves a SNARE protein in the cell. In some embodiments, the SNARE protein is selected from the group consisting of: VAMP1, VAMP2, VAMP3, SNAP-25, SNAP-23, syntaxin 1, and syntaxin 4. In some embodiments, the SNARE protein is VAMP1. In some embodiments, the chimeric neurotoxin cleaves between amino acid residues corresponding to A69 and D70 in SEQ ID NO: 31. In some embodiments, the SNARE protein is VAMP2. In some embodiments, the chimeric neurotoxin cleaves between amino acid residues corresponding to A67 and D68 in SEQ ID NO: 32. In some embodiments, the SNARE protein is VAMP3. In some embodiments, the chimeric neurotoxin cleaves between amino acid residues corresponding to A54 and D55 in SEQ ID NO: 33. In some embodiments, the SNARE protein is SNAP-23. In some embodiments, the SNARE protein is SNAP-25. In some embodiments, the SNARE protein is syntaxin 1. In some embodiments, the chimeric neurotoxin cleaves between amino acid residues corresponding to M182 and D183 in SEQ ID NO: 37. In some embodiments, the SNARE protein is syntaxin 4. In some embodiments, the chimeric neurotoxin cleaves between amino acid residues corresponding to K191 and D192 in SEQ ID NO: 38.

In some embodiments, the cell is a secretory cell. In some embodiments, the cell is a neuronal cell. In some embodiments, the chimeric neurotoxin polypeptide suppresses neuronal activity. In some embodiments, the chimeric neurotoxin polypeptide induces flaccid paralysis. In some embodiments, the cell is an immune cell. In some embodiments, the cell is a cultured cell. In some embodiments, the cell is in vivo. In some embodiments, the cell is from a mammal. In some embodiments, the mammal is a human. In some embodiments, the mammal is a rodent. In some embodiments, the rodent is a mouse. In some embodiments, the rodent is a rat. In some embodiments, the cell is an insect cell.

In some embodiments, the chimeric neurotoxin polypeptide does not cross react with an antibody against BoNT serotype A, B, C, D, E, F, G, or X.

Further provided herein are nucleic acid molecules comprising a polynucleotide encoding a polypeptide comprising an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5%, or 100% identical to the isolated BoNT/EN polypeptide, the modified BoNT/EN polypeptide, or the chimeric neurotoxin polypeptide described herein. Nucleic acid vectors comprising such nucleic acid molecule are also provided. Cells comprising the nucleic acid molecules or the nucleic acid vectors are provided. In some embodiments, the cell expresses the isolated BoNT/EN polypeptide, the modified BoNT/EN polypeptide, or the chimeric neurotoxin polypeptide described herein.

Other aspects of the present disclosure provide method of producing the isolated BoNT/EN polypeptide, the modified BoNT/EN polypeptide, or the chimeric neurotoxin polypeptide described herein, the method comprising the steps of culturing the cell expressing these polypeptides under conditions wherein said BoNT/EN polypeptide is produced. In some embodiments, the method further comprises recovering the BoNT/EN polypeptide, the modified BoNT/EN polypeptide, or the chimeric neurotoxin polypeptide from the culture.

Further provided herein are composition comprising the isolated BoNT/EN polypeptide, the modified BoNT/EN polypeptide, or the chimeric neurotoxin polypeptide described herein. In some embodiments, the composition is a pharmaceutical composition. In some embodiments, the pharmaceutical composition further comprises a pharmaceutically acceptable carrier.

Kits comprising the isolated BoNT/EN polypeptide, the modified BoNT/EN polypeptide, or the chimeric neurotoxin polypeptide, the nucleic acid encoding such polypeptides, the vector comprising such nucleic acids, the cell, or the composition described herein.

Other aspects of the present disclosure provide methods of treating a condition, the method comprising administering a therapeutically effective amount of the isolated BoNT/EN polypeptide, the modified BoNT/EN polypeptide, or the chimeric neurotoxin polypeptide, the nucleic acid, the vector, or the composition described herein to a subject to treat the condition.

In some embodiments, the condition is associated with overactive neurons or glands. In some embodiments, the condition is selected from the group consisting of: spasmodic dysphonia, spasmodic torticollis, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity and other voice disorders, spasmodic colitis, neurogenic bladder, anismus, limb spasticity, tics, tremors, bruxism, anal fissure, achalasia, dysphagia and other muscle tone disorders and other disorders characterized by involuntary movements of muscle groups, lacrimation, hyperhydrosis, excessive salivation, excessive gastrointestinal secretions, secretory disorders, pain from muscle spasms, headache pain, dennatological or aesthetic/cosmetic conditions, obesity/reduced appetite. In some embodiments, the condition is not associated with unwanted neuronal activity. In some embodiments, the condition is selected from the group consisting of: psoriasis, allergy, haemophagocytic lymphohistiocytosis, and alcoholic pancreatic disease. In some embodiments, the administering is via injection to where unwanted neuronal activity is present.

Other aspects of the present disclosure provide isolated BoNT/EN polypeptide, the modified BoNT/EN polypeptide, the chimeric neurotoxin polypeptide, the nucleic acid, the vector, or the composition, for use in treating a condition associated with unwanted neuronal activity or for use in medicine.

Yet another aspect of the present disclosure provide method of producing an neurotoxin polypeptide, the method comprising: i) obtaining a first neurotoxin fragment comprising a light chain (LC) and a N-terminal domain of a heavy chain ($H_N$), wherein the first neurotoxin fragment comprises a C-terminal LPXTGG (SEQ ID NO: 57) motif; ii) obtaining a second neurotoxin fragment comprising a C-terminal domain of the heavy chain ($H_C$); wherein the second neurotoxin fragment comprise a specific protease cleavage site at its N-terminus; iii) cleaving the second neurotoxin fragment with a specific protease, wherein the cleavage results in a free Glycine residue at the N-terminus; and iv) contacting the first neurotoxin fragment and the second neurotoxin fragment from (iii) in the presence of a transpeptidase, thereby ligating the first neurotoxin fragment and the second BoNT/EN fragment to form a ligated neurotoxin.

In some embodiments, the first neurotoxin fragment further comprises an affinity tag. In some embodiments, the affinity tag is fused to the first neurotoxin fragment at the N-terminus. In some embodiments, the affinity tag is fused to the first neurotoxin fragment at the C-terminus. In some embodiments, the affinity tag is selected from the group consisting of: His6, GST, Avi, Strep, S, MBP, Sumo, FLAG, HA, Myc, SBP, E, Calmodulin, Softag 1, Softag 3, TC, V5, VSV, Xpress, Halo, and Fc. In some embodiments, the second neurotoxin fragment further comprises an affinity tag. In some embodiments, the affinity tag is fused to the second neurotoxin fragment at the N-terminus. In some embodiments, affinity tag is fused to the second neurotoxin fragment at the C-terminus. In some embodiments, the affinity tag is selected from the group consisting of: His6, GST, Avi, Strep, S, MBP, Sumo, FLAG, HA, Myc, SBP. E, Calmodulin, Softag 1, Softag 3, TC, V5. VSV, Xpress, Halo, and Fc. In some embodiments, the protease is selected from the group consisting of: thrombin, TEV, PreScission® (3C protease), Enterokinase, and SUMO protease. In some embodiments, the cognate protease is thrombin. In some embodiments, the first neurotoxin fragment is from *Enterococcus faecium*. In some embodiments, the second neurotoxin fragment is from *Enterococcus faecium*. In some embodiments, the second neurotoxin fragment is from BoNT serotype A, B, C, D, E, F, G, or X. In some embodiments, the transpeptidase is a sortase. In some embodiments, the e is from *Staphylococcus aureus* (SrtA).

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

Figures 1C, 2A, 2B:
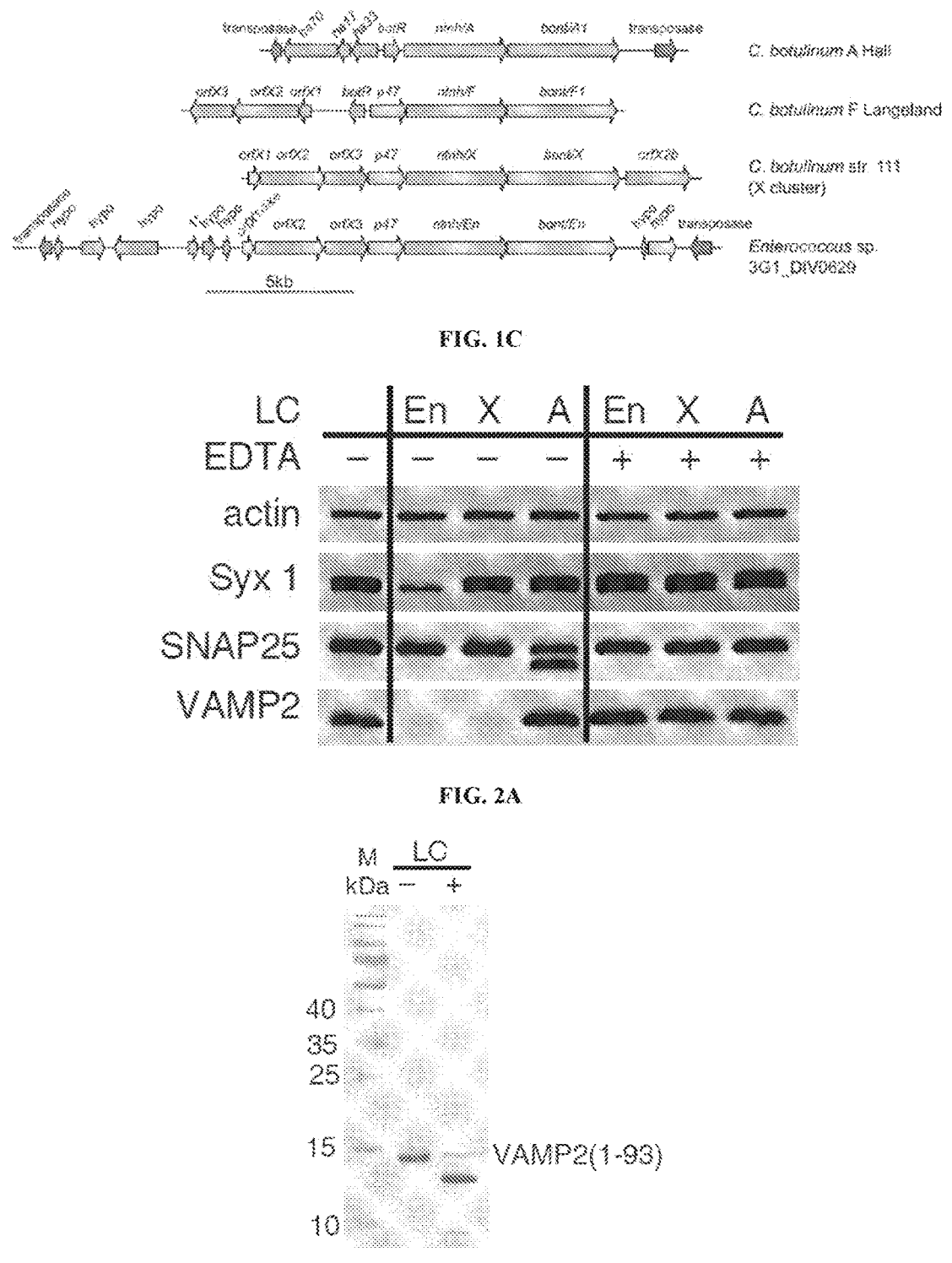

FIGS. 1A to 1C. Comparison of BoNT/EN to known BoNTs serotypes. (FIG. 1A) The maximum likelihood phylogeny of BoNT serotypes demonstrates that BoNT/EN forms a distinct lineage, grouping most closely with BoNT/X. (FIG. 1B) Upper panel: a schematic drawing of the three domains of BoNT/EN. Lower panel: a sliding sequence comparison window showing the percentage of identity between BoNT/EN versus other BoNTs. (FIG. 1C) The BoNT/EN gene cluster contains other hallmarks of BoNT gene clusters, including a neighboring ntnh-like gene as well as upstream orfX-like genes. The region is flanked with putative transposases, similar to other BoNT gene clusters.

FIGS. 2A to 2G. The LC of BoNT/EN cleaves VAMP1/2/3 at a unique site. (FIG. 2A) EN-LC, with or without EDTA, was incubated with BDE. Immunoblot analysis was carried out to detect syntaxin 1 (Syx 1), SNAP-25, and VAMP2. A-LC and X-LC were analyzed in parallel. Cleavage of VAMP2 by X-LC results in loss of immunoblot signals, while cleavage of SNAP-25 by A-LC generates a smaller fragment of SNAP-25 that can still be detected on immunoblot. Incubation with EN-LC resulted in loss of VAMP2 immunoblot signals. It also reduced the signal of Syx 1. EDTA blocked the activity of EN-, A-, and X-LCs. (FIG. 2B) VAMP2 (residues 1-93) was purified as a His6-tagged recombinant protein and incubated with EN-LC. Samples were analyzed by SDS-PAGE and Coomassie Blue staining. EN-LC converted VAMP2 (1-93) into two smaller fragments, indicating that EN-LC cleaved VAMP2. (FIG. 2C) VAMP2 (1-93) was incubated with EN-LC. Whole-protein samples were then analyzed by mass spectrometry (LC-MS/MS) to determine the precise molecular weight of cleaved fragments. The mass spectrometry data for the two cleavage products are color-coded respectively, with mass-to-charge ratio (m/z) noted for each signal. The molecular weight is deducted by multiplying m with z, followed by subtracting z. (FIG. 2D) Sequence alignment between VAMP family members, with cleavage sites for BoNT/B, D, F, G, X, tetanus neurotoxin (TeNT) and En marked in lighter grey. (FIG. 2E) HA-tagged VAMP1, 3, 7, and 8, and Myc-tagged Sec22b and Ykt6 were expressed in HEK293 cells via transient transfection. Cell lysates were incubated with EN-LC and subjected to immunoblot analysis detecting the HA or Myc tag. Actin served as a loading control. EN-LC cleaved VAMP1 and 3, but not other isoforms. (FIGS. 2F and 2G) Syx 1A, 1B, 2, 3, 4, SNAP-23, SNAP-25, and SNAP-29 were expressed in HEK293 cells. Cell lysates were incubated with EN-LC and subjected to immunoblot analysis. EN-LC cleaved Syx 1B, Syx 4, SNAP-23 and SNAP-25.

FIGS. 3A to 3C. BoNT/EN contains an inter-chain disulfide bond and cleaves both VAMP2 and SNAP-25 in neurons. (FIG. 3A) Sequence alignment of the linker regions between the LC and HC of the eight BoNTs plus BoNT/EN. To achieve better proteolytic activation of the LC-$H_N$ domain of BoNT/EN, a thrombin cleavage site was inserted into its linker region. (FIG. 3B) LC-$H_N$ of BoNT/EN was treated with thrombin and then analyzed by SDS-PAGE and Coomassie Blue staining, with or without DTT. (FIG. 3C) Cultured rat cortical neurons were exposed to LC-$H_N$ of BoNT/EN for 12 h. Cell lysates were harvested and immunoblot analysis carried out to detect Syx 1, SNAP-25, and VAMP2. Actin served as a loading control. Thrombin activated EN-LC-$H_N$ cleaved SNAP-25 and VAMP2 more efficiently than non-activated protein. SNAP-25 was detected with CI71.1 (SNAP-N), which recognizes the N-terminal region and did not detect any cleavage products. To further confirm the cleavage of SNAP-25, a second antibody which recognizes the C-terminus of SNAP-25 (residues 195-206, SNAP-C) was used to detect the C-terminal cleavage fragment (lower panel).

(FIG. 4A) A schematic drawing of the synthesis of full-length BoNT/EN using sortase ligation method. (FIG. 4B) Sortase ligation reaction mixture and indicated control components, with or without DTT, were analyzed by SDS-PAGE and Coomassie Blue staining. The molecular weight marker is in lane 1 (starting from the left side). Full-length BoNT/EN (EN-FL) is marked. It separated into two smaller bands in the presence of DTT, confirming that it is activated. (FIG. 4C) Cultured rat cortical neurons exposed to the same amount (15 μl) of sortase ligation mixture or indicated control components for 12 h in medium. Cell lysates were analyzed by immunoblot. Ligating EN-LC-$H_N$ and EN-$H_C$ together by sortase enhanced cleavage of VAMP2 and SNAP-25 only slightly compared to EN-LC-$H_N$/EN-$H_C$ mixture without sortase and EN-LC-$H_N$ alone, as titrating the sortase-ligated mixture by only 1:1.75 abolished any enhancement effect. (FIG. 4D) EN-FL linked by sortase reaction (1 μg) was injected into the gastrocnemius muscles of the right hind limb of mice (N=4). No paralysis was observed. The left limb was not injected with toxins, serving as a control. (FIG. 4E) A EN-A chimeric toxin was generated by ligating EN-LC-$H_N$ with A-$H_C$ by sortase, similar to generating EN-FL. The sortase ligation mixture and indicated control components were analyzed by SDS-PAGE and Coomassie Blue staining. (FIG. 4F) Rat cortical neurons were exposed to indicated control components or sortase-ligated EN-A mixture for 12 h in media.

Cell lysates were analyzed by immunoblot. Ligated EN-A resulted in a greatly enhanced cleavage of VAMP2 and SNAP-25 by ~1,000 folds compared to the mixture of ligating EN-LC-$H_N$ with A-$H_C$ without sortase. (FIG. 4G) EN-A linked by sortase reaction (1 ng) was injected into the gastrocnemius muscles of the right hind limb of mice (N=4). The injected limb developed typical flaccid paralysis, and the toes failed to spread within 12 h. (FIG. 4H) BoNT/A-G, BoNT/X, and BoNT/EN were subjected to dot blot analysis (0.2 μg per toxin, spotted on nitrocellulose membranes), using four horse antisera (trivalent anti-BoNT/A, B, and E, anti-BoNT/C, anti-BoNT/DC, and anti-BoNT/F), two goat antisera (anti-BoNT/G and anti-BoNT/D), as well as a rabbit polyclonal antisera against BoNT/X. BoNT/EN is composed of purified EN-LC-$H_N$ and EN-$H_C$ at 1:1 ratio. These antisera recognized their corresponding target toxins, yet none of them recognized BoNT/EN.

(FIG. 5A) GST-tagged VAMP2 (33-86) was incubated with or without EN-LC. Samples were analyzed by SDS-PAGE and Coomassie Blue staining. (FIGS. 5B and 5C) GST-tagged VAMP2 (33-86) was incubated with EN-LC. Samples were then analyzed by LC-MS/MS mass spectrometry. The mass spectrometry data for the C-terminal fragment generated by EN-LC in panel B, and the N-terminal fragment in panel C.

(FIGS. 6A and 6B) Recombinant GST-VAMP2, Syx 1B, and Syx 4 were purified and incubated with EN-LC for the indicated time. Samples were analyzed by SDS-PAGE and Coomassie Blue staining. (FIG. 6C) Recombinant Syx 1A, Syx 1B, and Syx 4 were incubated with high concentrations of EN-LC for the indicated time. Samples were analyzed by SDS-PAGE and Coomassie Blue staining. The cleavage products were marked with asterisks. (FIGS. 6D and 6E) The cleavage products described in panel C were analyzed by MS-LS/LS for Syx 1B (FIG. 6D) and Syx 4 (FIG. 6E). (FIG. 6F) The sequence alignment of Syx 1A, 1B and Syx 4 at the BoNT/EN cleavage site. BoNT/C cleavage site is also labeled.

(FIGS. 7A and 7B) Recombinant SNAP-25 and SNAP-23 were incubated with low levels or high levels of EN-LC for the indicated time. Low levels of EN-LC only cleaved SNAP-25, while high levels of EN-LC resulted in multiple cleavage bands. (FIG. 7C) SNAP-25 with a HA at its N-terminus was expressed in HEK293 cells. Cell lysates were incubated with EN-LC and then subjected to immunoblot analysis using three antibodies: SNAP-N Ab, SNAP-C Ab, and anti-HA. Only SNAP-C Ab was able to detect a cleavage product, which represents the C-terminal fragment of SNAP-25 generated by EN-LC.

DETAILED DESCRIPTION OF CERTAIN EMBODIMENTS

Figure 2E:
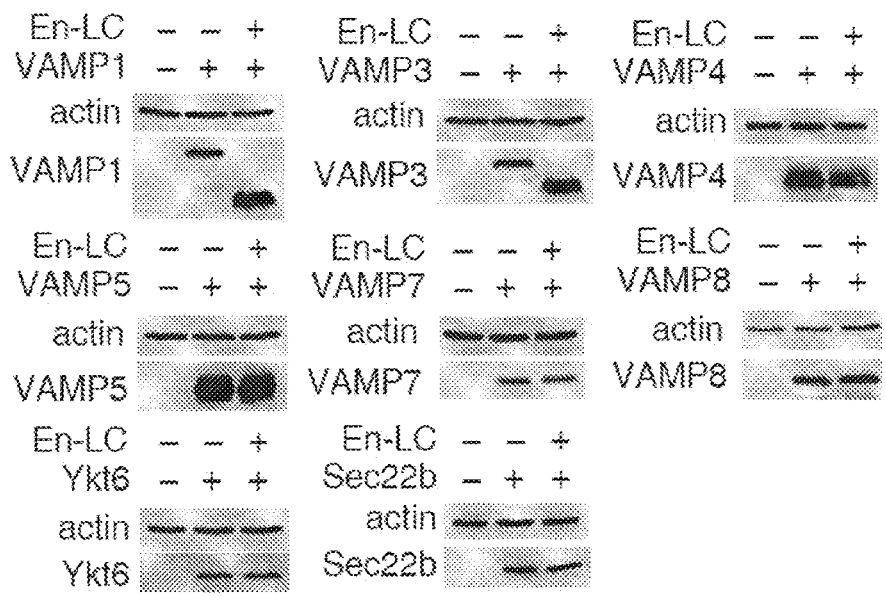

*Clostridium botulinum* neurotoxins (BoNTs) are a family of the most potent bacterial toxins and potential bioterrorism agents. BoNTs have only been identified within *Clostridium* species and its evolutionary origin remains a mystery. Recent studies revealed a homolog of BoNT in *Weissella oryzae*, a gram-positive bacterium[22,23]. It has been shown that the LC of this homolog is an active metalloprotease and cleaves recombinant VAMP2 under in vitro conditions. Thus, this homolog has been tentatively designated as BoNT/Wo[22]. However, BoNT/Wo is quite distant from BoNTs. First, the sequence identity between BoNT/Wo versus other BoNTs is only ~14-16%, which is far below the normal range for the members of BoNT family (~30-63%). Second, the two cysteines that form the essential disulfide bond in BoNTs are not conserved in BoNT/Wo, suggesting that it may have a distinct mode of action. Third, BoNT/Wo gene is not associated with any typical BoNT accessory proteins and it is not in a BoNT gene clusters.

Described herein, in some aspects, is a new member of the BoNT family that exists on a plasmid in an *Enterococcus faecium* bacterial strain. The strain was initially isolated from cow feces in the Cape Cod region in the U.S. It genome was sequenced in May, 2017, which revealed a novel BoNT resided in a BoNT gene cluster. It represents the first protein toxin identified in *E. faecium*, and the first BoNT gene cluster in a bacterial species outside of *Clostridium*. The new toxin polypeptide shares sequence homology with the *Clostridial botulinum* neurotoxin (BoNT) family, and is designated herein as "BoNT/EN." As demonstrated herein, the BoNT/EN cleaves VAMP1/2/3, the same substrate of BoNT/B, D, F, G and X, but at a novel site (D68-L93 in VAMP2). In addition, BoNT/EN cleaves multiple other SNARE proteins including SNAP-25, SNAP-23, syntaxin 1B and syntaxin 4 under in vitro conditions, and cleaves SNAP-25 efficiently within neurons. Although host species/cell types naturally targeted by BoNT/EN remains to be determined, BoNT/EN represents the first protein toxin identified in *E. faecium*. These findings showcase the capability of *E. faecium* to acquire a BoNT gene cluster, which could post a significant biosafety threat for such a commensal organism well-adapted in humans and animals and a leading cause of hospital-acquired multi-antibiotic resistant infections.

The term "*Enterococcus faecium* neurotoxin (BoNT/EN) polypeptide" encompasses any polypeptide or fragment from a *Enterococcus faecium* neurotoxin described herein. In some embodiments, the term BoNT/EN refers to a full-length BoNT/EN. In some embodiments, the term BoNT/EN refers to a fragment of the BoNT/EN that can execute the overall cellular mechanism, whereby a BoNT/EN enters a neuron and/or inhibits neurotransmitter release. In some embodiments, the term BoNT/EN simply refers to a fragment or a variant of the full-length BoNT/EN or BoNT/EN fragment, without requiring the fragment or variant to have any specific function or activity. For example, in some embodiments, a BoNT/EN polypeptide refers to the light chain (LC) of BoNT/EN. In some embodiments, a BoNT/EN polypeptide refers to the heavy chain ($H_C$) of BoNT/EN.

Figures 1A, 1B:
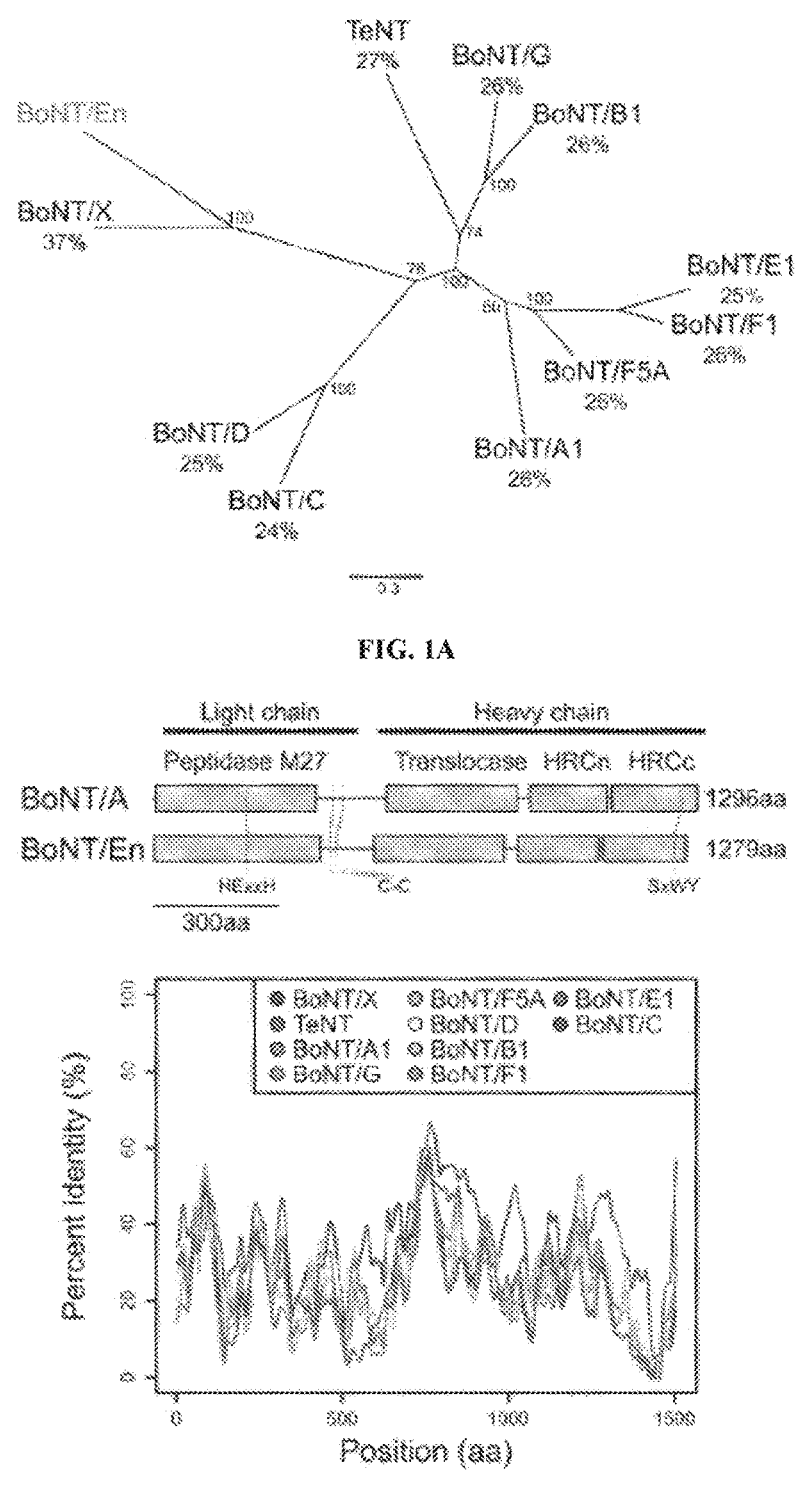

Like other BoNTs, the BoNT/EN is synthesized as one polypeptide comprising a heavy chain ($H_C$, herein termed "BoNT/EN-$H_C$") and a light chain (LC, herein termed "BoNT/EN-LC") linked by a linker region (e.g., in FIG. 1A), where a proteolytic cleavage occurs when BoNT/EN is processed into its mature form. The BoNT/EN-LC comprises a protease domain that cleaves the substrates of BoNT/EN, while the BoNT/EN-$H_C$ comprises a translocation domain and a receptor binding domain, which mediate the entering of BoNT/EN into a cell.

As used herein, the term "*Enterococcus faecium* neurotoxin (BoNT/EN) protease domain" is synonymous to "BoNT/EN-LC." The term means a BoNT domain that can execute the enzymatic target modification step of the intoxication process. A BoNT/EN protease domain specifically targets a BoNT/EN substrate and carries out the proteolytic cleavage of a *C. botulinum* toxin substrate including, e.g., SNARE proteins. In BoNT/EN, the protease domain or the LC corresponds to about amino acid 1-433 of BoNT/EN. The domain boundary may vary by about 25 amino acids. For example, the protease domain may correspond to amino acids 1-408 or 1-458 of BoNT/EN. In some embodiments, the protease domain corresponds to amino acids 1-433, 1-432, 1-431, 1-430, 1-429, 1-428, 1-427, 1-426, 1-425, 1-424, 1-434, 1-435, 1-436, 1-437, 1-438, 1-439, 1-440, 1-441, 1-442, 1-443, or 1-444 of BoNT/EN.

As used herein, the term "*Enterococcus faecium* neurotoxin (BoNT/EN) translocation domain" is synonymous with "BoNT/EN-$H_N$ domain" and means a BoNT/EN domain that can execute the translocation step of the intoxication process that mediates BoNT light chain translocation. "$H_N$" refers to the N-terminus of the heavy chain of a BoNT/EN. The $H_N$ domain facilitates the movement of a BoNT/EN light chain across a membrane into the cytoplasm of a cell.

As used herein, the term "linker region" refers to the amino acid sequence between a BoNT/EN protease domain (LC) and the translocation domain ($H_N$). The BoNT/EN linker region comprises two cysteines at position 424 and 438 that form an inter-molecular disulfide bond between the LC and $H_C$ in a mature form of BoNT/EN, which is required for BoNT/EN activity. Unlike the linker region for other BoNTs (e.g., BoNT/A, BoNT/B, or BoNT/X), the linker region of BoNT/EN does not contains a lysine. Modification of the BoNT/EN linker region is also contemplated herein, where a protease cleavage site is inserted into the BoNT/EN linker region to facilitate its processing.

As used herein, the term "BoNT/EN-LC-$H_N$" refers to a BoNT/EN polypeptide encompassing the protease domain, the linker region, and the translocation domain. The LC-$H_N$ polypeptide is considered to correspond to about amino acid 1-862 of BoNT/EN. The domain boundary may vary by about 25 amino acids. For example, the BoNT/EN-LC-$H_N$ polypeptide may correspond to about amino acid 1-837 or 1-887 of BoNT/EN. In some embodiments, the LC-$H_N$ polypeptide may correspond to amino acids 1-862, 1-863, 1-864, 1-865, 1-866, 1-867, 1-868, 1-869, 1-870, 1-871, 1-861, 1-860, 1-859, 1-858, 1-857, 1-856, 1-855, 1-854, 1-853, or 1-852 of BoNT/EN.

As used herein, the term "*Enterococcus faecium* neurotoxin (BoNT/EN) receptor-binding domain" is synonymous with "BoNT/EN-$H_C$ domain" and means the domain that executes the cell binding step of the intoxication process, including, e.g., the binding of BoNT-EN to a BoNT/EN-specific receptor system located on the plasma membrane surface of a target cell. The receptor binding domain, or the $H_C$, is considered to correspond to about amino acid 863-1279 of BoNT/EN. The domain boundary may vary by about 25 amino acids. For example, the receptor binding domain or $H_C$ may correspond to amino acids 838-1279 or 888-1279 of BoNT/EN. In some embodiments, the receptor binding domain or $H_C$ may correspond to amino acids 863-1279, 864-1279, 865-1279, 866-1279, 867-1279, 868-1279, 869-1279, 700-1279, 701-1279, 702-1279, 862-1279, 861-1279, 860-1279, 859-1279, 858-1279, 857-1279, 856-1279, 855-1279, 854-1279, or 853-1279 of BoNT/EN.

In some aspects, the present disclosure provide isolated BoNT/EN polypeptides. By "isolated" is meant a material (e.g., nucleic acids or proteins) that is free to varying degrees from components which normally accompany it as found in its native state. "Isolate" denotes a degree of separation from original source or surroundings, e.g., from a cell or from the natural source of the material (e.g., nucleic acids or proteins). An isolated polypeptide refers to a polypeptide that is "substantially pure", with respect to other components of a preparation (e.g., other polypeptides). For example, in some embodiments, it refers to a polypeptide that is at least about 50%, 60%>, 70%>, or 75%, preferably at least about 85%, more preferably at least about 90%, and most preferably at least about 95% pure, with respect to other components. In some embodiments, an isolated polypeptide refers to a preparation of polypeptides that contains fewer than about 20%, more preferably fewer than about 15%, 10%, 8%, 7%, most preferably fewer than about 5%, 4%, 3%, 2%, 1%, or less than 1%, of one or more other components (e.g., other polypeptides or cellular components).

In some embodiments, the isolated BoNT/EN polypeptide is a full length BoNT/EN polypeptide, and comprises an amino acid sequence that is at least 85% identical to SEQ ID NO: 1 (see Table 1). For example, the isolated BoNT/EN polypeptide may comprise an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to SEQ ID NO: 1. In some embodiments, the isolated BoNT/EN polypeptide comprises an amino acid sequence that is 85%, 86%, 87%, 88%, 89%, 90%, 91%, 92%, 93%, 94%, 95%, 96%, 97%, 98%, 99%, or 99.5% identical to SEQ ID NO: 1. In some embodiments, the isolated BoNT/EN polypeptide comprises the amino acid sequence of SEQ ID NO: 1. In some embodiments, the isolated BoNT/EN polypeptide consists of the amino acid sequence of SEQ ID NO: 1.

In some embodiments, the isolated BoNT/EN polypeptide is a BoNT/EN light chain (LC) polypeptide, and comprises an amino acid sequence that is at least 85% identical to SEQ ID NO: 2 (see Table 1). For example, the isolated BoNT/EN polypeptide may comprise an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to SEQ ID NO: 2. In some embodiments, the isolated BoNT/EN polypeptide comprises an amino acid sequence that is 85%, 86%, 87%. 88%, 89%, 90%, 91%, 92%, 93%, 94%, 95%, 96%, 97%, 98%, 99%, or 99.5% identical to SEQ ID NO: 2. In some embodiments, the isolated BoNT/EN polypeptide comprises the amino acid sequence of SEQ ID NO: 2. In some embodiments, the isolated BoNT/EN polypeptide consists of the amino acid sequence of SEQ ID NO: 2.

The BoNT/EN-LC polypeptide may be introduced alone into cells where the cleavage of a BoNT substrate (e.g., a SNARE protein) is desired for research or therapeutic purpose, by any known techniques of expression an exogenous protein in the art, e.g., transfection of LC coding sequence directly into cells, via lentiviral vectors, via AAV vectors, or fusing BoNT/EN-LC with cell penetrating peptides).

In some embodiments, the isolated BoNT/EN polypeptide is a BoNT/EN-LC-$H_N$ polypeptide that contains the light chain and the translocation domain of BoNT/EN. The translocation domain is the N-terminal half of the heavy chain. In some embodiments, the isolated BoNT/EN polypeptide comprises an amino acid sequence that is at least 85% identical to SEQ ID NO: 3 (see Table 1). For example, the isolated BoNT/EN polypeptide may comprise an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to SEQ ID NO: 3. In some embodiments, the isolated BoNT/EN polypeptide comprises an amino acid sequence that is 85%, 86%, 87%, 88%, 89%, 90%, 91%, 92%, 93%, 94%, 95%, 96%, 97%, 98%, 99%, or 99.5% identical to SEQ ID NO: 3. In some embodiments, the isolated BoNT/EN polypeptide comprises the amino acid sequence of SEQ ID NO: 3. In some embodiments, the isolated BoNT/EN polypeptide consists of the amino acid sequence of SEQ ID NO: 3.

In some embodiments, the isolated BoNT/EN polypeptide is the receptor binding domain of the BoNT/EN, which is the C-terminal half of the BoNT/EN heavy chain polypeptide. In some embodiments, the isolated BoNT/EN polypeptide comprises an amino acid sequence that is at least 85% identical to SEQ ID NO: 4 (see Table 1). For example, the isolated BoNT/EN polypeptide may comprise an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to SEQ ID NO: 4. In some embodiments, the isolated BoNT/EN polypeptide comprises an amino acid sequence that is 85%, 86%, 87%, 88%, 89%, 90%, 91%, 92%, 93%, 94%, 95%, 96%, 97%, 98%, 99%, or 99.5% identical to SEQ ID NO: 4. In some embodiments, the isolated BoNT/EN polypeptide comprises the amino acid sequence of SEQ ID NO: 4. In some embodiments, the isolated BoNT/EN polypeptide consists of the amino acid sequence of SEQ ID NO: 4.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

Other aspects of the present disclosure provide modified BoNT/EN polypeptides comprising (a) a protease domain; (b) a modified linker region; and (c) a translocation domain; wherein the modified linker region comprises a protease cleavage site. A "modified BoNT/EN" encompasses a BoNT comprising any modifications in the amino acid sequence, e.g., truncation, addition, amino acid substitution, and any combination thereof. In some embodiments, the linker region that connects the light chain and heavy chain of the BoNT/EN is modified.

As described herein, the natural linker region of BoNT/EN comprises two cysteines and there are 13 residues between the two cysteines, a length similar to the linker regions in other BoNTs. However, unlike other BoNTs, the BoNT/EN linker does not contain any lysines. As the endogenous protease that can efficiently activate BoNT/EN remains unknown, a cleavage site for a site-specific protease (e.g., thrombin) can be inserted in the BoNT/EN linker region, as a way to proteolytically separate EN-LC and $H_N$ (e.g., see FIG. 3A). The modified BoNT/EN can be proteolytically activated by the site-specific protease, whose cleavage site is inserted into the linker regions. Non-limiting examples of site-specific protease that may be used in accordance with the present disclosure include: thrombin, TEV, PreScission® (3C protease), Sortase, MMP-12, MMP-13, MMP-17, MMP-20, Granzyme-B, Enterokinase, SUMO protease, LysC, and trypsin. The cleavage site sequences of the site-specific proteases are provided in Table 2. As such, the modified linker region of the modified BoNT/EN comprises the amino acid sequence of SEQ ID NO: 41-47.

In some embodiments, the linker region of the BoNT/EN is replaced with a linker region from a *Clostridial botulinum* neurotoxin (BoNT), e.g., BoNT serotype A (BoNT/A), BoNT serotype B (BoNT/B), or BoNT serotype X (BoNT/X), as described in Zhang et al., *Nature Communications*, 8, Article number: 14130 (2017), incorporated herein by reference). The naturally occurring linker region of other BoNTs are provided in Table 2. In some embodiments, the modified linker region of the modified BoNT/EN comprises the amino acid sequence of SEQ ID NO: 48-55.

In some embodiments, the modified BoNT/EN is a modified BoNT/EN-LC-$H_N$ polypeptide with a modified linker region between the LC and the HN. In some embodiments, the modified BoNT/EN-LC-$H_N$ polypeptide comprises an amino acid sequence that is at least 85% identical to any one of SEQ ID NOs: 5-13 (see Table 3). For example, the modified BoNT/EN-LC-$H_N$ polypeptide may comprise an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to any one of SEQ ID NO: 5-13. In some embodiments, the modified BoNT/EN-LC-$H_N$ polypeptide comprises an amino acid sequence that is 85%, 86%, 87%, 88%, 89%, 90%. 91%, 92%, 93%, 94%, 95%, 96%, 97%, 98%, 99%, or 99.5% identical to any one of SEQ ID NO: 5-13. In some embodiments, the modified BoNT/EN-LC-$H_N$ polypeptide comprises the amino acid sequence of any one of SEQ ID NO: 5-13. In some embodiments, the modified BoNT/EN-LC-$H_N$ polypeptide consists of the amino acid sequence of any one of SEQ ID NO: 5-13.

In some embodiments, the modified BoNT/EN polypeptide further comprises a receptor binding domain. In some embodiments, the receptor binding domain is also from BoNT/EN. As such, the modified BoNT/EN is a modified full-length BoNT/EN polypeptide comprising a modified linker region as described herein. In some embodiments, the modified full-length BoNT/EN polypeptide comprises an amino acid sequence that is at least 85% identical to any one of SEQ ID NOs: 14-22 (see Table 3). For example, the modified full-length BoNT/EN polypeptide may comprise an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to any one of SEQ ID NO: 14-22. In some embodiments, the modified full-length BoNT/EN polypeptide comprises an amino acid sequence that is 85%, 86%, 87%, 88%, 89%, 90%. 91%, 92%, 93%, 94%, 95%, 96%, 97%, 98%, 99%, or 99.5% identical to any one of SEQ ID NO: 14-22. In some embodiments, the modified full-length BoNT/EN polypeptide comprises the amino acid sequence of any one of SEQ ID NO: 14-22. In some embodiments, the modified full-length BoNT/EN polypeptide consists of the amino acid sequence of any one of SEQ ID NO: 14-22.

Other aspects of the present disclosure provide chimeric toxins comprising: (a) a protease domain; (b) a translocation domain; and (c) a receptor binding domain; wherein the protease domain and the translocation domain are from a *Enterococcus faecium* neurotoxin (BoNT/EN), and wherein the receptor binding domain is from a *Clostridial botulinum* neurotoxin (BoNT). For example, the chimeric toxin described herein may comprise a BoNT/EN-LC-$H_N$ polypeptide and a receptor binding domain ($H_C$) from a BoNT selected from, without limitation: BoNT/A1, BoNT/A2, BoNT/B, BoNT/C, BoNT/D, BoNT/E, BoNT/F, BoNT/G, and BoNT/X. In some embodiments, the BoNT/EN-LC-$H_N$ polypeptide may be unmodified or modified (e.g., comprising a modified linker region as described herein).

For example, in some embodiments, an unmodified BoNT/EN-LC-$H_N$ comprises a linker region comprising the amino acid sequence of PNPHFSSQRGLSS (SEQ ID NO: 56). In some embodiments, a modified BoNT/EN-LC-$H_N$ comprises a linker region comprising the amino acid sequence of any one of SEQ ID NOs: 41-55.

In some embodiments, the chimeric toxin comprises an amino acid sequence that is at least 85% identical to any one of SEQ ID NOs: 23-30 (see Table 4). For example, the modified full-length BoNT/EN polypeptide may comprise an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5% identical to any one of SEQ ID NO: 23-30. In some embodiments, the modified full-length BoNT/EN polypeptide comprises an amino acid sequence that is 85%, 86%, 87%, 88%, 89%, 90%, 91%, 92%, 93%, 94%, 95%, 96%, 97%, 98%, 99%, or 99.5% identical to any one of SEQ ID NO: 23-30. In some embodiments, the modified full-length BoNT/EN polypeptide comprises the amino acid sequence of any one of SEQ ID NO: 23-30.

In some embodiments, the modified full-length BoNT/EN polypeptide consists of the amino acid sequence of any one of SEQ ID NO: 23-30.

To generate the chimeric toxins, e.g., the BoNT/EN-LC-$H_N$-A1-$H_C$ toxin, the BoNT/EN-LC-$H_N$ fragment (with or without a modified linker region) is fused to the receptor binding domain ($H_C$) of any one of BoNT/A (e.g., BoNT/A1 or BoNT/A2), BoNT/B, BoNT/C, BoNT/D, BoNT/E, BoNT/E, BoNT/F, and BoNT/G. One skilled in the art is familiar with methods of generate fusion proteins, e.g., using recombinant DNA technology.

Other aspects of the present disclosure provide the functional characterization of the BoNT/EN polypeptides. The BoNT/EN polypeptides, modified BoNT/EN polypeptides, and chimeric BoNT polypeptides of the present disclosure can bind and enter target cells, e.g., neurons, and cleave its substrate proteins, e.g. SNARE proteins. The term "SNARE proteins," as used herein, refers to SNAP (Soluble NSF Attachment Protein) Receptors, which is a large protein superfamily consisting of more than 60 members in yeast and mammalian cells. The primary role of SNARE proteins is to mediate vesicle fusion, i.e., the fusion of vesicles with their target membrane bound compartments (such as a lysosome). The best studied SNARE proteins are those that mediate docking of synaptic vesicles with the presynaptic membrane in neurons, e.g., SNAP-25, VAMP1, VAMP2, VAMP3, VAMP4, VAMP5, VAMP7, VAMP8, syntaxin1, and Ykt6. Several of these SNARE proteins are substrates of BoNTs. For example, VAMP1, VAMP2, VAMP3, SNAP-25, and syntaxin 1 have been shown to be cleaved by known BoNTs, e.g., BoNT/A and BoNT/B. It is shown herein that BoNT/EN cleaves at least VAMP1, VAMP2, VAMP3, SNAP-25, SNAP-23, syntaxin 1, and syntaxin 4.

The term "enters a cell," when used to describe the action of a BoNT/EN polypeptides, encompasses the binding of a BoNT/EN to cell, the internalization of the toxin, the translocation of the toxin light chain into the cytoplasm and the enzymatic modification of a BoNT substrate, e.g., a SNARE protein.

Another surprising finding of the present disclosure is that BoNT/EN cleaves VAMP proteins (e.g., VAMP1, VAMP2, or VAMP3) at a novel site what was not previously described. BoNT/EN was found herein to cleave between amino acids A69 and D70 of VAMP1 (SEQ ID NO: 31), between amino acids A67 and D68 of VAMP2 (SEQ ID NO: 32), and between amino acids A54 and D55 of VAMP3 (SEQ ID NO: 33). In some embodiments, BoNT/EN cleaves between amino acids M182 and D183 of syntaxin 1B (SEQ ID NO: 37), and cleaves between amino acids K191 and D192 of syntaxin 4 (SEQ ID NO: 38).

In some embodiments, the BoNT/EN polypeptide of the present disclosure cleaves a SNARE protein in a target cell. As used herein, a "target cell" means a cell that is a naturally occurring cell that BoNT/EN is capable of entering or intoxicating. In some embodiments, a target cell is a secretory cell, e.g., a neuron or a secretory immune cell. Examples of neurons that may be BoNT target cells include, without limitation, motor neurons; sensory neurons; autonomic neurons; such as, e.g., sympathetic neurons and parasympathetic neurons; non-peptidergic neurons, such as, e.g., cholinergic neurons, adrenergic neurons, noradrenergic neurons, serotonergic neurons, GABAergic neurons; and peptidergic neurons, such as, e.g., Substance P neurons, Calcitonin Gene Related Peptide neurons, vasoactive intestinal peptide neurons, Neuropeptide Y neurons, cholecystokinin neurons.

The BoNT/EN polypeptide of the present disclosure is able to target other types of secretory cells other than neurons. In some embodiments, the secretory cell targeted by the BoNT/EN polypeptide is a secretory immune cell. A "secretory immune cell," as used herein, refers to immune cells that secrets cytokines, chemokines, or antibodies. Such secretory immune cells may be innate immune cells including, without limitation, natural killer cells, mast cells, eosinophils, basophils, macrophages, neutrophils, and dendritic cells. Secretory immune cells that secret antibodies (e.g., white blood cells) may also be targeted by the BoNT polypeptides of the present disclosure. Non-limiting examples of antibody secreting cells include, without limitation, plasma B cells, plasmocytes, plasmacytes, and effector B cells. In some embodiments, the target cell is a cultured cell, e.g., a cultured neuron or a cultured secretory immune cell. In some embodiments, the target cell is in vivo. In some embodiments, target cell is from a mammal. In some embodiments, the mammal is a human. In embodiments, the mammal is a rodent, e.g., a mouse or a rat. In some embodiments, the target cell is an insect cell.

In some embodiments, the BoNT/EN polypeptide suppresses neuronal activity. "Suppress neuronal activity" means when a neuronal cell (one of the cell types targeted by BoNT/EN) is contacted with BoNT/EN, it's activity (e.g., activity in transmitting neuronal signals) is reduced by at least 20%, compared to without BoNT/EN. For example, the activity of a neuronal cell, when contacted with BoNT/EN, may be reduced by at least 20%, at least 30%, at least 40%, at least 50%, at least 60%, at least 70%, at least 80%, at least 90%, at least 95%, at least 99% or more, compared to without BoNT/EN. In some embodiments, the activity of a neuronal cell, when contacted with BoNT/EN, is reduced by 20%, 30%, 40%, 50%, 60%, 70%, 80%, 90%, 95%, 99%, or 100%, compared to without BoNT/EN.

In some embodiments, the BoNT polypeptide induces flaccid paralysis. "Flaccid paralysis" refers to a clinical manifestation characterized by weakness or paralysis and reduced muscle tone without other obvious cause (e.g., trauma).

In some embodiments, the BoNT polypeptide modulates immune response. "Modulate immune response" means when a secretory immune cell is contacted with BoNT/EN, it's activity (e.g., activity in producing an immune response) is changed (e.g., reduced) by at least 20%, compared to without BoNT/EN. For example, the activity of a secretory immune cell, when contacted with BoNT/EN, may be changed (e.g., reduced) by at least 20%, at least 30%, at least 40%, at least 50%, at least 60%, at least 70%, at least 80%, at least 90%, at least 95%, at least 99% or more, compared to without BoNT/EN. In some embodiments, the activity of a secretory immune cell, when contacted with BoNT/EN, is changed (e.g., reduced) by 20%, 30%, 40%, 50%, 60%, 70%, 80%, 90%, 95%, 99%, or 100%, compared to without BoNT/EN.

In some embodiments, the BoNT/EN polypeptide has reduced reactivity with an antibody against BoNT serotype A, B, C, D, E, F, G, or X. "Has reduced reactivity" means that the reactivity between BoNT/EN and an antibody against BoNT serotype A, B, C, D, E, F, G, or X is reduced by at least 20%, compared to the reactivity between a BoNT (e.g., serotype A, B, C, D, E, F, G, or X) and an antibody against such BoNT. For example, the reactivity between BoNT/EN and an antibody against BoNT serotype A, B, C, D, E, F, or G may be reduced by at least 20%, at least 30%, at least 40%, at least 50%, at least 60%, at least 70%, at least 80%, at least 90%, at least 95%, at least 99% or more, compared to the reactivity between a BoNT (e.g., serotype A, B, C, D, E, F, G, or X) and an antibody against such BoNT. In some embodiments, the reactivity between BoNT/EN and an antibody against BoNT serotype A, B, C, D, E, F, G, or X is reduced by 20%, 30%, 40%, 50%, 60%, 70%, 80%, 90%, 95%, 99% or more, compared to the reactivity between a BoNT (e.g., serotype A, B, C, D, E, F, G, or X) and an antibody against such BoNT. In some embodiments, the BoNT/EN polypeptide does not cross react with an antibody against BoNT serotype A, B, C, D, E, F, G, or X.

Other aspects of the present disclosure provide nucleic acids encoding the isolated BoNT/EN polypeptides, the modified BoNT/EN polypeptides, and the chimeric toxins described herein. The nucleic acids encoding the isolated polypeptide fragments of the present disclosure, may be DNA or RNA, double-stranded or single stranded. In certain aspects, the subject nucleic acids encoding the isolated polypeptide fragments are further understood to include nucleic acids encoding polypeptides that are variants of any one of the modified BoNT polypeptides described herein.

Variant nucleotide sequences include sequences that differ by one or more nucleotide substitutions, additions or deletions, such as allelic variants. In some embodiments, the nucleic acids comprise a polynucleotide encoding a polypeptide comprising an amino acid sequence that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.5%, or 100% identity to the isolated BoNT/EN polypeptides, the modified BoNT/EN polypeptides, and the chimeric toxins. In some embodiments, the isolated nucleic acid molecule of the present disclosure comprising a polynucleotide encoding a polypeptide comprising an amino acid sequence that has 85%, 86%, 87%, 88%, 89%, 90%, 91%, 92%, 93%, 94%, 95%, 96%, 97%, 98%, 99%, or 100% identity of any one of SEQ ID NOs: 1-30.

In some embodiments, such nucleic acids may be incorporated into vectors (e.g., cloning vectors or expression vectors). In some embodiments, the vectors may be adapted for expressing the encoded polypeptides in a cell (e.g., a bacterial cell, an insect cell, or a mammalian cell).

In some embodiments, the polynucleotide encoding the BoNT/EN polypeptide, the modified BoNT/EN polypeptide, or the chimeric toxin is operably linked to a promoter. A variety of promoters can be used for expression of the polypeptides described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter. Regulatable promoters can also be used. Such regulatable promoters include those using the lac repressor from *E. coli* as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)].

Other systems include FK506 dimer, VP16 or p65 using astradiol, RU486, diphenol murislerone, or rapamycin. Inducible systems are available from Invitrogen, Clontech and Ariad. Regulatable promoters that include a repressor with the operon can be used. In one embodiment, the lac repressor from *Escherichia coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (HCMV) major immediate-early promoter to create a tetR-tet operator system to control gene expression in mammalian cells. In one embodiment, a tetracycline inducible switch is used (Yao et al., Human Gene Therapy; Gossen et al., Natl. Acad. Sci. USA, 89:5547-5551 (1992); Shockett et al., Proc. Natl. Acad. Sci. USA, 92:6522-6526 (1995)).

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

An expression vector comprising the nucleic acid can be transferred to a host cell by conventional techniques (e.g., electroporation, liposomal transfection, and calcium phosphate precipitation) and the transfected cells are then cultured by conventional techniques to produce the polypeptides described herein. In some embodiments, the expression of the polypeptides described herein is regulated by a constitutive, an inducible or a tissue-specific promoter.

Also provided are cells comprising the nucleic acids or nucleic acid vectors, and cells expressing the BoNT/EN polypeptides, the modified BoNT/EN polypeptides, and the chimeric toxins described herein. The BoNT/EN polypeptides, the modified BoNT/EN polypeptides, and the chimeric toxins described herein will generally be produced by expression form recombinant nucleic acids in appropriate cells (e.g., *E. coli*, insect cells, or mammalian cells) and isolated.

The host cells used to express the isolated polypeptides described herein may be either bacterial cells such as *Escherichia coli*, or, preferably, eukaryotic cells. In particular, mammalian cells, such as Chinese hamster ovary cells (CHO), in conjunction with a vector such as the major intermediate early gene promoter element from human cytomegalovirus is an effective expression system for immunoglobulins (Foecking et al. (1986) "Powerful And Versatile Enhancer-Promoter Unit For Mammalian Expression Vectors," Gene 45:101-106; Cockett et al. (1990) "High Level Expression Of Tissue Inhibitor Of Metalloproteinases In Chinese Hamster Ovary Cells Using Glutamine Synthetase Gene Amplification," Biotechnology 8:662-667). A variety of host-expression vector systems may be utilized to express the isolated polypeptides described herein. Such host-expression systems represent vehicles by which the coding sequences of the isolate d polypeptides described herein may be produced and subsequently purified, but also represent cells which may, when transformed or transfected with the appropriate nucleotide coding sequences, express the isolated polypeptides described herein in situ. These include, but are not limited to, microorganisms such as bacteria (e.g., *E. coli* and *B. subtilis*) transformed with recombinant bacteriophage DNA, plasmid DNA or cosmid DNA expression vectors containing coding sequences for the isolated polypeptides described herein; yeast (e.g., *Saccharomyces pichia*) transformed with recombinant yeast expression vectors containing sequences encoding the isolated polypeptides described herein; insect cell systems infected with recombinant virus expression vectors (e.g., baclovirus) containing the sequences encoding the isolated polypeptides described herein; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the isolated polypeptides described herein; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the polypeptides being expressed. For example, when a large quantity of such a protein is to be produced, for the generation of pharmaceutical compositions of polypeptides described herein, vectors which direct the expression of high levels of fusion protein products that are readily purified may be desirable. Such vectors include, but are not limited, to the *E. coli* expression vector pUR278 (Rüther et al. (1983) "Easy Identification Of cDNA Clones," EMBO J. 2:1791-1794), in which the coding sequence may be ligated individually into the vector in frame with the lac Z coding region so that a fusion protein is produced; pIN vectors (Inouye et al. (1985) "Up-Promoter Mutations In The lpp Gene Of *Escherichia Coli*," Nucleic Acids Res. 13:3101-3110; Van Heeke et al. (1989) "Expression Of Human Asparagine Synthetase In *Escherichia Coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione.

The pGEX vectors are designed to include thrombin or factor Xa protease cleavage sites so that the cloned target gene product can be released from the GST moiety. In an insect system, *Autographa californica* nuclear polyhedrosis virus (AcNPV) is used as a vector to express foreign genes. The virus grows in *Spodoptera frugiperda* cells. The coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan et al. (1984) "Adenovirus Tripartite Leader Sequence Enhances Translation Of mRNAs Late After Infection," Proc. Natl. Acad. Sci. USA 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic.

The efficiency of expression may be enhanced by the inclusion of appropriate transcription enhancer elements, transcription terminators, etc. (see Bitter et al. (1987) "Expression And Secretion Vectors For Yeast," Methods in Enzymol. 153:516-544). In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. For example, in certain embodiments, the polypeptides described herein may be expressed as a single gene product (e.g., as a single polypeptide chain, i.e., as a polyprotein precursor), requiring proteolytic cleavage by native or recombinant cellular mechanisms to form separate polypeptides described herein.

The disclosure thus encompasses engineering a nucleic acid sequence to encode a polyprotein precursor molecule comprising the polypeptides described herein, which includes coding sequences capable of directing post translational cleavage of said polyprotein precursor. Post-translational cleavage of the polyprotein precursor results in the polypeptides described herein. The post translational cleavage of the precursor molecule comprising the polypeptides described herein may occur in vivo (i.e., within the host cell by native or recombinant cell systems/mechanisms, e.g. furin cleavage at an appropriate site) or may occur in vitro (e.g. incubation of said polypeptide chain in a composition comprising proteases or peptidases of known activity and/or in a composition comprising conditions or reagents known to foster the desired proteolytic action).

Purification and modification of recombinant proteins is well known in the art such that the design of the polyprotein precursor could include a number of embodiments readily appreciated by a skilled worker. Any known proteases or peptidases known in the art can be used for the described modification of the precursor molecule, e.g., thrombin or factor Xa (Nagai et al. (1985) "Oxygen Binding Properties Of Human Mutant Hemoglobins Synthesized In *Escherichia Coli*," Proc. Nat. Acad. Sci. USA 82:7252-7255, and reviewed in Jenny et al. (2003) "A Critical Review Of The Methods For Cleavage Of Fusion Proteins With Thrombin And Factor Xa," Protein Expr. Purif. 31:1-11, each of which is incorporated by reference herein in its entirety)), enterokinase (Collins-Racie et al. (1995) "Production Of Recombinant Bovine Enterokinase Catalytic Subunit In *Escherichia Coli* Using The Novel Secretory Fusion Partner DsbA," Biotechnology 13:982-987 hereby incorporated by reference herein in its entirety)), furin, and AcTEV (Parks et al. (1994) "Release Of Proteins And Peptides From Fusion Proteins Using A Recombinant Plant Virus Proteinase," Anal. Biochem. 216:413-417 hereby incorporated by reference herein in its entirety)) and the Foot and Mouth Disease Virus Protease C3.

Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 293T, 3T3, W138, BT483, Hs578T, HTB2, BT20 and T47D, CRL7030 and Hs578Bst.

For long-term, high-yield production of recombinant proteins, stable expression is preferred. For example, cell lines which stably express polypeptides described herein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the polypeptides described herein. Such engineered cell lines may be particularly useful in screening and evaluation of polypeptides that interact directly or indirectly with the polypeptides described herein.

A number of selection systems may be used, including but not limited to the herpes simplex virus thymidine kinase (Wigler et al. (1977) "Transfer of Purified Herpes Virus Thymidine Kinase Gene To Cultured Mouse Cells," Cell 11: 223-232), hypoxanthine-guanine phosphoribosyltransferase (Szybalska et al. (1992) "Use Of The HPRT Gene And The HAT Selection Technique In DNA-Mediated Transformation Of Mammalian Cells First Steps Toward Developing Hybridoma Techniques And Gene Therapy," Bioessays 14: 495-500), and adenine phosphoribosyltransferase (Lowy et al. (1980) "Isolation Of Transforming DNA: Cloning The Hamster aprt Gene," Cell 22: 817-823) genes can be employed in tk-, hgprt- or aprt-cells, respectively. Also, antimetabolite resistance can be used as the basis of selection for the following genes: dhfr, which confers resistance to methotrexate (Wigler et al. (1980) "Transformation Of Mammalian Cells With An Amplifiable Dominant-Acting Gene," Proc. Natl. Acad. Sci. USA 77:3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. USA 78: 1527-1531); gpt, which confers resistance to mycophenolic acid (Mulligan et al. (1981) "Selection For Animal Cells That Express The *Escherichia coli* Gene Coding For Xanthine-Guanine Phosphoribosyltransferase," Proc. Natl. Acad. Sci. USA 78: 2072-2076); neo, which confers resistance to the aminoglycoside G-418 (Tolstoshev (1993) "Gene Therapy, Concepts, Current Trials And Future Directions," Ann. Rev. Pharmacol. Toxicol. 32:573-596; Mulligan (1993) "The Basic Science Of Gene Therapy," Science 260:926-932; and Morgan et al. (1993) "Human Gene Therapy," Ann. Rev. Biochem. 62:191-217) and hygro, which confers resistance to hygromycin (Santerre et al. (1984) "Expression Of Prokaryotic Genes For Hygromycin B And G418 Resistance As Dominant-Selection Markers In Mouse L Cells," Gene 30:147-156). Methods commonly known in the art of recombinant DNA technology which can be used are described in Ausubel et al (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al. (1981) "A New Dominant Hybrid Selective Marker For Higher Eukaryotic Cells," J. Mol. Biol. 150:1-14.

The expression levels of the polypeptides described herein can be increased by vector amplification (for a review, see Bebbington and Hentschel, The use of vectors based on gene amplification for the expression of cloned genes in mammalian cells in DNA cloning, Vol. 3 (Academic Press, New York, 1987). When a marker in the vector system expressing a polypeptide described herein is amplifiable, increase in the level of inhibitor present in culture of host cell will increase the number of copies of the marker gene. Since the amplified region is associated with the nucleotide sequence of a polypeptide described herein or a polypeptide described herein, production of the polypeptide will also increase (Crouse et al. (1983) "Expression And Amplification Of Engineered Mouse Dihydrofolate Reductase Minigenes," Mol. Cell. Biol. 3:257-266).

Once a polypeptide described herein has been recombinantly expressed, it may be purified by any method known in the art for purification of polypeptides, polyproteins or antibodies (e.g., analogous to antibody purification schemes based on antigen selectivity) for example, by chromatography (e.g., ion exchange, affinity, particularly by affinity for the specific antigen (optionally after Protein A selection where the polypeptide comprises an Fe domain (or portion thereof)), and sizing column chromatography), centrifugation, differential solubility, or by any other standard technique for the purification of polypeptides or antibodies. Other aspects of the present disclosure relate to a cell comprising a nucleic acid described herein or a vector described herein.

The cell may be a prokaryotic or eukaryotic cell. In some embodiments, the cell in a mammalian cell. Exemplary cell types are described herein. Other aspects of the present disclosure related to a cell expressing the modified BoNT polypeptides described herein. The cell may be a prokaryotic or eukaryotic cell. In some embodiments, the cell in a mammalian cell. Exemplary cell types are described herein. The cell can be for propagation of the nucleic acid or for expression of the nucleic acid, or both. Such cells include, without limitation, prokaryotic cells including, without limitation, strains of aerobic, microaerophilic, capnophilic, facultative, anaerobic, gram-negative and gram-positive bacterial cells such as those derived from, e.g., *Escherichia coli, Bacillus subtilis, Bacillus licheniformis, Bacteroides fragilis, Clostridia perfringens, Clostridia difficile, Caulobacter crescentus, Lactococcus lactis, Methylobacterium extorquens, Neisseria meningirulls, Neisseria meningitidis, Pseudomonas fluorescens* and *Salmonella typhimurium*; and eukaryotic cells including, without limitation, yeast strains, such as, e.g., those derived from *Pichia pastoris, Pichia methanolica, Pichia angusta, Schizosaccharomyces pombe, Saccharomyces cerevisiae* and *Yarrowia lipolytica*; insect cells and cell lines derived from insects, such as, e.g., those derived from *Spodoptera frugiperda, Trichoplusia ni, Drosophila melanogaster* and *Manduca sexta*; and mammalian cells and cell lines derived from mammalian cells, such as, e.g., those derived from mouse, rat, hamster, porcine, bovine, equine, primate and human. Cell lines may be obtained from the American Type Culture Collection, European Collection of Cell Cultures and the German Collection of Microorganisms and Cell Cultures. Non-limiting examples of specific protocols for selecting, making and using an appropriate cell line are described in e.g., INSECT CELL CULTURE ENGINEERING (Mattheus F. A. Goosen et al. eds., Marcel Dekker, 1993); INSECT CELL CULTURES: FUNDAMENTAL AND APPLIED ASPECTS (J. M. Vlak et al. eds., Kluwer Academic Publishers, 1996); Maureen A. Harrison & Ian F. Rae. GENERAL TECHNIQUES OF CELL CULTURE (Cambridge University Press, 1997): CELL AND TISSUE CULTURE: LABORATORY PROCEDURES (Alan Doyle et al eds., John Wiley and Sons, 1998); R. Ian Freshney, CULTURE OF ANIMAL CELLS: A MANUAL OF BASIC TECHNIQUE (Wiley-Liss, 4.sup.th ed. 2000); ANIMAL CELL CULTURE: A PRACTICAL APPROACH (John R. W. Masters ed., Oxford University Press, 3.sup.rd ed. 2000); MOLECULAR CLONING A LABORATORY MANUAL, supra, (2001); BASIC CELL CULTURE: A PRACTICAL APPROACH (John M. Davis, Oxford Press, 2.sup.nd ed. 2002); and CURRENT PROTOCOLS IN MOLECULAR BIOLOGY, supra, (2004).

These protocols are routine procedures within the scope of one skilled in the art and from the teaching herein. Yet other aspects of the present disclosure relate to a method of producing a polypeptide described herein, the method comprising obtaining a cell described herein and expressing nucleic acid described herein in said cell. In some embodiments, the method further comprises isolating and purifying a polypeptide described herein.

In some embodiments, botulinum neurotoxin can be obtained by establishing and growing cultures of Clostridium botulinum in a fermenter and then harvesting and purifying the fermented mixture in accordance with known procedures. All the botulinum toxin serotypes are initially synthesized as inactive single chain proteins which must be cleaved or nicked by proteases to become neuroactive.

The bacterial strains that make botulinum toxin serotypes A and G possess endogenous proteases and serotypes A and G can therefore be recovered from bacterial cultures in predominantly their active form. In contrast, botulinum toxin serotypes C, D and E are synthesized by non-proteolytic strains and are therefore typically inactive when recovered from culture. Serotypes B and F are produced by both proteolytic and non-proteolytic strains and therefore can be recovered in either the active or inactive form. The proteolytic strains that produce, for example, the botulinum toxin type B serotype may only cleave a portion of the toxin produced. The production of BoNT/EN polypeptides using these strains are contemplated herein.

The exact proportion of nicked to un-nicked molecules depends on the length of incubation and the temperature of the culture. Therefore, a certain percentage of a preparation of, for example, the botulinum toxin type B toxin may be inactive. In one embodiment, the neurotoxin of the present disclosure is in an active state. In one embodiment, the neurotoxin is in an inactive state. In one embodiment, a combination of active and inactive neurotoxin is envisioned.

One aspect of the present disclosure provides alternative methods of producing full length BoNT/EN polypeptides (with or without modification in the linker region) or chimeric toxins via an in vitro transpeptidase reaction that ligates two non-toxic fragments of BoNTs. Such methods comprise the steps of: (i) obtaining a first BoNT fragment comprising a light chain (LC) and a N-terminal domain of a heavy chain ($H_N$), wherein the first BoNT fragment comprises a C-terminal LPXTGG (SEQ ID NO: 57) motif; (ii) obtaining a second BoNT fragment comprising a C-terminal domain of the heavy chain ($H_C$); wherein the second BoNT fragment comprise a specific protease cleavage site at its N-terminus; (iii) cleaving the second BoNT fragment with a specific protease, wherein the cleavage results in a free glycine residue at the N-terminus; and (iv) contacting the first BoNT fragment and the second BoNT fragment in the presence of a transpeptidase, thereby ligating the first BoNT fragment and the second BoNT fragment to form a ligated BoNT.

In some embodiments, the first BoNT fragment comprises the BoNT/EN-LC-$H_N$ polypeptide described herein fused to a C-terminal LPXTGG (SEQ ID NO: 57) motif (e.g., SEQ ID NO: 57), or any variants thereof. In some embodiments, the second BoNT fragment comprises the He polypeptide described herein, or any variants thereof (e.g., SEQ ID NO: 4). It is to be understood that any BoNT fragments or domains may be ligated using the methods described herein.

The methods described herein may also be used to generate chimeric toxins. For example, the first BoNT fragment may be from BoNT/EN, while the second BoNT fragment may be from BoNT serotype A, B, C, D, E, F, G, or X. One skilled in the art will be able to discern the combinations that may be made.

In some embodiments, the transpeptidase is a sortase. In some embodiments, the sortase is from Staphylococcus aureus (SrtA).

Other peptide ligation systems available in the art may also be used to ligate two non-toxic BoNT fragments. For example, an intein-mediated protein ligation reaction allows the ligation of a synthetic peptide or a protein with an N-terminal cysteine residue to the C-terminus of a bacterially expressed protein through a native peptide bond (Evans et al., (1998) Protein Sci. 7, 2256-2264, Dawson et al., (1994) Science 266, 776-779; Tam et al., (1995) Proc. Natl. Acad. Sci. USA 92, 12485-12489, Muir et al., (1998) Proc. Natl. Acad. Sci. USA95,6705-6710; Severinov and Muir (1998) J. Biol. Chem. 273, 16205-16209, the entire contents of which are incorporated herein by references). Kits are commercially available (e.g., from New England Biolabs) for intern-mediated protein ligation reactions.

In some embodiments, the first BoNT fragment further comprises an affinity tag. In some embodiments, the affinity tag is fused to first BoNT fragment at the N-terminus. In some embodiments, the affinity tag is fused to the first BoNT fragment at the C-terminus. In the event that the affinity tag is fused to the C-terminus of the first BoNT fragment, the transpeptidase cleaves between the T and G in the LPXTGG (SEQ ID NO: 57) motif and removes the affinity tag before ligating the first BoNT fragment and the second BoNT fragment.

In some embodiments, the second BoNT fragment further comprises an affinity tag. In some embodiments, the affinity tag is fused to the first BoNT fragment at the N-terminus. In some embodiments, the affinity tag is fused to the second BoNT fragment at the C-terminus. In the event that the affinity tag is fused to the N-terminus of the first BoNT fragment, the specific protease cleaves in the specific protease cleavage site and removes the affinity tag before ligating the first BoNT fragment and the second BoNT fragment by the transpeptidase.

An "affinity tag," as used herein, refers to a polypeptide sequence that can bind specifically to a substance or a moiety, e.g., a tag comprising six Histidines bind specifically to $Ni^{2+}$. Affinity tags may be appended to proteins to facilitate their isolation. The affinity tags are typically fused to proteins via recombinant DNA techniques known by those skilled in the art. The use of affinity tags to facilitate protein isolate is also well known in the art. Suitable affinity tags that may be used in accordance with the present disclosure include, without limitation, His6, GST, Avi, Strep, S, MBP, Sumo, FLAG, HA, Myc, SBP, E, Calmodulin, Softag 1, Softag 3, TC, V5, VSV, Xpress, Halo, and Fc.

The second BoNT fragment has a specific protease cleavage at the N-terminus. Cleavage of the site by the specific protease results to a free glycine residue at the N-terminus of the second BoNT fragment. Suitable specific protease that may be used in accordance with the present disclosure include, without limitation: thrombin, TEV, PreScission® (3C protease), Enterokinase, and SUMO protease. In some embodiments, the specific protease is thrombin, and the cleavage site is: LVPRIGS (SEQ ID NO: 41).

The BoNT/EN polypeptides, the modified BoNT/EN polypeptides, and the chimeric toxins described herein affords potential for therapeutic use. For example, in some embodiments, BoNT/EN is more potent compared to other BoNT serotypes. In other embodiments, BoNT/EN is more versatile and may be more effective in a wide range of cells due to its ability to cleave more substrates than other BoNT serotypes.

Thus, the present disclosure also provides compositions comprising the BoNT/EN polypeptides, the modified BoNT/EN polypeptides, or the chimeric toxins described herein. In some embodiments, the composition is a pharmaceutical composition. As it may also become clear later in the present disclosure, the pharmaceutical composition may further comprise other therapeutic agents suitable for the specific disease such composition is designed to treat. In some embodiments, the pharmaceutically composition further comprises pharmaceutically-acceptable carriers.

The term "pharmaceutically-acceptable carrier", as used herein, means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the polypeptide from one site (e.g., the delivery site) of the body, to another site (e.g., organ, tissue or portion of the body).

A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethylcellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide: (15) alginic acid; (16) pyrogEN-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, a BoNT polypeptide of the present disclosure in a composition is administered by injection, by means of a catheter, by means of a suppository, or by means of an implant, the implant being of a porous, non-porous, or gelatinous material, including a membrane, such as a sialastic membrane, or a fiber.

Typically, when administering the composition, materials to which the polypeptide of the disclosure does not absorb are used. In other embodiments, the polypeptides of the present disclosure are delivered in a controlled release system. Such compositions and methods for administration are provides in U.S. Patent publication No. 2007/0020295, the contents of which are herein incorporated by reference. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

The polypeptides of the present disclosure can be administered as pharmaceutical compositions comprising a therapeutically effective amount of a binding agent and one or more pharmaceutically compatible ingredients. In typical embodiments, the pharmaceutical composition is formulated in accordance with routine procedures as a pharmaceutical composition adapted for intravenous or subcutaneous administration to a subject, e.g., a human being.

Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration. A pharmaceutical composition for systemic administration may be a liquid, e.g., sterile saline, lactated Ringer's or Hank's solution. In addition, the pharmaceutical composition can be in solid forms and re-dissolved or suspended immediately prior to use. Lyophilized forms are also contemplated. The pharmaceutical composition can be contained within a lipid particle or vesicle, such as a liposome or microcrystal, which is also suitable for parenteral administration. The particles can be of any suitable structure, such as unilamellar or plurilamellar, so long as compositions are contained therein.

The polypeptides of the present disclosure can be entrapped in 'stabilized plasmid-lipid particles' (SPLP) containing the fusogenic lipid dioleoylphosphatidyletha-nolamine (DOPE), low levels (5-10 mol %) of cationic lipid, and stabilized by a polyethyleneglycol (PEG) coating (Zhang Y. P. et al., Gene Ther. 1999, 6:1438-47). Positively charged lipids such as N-[1-(2,3-dioleoyloxi)propyl]-N,N, N-trimethyl-amoniummethylsulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757. The pharmaceutical compositions of the present disclosure may be administered or packaged as a unit dose, for example.

The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle. In some embodiments, the polypeptides (e.g., modified or unmodified BoNT/EN or chimeric toxin) described herein may be conjugated to a therapeutic moiety, e.g., an antibiotic. Techniques for conjugating such therapeutic moieties to polypeptides, including e.g., Fc domains, are well known; see, e.g., Amon et al., "Monoclonal Antibodies For Immunotargeting Of Drugs In Cancer Therapy", in Monoclonal Antibodies And Cancer Therapy, Reisfeld et al. (eds.), 1985, pp. 243-56, Alan R. Liss, Inc.); Hellstrom et al., "Antibodies For Drug Delivery", in Controlled Drug Delivery (2nd Ed.), Robinson et al. (eds.), 1987, pp. 623-53. Marcel Dekker, Inc.); Thorpe, "Antibody Carriers Of Cytotoxic Agents In Cancer Therapy: A Review", in Monoclonal Antibodies '84: Biological And Clinical Applications, Pinchera et al. (eds.), 1985, pp. 475-506); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), 1985, pp. 303-16, Academic Press; and Thorpe et al. (1982) "The Preparation And Cytotoxic Properties Of Antibody-Toxin Conjugates," Immunol. Rev., 62:119-158. Further, the pharmaceutical composition can be provided as a pharmaceutical kit comprising (a) a container containing a polypeptide of the disclosure in lyophilized form and (b) a second container containing a pharmaceutically acceptable diluent (e.g., sterile water) for injection. The pharmaceutically acceptable diluent can be used for reconstitution or dilution of the lyophilized polypeptide of the disclosure. Optionally associated with such container(s) can be a notice in the form prescribed by a governmental agency regulating the manufacture, use or sale of pharmaceuticals or biological products, which notice reflects approval by the agency of manufacture, use or sale for human administration. In another aspect, an article of manufacture containing materials useful for the treatment of the diseases described above is included. In some embodiments, the article of manufacture comprises a container and a label.

Suitable containers include, for example, bottles, vials, syringes, and test tubes. The containers may be formed from a variety of materials such as glass or plastic. In some embodiments, the container holds a composition that is effective for treating a disease described herein and may have a sterile access port. For example, the container may be an intravenous solution bag or a vial having a stopper pierceable by a hypodermic injection needle. The active agent in the composition is an isolated polypeptide of the disclosure. In some embodiments, the label on or associated with the container indicates that the composition is used for treating the disease of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use.

The use of the BoNT/EN polypeptides (modified or unmodified), the chimeric toxin, the nucleic acids encoding these polypeptides, or the composition comprising such polypeptides may be used in medicine. In some embodiments, the BoNT/EN polypeptides (modified or unmodified), the chimeric toxin, the nucleic acids encoding these polypeptides, or the composition comprising such polypeptides are used for treating a condition associated with unwanted neuronal activity.

Thus, further provided herein are methods of treating a condition associated with unwanted neuronal activity, the method comprising administering a therapeutically effective amount of the modified or unmodified BoNT/EN, or the chimeric toxin polypeptide, or the pharmaceutical composition comprising such to a subject in need of to thereby treat the condition. In some embodiments, the modified or unmodified BoNT/EN, or the chimeric toxin polypeptide, or the pharmaceutic compositions of the present disclosure contact one or more neuron(s) exhibiting unwanted neuronal activity.

Conditions typically treated with a neurotoxin (e.g., skeletal muscle conditions, smooth muscle conditions, glandular conditions, a neuromuscular disorder, an autonomic disorder, pain, or an aesthetic/cosmetic condition) are associated with unwanted neuronal activity, as determined by the skilled practitioner. Administration is by a route that contacts an effective amount of the composition to neurons exhibiting the unwanted activity. In some embodiments, the condition may be associated with overactive neurons or glands. Specific conditions envisioned for treatment by the methods discussed herein include, without limitation, spasmodic dysphonia, spasmodic torticollis, laryngeal dystonia, oromandibular dysphonia, lingual dystonia, cervical dystonia, focal hand dystonia, blepharospasm, strabismus, hemifacial spasm, eyelid disorder, cerebral palsy, focal spasticity and other voice disorders, spasmodic colitis, neurogenic bladder, anismus, limb spasticity, tics, tremors, bruxism, anal fissure, achalasia, dysphagia and other muscle tone disorders and other disorders characterized by involuntary movements of muscle groups, lacrimation, hyperhydrosis, excessive salivation, excessive gastrointestinal secretions as well as other secretory disorders, pain from muscle spasms, headache pain. In addition, the present disclosure can be used to treat dermato logical or aesthetic/cosmetic conditions, for example, reduction of brow furrows, reduction of skin wrinkles.

In some embodiments, the modified or unmodified BoNT/EN, or the chimeric toxin polypeptide, or the pharmaceutical composition comprising such are used in the treatment of conditions associated with unwanted secretion activities in a wide range of cells. In some embodiments, the unwanted secretion is immune secretion. Conditions associated with unwanted immune secretion include, without limitation: inflammation, psoriasis, allergy, haemophagocytic lymphohistiocytosis, and alcoholic pancreatic disease.

The modified or unmodified BoNT/EN, the chimeric toxin polypeptide, or the pharmaceutical composition comprising such can also be used in the treatment of sports injuries. Borodic U.S. Pat. No. 5,053,005 discloses methods for treating juvenile spinal curvature, i.e. scoliosis, using

*botulinum* type A. The disclosure of Borodic is incorporated in its entirety herein by reference. In one embodiment, using substantially similar methods as disclosed by Borodic, a BoNT polypeptide can be administered to a mammal, preferably a human, to treat spinal curvature.

In some embodiments, the modified or unmodified BoNT/EN, the chimeric toxin polypeptide, or the pharmaceutical composition comprising such is administered to treat neuromuscular disorders using well known techniques that are commonly performed with *botulinum* type A. For example, the present disclosure can be used to treat pain, for example, headache pain, pain from muscle spasms and various forms of inflammatory pain. For example, Aoki U.S. Pat. No. 5,721,215 and Aoki U.S. Pat. No. 6,113,915 disclose methods of using *botulinum* toxin type A for treating pain. The disclosure of these two patents is incorporated in its entirety herein by reference.

Autonomic nervous system disorders can also be treated with a modified neurotoxin. For example, glandular malfunctioning is an autonomic nervous system disorder. Glandular malfunctioning includes excessive sweating and excessive salivation. Respiratory malfunctioning is another example of an autonomic nervous system disorder. Respiratory malfunctioning includes chronic obstructive pulmonary disease and asthma. Sanders et al. disclose methods for treating the autonomic nervous system; for example, treating autonomic nervous system disorders such as excessive sweating, excessive salivation, asthma, etc., using naturally existing *botulinum* toxins. The disclosure of Sander et al. is incorporated in its entirety by reference herein.

In one embodiment, substantially similar methods to that of Sanders et al. can be employed, but using the modified or unmodified BoNT/EN, the chimeric toxin polypeptide, or the pharmaceutical composition comprising such, to treat autonomic nervous system disorders such as the ones discussed above. For example, the modified or unmodified BoNT/EN, the chimeric toxin polypeptide, or the pharmaceutical composition comprising such polypeptide can be locally applied to the nasal cavity of the mammal in an amount sufficient to degenerate cholinergic neurons of the autonomic nervous system that control the mucous secretion in the nasal cavity. Pain that can be treated by a modified neurotoxin includes pain caused by muscle tension, or spasm, or pain that is not associated with muscle spasm. For example, Binder in U.S. Pat. No. 5,714,468 discloses that headache caused by vascular disturbances, muscular tension, neuralgia and neuropathy can be treated with a naturally occurring *botulinum* toxin, for example *botulinum* type A. The disclosures of Binder are incorporated in its entirety herein by reference.

In one embodiment, substantially similar methods to that of Binder can be employed, but using the modified or unmodified BoNT/EN, the chimeric toxin polypeptide, or the pharmaceutical composition comprising such described herein, to treat headache, especially the ones caused by vascular disturbances, muscular tension, neuralgia and neuropathy. Pain caused by muscle spasm can also be treated by an administration of the modified or unmodified BoNT/EN, the chimeric toxin polypeptide, or the pharmaceutical composition comprising such described herein. For example, a *botulinum* type E fused with a leucine-based motif, preferably at the carboxyl terminal of the *botulinum* type E light chain, can be administered intramuscularly at the pain/spasm location to alleviate pain. Furthermore, a modified neurotoxin can be administered to a mammal to treat pain that is not associated with a muscular disorder, such as spasm.

In one broad embodiment, methods of the present disclosure to treat non-spasm related pain include central administration or peripheral administration of the modified or unmodified BoNT/EN, the chimeric toxin polypeptide, or the pharmaceutical composition comprising such. For example, Foster et al. in U.S. Pat. No. 5,989,545 discloses that a *botulinum* toxin conjugated with a targeting moiety can be administered centrally (intrathecally) to alleviate pain. The disclosures of Foster et al. are incorporated in its entirety by reference herein.

In one embodiment, substantially similar methods to that of Foster et al. can be employed, but using the compositions described herein to treat pain. The pain to be treated can be an acute pain or chronic pain. An acute or chronic pain that is not associated with a muscle spasm can also be alleviated with a local, peripheral administration of the modified neurotoxin to an actual or a perceived pain location on the mammal.

In one embodiment, the modified or unmodified BoNT/EN, the chimeric toxin polypeptide, or the pharmaceutical composition comprising such is administered subcutaneously at or near the location of pain, for example, at or near a cut. In some embodiments, the modified neurotoxin is administered intramuscularly at or near the location of pain, for example, at or near a bruise location on the mammal. In some embodiments, the modified or unmodified BoNT/EN, the chimeric toxin polypeptide, or the pharmaceutical composition comprising such is injected directly into a joint of a mammal, for treating or alleviating pain caused by arthritic conditions. Also, frequent repeated injection or infusion of the modified neurotoxin to a peripheral pain location is within the scope of the present disclosure. Routes of administration for such methods are known in the art and easily adapted to the methods described herein by the skilled practitioner (e.g., see for example, Harrison's Principles of Internal Medicine (1998), edited by Anthony Fauci et al., $14^{th}$ edition, published by McGraw Hill).

By way of non-limiting example, the treatment of a neuromuscular disorder can comprise a step of locally administering an effective amount of the molecule to a muscle or a group of muscles, the treatment of an autonomic disorder can comprise a step of locally administering an effective of the molecule to a gland or glands, and the treatment of pain can comprise a step of administering an effective amount of the molecule the site of the pain. In addition, the treatment of pain can comprise a step of administering an effective amount of a modified neurotoxin to the spinal cord.

"A therapeutically effective amount" as used herein refers to the amount of each therapeutic agent of the present disclosure required to confer therapeutic effect on the subject, either alone or in combination with one or more other therapeutic agents. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons. Empirical considerations, such as the half-life, generally will contribute to the determination of the dosage. For example, therapeutic agents that are compatible with the human immune system, such as polypeptides comprising regions from humanized antibodies or fully human antibodies, may be used to prolong half-life of the polypeptide and to prevent the polypeptide being attacked by the host's immune system.

Frequency of administration may be determined and adjusted over the course of therapy, and is generally, but not necessarily, based on treatment and/or suppression and/or amelioration and/or delay of a disease. Alternatively, sustained continuous release formulations of a polypeptide may be appropriate. Various formulations and devices for achieving sustained release are known in the art. In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks: or once every month, every 2 months, or every 3 months, or longer. The progress of this therapy is easily monitored by conventional techniques and assays.

The dosing regimen (including the polypeptide used) can vary over time. In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the polypeptide (such as the half-life of the polypeptide, and other considerations well known in the art).

For the purpose of the present disclosure, the appropriate dosage of a therapeutic agent as described herein will depend on the specific agent (or compositions thereof) employed, the formulation and route of administration, the type and severity of the disease, whether the polypeptide is administered for preventive or therapeutic purposes, previous therapy, the subject's clinical history and response to the antagonist, and the discretion of the attending physician. Typically the clinician will administer a polypeptide until a dosage is reached that achieves the desired result.

Administration of one or more polypeptides can be continuous or intermittent, depending, for example, upon the recipient's physiological condition, whether the purpose of the administration is therapeutic or prophylactic, and other factors known to skilled practitioners. The administration of a polypeptide may be essentially continuous over a preselected period of time or may be in a series of spaced dose, e.g., either before, during, or after developing a disease. As used herein, the term "treating" refers to the application or administration of a polypeptide or composition including the polypeptide to a subject in need thereof.

"A subject in need thereof", refers to an individual who has a disease, a symptom of the disease, or a predisposition toward the disease, with the purpose to cure, heal, alleviate, relieve, alter, remedy, ameliorate, improve, or affect the disease, the symptom of the disease, or the predisposition toward the disease. In some embodiments, the subject has CDI. In some embodiments, the subject has cancer. In some embodiments, the subject is a mammal. In some embodiments, the subject is a non-human primate. In some embodiments, the subject is human. Alleviating a disease includes delaying the development or progression of the disease, or reducing disease severity. Alleviating the disease does not necessarily require curative results.

As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset.

As used herein "onset" or "occurrence" of a disease includes initial onset and/or recurrence. Conventional methods, known to those of ordinary skill in the art of medicine, can be used to administer the isolated polypeptide or pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir.

The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

As used herein, a "subject" refers to a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human.

The terms, "patient" and "subject" are used interchangeably herein. A subject can be male or female. A subject can be a fully developed subject (e.g., an adult) or a subject undergoing the developmental process (e.g., a child, infant or fetus). Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with unwanted neuronal activity. In addition, the methods and compositions described herein can be used to treat domesticated animals and/or pets.

Kits comprising the isolated BoNT/EN polypeptide, the modified BoNT/EN polypeptide, or the chimeric neurotoxin polypeptide, the nucleic acid encoding such polypeptides, the vector comprising such nucleic acids, the cell, or the composition described herein are also provided. The kit described herein may include one or more containers housing components. Specifically, such a kit may include one or more agents described herein (for example, a polypeptide, a nucleic acid, a vector, a cell, or a composition), along with instructions describing the intended application and the proper use of these agents. In certain embodiments, the kit may be suitable for a therapeutic purpose. The kit may further comprise components needed for using the agents.

Each components of the kits, where applicable, may be provided in liquid form (e.g., in solution), or in solid form, (e.g., a dry powder). In certain cases, some of the components may be constitutable or otherwise processable (e.g., to an active form), for example, by the addition of a suitable solvent or other species (for example, water or certain organic solvents), which may or may not be provided with the kit.

In some embodiments, the kits may optionally include instructions and/or promotion for use of the components provided. As used herein, "instructions" can define a component of instruction and/or promotion, and typically involve written instructions on or associated with packaging of the disclosure. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which can also reflects approval by the agency of manufacture, use or sale for animal administration. As used herein, "promoted" includes all methods of doing business including methods of education, hospital and other clinical instruction, scientific inquiry, drug discovery or development, academic research, pharmaceutical industry activity including pharmaceutical sales, and any advertising or other promotional activity including written, oral and electronic communication of any form, associated with the invention. Additionally, the kits may include other components depending on the specific application, as described herein.

The kits may contain any one or more of the components described herein in one or more containers. The components may be prepared sterilely, packaged in syringe and shipped refrigerated. Alternatively it may be housed in a vial or other container for storage. A second container may have other components prepared sterilely. Alternatively the kits may include the active agents premixed and shipped in a vial, tube, or other container.

The kits may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kits may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kits may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Protein and polypeptide sequences described herein are provided in Tables 1-5.

TABLE 1

| BoNT/EN Sequences (linker region is underlined) | | |
|---|---|---|
| Name | Amino Acid Sequence | SEQ ID NO |
| BoNT/En (stain *Enterococcus* sp. 3G1_DIV062, GenBank: OTO22244.1) Full-length | MVTINDLHYSDPIDEDNIINMRIPLYDLEVDDQFINHNVPDLKAFQVFPNVW VVPERYTFYSTMKNLDAPANPSRSSYYDPTYLQSDAEKEVFLQQMILLFKRI NSTQEGQQFLNLLSRSIPVPYESNGDVAMGTTQVIKQMDDKGNVLKHRRAHI IIYGPGPDLMAKGSKALTKSRETGRGCMAEIYFSPMYHKTYSTKLTNKNSLV DKSVQEFVPDPAVTLIHELCHGLHALYGIDLGNVGSWEFNSNPNSLFSSWFS SKEAVNFEEVMTFGGEDVKVIKSEIDKKIPGILNLIKTTVEPIINKITDPHD EMLQCLQSKYPSLKGTLGQFFDDTQLEKDIRDLWMVMNETMFAENLKALTR ARYLVPKVENIVQVDILSPNVYTIDKGFNHLSKGFKGQSVSQSYFRKISALA RGAVVRACPNPHFSSQRGLSSCIEILEDDLFIMSSKDSFTDTDFSEPSVGPV SYKAKKGADTILDSTLSNYDFSKEINFTSTVPIITVEDPLETDEDVPVISED RTVYVDDYTTFHFLEAQKIGKEVVPTQTKVVFTTNMEEALFDSKKVYTVPEN TASRINEAGTGIANGMMFYQWLKGIVQDFTEEATQKDTFDKISDVTMIVPYL GNILNIGNDIRKGDFMGAVELGGVTILLEAIPELTLPVLIGLTIIEDELEKE QVSQTVYNVLDKRDEKWEEVYGFVKQQWWMVHTQFETRILHAYQALNHQVE AIKANMTYQLANYRGNQEDKELLEKAIDDTLQSLYYAVDQAMHNIKRFLIQS SKSYLLNQMLPKTKEQLLAFDQQTLRNVNDFINKNQGVLGESLAKDLKKKVE KRLTSLPVFNLEDLPISEFEDLIHSHEIDIQDSEVLNIGVNNGKIQDLSGEN TPLTLGENLHIVNGRDNQAVRLNNQLDSKLEIQSRPNIHFTAFEDFSISIWI RCSMLRNNRNRGQKYTIIQQFNKYGWQLAIQDSVFVWTLHDTFNNQIQLTSG SALTNKNYLLQNFWLHITVTNKRSEKSRLYINGVLQDQKDISVLGNCHPKEP ILFSIQDNSDPNYFVRFEQFNVYRKALTDSEVNRLYWKYFEGSYLRDVWGER LTYNRDYYMQLSTLPGRGIKREYRTWSGFDYIILSELGTQKIPTHEVTYPKL YQGQKITIHSDGKNLEPHVKSNKNIRLKIDDFYIGVVNPFKLPEWRPESGAY VVTTYNHAEDLCLYFRTRSSSQSLYYGQLIMNDGRNKSLLNYTLKGSTYWIW SSAWYYENYNTSSKTAGNWYFIPVDEGWKED | 1 |

TABLE 1-continued

BoNT/EN Sequences (linker region is underlined)

| Name | Amino Acid Sequence | SEQ ID NO |
|---|---|---|
| BoNT/En-LC (1-433) | MVTINDLHYSDPIDEDNIINMRIPLYDLEVDDQFINHNVPDLKAFQVFPNVW VVPERYTFYSTMKNLDAPANPSRSSYYDPTYLQSDAEKEVFLQQMILLFKRI NSTQEGQQFLNLLSRSIPVPYESNGDVAMGTTQVIKQMDDKGNVLKHRRAHI IIYGPGPDLMAKGSKALTKSRETGRGCMAEIYFSPMYHKTYSTKLTNKNSLV DKSVQEFVPDPAVTLIHELCHGLHALYGIDLGNVGSWEFNSNPNSLFSSWFS SKEAVNFEEVMTFGGEDVKVIKSEIDKKIPGILNLIKTTVEPIINKITDPHD EMLQCLQSKYPSLKGTLGQFFFDDTQLEKDIRDLWMVMNETMFAENLKALTR ARYLVPKVENIVQVDILSPNVYTIDKGFNHLSKGFKGQSVSQSYFRKISALA RGAVVRA<u>CPNPHFSSQR</u> | 2 |
| BoNT/En-LC-$H_N$ (1-862) | MVTINDLHYSDPIDEDNIINMRIPLYDLEVDDQFINHNVPDLKAFQVFPNVW VVPERYTFYSTMKNLDAPANPSRSSYYDPTYLQSDAEKEVFLQQMILLFKRI NSTQEGQQFLNLLSRSIPVPYESNGDVAMGTTQVIKQMDDKGNVLKHRRAHI IIYGPGPDLMAKGSKALTKSRETGRGCMAEIYFSPMYHKTYSTKLTNKNSLV DKSVQEFVPDPAVTLIHELCHGLHALYGIDLGNVGSWEFNSNPNSLFSSWFS SKEAVNFEEVMTFGGEDVKVIKSEIDKKIPGILNLIKTTVEPIINKITDPHD EMLQCLQSKYPSLKGTLGQFFFDDTQLEKDIRDLWMVMNETMFAENLKALTR ARYLVPKVENIVQVDILSPNVYTIDKGFNHLSKGFKGQSVSQSYFRKISALA RGAVVRA<u>CPNPHFSSQRGLSSC</u>IEILEDDLFIMSSKDSFTDTDFSEPSVGPV SYKAKKGADTILDSTLSNYDFSKEINFTSTVPIITVEDPLETEDEDVPISED RTVYVDDYTTFHFLEAQKIGKEVVPTQTKVVFTTNMEEALFDSKKVYTVPEN TASRINEAGTGIANGMMFYQWLKGIVQDFTEEATQKDTFDKISDVTMIVPYL GNILNIGNDIRKGDFMGAVELGGVTILLEAIPELTLPVLIGLTIIEDELEKE QVSQTVYNVLDKRDEKWEEVYGFVKQQWWWMVHTQFETRILHAYQALNHQVE AIKANMTYQLANYRGNQEDKELLEKAIDDTLQSLYYAVDQAMHNIKRFLIQS SKSYLLNQMLPKTKEQLLAFDQQTLRNVNDFINKNQGVLGESLAKDLKKKVE KRLTSLPVFNLEDLPISEFEDLIHSHEIDI | 3 |
| BoNT/EN-Hc (863-1279) | QDSEVLNIGVNNGKIQDLSGENTPLTLGENLHIVNGRDNQAVRLNNQLDSKL EIQSRPNIHFTAFEDFSISIWIRCSMLRNNRNRGQKYTIIQQFNKYGWQLAI QDSVFVWTLHDTFNNQIQLTSGSALTNKNYLLQNFWLHITVTNKRSEKSRLY INGVLQDQKDISVLGNCHPKEPILFSIQDNSDPNYFVRFEQFNVYRKALTDS EVNRLYWKYFEGSYLRDVWGERLTYNRDYYMQLSTLPGRGIKREYRTWSGFD YIILSELGTQKIPTHEVTYPKLYQGQKITIHSDGKNLEPHVKSNKNIRLKID DFYIGVVNPFKLPEWRPESGAYVVTTYNHAEDLCLYFRTRSSSQSLYYGQLI MNDGRNKSLLNYTLKGSTYWIWSSAWYYENYNTSSKTAGNWYFIPVDEGWKE D | 4 |

TABLE 2

Protease Cleavage sites and Naturally BoNT Linker Regions ("|" indicates cleavage sites)

| Name | Amino Acid Sequence | SEQ ID NO |
|---|---|---|
| Thrombin cleavage site | LVPR\|GS | 41 |
| TEV cleavage site | ENLYFQ\|G | 42 |
| PreScission cleavage site | LEVLFQ\|GP | 43 |
| Factor Xa cleavage site | IEGR\| | 44 |
| Factor Xa cleavage site | IDGR\| | 45 |
| Enterokinase cleavage site | DDDDK\| | 46 |
| SUMO protease cleavage site | AHREQIGG\| | 47 |
| BoNT/A linker region | CVRGIITSKTKSLDKGYNKALNDLC | 48 |
| BoNT/B linker region | CKSVKAPGIC | 49 |
| BoNT/C linker region | CHKAIDGRSLYNKTLDC | 50 |
| BoNT/D linker region | CLRLTKNSRDDSTC | 51 |
| BoNT/E linker region | CKNIVSVKGIRKSIC | 52 |
| BoNT/F linker region | CKSVIPRKGTKAPPRLC | 53 |
| BoNT/G linker region | CKPVMYKNTGKSEQC | 54 |
| BoNT/X linker region | CPRNGLLYNAIYRNSKNYLNNIDLE DKKTTSKTNVSYPCSLLNGC | 55 |
| BoNT/EN linker region | CPNPHFSSQRGLSSC | 56 |

TABLE 3

Non-limiting, Exemplary Modified BoNT/EN Polypeptides

| Name | Amino Acid Sequence | SEQ ID NO |
| --- | --- | --- |
| BoNT/EN-LC-H$_N$ with modified linker containing thrombin cleavage site | MVTINDLHYSDPIDEDNIINMRIPLYDLEVDDQFINHNVPDLKAFQ VFPNVWVVPERYTFYSTMKNLDAPANPSRSSYYDPTYLQSDAEKEV FLQQMILLFKRINSTQEGQQFLNLLSRSIPVPYESNGDVAMGTTQV IKQMDDKGNVLKHRRAHIIYGPGPDLMAKGSKALTKSRETGRGCM AEIYFSPMYHKTYSTKLTNKNSLVDKSVQEFVPDPAVTLIHELCHG LHALYGIDLGNVGSWEFNSNPNSLFSSWFSSKEAVNFEEVMTFGGE DVKVIKSEIDKKIPGILNLIKTTVEPIINKITDPHDEMLQCLQSKY PSLKGTLGQFFFDDTQLEKDIRDLWMVMNETMFAENLKALTRARYL VPKVENIVQVDILSPNVYTIDKGFNHLSKGFKGQSVSQSYFRKISA LARGAVVRACPNPHFSSQLVPRGSLSSCIEILEDDLFIMSSKDSFT DTDFSEPSVGPVSYKAKKGADTILDSTLSNYDFSKEINFTSTVPII TVEDPLETDEDVPVISEDRTVYVDDYTTFHFLEAQKIGKEVVPTQT KVVFTTNMEEALFDSKKVYTVFENTASRINEAGTGIANGMMFYQWL KGIVQDFTEEATQKDTFDKISDVTMIVPYLGNILNIGNDIRKGDFM GAVELGGVTILLEAIPELTLPVLIGLTIIEDELEKEQVSQTVYNVL DKRDEKWEEVYGFVKQQWWWMVHTQFETRILHAYQALNHQVEAIKA NMTYQLANYRGNQEDKELLEKAIDDTLQSLYYAVDQAMHNIKRFLI QSSKSYLLNQMLPKTKEQLLAFDQQTLRNVNDFINKNQGVLGESLA KDLKKKVEKRLTSLPVFNLEDLPISEFEDLIHSHEIDI | 5 |
| BoNT/EN-LC-H$_N$ with BoNT/A linker | MVTINDLHYSDPIDEDNIINMRIPLYDLEVDDQFINHNVPDLKAFQ VFPNVWVVPERYTFYSTMKNLDAPANPSRSSYYDPTYLQSDAEKEV FLQQMILLFKRINSTQEGQQFLNLLSRSIPVPYESNGDVAMGTTQV IKQMDDKGNVLKHRRAHIIYGPGPDLMAKGSKALTKSRETGRGCM AEIYFSPMYHKTYSTKLTNKNSLVDKSVQEFVPDPAVTLIHELCHG LHALYGIDLGNVGSWEFNSNPNSLFSSWFSSKEAVNFEEVMTFGGE DVKVIKSEIDKKIPGILNLIKTTVEPIINKITDPHDEMLQCLQSKY PSLKGTLGQFFFDDTQLEKDIRDLWMVMNETMFAENLKALTRARYL VPKVENIVQVDILSPNVYTIDKGFNHLSKGFKGQSVSQSYFRKISA LARGAVVRACVRGIITSKTKSLDKGYNKALNDLCIEILEDDLFIMS SKDSFTDTDFSEPSVGPVSYKAKKGADTILDSTLSNYDFSKEINFT STVPIITVEDPLETDEDVPVISEDRTVYVDDYTTFHFLEAQKIGKE VVPTQTKVVFTTNMEEALFDSKKVYTVFENTASRINEAGTGIANGM MFYQWLKGIVQDFTEEATQKDTFDKISDVTMIVPYLGNILNIGNDI RKGDFMGAVELGGVTILLEAIPELTLPVLIGLTIIEDELEKEQVSQ TVYNVLDKRDEKWEEVYGFVKQQWWWMVHTQFETRILHAYQALNHQ VEAIKANMTYQLANYRGNQEDKELLEKAIDDTLQSLYYAVDQAMHN IKRFLIQSSKSYLLNQMLPKTKEQLLAFDQQTLRNVNDFINKNQGV LGESLAKDLKKKVEKRLTSLPVFNLEDLPISEFEDLIHSHEIDI | 6 |
| BoNT/EN-LC-H$_N$ with BoNT/B linker | MVTINDLHYSDPIDEDNIINMRIPLYDLEVDDQFINHNVPDLKAFQ VFPNVWVVPERYTFYSTMKNLDAPANPSRSSYYDPTYLQSDAEKEV FLQQMILLFKRINSTQEGQQFLNLLSRSIPVPYESNGDVAMGTTQV IKQMDDKGNVLKHRRAHIIYGPGPDLMAKGSKALTKSRETGRGCM AEIYFSPMYHKTYSTKLTNKNSLVDKSVQEFVPDPAVTLIHELCHG LHALYGIDLGNVGSWEFNSNPNSLFSSWFSSKEAVNFEEVMTFGGE DVKVIKSEIDKKIPGILNLIKTTVEPIINKITDPHDEMLQCLQSKY PSLKGTLGQFFFDDTQLEKDIRDLWMVMNETMFAENLKALTRARYL VPKVENIVQVDILSPNVYTIDKGFNHLSKGFKGQSVSQSYFRKISA LARGAVVRACKSVKAPGICIEILEDDLFIMSSKDSFTDTDFSEPSV GPVSYKAKKGADTILDSTLSNYDFSKEINFTSTVPIITVEDPLETD EDVPVISEDRTVYVDDYTTFHFLEAQKIGKEVVPTQTKVVFTTNME EALFDSKKVYTVFENTASRINEAGTGIANGMMFYQWLKGIVQDFTE EATQKDTFDKISDVTMIVPYLGNILNIGNDIRKGDFMGAVELGGVT ILLEAIPELTLPVLIGLTIIEDELEKEQVSQTVYNVLDKRDEKWEE VYGFVKQQWWWMVHTQFETRILHAYQALNHQVEAIKANMTYQLANY RGNQEDKELLEKAIDDTLQSLYYAVDQAMHNIKRFLIQSSKSYLLN QMLPKTKEQLLAFDQQTLRNVNDFINKNQGVLGESLAKDLKKKVEK RLTSLPVFNLEDLPISEFEDLIHSHEIDI | 7 |
| BoNT/EN-LC-H$_N$ with BoNT/C linker | MVTINDLHYSDPIDEDNIINMRIPLYDLEVDDQFINHNVPDLKAFQ VFPNVWVVPERYTFYSTMKNLDAPANPSRSSYYDPTYLQSDAEKEV FLQQMILLFKRINSTQEGQQFLNLLSRSIPVPYESNGDVAMGTTQV IKQMDDKGNVLKHRRAHIIYGPGPDLMAKGSKALTKSRETGRGCM AEIYFSPMYHKTYSTKLTNKNSLVDKSVQEFVPDPAVTLIHELCHG LHALYGIDLGNVGSWEFNSNPNSLFSSWFSSKEAVNFEEVMTFGGE DVKVIKSEIDKKIPGILNLIKTTVEPIINKITDPHDEMLQCLQSKY PSLKGTLGQFFFDDTQLEKDIRDLWMVMNETMFAENLKALTRARYL VPKVENIVQVDILSPNVYTIDKGFNHLSKGFKGQSVSQSYFRKISA LARGAVVRACHKAIDGRSLYNKTLDCIEILEDDLFIMSSKDSFTDT DFSEPSVGPVSYKAKKGADTILDSTLSNYDFSKEINFTSTVPIITV EDPLETDEDVPVISEDRTVYVDDYTTFHFLEAQKIGKEVVPTQTKV VFTTNMEEALFDSKKVYTVFENTASRINEAGTGIANGMMFYQWLKG IVQDFTEEATQKDTFDKISDVTMIVPYLGNILNIGNDIRKGDFMGA VELGGVTILLEAIPELTLPVLIGLTIIEDELEKEQVSQTVYNVLDK RDEKWEEVYGFVKQQWWWMVHTQFETRILHAYQALNHQVEAIKANM | 8 |

TABLE 3-continued

Non-limiting, Exemplary Modified BoNT/EN Polypeptides

| Name | Amino Acid Sequence | SEQ ID NO |
|---|---|---|
| | TYQLANYRGNQEDKELLEKAIDDTLQSLYYAVDQAMHNIKRFLIQS<br>SKSYLLNQMLPKTKEQLLAFDQQTLRNVNDFINKNQGVLGESLAKD<br>LKKKVEKRLTSLPVFNLEDLPISEFEDLIHSHEIDI | |
| BoNT/EN-LC-H$_N$<br>with BoNT/D<br>linker | MVTINDLHYSDPIDEDNIINMRIPLYDLEVDDQFINHNVPDLKAFQ<br>VFPNVWVVPERYTFYSTMKNLDAPANPSRSSYYDPTYLQSDAEKEV<br>FLQQMILLFKRINSTQEGQQFLNLLSRSIPVPYESNGDVAMGTTQV<br>IKQMDDKGNVLKHRRAHIIYGPGPDLMAKGSKALTKSRETGRGCM<br>AEIYFSPMYHKTYSTKLTNKNSLVDKSVQEFVPDPAVTLIHELCHG<br>LHALYGIDLGNVGSWEFNSNPNSLFSSWFSSKEAVNFEEVMTFGGE<br>DVKVIKSEIDKKIPGILNLIKTTVEPIINKITDPHDEMLQCLQSKY<br>PSLKGTLGQFFFDDTQLEKDIRDLWMVMNETMFAENLKALTRARYL<br>VPKVENIVQVDILSPNVYTIDKGFNHLSKGFKGQSVSQSYFRKISA<br>LARGAVVRACLRLTKNSRDDSTCIEILEDDLFIMSSKDSFTDTDFS<br>EPSVGPVSYKAKKGADTILDSTLSNYDFSKEINFTSTVPIITVEDP<br>LETDEDVPVISEDRTVYVDDYTTFHFLEAQKIGKEVVPTQTKVVFT<br>TNMEEALFDSKKVYTVFENTASRINEAGTGIANGMMFYQWLKGIVQ<br>DFTEEATQKDTFDKISDVTMIVPYLGNILNIGNDIRKGDFMGAVEL<br>GGVTILLEAIPELTLPVLIGLTIIEDELEKEQVSQTVYNVLDKRDE<br>KWEEVYGFVKQQWWWMVHTQFETRILHAYQALNHQVEAIKANMTYQ<br>LANYRGNQEDKELLEKAIDDTLQSLYYAVDQAMHNIKRFLIQSSKS<br>YLLNQMLPKTKEQLLAFDQQTLRNVNDFINKNQGVLGESLAKDLKK<br>KVEKRLTSLPVFNLEDLPISEFEDLIHSHEIDI | 9 |
| BoNT/EN-LC-H$_N$<br>with BoNT/E<br>linker | MVTINDLHYSDPIDEDNIINMRIPLYDLEVDDQFINHNVPDLKAFQ<br>VFPNVWVVPERYTFYSTMKNLDAPANPSRSSYYDPTYLQSDAEKEV<br>FLQQMILLFKRINSTQEGQQFLNLLSRSIPVPYESNGDVAMGTTQV<br>IKQMDDKGNVLKHRRAHIIYGPGPDLMAKGSKALTKSRETGRGCM<br>AEIYFSPMYHKTYSTKLTNKNSLVDKSVQEFVPDPAVTLIHELCHG<br>LHALYGIDLGNVGSWEFNSNPNSLFSSWFSSKEAVNFEEVMTFGGE<br>DVKVIKSEIDKKIPGILNLIKTTVEPIINKITDPHDEMLQCLQSKY<br>PSLKGTLGQFFFDDTQLEKDIRDLWMVMNETMFAENLKALTRARYL<br>VPKVENIVQVDILSPNVYTIDKGFNHLSKGFKGQSVSQSYFRKISA<br>LARGAVVRACKNIVSVKGIRKSICIEILEDDLFIMSSKDSFTDTDF<br>SEPSVGPVSYKAKKGADTILDSTLSNYDFSKEINFTSTVPIITVED<br>PLETDEDVPVISEDRTVYVDDYTTFHFLEAQKIGKEVVPTQTKVVF<br>TTNMEEALFDSKKVYTVFENTASRINEAGTGIANGMMFYQWLKGIV<br>QDFTEEATQKDTFDKISDVTMIVPYLGNILNIGNDIRKGDFMGAVE<br>LGGVTILLEAIPELTLPVLIGLTIIEDELEKEQVSQTVYNVLDKRD<br>EKWEEVYGFVKQQWWWMVHTQFETRILHAYQALNHQVEAIKANMTY<br>QLANYRGNQEDKELLEKAIDDTLQSLYYAVDQAMHNIKRFLIQSSK<br>SYLLNQMLPKTKEQLLAFDQQTLRNVNDFINKNQGVLGESLAKDLK<br>KKVEKRLTSLPVFNLEDLPISEFEDLIHSHEIDI | 10 |
| BoNT/EN-LC-H$_N$<br>with BoNT/F<br>linker | MVTINDLHYSDPIDEDNIINMRIPLYDLEVDDQFINHNVPDLKAFQ<br>VFPNVWVVPERYTFYSTMKNLDAPANPSRSSYYDPTYLQSDAEKEV<br>FLQQMILLFKRINSTQEGQQFLNLLSRSIPVPYESNGDVAMGTTQV<br>IKQMDDKGNVLKHRRAHIIYGPGPDLMAKGSKALTKSRETGRGCM<br>AEIYFSPMYHKTYSTKLTNKNSLVDKSVQEFVPDPAVTLIHELCHG<br>LHALYGIDLGNVGSWEFNSNPNSLFSSWFSSKEAVNFEEVMTFGGE<br>DVKVIKSEIDKKIPGILNLIKTTVEPIINKITDPHDEMLQCLQSKY<br>PSLKGTLGQFFFDDTQLEKDIRDLWMVMNETMFAENLKALTRARYL<br>VPKVENIVQVDILSPNVYTIDKGFNHLSKGFKGQSVSQSYFRKISA<br>LARGAVVRACKSVIPRKGTKAPPRLCIEILEDDLFIMSSKDSFTDT<br>DFSEPSVGPVSYKAKKGADTILDSTLSNYDFSKEINFTSTVPIITV<br>EDPLETDEDVPVISEDRTVYVDDYTTFHFLEAQKIGKEVVPTQTKV<br>VFTTNMEEALFDSKKVYTVFENTASRINEAGTGIANGMMFYQWLKG<br>IVQDFTEEATQKDTFDKISDVTMIVPYLGNILNIGNDIRKGDFMGA<br>VELGGVTILLEAIPELTLPVLIGLTIIEDELEKEQVSQTVYNVLDK<br>RDEKWEEVYGFVKQQWWWMVHTQFETRILHAYQALNHQVEAIKANM<br>TYQLANYRGNQEDKELLEKAIDDTLQSLYYAVDQAMHNIKRFLIQS<br>SKSYLLNQMLPKTKEQLLAFDQQTLRNVNDFINKNQGVLGESLAKD<br>LKKKVEKRLTSLPVFNLEDLPISEFEDLIHSHEIDI | 11 |
| BoNT/EN-LC-H$_N$<br>with BoNT/G<br>linker | MVTINDLHYSDPIDEDNIINMRIPLYDLEVDDQFINHNVPDLKAFQ<br>VFPNVWVVPERYTFYSTMKNLDAPANPSRSSYYDPTYLQSDAEKEV<br>FLQQMILLFKRINSTQEGQQFLNLLSRSIPVPYESNGDVAMGTTQV<br>IKQMDDKGNVLKHRRAHIIYGPGPDLMAKGSKALTKSRETGRGCM<br>AEIYFSPMYHKTYSTKLTNKNSLVDKSVQEFVPDPAVTLIHELCHG<br>LHALYGIDLGNVGSWEFNSNPNSLFSSWFSSKEAVNFEEVMTFGGE<br>DVKVIKSEIDKKIPGILNLIKTTVEPIINKITDPHDEMLQCLQSKY<br>PSLKGTLGQFFFDDTQLEKDIRDLWMVMNETMFAENLKALTRARYL<br>VPKVENIVQVDILSPNVYTIDKGFNHLSKGFKGQSVSQSYFRKISA<br>LARGAVVRACKPVMYKNTGKSEQCIEILEDDLFIMSSKDSFTDTDF<br>SEPSVGPVSYKAKKGADTILDSTLSNYDFSKEINFTSTVPIITVED<br>PLETDEDVPVISEDRTVYVDDYTTFHFLEAQKIGKEVVPTQTKVVF | 12 |

TABLE 3-continued

Non-limiting, Exemplary Modified BoNT/EN Polypeptides

| Name | Amino Acid Sequence | SEQ ID NO |
|---|---|---|
| | TTNMEEALFDSKKVYTVFENTASRINEAGTGIANGMMFYQWLKGIV QDFTEEATQKDTFDKISDVTMIVPYLGNILNIGNDIRKGDFMGAVE LGGVTILLEAIPELTLPVLIGLTIIEDELEKEQVSQTVYNVLDKRD EKWEEVYGFVKQQWWWMVHTQFETRILHAYQALNHQVEAIKANMTY QLANYRGNQEDKELLEKAIDDTLQSLYYAVDQAMHNIKRFLIQSSK SYLLNQMLPKTKEQLLAFDQQTLRNVNDFINKNQGVLGESLAKDLK KKVEKRLTSLPVFNLEDLPISEFEDLIHSHEIDI | |
| BoNT/EN-LC-H$_N$ with BoNT/X linker | MVTINDLHYSDPIDEDNIINMRIPLYDLEVDDQFINHNVPDLKAFQ VFPNVWVVPERYTFYSTMKNLDAPANPSRSSYYDPTYLQSDAEKEV FLQQMILLFKRINSTQEGQQFLNLLSRSIPVPYESNGDVAMGTTQV IKQMDDKGNVLKHRRAHIIYGPGPDLMAKGSKALTKSRETGRGCM AEIYFSPMYHKTYSTKLTNKNSLVDKSVQEFVPDPAVTLIHELCHG LHALYGIDLGNVGSWEFNSNPNSLFSSWFSSKEAVNFEEVMTFGGE DVKVIKSEIDKKIPGILNLIKTTVEPIINKITDPHDEMLQCLQSKY PSLKGTLGQFFFDDTQLEKDIRDLWMVMNETMFAENLKALTRARYL VPKVENIVQVDILSPNVYTIDKGFNHLSKGFKGQSVSQSYFRKISA LARGAVVRACPRNGLLYNAIYRNSKNYLNNIDLEDKKTTSKTNVSY PCSLLNGCIEILEDDLFIMSSKDSFTDTDFSEPSVGPVSYKAKKGA DTILDSTLSNYDFSKEINFTSTVPIITVEDPLETEDVPVISEDRT VYVDDYTTFHFLEAQKIGKEVVPTQTKVVFTTNMEEALFDSKKVYT VFENTASRINEAGTGIANGMMFYQWLKGIVQDFTEEATQKDTFDKI SDVTMIVPYLGNILNIGNDIRKGDFMGAVELGGVTILLEAIPELTL PVLIGLTIIEDELEKEQVSQTVYNVLDKRDEKWEEVYGFVKQQWWW MVHTQFETRILHAYQALNHQVEAIKANMTYQLANYRGNQEDKELLE KAIDDTLQSLYYAVDQAMHNIKRFLIQSSKSYLLNQMLPKTKEQLL AFDQQTLRNVNDFINKNQGVLGESLAKDLKKKVEKRLTSLPVFNLE DLPISEFEDLIHSHEIDI | 13 |
| BoNT/EN full length with modified linker containing thrombin cleavage site | MVTINDLHYSDPIDEDNIINMRIPLYDLEVDDQFINHNVPDLKAFQ VFPNVWVVPERYTFYSTMKNLDAPANPSRSSYYDPTYLQSDAEKEV FLQQMILLFKRINSTQEGQQFLNLLSRSIPVPYESNGDVAMGTTQV IKQMDDKGNVLKHRRAHIIYGPGPDLMAKGSKALTKSRETGRGCM AEIYFSPMYHKTYSTKLTNKNSLVDKSVQEFVPDPAVTLIHELCHG LHALYGIDLGNVGSWEFNSNPNSLFSSWFSSKEAVNFEEVMTFGGE DVKVIKSEIDKKIPGILNLIKTTVEPIINKITDPHDEMLQCLQSKY PSLKGTLGQFFFDDTQLEKDIRDLWMVMNETMFAENLKALTRARYL VPKVENIVQVDILSPNVYTIDKGFNHLSKGFKGQSVSQSYFRKISA LARGAVVRACPNPHFSSQLVPRGSLSSCIEILEDDLFIMSSKDSFT DTDFSEPSVGPVSYKAKKGADTILDSTLSNYDFSKEINFTSTVPII TVEDPLETEDVPVISEDRTVYVDDYTTFHFLEAQKIGKEVVPTQT KVVFTTNMEEALFDSKKVYTVFENTASRINEAGTGIANGMMFYQWL KGIVQDFTEEATQKDTFDKISDVTMIVPYLGNILNIGNDIRKGDFM GAVELGGVTILLEAIPELTLPVLIGLTIIEDELEKEQVSQTVYNVL DKRDEKWEEVYGFVKQQWWWMVHTQFETRILHAYQALNHQVEAIKA NMTYQLANYRGNQEDKELLEKAIDDTLQSLYYAVDQAMHNIKRFLI QSSKSYLLNQMLPKTKEQLLAFDQQTLRNVNDFINKNQGVLGESLA KDLKKKVEKRLTSLPVFNLEDLPISEFEDLIHSHEIDIQDSEVLNI GVNNGKIQDLSGENTPLTLGENLHIVNGRDNQAVRLNNQLDSKLEI QSRPNIHFTAFEDFSISIWIRCSMLRNNRNRGQKYTIIQQFNKYGW QLAIQDSVFVWTLHDTFNNQIQLTSGSALTNKNYLLQNFWLHITVT NKRSEKSRLYINGVLQDKDISVLGNCHPKEPILFSIQDNSDPNYF VRFEQFNVYRKALTDSEVNRLYWKYFEGSYLRDVWGERLTYNRDYY MQLSTLPGRGIKREYRTWSGFDYIILSELGTQKIPTHEVTYPKLYQ GQKITIHSDGKNLEPHVKSNKNIRLKIDDFYIGVVNPFKLPEWRPE SGAYVVTTYNHAEDLCLYFRTRSSSQSLYYGQLIMNDGRNKSLLNY TLKGSTYWIWSSAWYYENYNTSSKTAGNWYFIPVDEGWKED | 14 |
| BoNT/EN full length with BoNT/A linker | MVTINDLHYSDPIDEDNIINMRIPLYDLEVDDQFINHNVPDLKAFQ VFPNVWVVPERYTFYSTMKNLDAPANPSRSSYYDPTYLQSDAEKEV FLQQMILLFKRINSTQEGQQFLNLLSRSIPVPYESNGDVAMGTTQV IKQMDDKGNVLKHRRAHIIYGPGPDLMAKGSKALTKSRETGRGCM AEIYFSPMYHKTYSTKLTNKNSLVDKSVQEFVPDPAVTLIHELCHG LHALYGIDLGNVGSWEFNSNPNSLFSSWFSSKEAVNFEEVMTFGGE DVKVIKSEIDKKIPGILNLIKTTVEPIINKITDPHDEMLQCLQSKY PSLKGTLGQFFFDDTQLEKDIRDLWMVMNETMFAENLKALTRARYL VPKVENIVQVDILSPNVYTIDKGFNHLSKGFKGQSVSQSYFRKISA LARGAVVRACVRGIITSKTKSLDKGYNKALNDLCIEILEDDLFIMS SKDSFTDTDFSEPSVGPVSYKAKKGADTILDSTLSNYDFSKEINFT STVPIITVEDPLETEDVPVISEDRTVYVDDYTTFHFLEAQKIGKE VVPTQTKVVFTTNMEEALFDSKKVYTVFENTASRINEAGTGIANG MFYQWLKGIVQDFTEEATQKDTFDKISDVTMIVPYLGNILNIGNDI RKGDFMGAVELGGVTILLEAIPELTLPVLIGLTIIEDELEKEQVSQ TVYNVLDKRDEKWEEVYGFVKQQWWWMVHTQFETRILHAYQALNHQ VEAIKANMTYQLANYRGNQEDKELLEKAIDDTLQSLYYAVDQAMHN IKRFLIQSSKSYLLNQMLPKTKEQLLAFDQQTLRNVNDFINKNQGV | 15 |

TABLE 3-continued

Non-limiting, Exemplary Modified BoNT/EN Polypeptides

| Name | Amino Acid Sequence | SEQ ID NO |
|---|---|---|
| | LGESLAKDLKKKVEKRLTSLPVFNLEDLPISEFEDLIHSHEIDIQD<br>SEVLNIGVNNGKIQDLSGENTPLTLGENLHIVNGRDNQAVRLNNQL<br>DSKLEIQSRPNIHFTAFEDFSISIWIRCSMLRNNRNRGQKYTIIQQ<br>FNKYGWQLAIQDSVFVWTLHDTFNNQIQLTSGSALTNKNYLLQNFW<br>LHITVTNKRSEKSRLYINGVLQDQKDISVLGNCHPKEPILFSIQDN<br>SDPNYFVRFEQFNVYRKALTDSEVNRLYWKYFEGSYLRDVWGERLT<br>YNRDYYMQLSTLPGRGIKREYRTWSGFDYIILSELGTQKIPTHEVT<br>YPKLYQGQKITIHSDGKNLEPHVKSNKNIRLKIDDFYIGVVNPFKL<br>PEWRPESGAYVVTTYNHAEDLCLYFRTRSSSQSLYYGQLIMNDGRN<br>KSLLNYTLKGSTYWIWSSAWYYENYNTSSKTAGNWYFIPVDEGWKE<br>D | |
| BoNT/EN full<br>length with<br>BoNT/B linker | MVTINDLHYSDPIDEDNIINMRIPLYDLEVDDQFINHNVPDLKAFQ<br>VFPNVWVVPERYTFYSTMKNLDAPANPSRSSYYDPTYLQSDAEKEV<br>FLQQMILLFKRINSTQEGQQFLNLLSRSIPVPYESNGDVAMGTTQV<br>IKQMDDKGNVLKHRRAHIIYGPGPDLMAKGSKALTKSRETGRGCM<br>AEIYFSPMYHKTYSTKLTNKNSLVDKSVQEFVPDPAVTLIHELCHG<br>LHALYGIDLGNVGSWEFNSNPNSLFSSWFSSKEAVNFEEVMTFGGE<br>DVKVIKSEIDKKIPGILNLIKTTVEPIINKITDPHDEMLQCLQSKY<br>PSLKGTLGQFFFDDTQLEKDIRDLWMVMNETMFAENLKALTRARYL<br>VPKVENIVQVDILSPNVYTIDKGFNHLSKGFKGQSVSQSYFRKISA<br>LARGAVVRACKSVKAPGICIEILEDDLFIMSSKDSFTDTDFSEPSV<br>GPVSYKAKKGADTILDSTLSNYDFSKEINFTSTVPIITVEDPLETD<br>EDVPVISEDRTVYVDDYTTFHFLEAQKIGKEVVPTQTKVVFTTNME<br>EALFDSKKVYTVFENTASRINEAGTGIANGMMFYQWLKGIVQDFTE<br>EATQKDTFDKISDVTMIVPYLGNILNIGNDIRKGDFMGAVELGGVT<br>ILLEAIPELTLPVLIGLTIIEDELEKEQVSQTVYNVLDKRDEKWEE<br>VYGFVKQQWWWMVHTQFETRILHAYQALNHQVEAIKANMTYQLANY<br>RGNQEDKELLEKAIDDTLQSLYYAVDQAMHNIKRFLIQSSKSYLLN<br>QMLPKTKEQLLAFDQQTLRNVNDFINKNQGVLGESLAKDLKKKVEK<br>RLTSLPVFNLEDLPISEFEDLIHSHEIDIQDSEVLNIGVNNGKIQD<br>LSGENTPLTLGENLHIVNGRDNQAVRLNNQLDSKLEIQSRPNIHFT<br>AFEDFSISIWIRCSMLRNNRNRGQKYTIIQQFNKYGWQLAIQDSVF<br>VWTLHDTFNNQIQLTSGSALTNKNYLLQNFWLHITVTNKRSEKSRL<br>YINGVLQDQKDISVLGNCHPKEPILFSIQDNSDPNYFVRFEQFNVY<br>RKALTDSEVNRLYWKYFEGSYLRDVWGERLTYNRDYYMQLSTLPGR<br>GIKREYRTWSGFDYIILSELGTQKIPTHEVTYPKLYQGQKITIHSD<br>GKNLEPHVKSNKNIRLKIDDFYIGVVNPFKLPEWRPESGAYVVTTY<br>NHAEDLCLYFRTRSSSQSLYYGQLIMNDGRNKSLLNYTLKGSTYWI<br>WSSAWYYENYNTSSKTAGNWYFIPVDEGWKED | 16 |
| BoNT/EN full<br>length with<br>BoNT/C linker | MVTINDLHYSDPIDEDNIINMRIPLYDLEVDDQFINHNVPDLKAFQ<br>VFPNVWVVPERYTFYSTMKNLDAPANPSRSSYYDPTYLQSDAEKEV<br>FLQQMILLFKRINSTQEGQQFLNLLSRSIPVPYESNGDVAMGTTQV<br>IKQMDDKGNVLKHRRAHIIYGPGPDLMAKGSKALTKSRETGRGCM<br>AEIYFSPMYHKTYSTKLTNKNSLVDKSVQEFVPDPAVTLIHELCHG<br>LHALYGIDLGNVGSWEFNSNPNSLFSSWFSSKEAVNFEEVMTFGGE<br>DVKVIKSEIDKKIPGILNLIKTTVEPIINKITDPHDEMLQCLQSKY<br>PSLKGTLGQFFFDDTQLEKDIRDLWMVMNETMFAENLKALTRARYL<br>VPKVENIVQVDILSPNVYTIDKGFNHLSKGFKGQSVSQSYFRKISA<br>LARGAVVRACHKAIDGRSLYNKTLDCIEILEDDLFIMSSKDSFTDT<br>DFSEPSVGPVSYKAKKGADTILDSTLSNYDFSKEINFTSTVPIITV<br>EDPLETDEDVPVISEDRTVYVDDYTTFHFLEAQKIGKEVVPTQTKV<br>VFTTNMEEALFDSKKVYTVFENTASRINEAGTGIANGMMFYQWLK<br>IVQDFTEEATQKDTFDKISDVTMIVPYLGNILNIGNDIRKGDFMGA<br>VELGGVTILLEAIPELTLPVLIGLTIIEDELEKEQVSQTVYNVLDK<br>RDEKWEEVYGFVKQQWWWMVHTQFETRILHAYQALNHQVEAIKANM<br>TYQLANYRGNQEDKELLEKAIDDTLQSLYYAVDQAMHNIKRFLIQS<br>SKSYLLNQMLPKTKEQLLAFDQQTLRNVNDFINKNQGVLGESLAKD<br>LKKKVEKRLTSLPVFNLEDLPISEFEDLIHSHEIDIQDSEVLNIGV<br>NNGKIQDLSGENTPLTLGENLHIVNGRDNQAVRLNNQLDSKLEIQS<br>RPNIHFTAFEDFSISIWIRCSMLRNNRNRGQKYTIIQQFNKYGWQL<br>AIQDSVFVWTLHDTFNNQIQLTSGSALTNKNYLLQNFWLHITVTNK<br>RSEKSRLYINGVLQDQKDISVLGNCHPKEPILFSIQDNSDPNYFVR<br>FEQFNVYRKALTDSEVNRLYWKYFEGSYLRDVWGERLTYNRDYYMQ<br>LSTLPGRGIKREYRTWSGFDYIILSELGTQKIPTHEVTYPKLYQGQ<br>KITIHSDGKNLEPHVKSNKNIRLKIDDFYIGVVNPFKLPEWRPESG<br>AYVVTTYNHAEDLCLYFRTRSSSQSLYYGQLIMNDGRNKSLLNYTL<br>KGSTYWIWSSAWYYENYNTSSKTAGNWYFIPVDEGWKED | 17 |
| BoNT/EN full<br>length with<br>BoNT/D linker | MVTINDLHYSDPIDEDNIINMRIPLYDLEVDDQFINHNVPDLKAFQ<br>VFPNVWVVPERYTFYSTMKNLDAPANPSRSSYYDPTYLQSDAEKEV<br>FLQQMILLFKRINSTQEGQQFLNLLSRSIPVPYESNGDVAMGTTQV<br>IKQMDDKGNVLKHRRAHIIYGPGPDLMAKGSKALTKSRETGRGCM<br>AEIYFSPMYHKTYSTKLTNKNSLVDKSVQEFVPDPAVTLIHELCHG<br>LHALYGIDLGNVGSWEFNSNPNSLFSSWFSSKEAVNFEEVMTFGGE | 18 |

TABLE 3-continued

Non-limiting, Exemplary Modified BoNT/EN Polypeptides

| Name | Amino Acid Sequence | SEQ ID NO |
|---|---|---|
| | DVKVIKSEIDKKIPGILNLIKTTVEPIINKITDPHDEMLQCLQSKY PSLKGTLGQFFFDDTQLEKDIRDLWMVMNETMFAENLKALTRARYL VPKVENIVQVDILSPNVYTIDKGFNHLSKGFKGQSVSQSYFRKISA LARGAVVRAC<u>LRLTKNSRDDST</u>CIEILEDDLFIMSSKDSFTDTDFS EPSVGPVSYKAKKGADTILDSTLSNYDFSKEINFTSTVPIITVEDP LETDEDVPVISEDRTVYVDDYTTFHFLEAQKIGKEVVPTQTKVVFT TNMEEALFDSKKVYTVFENTASRINEAGTGIANGMMFYQWLKGIVQ DFTEEATQKDTFDKISDVTMIVPYLGNILNIGNDIRKGDFMGAVEL GGVTILLEAIPELTLPVLIGLTIIEDELEKEQVSQTVYNVLDKRDE KWEEVYGFVKQQWWWMVHTQFETRILHAYQALNHQVEAIKANMTYQ LANYRGNQEDKELLEKAIDDTLQSLYYAVDQAMHNIKRFLIQSSKS YLLNQMLPKTKEQLLAFDQQTLRNVNDFINKNQGVLGESLAKDLKK KVEKRLTSLPVFNLEDLPISEFEDLIHSHEIDIQDSEVLNIGVNNG KIQDLSGENTPLTLGENLHIVNGRDNQAVRLNNQLDSKLEIQSRPN IHFTAFEDFSISIWIRCSMLRNNRNRGQKYTIIQQFNKYGWQLAIQ DSVFVWTLHDTFNNQIQLTSGSALTNKNYLLQNFWLHITVTNKRSE KSRLYINGVLQDQKDISVLGNCHPKEPILFSIQDNSDPNYFVRFEQ FNVYRKALTDSEVNRLYWKYFEGSYLRDVWGERLTYNRDYYMQLST LPGRGIKREYRTWSGFDYIILSELGTQKIPTHEVTYPKLYQGQKIT IHSDGKNLEPHVKSNKNIRLKIDDFYIGVVNPFKLPEWRPESGAYV VTTYNHAEDLCLYFRTRSSSQSLYYGQLIMNDGRNKSLLNYTLKGS TYWIWSSAWYYENYNTSSKTAGNWYFIPVDEGWKED | |
| BoNT/EN full length with BoNT/E linker | MVTINDLHYSDPIDEDNIINMRIPLYDLEVDDQFINHNVPDLKAFQ VFPNVWVVPERYTFYSTMKNLDAPANPSRSSYYDPTYLQSDAEKEV FLQQMILLFKRINSTQEGQQFLNLLSRSIPVPYESNGDVAMGTTQV IKQMDDKGNVLKHRRAHIIYGPGPDLMAKGSKALTKSRETGRGCM AEIYFSPMYHKTYSTKLTNKNSLVDKSVQEFVPDDPAVTLIHELCHG LHALYGIDLGNVGSWEFNSNPNSLFSSWFSSKEAVNFEEVMTFGGE DVKVIKSEIDKKIPGILNLIKTTVEPIINKITDPHDEMLQCLQSKY PSLKGTLGQFFFDDTQLEKDIRDLWMVMNETMFAENLKALTRARYL VPKVENIVQVDILSPNVYTIDKGFNHLSKGFKGQSVSQSYFRKISA LARGAVVRAC<u>KNIVSVKGIRKS</u>ICIEILEDDLFIMSSKDSFTDTDF SEPSVGPVSYKAKKGADTILDSTLSNYDFSKEINFTSTVPIITVED PLETDEDVPVISEDRTVYVDDYTTFHFLEAQKIGKEVVPTQTKVVF TTNMEEALFDSKKVYTVFENTASRINEAGTGIANGMMFYQWLKGIV QDFTEEATQKDTFDKISDVTMIVPYLGNILNIGNDIRKGDFMGAVE LGGVTILLEAIPELTLPVLIGLTIIEDELEKEQVSQTVYNVLDKRD EKWEEVYGFVKQQWWWMVHTQFETRILHAYQALNHQVEAIKANMTY QLANYRGNQEDKELLEKAIDDTLQSLYYAVDQAMHNIKRFLIQSSK SYLLNQMLPKTKEQLLAFDQQTLRNVNDFINKNQGVLGESLAKDLK KKVEKRLTSLPVFNLEDLPISEFEDLIHSHEIDIQDSEVLNIGVNN GKIQDLSGENTPLTLGENLHIVNGRDNQAVRLNNQLDSKLEIQSRP NIHFTAFEDFSISIWIRCSMLRNNRNRGQKYTIIQQFNKYGWQLAI QDSVFVWTLHDTFNNQIQLTSGSALTNKNYLLQNFWLHITVTNKRS EKSRLYINGVLQDQKDISVLGNCHPKEPILFSIQDNSDPNYFVRFE QFNVYRKALTDSEVNRLYWKYFEGSYLRDVWGERLTYNRDYYMQLS TLPGRGIKREYRTWSGFDYIILSELGTQKIPTHEVTYPKLYQGQKI TIHSDGKNLEPHVKSNKNIRLKIDDFYIGVVNPFKLPEWRPESGAY VVTTYNHAEDLCLYFRTRSSSQSLYYGQLIMNDGRNKSLLNYTLKG STYWIWSSAWYYENYNTSSKTAGNWYFIPVDEGWKED | 19 |
| BoNT/EN full length with BoNT/F linker | MVTINDLHYSDPIDEDNIINMRIPLYDLEVDDQFINHNVPDLKAFQ VFPNVWVVPERYTFYSTMKNLDAPANPSRSSYYDPTYLQSDAEKEV FLQQMILLFKRINSTQEGQQFLNLLSRSIPVPYESNGDVAMGTTQV IKQMDDKGNVLKHRRAHIIYGPGPDLMAKGSKALTKSRETGRGCM AEIYFSPMYHKTYSTKLTNKNSLVDKSVQEFVPDDPAVTLIHELCHG LHALYGIDLGNVGSWEFNSNPNSLFSSWFSSKEAVNFEEVMTFGGE DVKVIKSEIDKKIPGILNLIKTTVEPIINKITDPHDEMLQCLQSKY PSLKGTLGQFFFDDTQLEKDIRDLWMVMNETMFAENLKALTRARYL VPKVENIVQVDILSPNVYTIDKGFNHLSKGFKGQSVSQSYFRKISA LARGAVVRAC<u>SVIPRKGTKAPPRL</u>CIEILEDDLFIMSSKDSFTDT DFSEPSVGPVSYKAKKGADTILDSTLSNYDFSKEINFTSTVPIITV EDPLETDEDVPVISEDRTVYVDDYTTFHFLEAQKIGKEVVPTQTKV VFTTNMEEALFDSKKVYTVFENTASRINEAGTGIANGMMFYQWLKG IVQDFTEEATQKDTFDKISDVTMIVPYLGNILNIGNDIRKGDFMGA VELGGVTILLEAIPELTLPVLIGLTIIEDELEKEQVSQTVYNVLDK RDEKWEEVYGFVKQQWWWMVHTQFETRILHAYQALNHQVEAIKANM TYQLANYRGNQEDKELLEKAIDDTLQSLYYAVDQAMHNIKRFLIQS SKSYLLNQMLPKTKEQLLAFDQQTLRNVNDFINKNQGVLGESLAKD LKKKVEKRLTSLPVFNLEDLPISEFEDLIHSHEIDIQDSEVLNIGV NNGKIQDLSGENTPLTLGENLHIVNGRDNQAVRLNNQLDSKLEIQS RPNIHFTAFEDFSISIWIRCSMLRNNRNRGQKYTIIQQFNKYGWQL AIQDSVFVWTLHDTFNNQIQLTSGSALTNKNYLLQNFWLHITVTNK RSEKSRLYINGVLQDQKDISVLGNCHPKEPILFSIQDNSDPNYFVR FEQFNVYRKALTDSEVNRLYWKYFEGSYLRDVWGERLTYNRDYYMQ | 20 |

TABLE 3-continued

Non-limiting, Exemplary Modified BoNT/EN Polypeptides

| Name | Amino Acid Sequence | SEQ ID NO |
|------|---------------------|-----------|
|  | LSTLPGRGIKREYRTWSGFDYIILSELGTQKIPTHEVTYPKLYQGQ KITIHSDGKNLEPHVKSNKNIRLKIDDFYIGVVNPFKLPEWRPESG AYVVTTYNHAEDLCLYFRTRSSSQSLYYGQLIMNDGRNKSLLNYTL KGSTYWIWSSAWYYENYNTSSKTAGNWYFIPVDEGWKED |  |
| BoNT/EN full length with BoNT/G linker | MVTINDLHYSDPIDEDNIINMRIPLYDLEVDDQFINHNVPDLKAFQ VFPNVWVPERYTFYSTMKNLDAPANPSRSSYYDPTYLQSDAEKEV FLQQMILLFKRINSTQEGQQFLNLLSRSIPVPYESNGDVAMGTTQV IKQMDDKGNVLKHRRAHIIYGPGPDLMAKGSKALTKSRETGRGCM AEIYFSPMYHKTYSTKLTNKNSLVDKSVQEFVPDPAVTLIHELCHG LHALYGIDLGNVGSWEFNSNPNSLFSSWFSSKEAVNFEEVMTFGGE DVKVIKSEIDKKIPGILNLIKTTVEPIINKITDPHDEMLQCLQSKY PSLKGTLGQFFFDDTQLEKDIRDLWMVMNETMFAENLKALTRARYL VPKVENIVQVDILSPNVYTIDKGFNHLSKGFKGQSVSQSYFRKISA LARGAVVRACKPVMYKNTGKSEQCIEILEDDLFIMSSKDSFTDTDF SEPSVGPVSYKAKKGADTILDSTLSNYDFSKEINFTSTVPIITVED PLETDEDVPVISEDRTVYVDDYTTFHFLEAQKIGKEVVPTQTKVVF TTNMEEALFDSKKVYTVFENTASRINEAGTGIANGMMFYQWLKGIV QDFTEEATQKDTFDKISDVTMIVPYLGNILNIGNDIRKGDFMGAVE LGGVTILLEAIPELTLPVLIGLTIIEDELEKEQVSQTVYNVLDKRD EKWEEVYGFVKQQWWWMVHTQFETRILHAYQALNHQVEAIKANMTY QLANYRGNQEDKELLEKAIDDTLQSLYYAVDQAMHNIKRFLIQSSK SYLLNQMLPKTKEQLLAFDQQTLRNVNDFINKNQGVLGESLAKDLK KKVEKRLTSLPVFNLEDLPISEFEDLIHSHEIDIQDSEVLNIGVNN GKIQDLSGENTPLTLGENLHIVNGRDNQAVRLNNQLDSKLEIQSRP NIHFTAFEDFSISIWIRCSMLRNNRNRGQKYTIIQQFNKYGWQLAI QDSVFVWTLHDTFNNQIQLTSGSALTNKNYLLQNFWLHITVTNKRS EKSRLYINGVLQDQKDISVLGNCHPKEPILFSIQDNSDPNYFVRFE QFNVYRKALTDSEVNRLYWKYFEGSYLRDVWGERLTYNRDYYMQLS TLPGRGIKREYRTWSGFDYIILSELGTQKIPTHEVTYPKLYQGQKI TIHSDGKNLEPHVKSNKNIRLKIDDFYIGVVNPFKLPEWRPESGAY VVTTYNHAEDLCLYFRTRSSSQSLYYGQLIMNDGRNKSLLNYTLKG STYWIWSSAWYYENYNTSSKTAGNWYFIPVDEGWKED | 21 |
| BoNT/EN full length with BoNT/X linker | MVTINDLHYSDPIDEDNIINMRIPLYDLEVDDQFINHNVPDLKAFQ VFPNVWVPERYTFYSTMKNLDAPANPSRSSYYDPTYLQSDAEKEV FLQQMILLFKRINSTQEGQQFLNLLSRSIPVPYESNGDVAMGTTQV IKQMDDKGNVLKHRRAHIIYGPGPDLMAKGSKALTKSRETGRGCM AEIYFSPMYHKTYSTKLTNKNSLVDKSVQEFVPDPAVTLIHELCHG LHALYGIDLGNVGSWEFNSNPNSLFSSWFSSKEAVNFEEVMTFGGE DVKVIKSEIDKKIPGILNLIKTTVEPIINKITDPHDEMLQCLQSKY PSLKGTLGQFFFDDTQLEKDIRDLWMVMNETMFAENLKALTRARYL VPKVENIVQVDILSPNVYTIDKGFNHLSKGFKGQSVSQSYFRKISA LARGAVVRAC<u>PRNGLLYNAIYRNSKNYLNNIDLEDKKTTSKTNVSY PCSLLNGC</u>IEILEDDLFIMSSKDSFTDTDFSEPSVGPVSYKAKKGA DTILDSTLSNYDFSKEINFTSTVPIITVEDPLETDEDVPVISEDRT VYVDDYTTFHFLEAQKIGKEVVPTQTKVVFTTNMEEALFDSKKVYT VFENTASRINEAGTGIANGMMFYQWLKGIVQDFTEEATQKDTFDKI SDVTMIVPYLGNILNIGNDIRKGDFMGAVELGGVTILLEAIPELTL PVLIGLTIIEDELEKEQVSQTVYNVLDKRDEKWEEVYGFVKQQWWW MVHTQFETRILHAYQALNHQVEAIKANMTYQLANYRGNQEDKELLE KAIDDTLQSLYYAVDQAMHNIKRFLIQSSKSYLLNQMLPKTKEQLL AFDQQTLRNVNDFINKNQGVLGESLAKDLKKKVEKRLTSLPVFNLE DLPISEFEDLIHSHEIDIQDSEVLNIGVNNGKIQDLSGENTPLTLG ENLHIVNGRDNQAVRLNNQLDSKLEIQSRPNIHFTAFEDFSISIWI RCSMLRNNRNRGQKYTIIQQFNKYGWQLAIQDSVFVWTLHDTFNNQ IQLTSGSALTNKNYLLQNFWLHITVTNKRSEKSRLYINGVLQDQKD ISVLGNCHPKEPILFSIQDNSDPNYFVRFEQFNVYRKALTDSEVNR LYWKYFEGSYLRDVWGERLTYNRDYYMQLSTLPGRGIKREYRTWSG FDYIILSELGTQKIPTHEVTYPKLYQGQKITIHSDGKNLEPHVKSN KNIRLKIDDFYIGVVNPFKLPEWRPESGAYVVTTYNHAEDLCLYFR TRSSSQSLYYGQLIMNDGRNKSLLNYTLKGSTYWIWSSAWYYENYN TSSKTAGNWYFIPVDEGWKED | 22 |

TABLE 4

Non-limiting, Exemplary Chimeric Toxins

| Name | Amino Acid Sequence | SEQ ID NO |
|---|---|---|
| BoNT/EN-LC-H$_N$ and BoNT/A1-H$_C$ | MVTINDLHYSDPIDEDNIINMRIPLYDLEVDDQFINHNVPDLKAFQVFPN VWVVPERYTFYSTMKNLDAPANPSRSSYYDPTYLQSDAEKEVFLQQMILL FKRINSTQEGQQFLNLLSRSIPVPYESNGDVAMGTTQVIKQMDDKGNVLK HRRAHIIIYGPGPDLMAKGSKALTKSRETGRGCMAEIYFSPMYHKTYSTK LTNKNSLVDKSVQEFVPDPAVTLIHELCHGLHALYGIDLGNVGSWEFNSN PNSLFSSWFSSKEAVNFEEVMTFGGEDVKVIKSEIDKKIPGILNLIKTTV EPIINKITDPHDEMLQCLQSKYPSLKGTLGQFFFDDTQLEKDIRDLWMVM NETMFAENLKALTRARYLVPKVENIVQVDILSPNVYTIDKGFNHLSKGFK GQSVSQSYFRKISALARGAVVRACPNPHFSSQRGLSSCIEILEDDLFIMS SKDSFTDTDFSEPSVGPVSYKAKKGADTILDSTLSNYDFSKEINFTSTVP IITVEDPLETDEDVPVISEDRTVYVDDYTTFHFLEAQKIGKEVVPTQTKV VFTTNMEEALFDSKKVYTVFENTASRINEAGTGIANGMMFYQWLKGIVQD FTEEATQKDTFDKISDVTMIVPYLGNILNIGNDIRKGDFMGAVELGGVTI LLEAIPELTLPVLIGLTIIEDELEKEQVSQTVYNVLDKRDEKWEEVYGFV KQQWWWMVHTQFETRILHAYQALNHQVEAIKANMTYQLANYRGNQEDKEL LEKAIDDTLQSLYYAVDQAMHNIKRFLIQSSKSYLLNQMLPKTKEQLLAF DQQTLRNVNDFINKNQGVLGESLAKDLKKKVEKRLTSLPVFNLEDLPISE FEDLIHSHEIDIIINTSILNLRYESNHLIDLSRYASKINIGSKVNFDPID KNQIQLFNLESSKIEVILKNAIVYNSMYENFSTSFWIRIPKYFNSISLNN EYTIINCMENNSGWKVSLNYGEIIWTLQDTQEIKQRVVFKYSQMINISDY INRWIFVTITNNRLNNSKIYINGRLIDQKPISNLGNIHASNNIMFKLDGC RDTHRYIWIKYFNLFDKELNEKEIKDLYDNQSNSGILKDFWGDYLQYDKP YYMLNLYDPNKYVDVNNVGIRGYMYLKGPRGSVMTTNIYLNSSLYRGTKF IIKKYASGNKDNIVRNNDRVYINVVVKNKEYRLATNASQAGVEKILSALE IPDVGNLSQVVVMKSKNDQGITNKCKMNLQDNNGNDIGFIGFHQFNNIAK LVASNWYNRQIERSSRTLGCSWEFIPVDDGWGERPL | 23 |
| BoNT/EN-LC-H$_N$ and BoNT/B1-H$_C$ | MVTINDLHYSDPIDEDNIINMRIPLYDLEVDDQFINHNVPDLKAFQVFPN VWVVPERYTFYSTMKNLDAPANPSRSSYYDPTYLQSDAEKEVFLQQMILL FKRINSTQEGQQFLNLLSRSIPVPYESNGDVAMGTTQVIKQMDDKGNVLK HRRAHIIIYGPGPDLMAKGSKALTKSRETGRGCMAEIYFSPMYHKTYSTK LTNKNSLVDKSVQEFVPDPAVTLIHELCHGLHALYGIDLGNVGSWEFNSN PNSLFSSWFSSKEAVNFEEVMTFGGEDVKVIKSEIDKKIPGILNLIKTTV EPIINKITDPHDEMLQCLQSKYPSLKGTLGQFFFDDTQLEKDIRDLWMVM NETMFAENLKALTRARYLVPKVENIVQVDILSPNVYTIDKGFNHLSKGFK GQSVSQSYFRKISALARGAVVRACPNPHFSSQRGLSSCIEILEDDLFIMS SKDSFTDTDFSEPSVGPVSYKAKKGADTILDSTLSNYDFSKEINFTSTVP IITVEDPLETDEDVPVISEDRTVYVDDYTTFHFLEAQKIGKEVVPTQTKV VFTTNMEEALFDSKKVYTVFENTASRINEAGTGIANGMMFYQWLKGIVQD FTEEATQKDTFDKISDVTMIVPYLGNILNIGNDIRKGDFMGAVELGGVTI LLEAIPELTLPVLIGLTIIEDELEKEQVSQTVYNVLDKRDEKWEEVYGFV KQQWWWMVHTQFETRILHAYQALNHQVEAIKANMTYQLANYRGNQEDKEL LEKAIDDTLQSLYYAVDQAMHNIKRFLIQSSKSYLLNQMLPKTKEQLLAF DQQTLRNVNDFINKNQGVLGESLAKDLKKKVEKRLTSLPVFNLEDLPISE FEDLIHSHEIDIILNNIILNLRYKDNNLIDLSGYGAKVEVDGVELNDKN QFKLTSSANSKIRVTQNQNIIFNSVFLDFSVSFWIRIPKYKNDGIQNYIH NEYTIINCMKNNSGWKISIRGNRIIWTLIDINGKTKSVFFEYNIREDISE YINRWFFVTITNNLNNAKIYINGKLESNTDIKDIREVIANGEIIFKLDGD IDRTQFIWMKYFSIFNTELSQSNIEERYKIQSYSEYLKDFWGNPLMYNKE YYMFNAGNKNSYIKLKKDSPVGEILTRSKYNQNSKYINYRDLYIGEKFII RRKSNSQSINDDIVRKEDYIYLDFFNLNQEWRVYTYKYFKKEEEKLFLAP ISDSDEFYNTIQIKEYDEQPTYSCQLLFKKDEESTDEIGLIGIHRFYESG IVFEEYKDYFCISKWYLKEVKRKPYNLKLGCNWQFIPKDEGWTE | 24 |
| BoNT/EN-LC-H$_N$ and BoNT/C1-H$_C$ | MVTINDLHYSDPIDEDNIINMRIPLYDLEVDDQFINHNVPDLKAFQVFPN VWVVPERYTFYSTMKNLDAPANPSRSSYYDPTYLQSDAEKEVFLQQMILL FKRINSTQEGQQFLNLLSRSIPVPYESNGDVAMGTTQVIKQMDDKGNVLK HRRAHIIIYGPGPDLMAKGSKALTKSRETGRGCMAEIYFSPMYHKTYSTK LTNKNSLVDKSVQEFVPDPAVTLIHELCHGLHALYGIDLGNVGSWEFNSN PNSLFSSWFSSKEAVNFEEVMTFGGEDVKVIKSEIDKKIPGILNLIKTTV EPIINKITDPHDEMLQCLQSKYPSLKGTLGQFFFDDTQLEKDIRDLWMVM NETMFAENLKALTRARYLVPKVENIVQVDILSPNVYTIDKGFNHLSKGFK GQSVSQSYFRKISALARGAVVRACPNPHFSSQRGLSSCIEILEDDLFIMS SKDSFTDTDFSEPSVGPVSYKAKKGADTILDSTLSNYDFSKEINFTSTVP IITVEDPLETDEDVPVISEDRTVYVDDYTTFHFLEAQKIGKEVVPTQTKV VFTTNMEEALFDSKKVYTVFENTASRINEAGTGIANGMMFYQWLKGIVQD FTEEATQKDTFDKISDVTMIVPYLGNILNIGNDIRKGDFMGAVELGGVTI LLEAIPELTLPVLIGLTIIEDELEKEQVSQTVYNVLDKRDEKWEEVYGFV KQQWWWMVHTQFETRILHAYQALNHQVEAIKANMTYQLANYRGNQEDKEL LEKAIDDTLQSLYYAVDQAMHNIKRFLIQSSKSYLLNQMLPKTKEQLLAF DQQTLRNVNDFINKNQGVLGESLAKDLKKKVEKRLTSLPVFNLEDLPISE FEDLIHSHEIDINDSKILSLQNRKTLVDTSGYNAEVSEEGDVQLNPIF PFDFKLGSSGEDRGKVIVTQNENIVYNSMYESFSISFWIRINKWVSNLPG YTIIDSVKNNSGWSIGIISNFLVFTLKQNEDSEQSINFSYDISNNAPGYN KWFFVTVTNNMMGNMKIYINGKLIDTIKVKELTGINFSKTITFEINKIPD | 25 |

TABLE 4-continued

Non-limiting, Exemplary Chimeric Toxins

| Name | Amino Acid Sequence | SEQ ID NO |
|---|---|---|
| | TGLITSDSDNINMWIRDFYIFAKELDGKDINILFNSLQYTNVVKDYWGND<br>LRYNKEYYMVNIDYLNRYMYANSRQIVFNTRRNNNDFNEGYKIIIKRIRG<br>NTNDTRVRGGDILYFDMTINNKAYNLFMKNETMYADNHSTEDIYAIGLRE<br>QTKDINDNIIFQIQPMNNTYYYASQIFKSNFNGENISGICSIGTYRFRLG<br>GDWYRHNYLVPTVKQGNYASLLESTSTHWGFVPVSE | |
| BoNT/EN-LC-H$_N$ and BoNT/X-H$_C$ | MVTINDLHYSDPIDEDNIINMRIPLYDLEVDDQFINHNVPDLKAFQVFPN<br>VWVVPERYTFYSTMKNLDAPANPSRSSYYDPTYLQSDAEKEVFLQQMILL<br>FKRINSTQEGQQFLNLLSRSIPVPYESNGDVAMGTTQVIKQMDDKGNVLK<br>HRRAHIIIYGPGPDLMAKGSKALTKSRETGRGCMAEIYFSPMYHKTYSTK<br>LTNKNSLVDKSVQEFVPDPAVTLIHELCHGLHALYGIDLGNVGSWEFNSN<br>PNSLFSSWFSSKEAVNFEEVMTFGGEDVKVIKSEIDKKIPGILNLIKTTV<br>EPIINKITDPHDEMLQCLQSKYPSLKGTLGQFFFDDTQLEKDIRDLWMVM<br>NETMFAENLKALTRARYLVPKVENIVQVDILSPNVYTIDKGFNHLSKGFK<br>GQSVSQSYFRKISALARGAVVRA<u>CPNPHFSSQRGLSSC</u>IEILEDDLFIMS<br>SKDSFTDTDFSEPSVGPVSYKAKKGADTILDSTLSNYDFSKEINFTSTVP<br>IIITVEDPLETDEDVPVISEDRTVYVDDYTTFHFLEAQKIGKEVVPTQTKV<br>VFTTNMEEALFDSKKVYTVFENTASRINEAGTGIANGMMFYQWLKGIVQD<br>FTEEATQKDTFDKISDVTMIVPYLGNILNIGNDIRKGDFMGAVELGGVTI<br>LLEAIPELTLPVLIGLTIIEDELEKEQVSQTVYNVLDKRDEKWEEVYGFV<br>KQQWWWMVHTQFETRILHAYQALNHQVEAIKANMTYQLANYRGNQEDKEL<br>LEKAIDDTLQSLYYAVDQAMHNIKRFLIQSSKSYLLNQMLPKTKEQLLAF<br>DQQTLRNVNDFINKNQGVLGESLAKDLKKKVEKRLTSLPVFNLEDLPISE<br>FEDLIHSHEIDIEDYEVLNLGAEDGKIKDLSGTTSDINIGSDIELADGRE<br>NKAIKIKGSENSTIKIAMNKYLRFSATDNFSISFWIKHPKPTNLLNNGIE<br>YTLVENFNQRGWKISIQDSKLIWYLRDHNNSIKIVTPDYIAFNGWNLITI<br>TNNRSKGSIVYVNGSKIEEKDISSIWNTEVDDPIIFRLKNNRDTQAFTLL<br>DQFSIYRKELNQNEVVKLYNYYFNSNYIRDIWGNPLQYNKKYYLQTQDKP<br>GKGLIREYWSSFGYDYVILSDSKTITFPNNIRYGALYNGSKVLIKNSKKL<br>DGLVRNKDFIQLEIDGYNMGISADRFNEDTNYIGTTYGTTHDLTTDFEII<br>QRQEKYRNYCQLKTPYNIFHKSGLMSTETSKPTFHDYRDWVYSSAWYFQN<br>YENLNLRKHTKTNWYFIPKDEGWDED | 26 |
| BoNT/EN-LC-H$_N$ (with modified linker containing thrombin cleavage site) and BoNT/A1-H$_C$ | MVTINDLHYSDPIDEDNIINMRIPLYDLEVDDQFINHNVPDLKAFQVFPN<br>VWVVPERYTFYSTMKNLDAPANPSRSSYYDPTYLQSDAEKEVFLQQMILL<br>FKRINSTQEGQQFLNLLSRSIPVPYESNGDVAMGTTQVIKQMDDKGNVLK<br>HRRAHIIIYGPGPDLMAKGSKALTKSRETGRGCMAEIYFSPMYHKTYSTK<br>LTNKNSLVDKSVQEFVPDPAVTLIHELCHGLHALYGIDLGNVGSWEFNSN<br>PNSLFSSWFSSKEAVNFEEVMTFGGEDVKVIKSEIDKKIPGILNLIKTTV<br>EPIINKITDPHDEMLQCLQSKYPSLKGTLGQFFFDDTQLEKDIRDLWMVM<br>NETMFAENLKALTRARYLVPKVENIVQVDILSPNVYTIDKGFNHLSKGFK<br>GQSVSQSYFRKISALARGAVVRA<u>CPNPHFSSQLVPRGSLSSC</u>IEILEDDL<br>FIMSSKDSFTDTDFSEPSVGPVSYKAKKGADTILDSTLSNYDFSKEINFT<br>STVPIIITVEDPLETDEDVPVISEDRTVYVDDYTTFHFLEAQKIGKEVVPT<br>QTKVVFTTNMEEALFDSKKVYTVFENTASRINEAGTGIANGMMFYQWLKG<br>IVQDFTEEATQKDTFDKISDVTMIVPYLGNILNIGNDIRKGDFMGAVELG<br>GVTILLEAIPELTLPVLIGLTIIEDELEKEQVSQTVYNVLDKRDEKWEEV<br>YGFVKQQWWWMVHTQFETRILHAYQALNHQVEAIKANMTYQLANYRGNQE<br>DKELLEKAIDDTLQSLYYAVDQAMHNIKRFLIQSSKSYLLNQMLPKTKEQ<br>LLAFDQQTLRNVNDFINKNQGVLGESLAKDLKKKVEKRLTSLPVFNLEDL<br>PISEFEDLIHSHEIDIIINTSILNLRYESNHLIDLSRYASKINIGSKVNF<br>DPIDKNQIQLFNLESSKIEVILKNAIVYNSMYENFSTSFWIRIPKYFNSI<br>SLNNEYTIINCMENNSGWKVSLNYGEIIWTLQDTQEIKQRVVFKYSQMIN<br>ISDYINRWIFVTITNNRLNNSKIYINGRLIDQKPISNLGNIHASNNIMFK<br>LDGCRDTHRYIWIKYFNLFDKELNEKEIKDLYDNQSNSGILKDFWGDYLQ<br>YDKPYYMLNLYDPNKYVDVNNVGIRGYMYLKGPRGSVMTTNIYLNSSLYR<br>GTKFIIKKYASGNKDNIVRNNDRVYINVVVKNKEYRLATNASQAGVEKIL<br>SALEIPDVGNLSQVVVMKSKNDQGITNKCKMNLQDNNGNDIGFIGFHQFN<br>NIAKLVASNWYNRQIERSSRTLGCSWEFIPVDDGWGERPL | 27 |
| BoNT/EN-LC-H$_N$ (with modified linker containing thrombin cleavage site) and BoNT/B1-H$_C$ | MVTINDLHYSDPIDEDNIINMRIPLYDLEVDDQFINHNVPDLKAFQVFPN<br>VWVVPERYTFYSTMKNLDAPANPSRSSYYDPTYLQSDAEKEVFLQQMILL<br>FKRINSTQEGQQFLNLLSRSIPVPYESNGDVAMGTTQVIKQMDDKGNVLK<br>HRRAHIIIYGPGPDLMAKGSKALTKSRETGRGCMAEIYFSPMYHKTYSTK<br>LTNKNSLVDKSVQEFVPDPAVTLIHELCHGLHALYGIDLGNVGSWEFNSN<br>PNSLFSSWFSSKEAVNFEEVMTFGGEDVKVIKSEIDKKIPGILNLIKTTV<br>EPIINKITDPHDEMLQCLQSKYPSLKGTLGQFFFDDTQLEKDIRDLWMVM<br>NETMFAENLKALTRARYLVPKVENIVQVDILSPNVYTIDKGFNHLSKGFK<br>GQSVSQSYFRKISALARGAVVRA<u>CPNPHFSSQLVPRGSLSSC</u>IEILEDDL<br>FIMSSKDSFTDTDFSEPSVGPVSYKAKKGADTILDSTLSNYDFSKEINFT<br>STVPIIITVEDPLETDEDVPVISEDRTVYVDDYTTFHFLEAQKIGKEVVPT<br>QTKVVFTTNMEEALFDSKKVYTVFENTASRINEAGTGIANGMMFYQWLKG<br>IVQDFTEEATQKDTFDKISDVTMIVPYLGNILNIGNDIRKGDFMGAVELG<br>GVTILLEAIPELTLPVLIGLTIIEDELEKEQVSQTVYNVLDKRDEKWEEV<br>YGFVKQQWWWMVHTQFETRILHAYQALNHQVEAIKANMTYQLANYRGNQE | 28 |

TABLE 4-continued

Non-limiting, Exemplary Chimeric Toxins

| Name | Amino Acid Sequence | SEQ ID NO |
|---|---|---|
| | DKELLEKAIDDTLQSLYYAVDQAMHNIKRFLIQSSKSYLLNQMLPKTKEQ<br>LLAFDQQTLRNVNDFINKNQGVLGESLAKDLKKKVEKRLTSLPVFNLEDL<br>PISEFEDLIHSHEIDIILNNIILNLRYKDNNLIDLSGYGAKVEVYDGVEL<br>NDKNQFKLTSSANSKIRVTQNQNIIFNSVFLDFSVSFWIRIPKYKNDGIQ<br>NYIHNEYTIINCMKNNSGWKISIRGNRIIWTLIDINGKTKSVFFEYNIRE<br>DISEYINRWFFVTITNNLNNAKIYINGKLESNTDIKDIREVIANGEIIPK<br>LDGDIDRTQFIWMKYFSIFNTELSQSNIEERYKIQSYSEYLKDFWGNPLM<br>YNKEYYMFNAGNKNSYIKLKKDSPVGEILTRSKYNQNSKYINYRDLYIGE<br>KFIIRRKSNSQSINDDIVRKEDYIYLDFFNLNQEWRVYTYKYFKKEEEKL<br>FLAPISDSDEFYNTIQIKEYDEQPTYSCQLLFKKDEESTDEIGLIGIHRF<br>YESGIVFEEYKDYFCISKWYLKEVKRKPYNLKLGCNWQFIPKDEGWTE | |
| BoNT/EN-LC-H$_N$ (with modified linker containing thrombin cleavage site) and BoNT/C1-H$_C$ | MVTINDLHYSDPIDEDNIINMRIPLYDLEVDDQFINHNVPDLKAFQVFPN<br>VWVVPERYTFYSTMKNLDAPANPSRSSYYDPTYLQSDAEKEVFLQQMILL<br>FKRINSTQEGQQFLNLLSRSIPVPYESNGDVAMGTTQVIKQMDDKGNVLK<br>HRRAHIIIYGPGPDLMAKGSKALTKSRETGRGCMAEIYFSPMYHKTYSTK<br>LTNKNSLVDKSVQEFVPDPAVTLIHELCHGLHALYGIDLGNVGSWEFNSN<br>PNSLFSSWFSSKEAVNFEEVMTFGGEDVKVIKSEIDKKIPGILNLIKTTV<br>EPIINKITDPHDEMLQCLQSKYPSLKGTLGQFFFDDTQLEKDIRDLWMVM<br>NETMFAENLKALTRARYLVPKVENIVQVDILSPNVYTIDKGFNHLSKGFK<br>GQSVSQSYFRKISALARGAVVRACPNPHFSSQLVPRGSLSSCIEILEDDL<br>FIMSSKDSFTDTDFSEPSVGPVSYKAKKGADTILDSTLSNYDFSKEINFT<br>STVPIITVEDPLETDEDVPVISEDRTVYVDDYTTFHFLEAQKIGKEVVPT<br>QTKVVFTTNMEEALFDSKKVYTVFENTASRINEAGTGIANGMMFYQWLKG<br>IVQDFTEEATQKDTFDKISDVTMIVPYLGNILNIGNDIRKGDFMGAVELG<br>GVTILLEAIPELTLPVLIGLTIIEDELEKEQVSQTVYNVLDKRDEKWEEV<br>YGFVKQQWWWMVHTQFETRILHAYQALNHQVEAIKANMTYQLANYRGNQE<br>DKELLEKAIDDTLQSLYYAVDQAMHNIKRFLIQSSKSYLLNQMLPKTKEQ<br>LLAFDQQTLRNVNDFINKNQGVLGESLAKDLKKKVEKRLTSLPVFNLEDL<br>PISEFEDLIHSHEIDIINDSKILSLQNRKNTLVDTSGYNAEVSEEGDVQL<br>NPIFPFDFKLGSSGEDRGKVIVTQNENIVYNSMYESFSISFWIRINKWVS<br>NLPGYTIIDSVKNNSGWSIGIISNFLVFTLKQNEDSEQSINFSYDISNNA<br>PGYNKWFFVTVTNNMMGNMKIYINGKLIDTIKVKELTGINFSKTITFEIN<br>KIPDTGLITSDSDNINMWIRDFYIFAKELDGKDINILFNSLQYTNVVKDY<br>WGNDLRYNKEYYMVNIDYLNRYMYANSRQIVFNTRRNNNDFNEGYKIIIK<br>RIRGNTNDTRVRGGDILYFDMTINNKAYNLFMKNETMYADNHSTEDIYAI<br>GLREQTKDINDNIIFQIQPMNNTYYYASQIFKSNFNGENISGICSIGTYR<br>FRLGGDWYRHNYLVPTVKQGNYASLLESTSTHWGFVPVSE | 29 |
| BoNT/EN-LC-H$_N$ (with modified linker containing thrombin cleavage site) and BoNT/X-H$_C$ | MVTINDLHYSDPIDEDNIINMRIPLYDLEVDDQFINHNVPDLKAFQVFPN<br>VWVVPERYTFYSTMKNLDAPANPSRSSYYDPTYLQSDAEKEVFLQQMILL<br>FKRINSTQEGQQFLNLLSRSIPVPYESNGDVAMGTTQVIKQMDDKGNVLK<br>HRRAHIIIYGPGPDLMAKGSKALTKSRETGRGCMAEIYFSPMYHKTYSTK<br>LTNKNSLVDKSVQEFVPDPAVTLIHELCHGLHALYGIDLGNVGSWEFNSN<br>PNSLFSSWFSSKEAVNFEEVMTFGGEDVKVIKSEIDKKIPGILNLIKTTV<br>EPIINKITDPHDEMLQCLQSKYPSLKGTLGQFFFDDTQLEKDIRDLWMVM<br>NETMFAENLKALTRARYLVPKVENIVQVDILSPNVYTIDKGFNHLSKGFK<br>GQSVSQSYFRKISALARGAVVRACPNPHFSSQLVPRGSLSSCIEILEDDL<br>FIMSSKDSFTDTDFSEPSVGPVSYKAKKGADTILDSTLSNYDFSKEINFT<br>STVPIITVEDPLETDEDVPVISEDRTVYVDDYTTFHFLEAQKIGKEVVPT<br>QTKVVFTTNMEEALFDSKKVYTVFENTASRINEAGTGIANGMMFYQWLKG<br>IVQDFTEEATQKDTFDKISDVTMIVPYLGNILNIGNDIRKGDFMGAVELG<br>GVTILLEAIPELTLPVLIGLTIIEDELEKEQVSQTVYNVLDKRDEKWEEV<br>YGFVKQQWWWMVHTQFETRILHAYQALNHQVEAIKANMTYQLANYRGNQE<br>DKELLEKAIDDTLQSLYYAVDQAMHNIKRFLIQSSKSYLLNQMLPKTKEQ<br>LLAFDQQTLRNVNDFINKNQGVLGESLAKDLKKKVEKRLTSLPVFNLEDL<br>PISEFEDLIHSHEIDIEDYEVLNLGAEDGKIKDLSGTTSDINIGSDIELA<br>DGRENKAIKIKGSENSTIKIAMNKYLRFSATDNFSISFWIKHPKPTNLLN<br>NGIEYTLVENFNQRGWKISIQDSKLIWYLRDHNNSIKIVTPDYIAFNGWN<br>LITITNNRSKGSIVYVNGSKIEEKDISSIWNTEVDDPIIFRLKNNRDTQA<br>FTLLDQFSIYRKELNQNEVVKLYNYYFNSNYIRDIWGNPLQYNKKYYLQT<br>QDKPGKGLIREYWSSFGYDYVILSDSKTITFPNNIRYGALYNGSKVLIKN<br>SKKLDGLVRNKDFIQLEIDGYNMGISADRFNEDTNYIGTTYGTTHDLTTD<br>FEIIQRQEKYRNYCQLKTPYNIFHKSGLMSTETSKPTFHDYRDWVYSSAW<br>YFQNYENLNLRKHTKTNWYFIPKDEGWDED | 30 |

TABLE 5

| Name | Amino Acid Sequence | SEQ ID NO |
|---|---|---|
| human VAMP1 (*Homo sapiens*, GenBank: CAG47027.1) | MSAPAQPPAEGTEGTAPGGGPPGPPPNMTSNRRLQQTQAQVEEVVDIIR VNVDKVLERDQKLSELDDR̲ADALQAGASQFESSAAKLKRKYWWKNCKMM IMLGAICAIIVVVIVRRD | 31 |
| human VAMP2 (*Homo sapiens*, GenBank: AAF15551.1) | MSATAATAPPAAPAGEGGPPAPPPNLTSNRRLQQTQAQVDEVVDIMRVN VDKVLERDQKLSELDDR̲ADALQAGASQFETSAAKLKRKYWWKNLKMMII LGVICAIILIIIIVYFSS | 32 |
| human VAMP3 (*Homo sapiens*, GenBank: CAG46942.1) | MSTGPTAATGSNRRLQQTQNQVDEVVDIMRVNVDKVLERDQKLSELDDR̲ ADALQAGASQFETSAAKLKRKYWWKNCKMWAIGITVLVIFIIIIVWVV SS | 33 |
| SNAP-23 (*Homo sapiens*, GenBank: AAC50537.1) | MDNLSSEEIQQRAHQITDESLESTRRILGLAIESQDAGIKTITMLDEQK EQLNRIEEGLDQINKDMRETEKTLTELNKCCGLCVCPCNRTKNFESGKA YKTTWGDGGENSPCNVVSKQPGPVTNGQLQQPTTGAVSGGYIKRITNDA REDEMEENLTQVGSILGNLKDMALNIGNEIDAQNPQIKRITDKADTNRD RIDIANARAKKLIDS | 34 |
| human SNAP-25 (*Homo sapiens*, GenBank: AAH10647.1) | MAEDADMRNELEEMQRRADQLADESLESTRRMLQLVEESKDAGIRTLVM LDEQGEQLDRVEEGMNHINQDMKEAEKNLKDLGKCCGLFICPCNKLKSS DAYKKAWGNNQDGVVASQPARVVDEREQMAISGGFIRRVTNDARENEMD ENLEQVSGIIGNLRHMALDMGNEIDTQNRQIDRIMEKADSNKTRIDEAN QRATKMLGSG | 35 |
| human syntaxin1A (*Homo sapiens*, GenBank: EAW69649.1) | MDEFFEQVEEIRGFIDKIAENVEEVKRKHSAILASPNPDEKTKEELEEL MSDIKKTANKVRSKLKSIEQSIEQEEGLNRSSADLRIRKTQHSTLSRKF VEVMSEYNATQSDYRERCKGRIQRQLEITGRTTTSEELEDMLESGNPAI FASGIIMDSSISKQALSEIETRHSEIIKLENSIRELHDMFMDMAMLVES QGEMIDRIEYNVEHAVDYVERAVSDTKKAVKYQSKARRKKIMIIICCVI LGIVIASTVGGIFA | 36 |
| human syntaxin1B (*Homo sapiens*, GenBank: BAA07152.1) | MKDRTQVLRTRRNSDDKEEVVHVDRDHFMDEFFEQEEEIRGCIEKLSED VEQVKKQHSAILAAPNPDERTKQELEDLTADIKKTANKVRSKLKAIEQS IEQEEGSTAPRPILRIRKTQHSTLSRKFVEVMTEYNATQSKYRDRCKDR IQRQLEITGRTTTNEELEDMLESGKLPIFTDDIKMD̲SQMTKQALNEIET RHNEIIKLETSIRELHDMFVDMAMLVESQGEMIDRI̲EYNVEHSVDYVER AVSDTKKAVKYQSKARRKKIIIIICCVVLGVVLASSIGCTLGL | 37 |
| human syntaxin4 (*Homo sapiens*, GenBank: AAH02436.1) | MRDRTHELRQGDDSSEEDKERVALVVHPGTARLGSPDEEFFHKVRTIR QTIVKLGNKVQELEKQQVTILATPLPEESMKQELQNLRDEIKQLGREIR LQLKAIEPQKEEADENYNSVNTRMRKTQHGVLSQQFVELINKCNSMQSE YREKNVERIRRQLKITNAGMVSDEELEQMLDSGQSEVFVSNILK̲DTQVT RQALNEISARHSEIQQLERSIRELHDIFTFLATEVEMQGEMINRIEKNI LSSADYVERGQEHVKTALENQKKARKKKVLIAICVSITVVLLAVIIGVT VVG | 38 |
| fly VAMP (*Drosophila melanogaster*, GenBank: NP_001246547.1) | MGKKDKNKEQADAAPAGADAPPNAGAPAGEGGDGEIVGGPHNPQQIAAQK RLQQTQAQVDEVVDIMRTNVEKVLERDSKLSELDDR̲ADALQQGASQFEQ QAGKLRKFWLQNLKMMIIMGVIGLVVVGIIAKKDEE | 39 |
| fly SNAP25 isoform A (*Drosophila melanogaster*, GenBank: EAA46071.2) | MPADPSEEVAPQVPKTELEELQINAQGVADESLESTRRMLALCEESKEA GIRTLVALDDQGEQLDRIEEGMDQINADMREAEKNLSGMEKCCGICVLP CNKSQSFKEDDGTWKGNDDGKVVNNQPQRVMDDRNGMMAQAGYIGRITN DAREDEMEENMGQVNTMIGNLRNMALDMGSELENQNRQIDRINRKGESN EARIAVANQRAHQLLK | 40 |

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Identification and characterization of a *botulinum* neurotoxin-like toxin in *Enterococcus faecium botulinum* neurotoxins (BoNTs) are the most potent bacterial toxins known and the causative agents for the disease botulism[1-3]. Unlike many other deadly toxins, the general population is not immunized against BoNTs since botulism is a rare disease. This lack of immunity, combined with the extreme potency of BoNTs, are the reasons for BoNTs to be considered as one of the six most dangerous potential bioterrorism agents (Category A and Tier 1) by the Center for Disease Control and Prevention in the U.S[4]. On the other hand, lack of immunity also allows the utilization of BoNTs to treat a growing list of medical conditions ranging from muscle spasms to chronic pain, as well as for cosmetic applications[5,6].

BoNTs are synthesized as a single polypeptide of ~150 kDa, which requires further proteolytic cleavage to separate it into two chains: the N-terminal light chain (LC, ~50 kDa) and the C-terminal heavy chain ($H_C$, ~100 kDa)[1-3]. The two chains remain connected via a single inter-chain disulfide bond, which is essential for the activity of BoNTs. The LC functions as a zinc-dependent metalloprotease. The $H_C$ contains two functional domains: the N-terminal translocation domain ($H_N$, ~50 kDa) and the C-terminal receptor-binding domain ($H_C$, ~50 kDa). BoNTs act by first binding to their specific neuronal receptors via its $H_C$, entering neurons via receptor-mediated endocytosis, followed by delivering the LC through $H_N$ across endosomal membranes into the cytosol. The disulfide bond is reduced in the reducing environment of the cytosol and the LC is released to cleave its cellular target proteins.

There are seven well-established major serotypes of BoNTs (BoNT/A-G), based on lack of cross-neutralization by their specific antisera. They share the same mode of action[1-3] The LCs of BoNT/A, C, and E cleaves a peripheral membrane protein SNAP-25. The LCs of BoNT/B, D, F, and G cleave homologous vesicle membrane protein VAMP1, 2, and 3. In addition, the LC of BoNT/C also cleaves a plasma membrane protein syntaxin 1 (Syx 1). These three sets of proteins form the core machinery that mediates fusion of synaptic vesicle membranes to plasma membranes and are the prototype of the SNARE protein family (soluble NSF attachment protein receptor), which mediates various membrane fusion events in eukaryotic cells[7,8]. Cleaving any one of these three proteins is sufficient to block synaptic vesicle exocytosis required for releasing neurotransmitters. Besides these seven serotypes, a new serotype, tentatively named BoNT/X, was recently identified[9]. It cleaves not only VAMP1, 2, and 3, but also additional members of SNARE proteins VAMP4, VAMP5, and Ykt6. The physiological consequence of cleaving these additional SNARE proteins remains to be determined.

The BoNT genes are always present within two types of conserved gene clusters and are co-expressed together with accessary proteins[10]. Both clusters express a ~150 kDa protein NTNHA (non-toxic non-hemagglutinin protein) preceding the toxin, which forms a pH-dependent complex with BoNTs and protects them from proteases in the gastrointestinal (GI) tract[11]. One gene cluster contains additional proteins known as HA17, HA33, and HA70, which form a complex with BoNT/NTNHA and facilitate the absorption of toxins across the epithelial barrier[12-14]. The other type of gene cluster encodes a few proteins with unknown functions designated as OrfX1, OrfX2, OrfX3, and P47[10].

The BoNT clusters exist in diverse groups of gram-positive spore-forming bacteria within *Clostridium*[10]. Most are known as *C. botulinum* based on their ability to produce toxins, although these strains can be phylogenetically distinct. In addition, BoNT/E is also found in strains known as *C. butyricum* and BoNT/F can be found in the strain classified as *C. baratii*. Multiple mechanisms contribute to horizontal gene transfer and recombination of BoNT clusters between different strains, including being located on plasmids or phages and the presence of transposases or Insertion Sequence (IS). The mobility of BoNT genes provides the opportunity for toxin genes to diversify and evolve in distinct genetic background and ecological niches. Recent genomic studies revealed a growing number of subtype and mosaic toxins[15-21].

BoNTs have only been identified within *Clostridium* species and its evolutionary origin remains a mystery. Recent studies revealed a homolog of BoNT in *Weissella oryzae*, a gram-positive bacterium[22,23]. It has been shown that the LC of this homolog is an active metalloprotease and cleaves recombinant VAMP2 under in vitro conditions. Thus, this homolog has been tentatively designated as BoNT/Wo[22]. However, BoNT/Wo is quite distant from BoNTs. First, the sequence identity between BoNT/Wo versus other BoNTs is only ~14-16%, which is far below the normal range for the members of BoNT family (~30-63%). Second, the two cysteines that form the essential disulfide bond in BoNTs are not conserved in BoNT/Wo, suggesting that it may have a distinct mode of action. Third, BoNT/Wo gene is not associated with any typical BoNT accessory proteins and it is not in a BoNT gene clusters.

It is reported herein that a new member of BoNT exists on a plasmid in an *Enterococcus faecium* strain. The strain was initially isolated from cow feces in the Cape Cod region in the U.S. It genome was sequenced in May, 2017, which revealed a novel BoNT resided in a BoNT gene cluster. This toxin was found to cleave VAMP2 at a novel site distinct from known cleavage sites for other BoNTs. It was also found to cleave SNAP-25 efficiently in neurons. It represents the first protein toxin identified in *E. faecium*, and the first BoNT gene cluster in a bacterial species outside of *Clostridium*.

Results

An *E. faecium* Strain Contains a Novel BoNT Gene

To monitor the emergence of new BoNTs, public sequence databases have been periodically surveyed, using known BoNT sequences as probes. A recent search in May, 2017 revealed a novel BoNT gene in the draft genome of an *E. faecium* strain (strain DIV0629, GenBank: OTO22244.1), tentatively designated as BoNT/EN. The protein sequence of BoNT/EN shows 29%-38.7% identity to other BoNTs and it is most closely related to BoNT/X in phylogenetic analysis (FIG. 1A). The low level of identity is distributed across the length of BoNT/EN, indicating that it is not a mosaic toxin (FIG. 1B). The overall BoNT domain arrangement and all key functional motifs are conserved in BoNT/EN (FIG. 1B), including a zinc-dependent protease motif HExxH (residues H225-H229) in the LC[24], two cysteines that potentially form the inter-chain disulfide bond (C424 and C438), and a ganglioside-binding motif SxWY in the $H_C$ (residues S1250 to Y1253)[25].

Similar to the other BoNTs, the BoNT/EN gene is located within a gene cluster and it is preceded by a potential NTNHA gene (FIG. 1C). The BoNT/EN cluster is similar to the OrfX cluster for BoNT/X, E, F and members of BoNT/A, containing potentially orfX2, orfX3, and p47 genes (FIG. 1D). A gene located at the N-terminal of orfX2 showed some similarity to orfX1, although the homology is low, which was designated as orfX1-like gene. Interestingly, the reading frame of the three orfX genes is in the same direction as NTNHA and BoNT/EN genes. This directional arrangement is the same in the BoNT/X cluster[9], while it is usually opposite to NTNHA/BoNT genes in other OrfX clusters.

The LC of BoNT/EN Cleaves VAMP1/2/3 at a Novel Site

To characterize the function of BoNT/EN experimentally, it was first examined whether its LC (EN-LC) is capable of cleaving neuronal SNARE proteins. Recombinant EN-LC (residues 1-434) was produced as a His6-tagged recombinant protein and incubated with rat brain detergent extracts (BDE). The LC of BoNT/X (X-LC), which cleaves VAMP2, and the LC of BoNT/A (A-LC), which cleaves SNAP-25, were analyzed in parallel as controls. Similar to X-LC, incubation of BDE with EN-LC resulted in disappearance of VAMP2 immunoblot signals (FIG. 2A). Pre-incubation of EN-LC with EDTA, which inhibits metalloprotease activity, protected VAMP2[24]. In addition to VAMP2, EN-LC reduced the immunoblot signal of Syx 1 as well, suggesting that EN-LC might be able to cleave additional SNARE proteins.

Figure 5A:
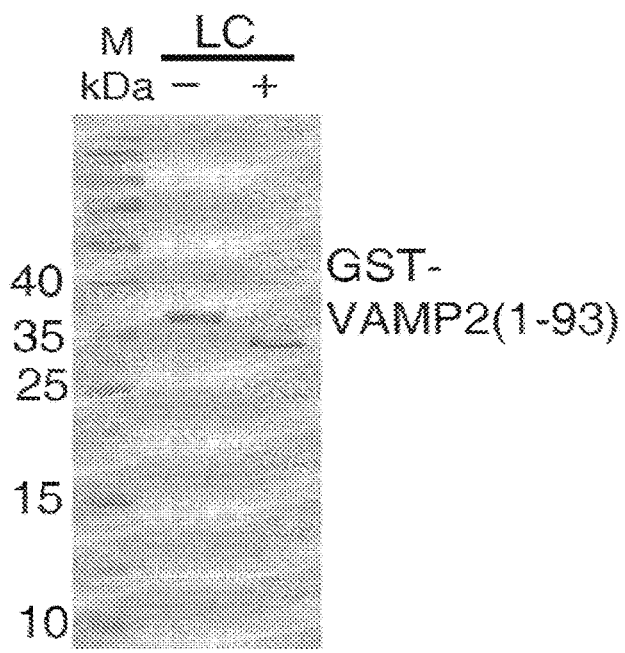
FIGS. 5A to 5C. Identification of the cleavage site on GST-VAMP2 (33-86) by EN-LC.
Figure 5B:
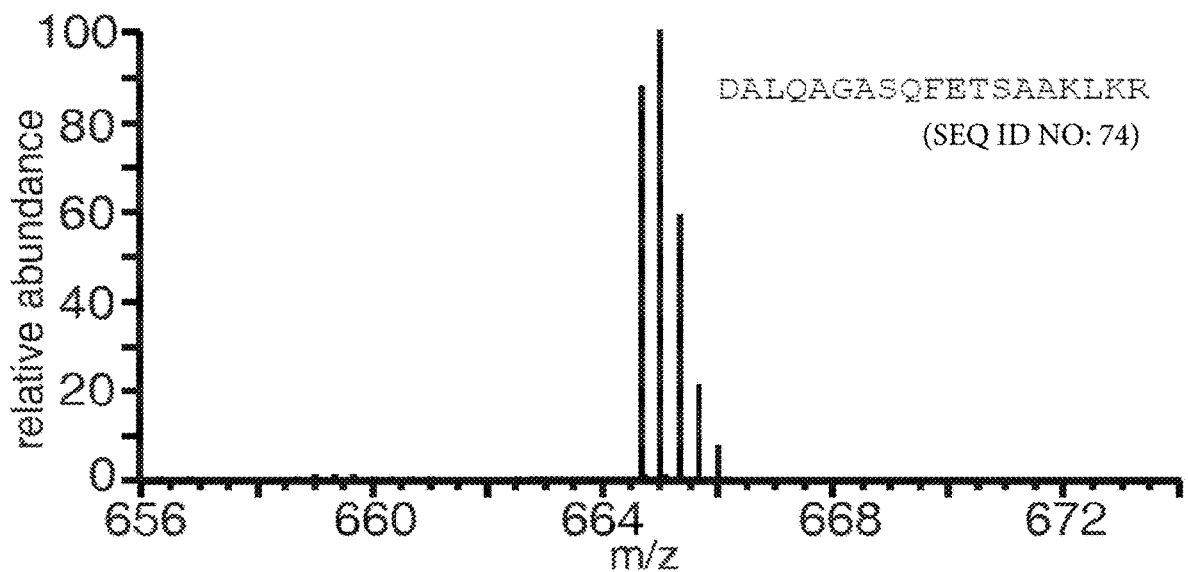
Figure 5C:
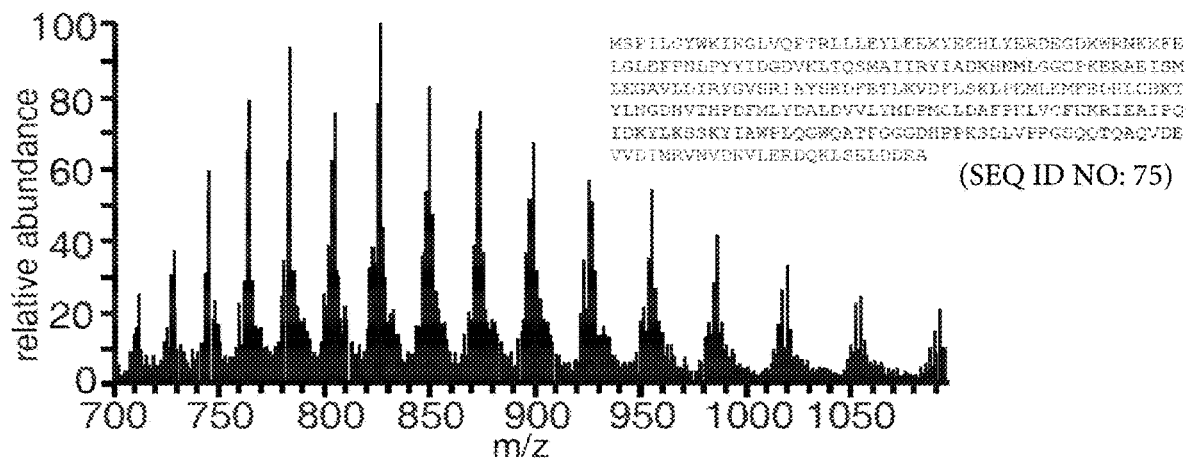

Cleavage of VAMP2 by EN-LC was next analyzed using recombinantly produced His6-tagged VAMP2 fragment (residues 1-93). As shown in FIG. 2B, incubation with EN-LC generated two smaller fragments, confirming that VAMP2 was cleaved. To identify the cleavage site, the samples were analyzed by lipid chromatography-tandem mass spectrometry (LC-MS/MS, FIG. 2C). A single dominant peptide peak appeared after incubation with EN-LC, which matched the sequence of D68-L93 (FIG. 2C, lower panel). The corresponding N-terminal fragment was also identified (FIG. 2C, upper panel). To further confirm these findings, a different VAMP2 recombinant protein was analyzed: a glutathione S-transferase (GST) tagged VAMP2 (residues 33-86) using LC-MS/MS. Incubation with EN-LC generated a single dominant peptide that matched D68-R86, while the corresponding N-terminal fragment was also identified (FIG. 5). Together, these findings demonstrate that EN-LC cleaves VAMP2 once between A67 and D68.

A67-D68 is a novel cleavage site distinct from all other sites targeted by known BoNTs (FIG. 2D). It is one amino acid to the right of the cleavage site for BoNT/X[9]. It was also examined whether other members of VAMP family, including VAMP1, 3, 4, 5, 7, 8, Sec22b and Ykt6, can be cleaved by EN-LC. These VAMP members were expressed in HEK293 cells via transient transfection. Cell lysates were incubated with EN-LC. VAMP1 and VAMP3 are highly homologous to VAMP2, and both of them were cleaved by EN-LC (FIG. 2E). None of other VAMP members were cleaved, demonstrating a degree of specificity of EN-LC.

EN-LC is Capable of Cleaving Additional SNARE Proteins In Vitro

Figure 2F:
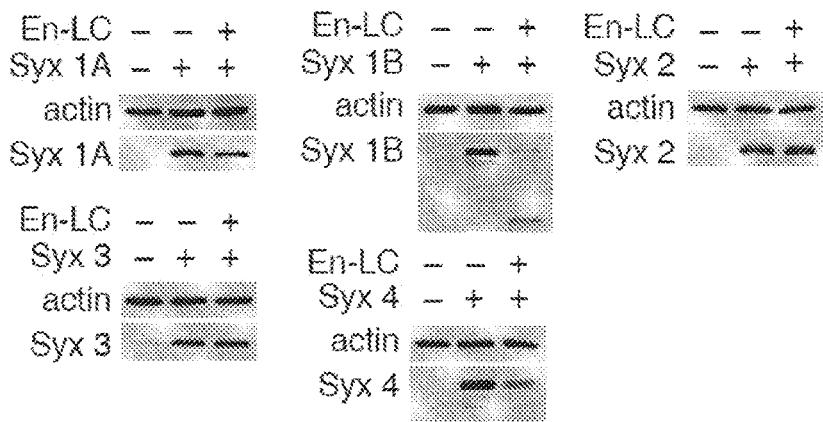
Figure 2G:
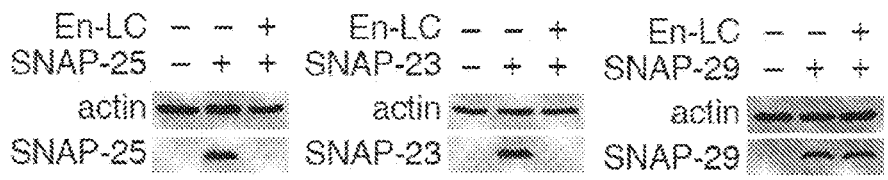

It was next examined whether EN-LC can cleave Syx 1, which includes two homologous isoforms, Syx 1A and Syx 1B. The antibody utilized in FIG. 2A recognizes both isoforms. Syx 1A and Syx 1B were expressed in HEK293 cells, respectively. Cell lysates were then incubated with EN-LC. Other closely related Syx family members were also examined, including Syx 2, 3, and 4. As shown in FIG. 2F, Syx 1A, 2, and 3 were not cleaved under the present assay conditions, while Syx 1B and Syx 4 were cleaved. It was further examined whether SNAP-25 and two of its closely related family members SNAP-23 and SNAP-29 can be cleaved by EN-LC using the same approach. As shown in FIG. 2G, both SNAP-25 and SNAP-23 were cleaved by EN-LC, while SNAP-29 was not. The finding that SNAP-25 was cleaved by EN-LC was a surprise, as no significant reduction of SNAP-25 in BDE after incubation with EN-LC was observed (FIG. 2A). The reason for this discrepancy between BDE and HEK293 cell lysates is unknown.

Figure 7A:
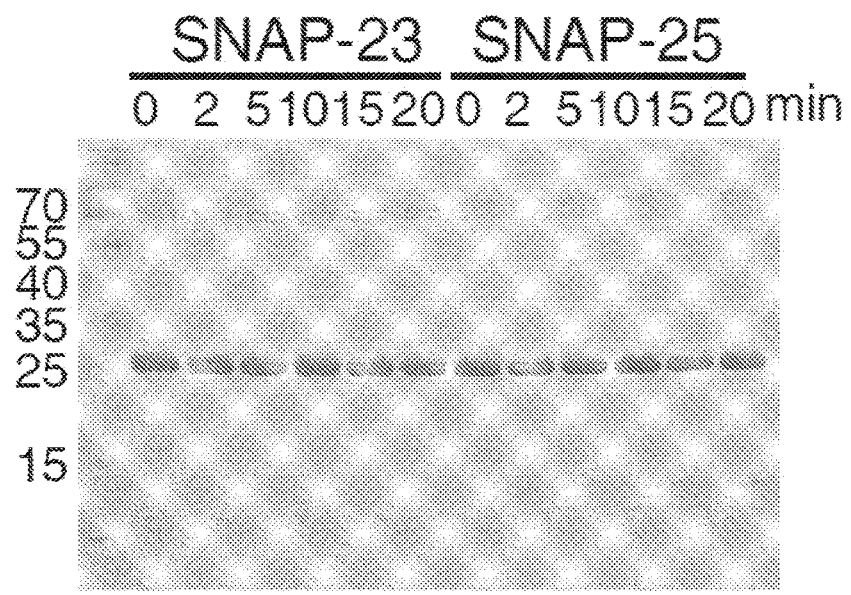
FIGS. 7A to 7C. EN-LC cleaves recombinant SNAP-25 and SNAP-23 inefficiently in vitro.

To directly compare the cleavage efficacy of EN-LC toward different SNARE proteins, His6-tagged cytosolic fragments of Syx 1B and Syx 4 were produced, as well as full-length SNAP-25 and SNAP-23. The same amounts of these recombinant proteins were incubated with the identical amount of EN-LC. Cleavage of these proteins over time was monitored on SDS-PAGE gel with Coomassie Blue staining. GST-VAMP2 (33-86) was analyzed in parallel as a control. While VAMP2 was cleaved within a few minutes, only a minor cleavage of Syx 1B and SNAP-25 was observed, and no cleavage of Syx 4 and SNAP-23 was detectable within twenty minutes (FIGS. 5A, 5B, and 7A). These results suggest that EN-LC cleaves recombinant VAMP2 far more efficiently than other SNAREs in vitro.

Figure 6A:
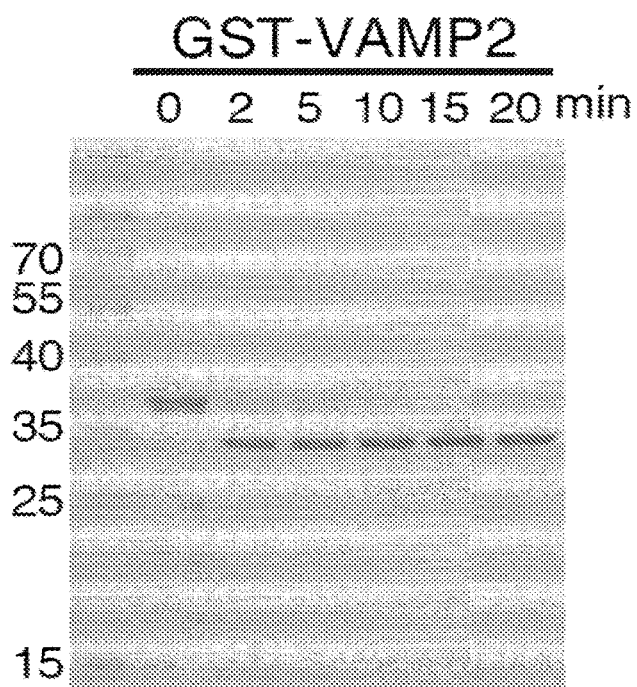
FIGS. 6A to 6F. EN-LC cleaves Syx 1B and Syx 4 at a conserved site, but inefficiently.
Figure 6B:
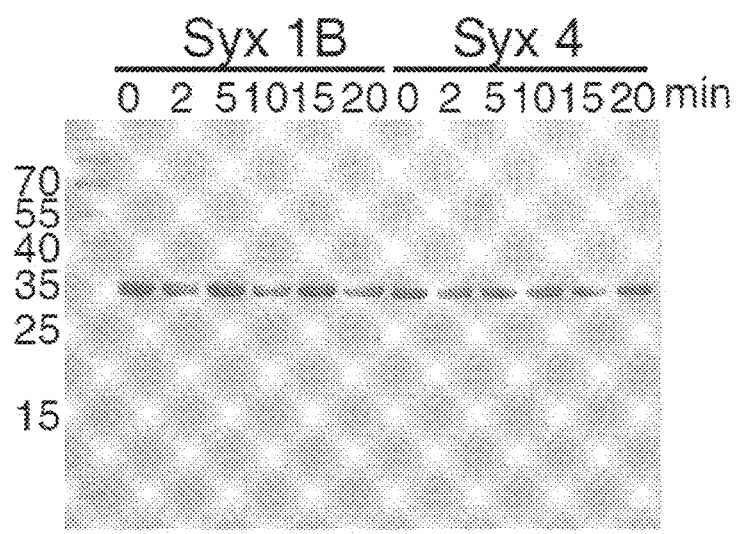
Figure 6C:
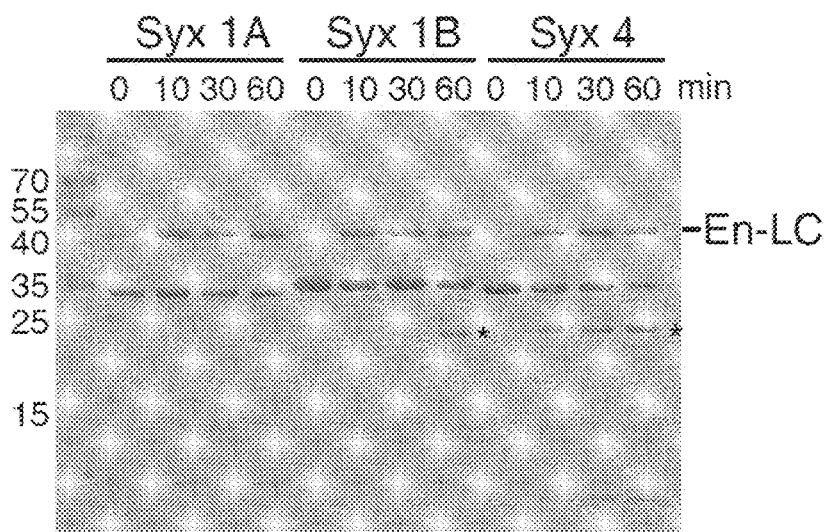
Figure 6D:
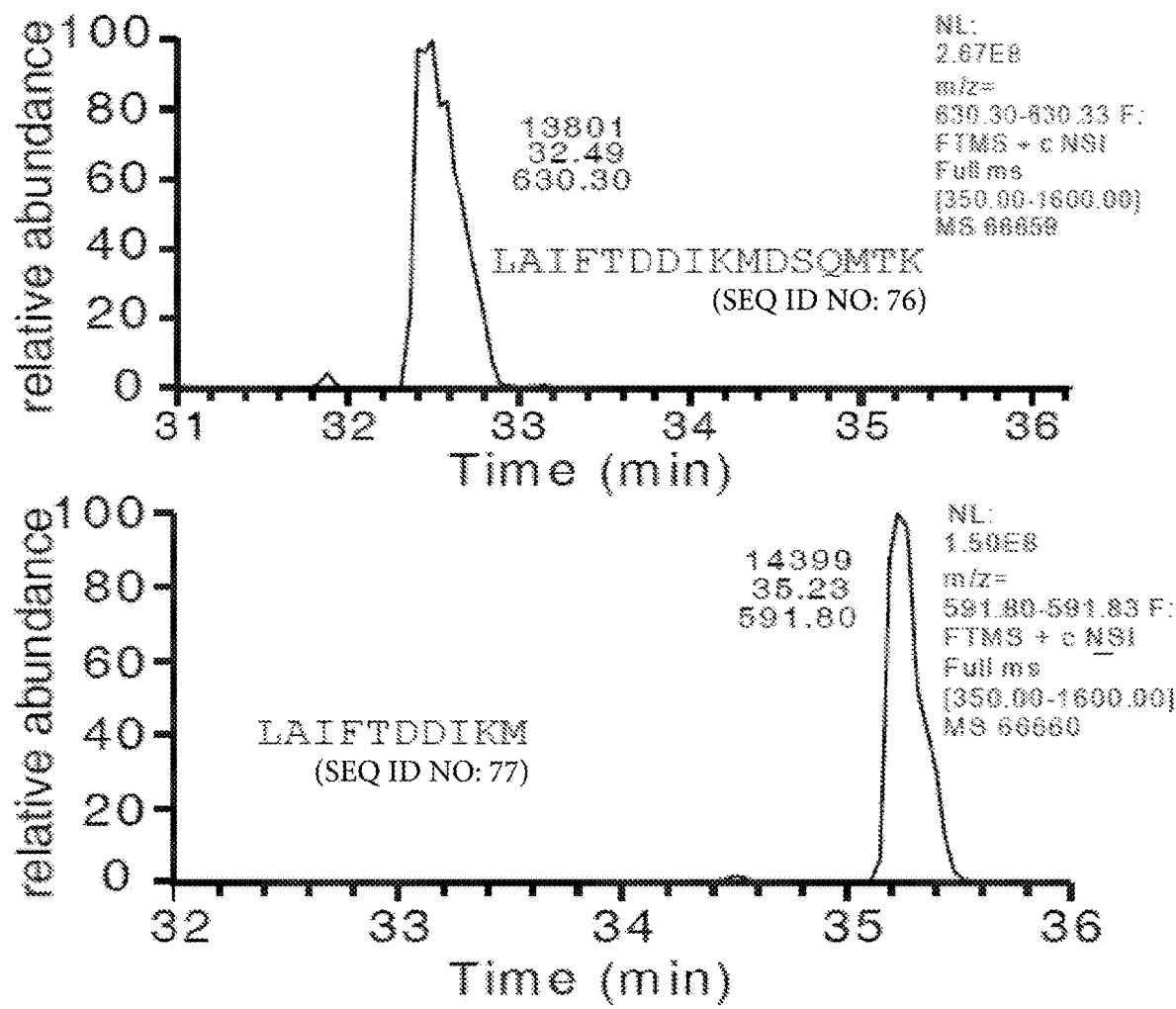
Figures 6E, 6F:
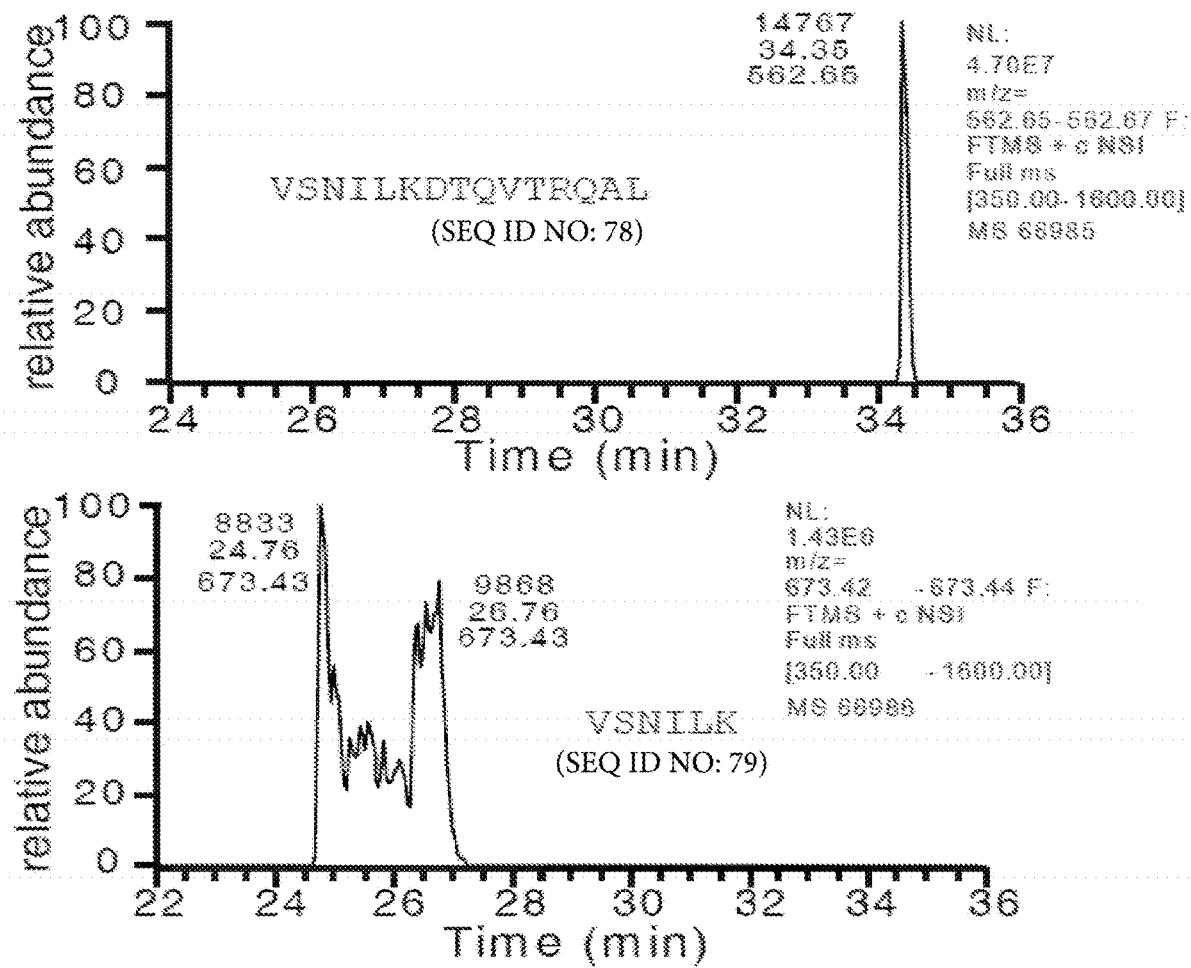

Increasing the concentration of EN-LC and incubation time enhanced the cleavage of Syx 1B and also resulted in detectable cleavage of Syx 4 (FIG. 6C). By mass spectrometry analysis of the intact proteins versus their fragments generated by EN-LC, the cleavage sites were mapped to between M182-D183 in Syx 1B and K191-D192 in Syx 4 (FIGS. 6D and 6E). These two sites are at homologous locations between Syx 1B and Syx 4, suggesting a degree of specificity for the cleavage events (FIG. 6F). All SNARE proteins contain SNARE domains required to form the 4-helical bundle of SNARE complexes. The cleavage sites for BoNTs are usually located within the SNARE domain[26], yet the BoNT/EN cleavage site on Syx 1B and Syx 4 is located between the N-terminal domain of Syx (known as Habc domain) and its C-terminal SNARE domain.

Figure 7B:
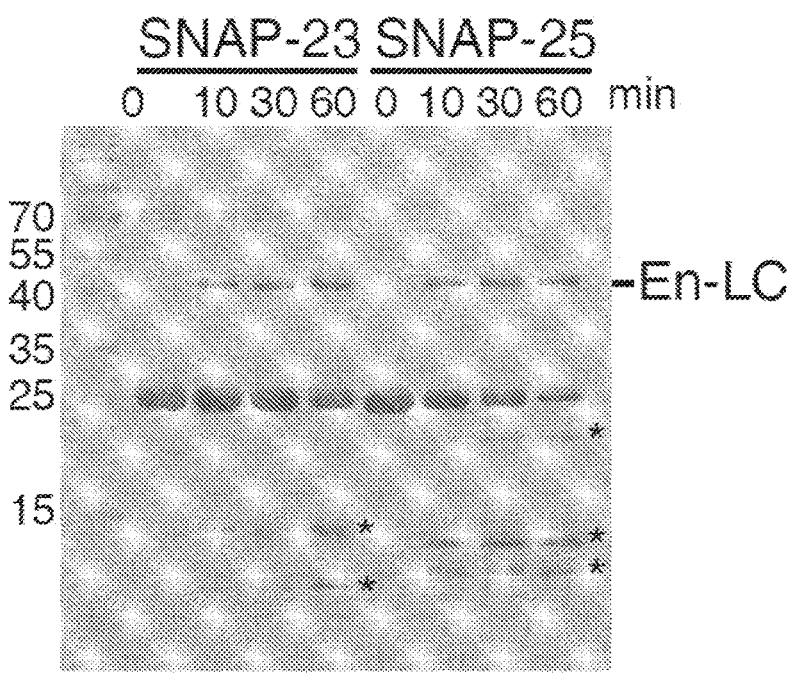
Figure 7C:
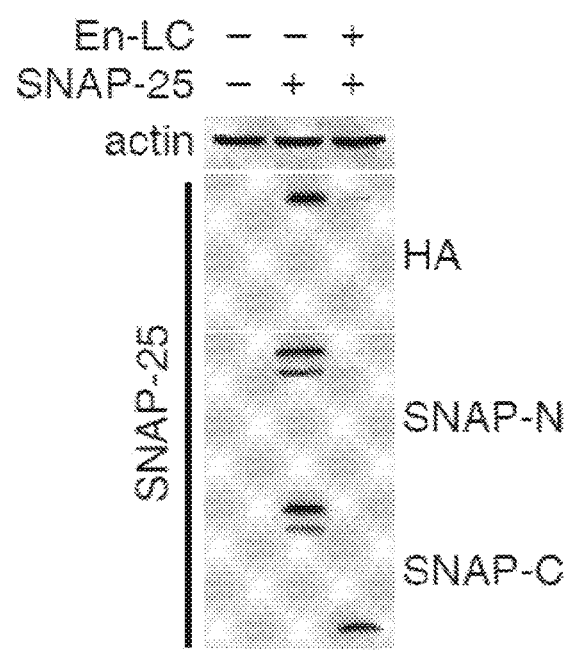

Identification of the cleavage site in SNAP-25 and SNAP-23 turned out to be problematic, as increasing EN-LC concentrations and incubation time resulted in multiple smear bands, which did not yield any clear cutting site by mass spectrometry analysis (FIGS. 7A to 7C). It is possible that either high levels of EN-LC may have resulted in multiple cutting events in SNAP-25 in vitro, or the cleavage products are susceptible to degradation. As high levels of EN-LC and long incubation time were utilized to cleave SNAP-23, SNAP-25, Syx 1B and Syx 4, the physiological relevance of these low-efficiency cleavage events observed in vitro needs to be validated in cells.

The Inter-Chain Disulfide Bond in BoNT/EN

It was next examined whether the EN-LC is connected to its $H_C$ via an inter-chain disulfide bond. Sequence alignment showed two cysteine residues at expected locations, with one at the C-terminus of EN-LC, and the other at the N-terminus of EN-$H_N$ (FIG. 3A). The linker region between two cysteines contains 13 residues, a length similar to the linker regions in other BoNTs, but the BoNT/EN linker is the only one without a single lysine. As the endogenous protease that can efficiently activate BoNT/EN remains unknown, a thrombin cleavage site was inserted in the BoNT/EN linker region, as a way to proteolytically separate EN-LC and $H_N$ (FIG. 3A). This modified EN-LC-$H_N$ behaves as expected after incubation with thrombin: it stays as a single band without reducing agent (−DTT), and separated into two bands in the presence of DTT (FIG. 3B), confirming the existence of the inter-chain disulfide bond.

BoNT/EN cleaves both VAMP2 and SNAP-25 in neurons Incubation of nanomolar concentrations of LC-H$_N$ of BoNTs in the medium often results in non-specific entry of some LC-H$_N$ into neurons[9,27], which provides a convenient way to examine the action of EN-LC within neurons in a more physiologically relevant manner than in vitro assays. Primary cultured rat cortical neurons were used as a model. Exposing neurons to EN-LC-H$_N$ resulted in a loss of both VAMP2 and SNAP-25 immunoblot signals in a concentration-dependent manner (FIG. 3C), suggesting that these two SNARE proteins are efficiently cleaved. Proteolytic activation of EN-LC-H$_N$ with thrombin increased the potency of EN-LC-H$_N$ as expected (FIG. 3C).

The epitope of the SNAP-25 antibody (CI 71.1,) used here is located within the N-terminal residues 20-40 (designated as SNAP-N), which did not detect any cleavage product (FIG. 3C). To further evaluate the cleavage of SNAP-25 in neurons, a different SNAP-25 antibody raised against its C-terminal sequence (residues 195-206, designated as SNAP-C Ab) was next utilized. This antibody detected both full-length SNAP-25 and a cleavage product with a smaller molecular weight (FIG. 3C). The intensity of the immunoblot of this cleavage product eventually reached similar levels as the endogenous SNAP-25 in neurons that have not exposed to any toxins, suggesting that this fragment was stable and was not further processed in neurons. The molecular weight of this fragment is ~12-13 kDa, suggesting that the cleavage site is located around the middle of SNAP-25.

It is puzzling that there was no corresponding N-terminal fragment detectable by SNAP-N Ab. To further confirm this finding, SNAP-25 expressed in HEK293 cells, which contains a HA tag on its N-terminus, was re-analyzed with three different antibodies: SNAP-N Ab, anti-HA tag, and SNAP-C Ab. While SNAP-C Ab recognized the C-terminal fragment of SNAP-25 as expected, neither 71.1 nor anti-HA detected any N-terminal cleavage fragments in immunoblot analysis (FIG. 7C). It is possible that the N-terminal region is degraded into smaller pieces.

Interestingly, SNAP-25 was cleaved by BoNT/EN at a rate similar to VAMP2 in neurons (FIG. 3C), despite that recombinant SNAP-25 is hardly cleaved by EN-LC (FIG. 7A). This is not without precedence: BoNT/C also cleaves SNAP-25 efficiently in cells, but inefficiently in vitro[28]. It has been proposed that the optimal cleavage of SNAP-25 by BoNT/C requires the presence of a proper membrane environment, which could be also a requirement for BoNT/EN[28]. In contrast to SNAP-25, Syx 1 (including both Syx 1A and 1B) was not cleaved by BoNT/EN in neurons (FIG. 3C). This is likely because cleavage of Syx 1 is inefficient and requires high levels of EN-LC that can only be achieved under in vitro incubations (FIGS. 6A to 6F), although the possibility that the optimal condition for cleavage of Syx 1 might be missing in cortical neurons cannot be excluded. In summary, VAMP2 and SNAP-25, but not Syx 1, are physiologically relevant targets for BoNT/EN in cortical neurons.

Testing Ligated BoNT/EN on Rat and Mouse Neurons

Figure 4A:
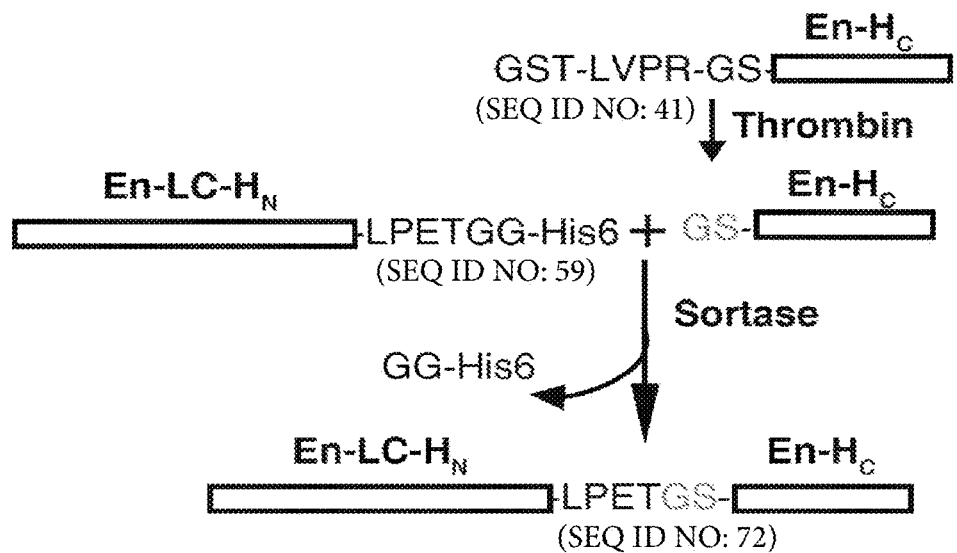
FIGS. 4A to 4H. Testing full-length BoNT/EN on cultured neurons and in vivo in mice.
Figure 4B:
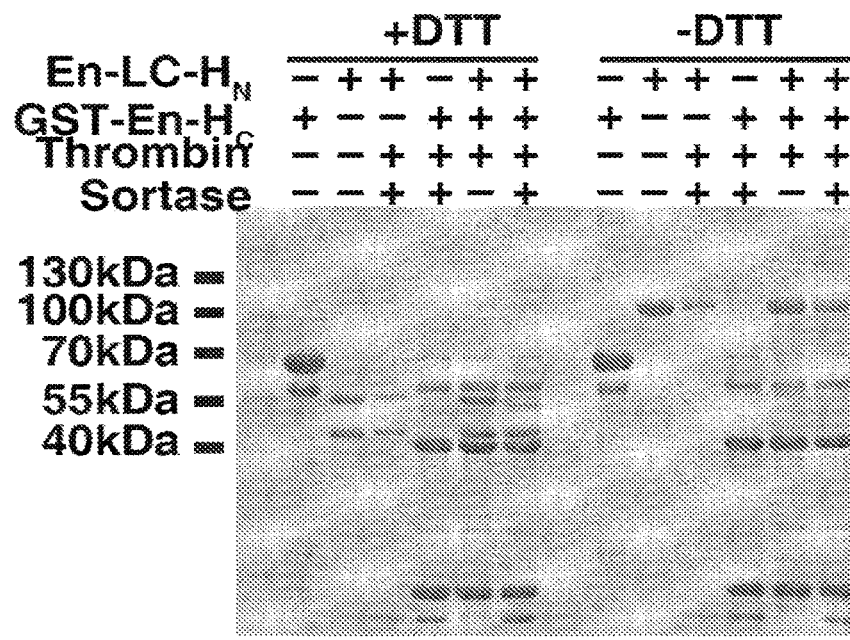

The activity of full-length BoNT/EN was next sought to be assessed. Due to biosafety considerations, it was decided not to clone the full-length toxin gene. Instead, a limited amount of full-length BoNT/EN was produced in test tubes utilizing sortase-mediated ligation method as previously described[9,29,30]. Briefly, two nontoxic fragments of BoNT/EN, EN-LC-H$_N$ and the H$_C$ of En (EN-H$_C$) were produced in E. coli separately. The EN-LC-H$_N$ contains a LPETGG (SEQ ID NO: 59) motif and a His6 tag at its C-terminus. EN-H$_C$ contains a GST tag and a thrombin cleavage site at its N-terminus (FIG. 4A). Incubation with thrombin releases EN-H$_C$ with a free glycine at its N-terminus, which can then be ligated to the LPETGG (SEQ ID NO: 59) motif in EN-LC-H$_N$ by the transpeptidase sortase (FIG. 4A). By controlling the levels of precursor proteins in the reaction, the amount of ligated full-length toxin can be strictly limited to ensure biosafety. The downside of this approach is that the toxicity of ligated toxins may not accurately reflect the potency of native toxins, as isolated toxin domains may encounter folding issues. Indeed, EN-H$_C$ showed poor solubility once cleaved from the GST tag, which limited the efficiency of sortase-mediated ligation. Nevertheless, a low level of full-length BoNT/EN can be generated using this approach (FIG. 4B).

Figure 4C:
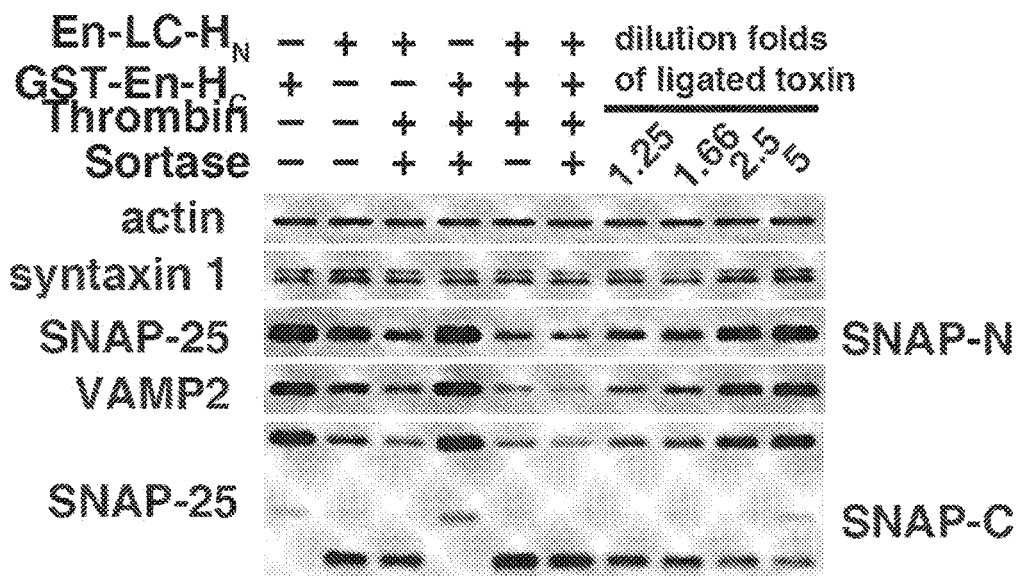

The ligated toxins on cultured rat cortical neurons were first evaluated. Neurons were exposed to the sortase-mediated ligation mixture, as well as three control mixtures lacking EN-H$_C$, EN-LC-H$_N$, or sortase, respectively. Cleavage of VAMP2 and SNAP-25 was analyzed by immunoblot. As shown in FIG. 4C, the presence of EN-LC-H$_N$ resulted in some cleavage of VAMP2 in neurons due to its high concentration in the reaction mixture. Ligation by sortase only slightly increased the cleavage of VAMP2 and SNAP-25 in neurons compared to the mixture without sortase, with estimated enhancement less than 2-fold (FIG. 4C). These results raise the doubt whether there are specific high-affinity receptors for BoNT/EN expressed in rat cortical neurons.

Figure 4D:
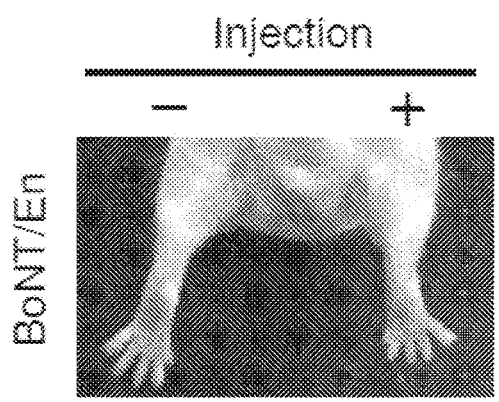

It was next assessed whether ligated BoNT/EN is toxic in vivo in mice, utilizing a well-established non-lethal assay known as the Digit Abduction Score (DAS) assay[31]. This assays measures the degree of local paralysis following injection of toxins into the gastrocnemius muscles of the mouse hind limb. The typical botulism type flaccid paralysis can be detected by the failure to spread the toes in startle responses. It was found that injecting as high as 1 μg of ligated BoNT/EN did not induce any paralysis in mice, suggesting that the ligated BoNT/EN is not toxic in mice at this level (FIG. 4D).

Figure 4E:
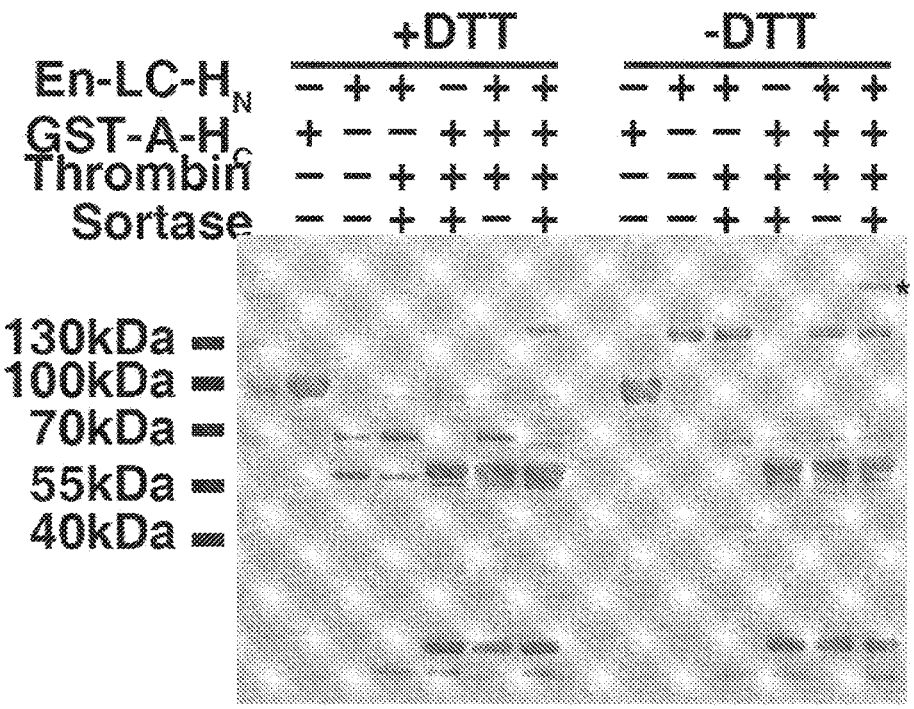
Figure 4F:
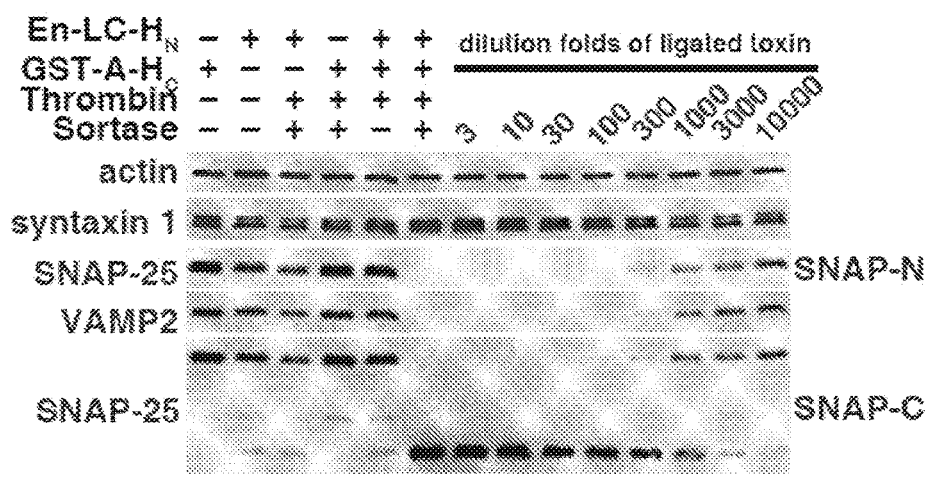
Figure 4G:
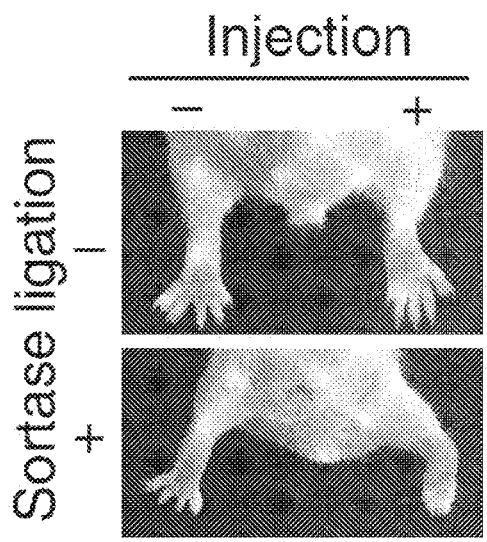

To determine whether the lack of activity of ligated BoNT/EN is due to its LC-H$_N$ part or H$_C$, a chimeric toxin was next generated by ligating EN-LC-H$_N$ with the H$_C$ of BoNT/A (A-H$_C$) using sortase-mediated ligation, which cleaved VAMP2 and SNAP-25 in neurons (FIGS. 4E and 4F). BoNT/A utilizes synaptic vesicle protein SV2 as its protein receptor and complex gangliosides as co-receptors, which are abundantly expressed in cortical neurons[32,33]. The presence of A-H$_C$ in this chimeric toxin facilitated entry into cultured rat cortical neurons by at least 1,000 fold: an estimated 1:1000 dilution of the chimeric toxin mixture cleaved similar levels of VAMP2 and SNAP-25 as the undiluted mixture of EN-LC-H$_N$ and A-H$_C$ without sortase (FIG. 4F). Consistently, injecting as low as 1 ng of the chimeric toxin paralyzed the mouse limb muscle in DAS assays (FIG. 4G). These results suggest that either the EN-H$_C$ purified in isolation has folding issues or high-affinity receptors for BoNT/EN are not present in rat cortical neurons and mouse motor nerves.

BoNT/EN was not Recognized by Antisera Against Other BoNTs

Figure 4H:
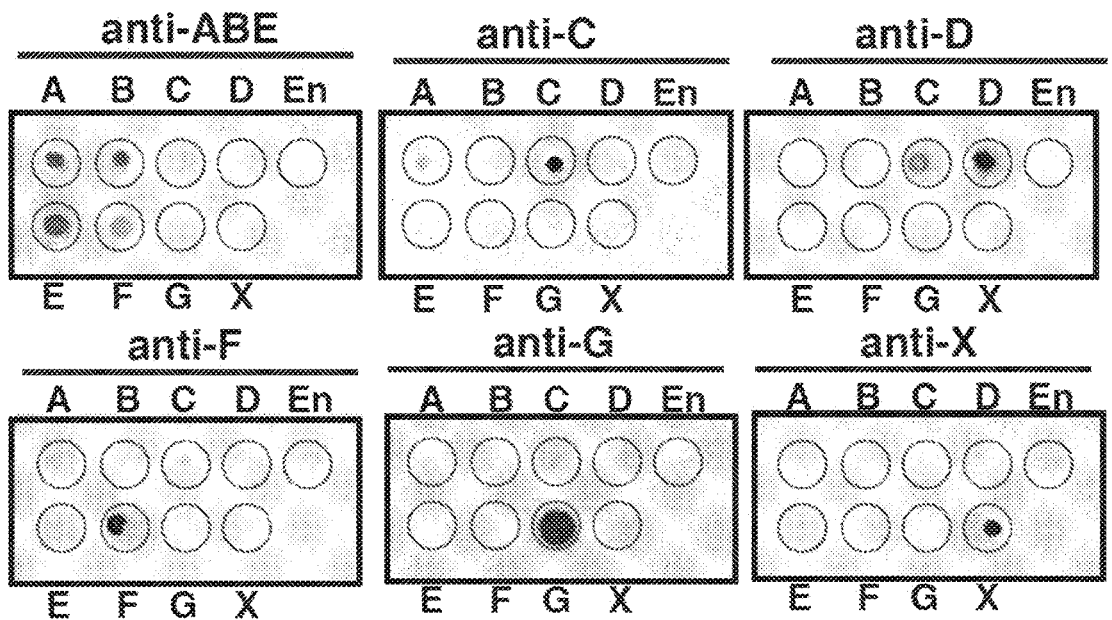

To further establish BoNT/EN as a new serotype of BoNTs, dot blot assays were carried out using antisera raised against other BoNTs, including all the seven major serotypes (BoNT/A-G) as well as the newly identified BoNT/X. Four horse antisera (trivalent anti-BoNT/A, B, and E, anti-BoNT/C, anti-BoNT/F) and two goat antisera (anti-BoNT/D and anti-BoNT/G) were utilized, which have been previously validated[9]. A rabbit polyclonal antibody against BoNT/X was also developed using inactive full-length BoNT/X as the antigen. As shown in FIG. 4H, these antisera recognized their corresponding BoNTs, but none recognized BoNT/EN (a mixture of EN-LC-$H_N$ and EN-$H_C$), confirming that BoNT/EN is a new BoNT serotype.

DISCUSSION

BoNT/EN represents the first case that a BoNT cluster is present in a bacterial species outside of Clostridium. BoNT/EN is most similar to BoNT/X, which was recently identified in C. botulinum strain 111[9]. The gene clusters of BoNT/EN and BoNT/X also shared the same directional arrangement that is unique to these two toxins, further suggesting that BoNT/EN and BoNT/X may form a unique branch within the BoNT family. It is possible that additional members of this branch exist in nature.

BoNT/EN cleaved VAMP2 and SNAP-25 with similar rates in neurons, suggesting that both VAMP2 and SNAP-25 are relevant toxin targets. This dual substrate phenomenon is similar to BoNT/C, which cleaves both SNAP-25 and Syx 1[28,34,35]. BoNT/EN showed low efficacy in cleaving recombinant SNAP-25 in vitro. This is also similar to BoNT/C, which can only cleave SNAP-25 efficiently in cells, but not in vitro[28]. Although the mechanism for this difference remains to be fully established, it is likely that proper localization of SNAP-25 to neuronal membranes is required to provide the optimal recognition/cleavage condition for BoNT/EN and BoNT/C.

Under in vitro assay conditions, BoNT/EN is capable of cleaving Syx 1B and Syx 4 in cell lysates. It cleaves recombinant cytoplasmic domains of Syx 1B and Syx 4 at a site that is spatially conserved between Syx 1B and Syx 4, suggesting a degree of specificity. However, Syx 1B in neurons was not cleaved by BoNT/EN. This is likely because low levels of toxins that successfully translocated into neurons are not sufficient to cleave Syx 1B. On the other hand, the possibilities that the cellular environment of Syx 1B in cortical neurons prevents its cleavage by BoNT/EN cannot be excluded. The drastic differences observed for both SNAP-25 and Syx 1B under in vitro conditions versus in neurons demonstrate the importance of validating any toxin-mediated cleavage events by loading toxins into live neurons, rather than relying solely on in vitro analysis with high levels of toxin LC proteins. SNAP-23 and Syx 4 are not expressed at detectable levels in rat cortical neurons[36]. Whether they and other SNARE proteins can be cleaved efficiently in relevant cell types remain to be determined.

The degree of enhanced entry into cortical neurons for ligated BoNT/EN is rather minimal compared to EN-LC-$H_N$. In contrast, ligating EN-LC-$H_N$ with A-$H_C$ resulted in at least 1,000-old increases in potency on cortical neurons. Consistently, full-length BoNT/EN generated by sortase-mediated ligation did not induce any paralysis at the dose as high as 1 µg, while the chimeric toxin containing A-He induced flaccid paralysis at 1 ng. These data suggest that rat/mouse neurons may not contain the proper high-affinity receptors for BoNT/EN. However, the possibility that EN-He purified in isolation may have folding issues cannot be excluded. It will be important to produce native full-length BoNT/EN in order to fully evaluate its potential toxicity and biosafety risks. Most BoNTs requires both gangliosides as low-affinity attachment factors and specific protein receptors in a double-receptor model[37,38]. BoNT/EN has the typical ganglioside-binding motif (SxWY) within its He, which may mediate low affinity attachment to rat/mouse neurons. Besides gangliosides, BoNT/EN may require additional high-affinity receptors that are not expressed or have altered sequences in rat/mouse neurons.

VAMP2 and SNAP-25 are also involved in secretion events in many non-neuronal cells and the homologs of VAMP2 and SNAP-25 exist throughout eukaryotic species, it is also possible that BoNT/EN may target cell types other than cortical neurons and motor neurons, or even species other than mammals via its unique $H_C$. Enterococci are widespread in nature and colonize the GI tracts of most land animals, including insects and other invertebrates[39-42]. Understanding the receptor-binding properties of BoNT/EN will be crucial to establishing the exact species and cell type specificity for BoNT/EN.

BoNT/EN also represents the first protein toxin identified in E. faecium[40]. With the ability to rapidly obtain new traits on mobile elements, enterococci have acquired and transmitted a variety of antibiotic resistances to both gram-positive and gram negative species[40]. It is always theoretically possible for enterococci to acquire/transmit deadly toxins as well. The discovery of BoNT/EN now sets the first example demonstrating this possibility. Questions remain unknown including the evolutionary origin of BoNT/EN and the specific host species/cell types targeted by BoNT/EN. The capability of E. faecium to acquire a functional BoNT gene cluster could create emerging strains with unwanted consequences for such a well-adapted commensal organism and a leading cause of multi-antibiotic resistant infections[40,43].

Methods

Materials: Mouse monoclonal antibodies for Syx 1 (HPC-1), SNAP-25 (C171.2), VAMP2 (C169.1) were generously provided by E. Chapman (Madison, WI) and are available from Synaptic Systems (Goettingen, Germany). Rabbit polyclonal antibody against VAMP4, Sec22b, Syx 2, Syx 3 and Syx 4 were purchased from Synaptic Systems (Cat. No. 136002, No. 186003, No. 110022, No. 110032 and No. 110042, respectively). The following mouse monoclonal antibodies were purchased from indicated vendors: actin (Sigma, AC-15); anti-HA (Covance, 16B12); anti-Myc (Millipore, 9E10); anti-SNAP-25 (Abcam, ab5666). Equine polyclonal antisera against BoNT/A/B/E, BoNT/C, BoNT/DC, BoNT/F, and goat polyclonal antisera against BoNT/G were generously provided by S. Sharma (FDA). Goat polyclonal antibody against BoNT/D was purchased from Fisher Scientific (NB10062469). BoNTs were purchased from Metabiologics (Madison, WI).

cDNA and constructs: The cDNAs encoding EN-LC (residues 1-434), EN-$H_C$ (residues 863-11279), EN-$H_N$ (residues 436-862), and X-LC (residues 1-439, GenBank No. WP045538952.1) were synthesized by GenScript (New Brunswick, NJ). The cDNA encoding EN-LC-$H_N$ was generated in-house using the Gibson assembly method with a thrombin protease cleavage site inserted between Q432 and L435. EN-LC, X-LC, A-LC (residues 1-425) were cloned into pET28 vectors with His6-tag on their N-termini. EN-$H_C$ and A-$H_C$ (residues 875-1297, GenBank No. AF488749) were cloned into pGEX4T to express as GST-tagged proteins. EN-LC-$H_N$ was cloned into a pET22b vector, with the peptide sequence LPETGG (SEQ ID NO: 59) fused to their C-termini, followed by a His6-tag, and were purified as His6-tagged proteins. VAMP2 (1-93) was cloned into pET28 vector with a His6-tag on the N-terminus and pGEX4T vector and expressed as a GST-tagged protein. Full-length mouse VAMP1, 3, and rat VAMP7, 8 were cloned into a modified pcDNA3.1 vectors, with a HA tag fused to their C-termini. Constructs expressing full-length rat Ykt6 and mouse Sec22b, in pcDNA3.1 vector with an N-terminal Myc tag, were generously provided by J. Hay (Missoula, MT). Full-length Syx 1A, Syx 1B, Syx 2, Syx 3, Syy 4, SNAP-23 and SNAP-29 were cloned into Syn-lox vector between BamHI/NotI with an exception that syntaxin 1B is fused with a HA tag to their N-termini. Full-length SNAP-25 was cloned into pcDNA3.1 vectors between BamHI/NotI, with a HA tag fused to their N-termini. Syx 1A (1-265), Syx 1B (1-251), Syx 4 (1-273), SNAP-23 and SNAP-25 were cloned between NheI/NotI sites in pET28a and expressed as His6-tagged proteinsThe construct encoding His6-tagged sortase (SrtA*) was generously provided by B. Pentelute (Boston, MA) and has been described previously[30].

Bioinformatical analysis: BoNT/EN was discovered using blastp with BoNT/X as a query sequence against the nr database with default parameters (BLOSUM62, gap existence=11, gap extension=1, with conditional compositional score matrix adjustment). As of April 2017, this search space covered a total of 231,827,651,552 bases and 200,877,884 sequences. Domains were annotated using the hmmsearch command of the HMMER package against the Pfam database (v31.0, citation). Genomic architecture visualized using genoplotR (v0.8.6, citation) in R (v3.4.1). BoNT sequences representing all major lineages (A-G, FSA, and X) were aligned in a multiple alignment using ClustalO (v1.2.1), then pairwise identity between BoNT/EN and the others was calculated in a 50 amino acid sliding window across the length of the multiple alignment with a step of 1. Regression splines were calculated using the splines base package in R.

Production of BoNT/X polyclonal antibody: An inactive full length BoNT/X mutant (R360A/Y363F, BoNT/$X_{RY}$) was expressed and purified as described previously[9], using pET22b vector encoding BoNT/$X_{RY}$ with the His6-tag on its C-terminus for expression in *E. coli* BL21 (DE3). Antibody production was carried out by EZBiolab Inc. (USA). The immunogen (BoNT/$X_{RY}$) was diluted with physiological saline and then mixed with the corresponding adjuvant (Freund's complete adjuvant) for 1:1. Antigens and adjuvants are completely mixed to form a stable emulsion and then the emulsion was injected in New Zealand white rabbits using a back multipoint injection method, 0.1 ml per point. After 2 weeks interval, subsequent immunizations are performed with Freund's incomplete adjuvant on different points. The amount of antigen per immunization was 100 μg. The number of immunizations was four times. The titer was tested with ELISA after four times of immunization. Rabbit blood was collected from the carotid artery. The sera were purified by protein A-chromatography and then dialyzed against PBS buffer and then lyophilized.

Protein purification: *E. coli* BL21 (DE3) was utilized for protein expression. In general, induction of expression was carried out with 0.1 mM IPTG at 22° C. overnight. Bacterial pellets were disrupted in lysis buffer (50 mM Tris pH 7.5, 150 mM NaCl) by sonication, and supernatants were collected after centrifugation at 20,000 g for 30 min at 4° C. Protein purification was carried out using AKTA Prime FPLC system (GE) and purified proteins were further desalted with a PD-10 column (GE, 17-0851-01).

Cleavage of SNARE proteins in rat brain detergent extracts (BDE): Rat brain was homogenized in 15 ml 320 mM sucrose buffer, followed by centrifugation at 5000 rpm for 2 min at 4° C. Supernatants were collected and centrifuged at 11,000 rpm for 12 min. The pellet was collected and solubilized for 30 min in 15 ml Tris-buffered saline (TBS: 20 mM Tris, 150 mM NaCl) plus 2% of Triton X-100 and a cocktail of protease inhibitors (Roche, CA). Samples were subsequently centrifuged at 17,000 rpm for 20 min to remove insoluble materials. The final BDE concentration was ~2 mg/ml proteins. BDE (60 μl) were incubated with EN-LC (2 μM), X-LC (2 μM), or A-LC (2 μM), for 1 hour at 37° C., and then analyzed by immunoblot using the enhanced chemiluminescence (ECL) method (Pierce). As controls, LCs were pre-incubated with 20 mM EDTA for 20 minutes at room temperature (RT) prior to adding into BDE.

Cleavage of recombinant VAMPs, Syntaxins and SNAPs by EN-LC: VAMP2 (1-93) was expressed and purified as a His6-tagged protein and also GST-tagged proteins. Syx 1A (1-265), Syx 1B (1-251), Syx 4 (1-273), SNAP-23 and SNAP-25 were expressed and purified as His6-tagged proteins. These proteins (0.3 mg/ml) were incubated with 0.1 or 6 μM EN-LC in TBS buffer for indicated times at 37° C. Samples were either analyzed by SDS-PAGE gels and Coomassie Blue staining, or subjected to mass spectrometry analysis.

Cleavage of VAMPs, Syntaxins and SNAPs in cell lysates: Full-length HA-tagged VAMP1, 3, 7, 8, Syx 1B, SNAP-25 and Myc-tagged Sec22b, and Ykt6 and Syx 1A, Syx 2, Syx 3, Syx 4, SNAP-23 and SNAP-29 in syn-lox vector without any tag were transfected into HEK293 cells using PolyJet transfection reagents (SignaGen, MD) following the manufacturer's instructions. Cell lysates were harvested 48 h later in RIPA buffer (50 mM Tris, 1% NP40, 150 mM NaCl, 0.5% sodium deoxycholate, 0.1% SDS, 400 μl per 10-cm dish) plus a protease inhibitor cocktail (Sigma-Aldrich). Cell lysates (250 μl) were incubated with X-LC (2 μM) for 1 hour at 37° C. Samples were then analyzed by immunoblot.

Identification of cleavage sites in VAMPs by LC-MS/MS: Samples were analyzed at Taplin Biological Mass Spectrometry Core Facility at Harvard Medical School. For VAMP2, whole-protein samples were loaded onto a 100 μm internal diameter C18 reverse-phase HPLC column packed with 3 cm of beads off-line using a pressure cell. The column was re-attached to an Accela 600 Pump (Thermo Fisher Scientific). A rapid gradient of increasing acetonitrile was used to elute the protein/peptide from the HPLC column. As peptides eluted, they were subjected to electrospray ionization and then placed into an LTQ Orbitrap Velos Pro ion-trap mass spectrometer to acquire a high resolution FTMS scan at 60,000 resolution, a second scan at low resolution in the ion trap, and a final scan to perform data-dependent MS/MS. The charge state envelopes were de-convoluted manually to obtain mono-isotopic masses when possible or average masses for the proteins. Peptide and protein identity were determined by matching protein databases with the acquired fragmentation pattern using the software program Sequest (Thermo Fisher Scientific). All databases include a reversed version of all the sequences and the data were filtered to 1-2% percent peptide false-discovery rate.

For Syx 1B, Syx 4, SNAP-23 and SNAP-25, samples were first separated on SDS-PAGE. Proteins bands were excised and cut into approximately 1 $mm^3$ pieces. Gel pieces were incubated with 50 mM ammonium bicarbonate solution containing 12.5 ng/μl modified sequencing-grade chymotrypsin or trypsin (Roche Diagnostics). Samples were digested over-night at room temperature. Peptides were then extracted and separated with reverse-phase HPLC. As peptides were eluted they were subjected to electrospray ionization and transferred into an LTQ Orbitrap Velos Pro ion-trap mass spectrometer (Thermo Fisher Scientific).

Eluted peptides were detected, isolated, and fragmented to produce a tandem mass spectrum of specific fragment ions for each peptide.

Neuron culture and immunoblot analysis: Primary rat cortical neurons were prepared from E18-19 embryos using a papain dissociation kit (Worthington Biochemical), as described previously[44]. Neurons were exposed to BoNT/EN fragments or sortase ligation mixture added to culture medium for 12 h. Neurons were then lysed with RIPA buffer (50 mM Tris, 1% NP40, 150 mM NaCl, 0.5% sodium deoxycholate, 0.1% SDS) plus a protease inhibitor cocktail (Sigma-Aldrich). Lysates were centrifuged for 10 min at maximum speed using a microcentrifuge at 4° C. Supernatants were subjected to SDS-PAGE and immunoblot analysis.

Dot blot: BoNTs (0.2 μg in 1 μl) were spotted onto nitrocellulose membranes and dried (10 minutes at RT). The membranes were blocked with 5% milk in TBST (TBS plus 0.05% Tween20) for 30 min and then incubated with appropriate antisera (1:500 dilution) for 30 min. The membranes were then washed three times with TBST and incubated with 1RP (horseradish peroxidase)-conjugated secondary antibodies for 30 min, washed three more times with TBST, and analyzed by the ECL method. It is noted that the BoNT/EN sample was composed of EN-LC-$H_N$ and GST-EN-$H_C$ at 1:1 ratio.

Sortase-mediated ligation: GST-EN-He or GST-A-$H_C$ was cleaved overnight at 4° C. by thrombin before being added into the ligation reaction mixture. Ligation reaction was set up in 50 μl TBS buffer with EN-LC-$H_N$ (5 μM) pre-treated with or without thrombin, EN-He (15 μM) or A-$H_C$ (15 μM), $Ca^{2+}$ (10 mM), and sortase (2 μM), for 40 min at RT.

DAS assay: EN-FL and EN-A chimeric toxin (EN-LC-$H_N$-A-$H_C$) were generated by sortase-mediated ligation. Mice (CD-1 strain, 21-25 g, n=4) were anesthetized with isoflurane (3-4%) and injected with EN-FL (1 μg) and EN-A (1 ng) using a 30-gauge needle attached to a sterile Hamilton syringe, into the gastrocnemius muscles of the right hind limb. Muscle paralysis and the spread of hind paw in the startle response were examined 24 h after injection.

REFERENCES

1. Schiavo, G., Matteoli, M. & Montecucco, C. Neurotoxins affecting neuroexocytosis. *Physiol Rev* 80, 717-766 (2000).
2. Montal, M. botulinum neurotoxin: a marvel of protein design. *Annu Rev Biochem* 79, 591-617 (2010).
3. Rossetto, O., Pirazzini, M. & Montecucco, C. *botulinum* neurotoxins: genetic, structural and mechanistic insights. *Nat Rev Microbiol* 12, 535-549 (2014).
4. Amon, S. S., Schechter, R., Inglesby, T. V., Henderson, D. A., Bartlett, J. G., Ascher, M. S., Eitzen, E., Fine, A. D., Hauer, J., Layton, M., Lillibridge, S., Osterholm, M. T., O'Toole, T., Parker, G., Perl, T. M., Russell, P. K., Swerdlow, D. L. & Tonat, K. *botulinum* toxin as a biological weapon: medical and public health management. *Jama* 285, 1059-1070 (2001).
5. Johnson, E. A. Clostridial toxins as therapeutic agents: benefits of nature's most toxic proteins. *Annu Rev Microbiol* 53, 551-575 (1999).
6. Montecucco, C. & Molgo, J. Botulinal neurotoxins: revival of an old killer. *Curr Opin Pharmacol* 5, 274-279 (2005).
7. Jahn, R. & Scheller, R. H. SNAREs—engines for membrane fusion. *Nat Rev Mol Cell Biol* 7, 631-643 (2006).
8. Sudhof, T. C. & Rothman, J. E. Membrane fusion: grappling with SNARE and SM proteins. *Science* 323, 474-477 (2009).
9. Zhang, S., Masuyer, G., Zhang, J., Shen, Y., Lundin, D., Henriksson, L., Miyashita, S. I., Martinez-Carranza, M., Dong, M. & Stenmark, P. Identification and characterization of a novel *botulinum* neurotoxin. *Nat Commun* 8, 14130 (2017).
10. Hill, K. K., Xie, G., Foley, B. T. & Smith, T. J. Genetic diversity within the *botulinum* neurotoxin-producing bacteria and their neurotoxins. *Toxicon* 107, 2-8 (2015).
11. Gu, S., Rumpel, S., Zhou, J., Strotmeier, J., Bigalke, H., Perry, K., Shoemaker, C. B., Rummel, A. & Jin, R. *botulinum* neurotoxin is shielded by NTNHA in an interlocked complex. *Science* 335, 977-981 (2012).
12. Lee, K., Zhong, X., Gu, S., Kruel, A. M., Dorner, M. B., Perry, K., Rummel, A., Dong, M. & Jin, R. Molecular basis for disruption of E-cadherin adhesion by *botulinum* neurotoxin A complex. *Science* 344, 1405-1410 (2014).
13. Lee, K., Gu, S., Jin, L., Le, T. T., Cheng, L. W., Strotmeier, J., Kruel, A. M., Yao, G., Perry, K., Rummel, A. & Jin, R. Structure of a bimodular *botulinum* neurotoxin complex provides insights into its oral toxicity. *PLoS Pathog* 9, e1003690 (2013).
14. Sugawara, Y., Matsumura, T., Takegahara, Y., Jin, Y., Tsukasaki, Y., Takeichi, M. & Fujinaga, Y. *botulinum* hemagglutinin disrupts the intercellular epithelial barrier by directly binding E-cadherin. *J Cell Biol* 189, 691-700 (2010).
15. Smith, T. J., Lou, J., Geren, I. N., Forsyth, C. M., Tsai, R., Laporte, S. L., Tepp, W. H., Bradshaw, M., Johnson, E. A., Smith, L. A. & Marks, J. D. Sequence variation within *botulinum* neurotoxin serotypes impacts antibody binding and neutralization. *Infect Immun* 73, 5450-5457 (2005).
16. Hill, K. K., Smith, T. J., Helma, C. H., Ticknor, L. O., Foley, B. T., Svensson, R. T., Brown, J. L., Johnson, E. A., Smith, L. A., Okinaka, R. T., Jackson, P. J. & Marks, J. D. Genetic diversity among *botulinum* Neurotoxin-producing clostridial strains. *J Bacteriol* 189, 818-832 (2007).
17. Montecucco, C. & Rasotto, M. B. On *botulinum* neurotoxin variability. *MBio* 6(2015).
18. Dover, N., Barash, J. R., Hill, K. K., Xie, G. & Arnon, S. S. Molecular characterization of a novel *botulinum* neurotoxin type H gene. *J Infect Dis* 209, 192-202 (2014).
19. Barash, J. R. & Arnon, S. S. A novel strain of *Clostridium botulinum* that produces type B and type H *botulinum* toxins. *J Infect Dis* 209, 183-191 (2014).
20. Maslanka, S. E., Luquez, C., Dykes, J. K., Tepp, W. H., Pier, C. L., Pellett, S., Raphael, B. H., Kalb, S. R., Barr, J. R., Rao, A. & Johnson, E. A. A Novel *botulinum* Neurotoxin, Previously Reported as Serotype H, Has a Hybrid-Like Structure With Regions of Similarity to the Structures of Serotypes A and F and Is Neutralized With Serotype A Antitoxin. *J Infect Dis* (2015).
21. Kalb, S. R., Baudys, J., Raphael, B. H., Dykes, J. K., Luquez, C., Maslanka, S. E. & Barr, J. R. Functional characterization of *botulinum* neurotoxin serotype H as a hybrid of known serotypes F and A (BoNT F/A). *Anal Chem* 87, 3911-3917 (2015).
22. Zornetta, T., Azarnia Tehran, D., Arrigoni, G., Anniballi, F., Bano, L., Leka, O., Zanotti, G., Binz, T. & Montecucco, C. The first non *Clostridial botulinum*-like toxin cleaves VAMP within the juxtamembrane domain. *Sci Rep* 6, 30257 (2016).

23. Mansfield, M. J., Adams, J. B. & Doxey, A. C. botulinum neurotoxin homologs in non-Clostridium species. *FEBS Lett* 589, 342-348 (2015).
24. Schiavo, G., Benfenati, F., Poulain, B., Rossetto, O., Polverino de Laureto, P., DasGupta, B. R. & Montecucco, C. Tetanus and botulinum-B neurotoxins block neurotransmitter release by proteolytic cleavage of synaptobrevin. *Nature* 359, 832-835 (1992).
25. Rummel, A., Mahrhold, S., Bigalke, H. & Binz, T. The HCC-domain of botulinum neurotoxins A and B exhibits a singular ganglioside binding site displaying serotype specific carbohydrate interaction. *Mol Microbiol* 51, 631-643 (2004).
26. Rossetto, O., Schiavo, G., Montecucco, C., Poulain, B., Deloye, F., Lozzi, L. & Shone, C. C. SNARE motif and neurotoxins. *Nature* 372, 415-416 (1994).
27. Chaddock, J. A., Herbert, M. H., Ling, R. J., Alexander, F. C., Fooks, S. J., Revell, D. F., Quinn, C. P., Shone, C. C. & Foster, K. A. Expression and purification of catalytically active, non-toxic endopeptidase derivatives of *Clostridium botulinum* toxin type A. *Protein Expr Purif* 25, 219-228 (2002).
28. Foran, P., Lawrence, G. W., Shone, C. C., Foster, K. A. & Dolly, J. O. botulinum neurotoxin C1 cleaves both syntaxin and SNAP-25 in intact and permeabilized chromaffin cells: correlation with its blockade of catecholamine release. *Biochemistry* 35, 2630-2636 (1996).
29. Popp, M. W., Antos, J. M., Grotenbreg, G. M., Spooner, E. & Ploegh, H. L. Sortagging: a versatile method for protein labeling. *Nat Chem Biol* 3, 707-708 (2007).
30. McCluskey, A. J. & Collier, R. J. Receptor-directed chimeric toxins created by sortase-mediated protein fusion. *Mol Cancer Ther* 12, 2273-2281 (2013).
31. Aoki, K. R. A comparison of the safety margins of botulinum neurotoxin serotypes A, B, and F in mice. *Toxicon* 39, 1815-1820 (2001).
32. Dong, M., Yeh, F., Tepp, W. H., Dean, C., Johnson, E. A., Janz, R. & Chapman, E. R. SV2 is the protein receptor for botulinum neurotoxin A. *Science* 312, 592-596 (2006).
33. Mahrhold, S., Rummel, A., Bigalke, H., Davletov, B. & Binz, T. The synaptic vesicle protein 2C mediates the uptake of botulinum neurotoxin A into phrenic nerves. *FEBS Lett* 580, 2011-2014 (2006).
34. Schiavo, G., Shone, C. C., Bennett, M. K., Scheller, R. H. & Montecucco, C. botulinum neurotoxin type C cleaves a single Lys-Ala bond within the carboxyl-terminal region of syntaxins. *J Biol Chem* 270, 10566-10570 (1995).
35. Blasi, J., Chapman, E. R., Yamasaki, S., Binz, T., Niemann, H. & Jahn, R. botulinum neurotoxin C1 blocks neurotransmitter release by means of cleaving HPC-1/syntaxin. *Embo J* 12, 4821-4828 (1993).
36. Peng, L., Liu, H., Ruan, H., Tepp, W. H., Stoothoff, W. H., Brown, R. H., Johnson, E. A., Yao, W.-D., Zhang, S.-C. & Dong, M. Cytotoxicity of botulinum neurotoxins reveals a direct role of syntaxin 1 and SNAP-25 in neuron survival. *Nat Commun* 4, 1472 (2013).
37. Montecucco, C. How do tetanus and botulinum toxins bind to neuronal membranes? *TIBS* 11, 314-317 (1986).
38. Rummel, A. The long journey of botulinum neurotoxins into the synapse. *Toxicon* 107, 9-24 (2015).
39. Lebreton, F., Manson, A. L., Saavedra, J. T., Straub, T. J., Earl, A. M. & Gilmore, M. S. Tracing the Enterococci from Paleozoic Origins to the Hospital. *Cell* 169, 849-861 e813 (2017).
40. Van Tyne, D. & Gilmore, M. S. Friend turned foe: evolution of enterococcal virulence and antibiotic resistance. *Annu Rev Microbiol* 68, 337-356 (2014).
41. Martin, J. D. & Mundt, J. O. Enterococci in insects. *Appl Microbiol* 24, 575-580 (1972).
42. Mundt, J. O. Occurrence of enterococci in animals in a wild environment. *Appl Microbiol* 11, 136-140 (1963).
43. Schloissnig, S., Arumugam, M., Sunagawa, S., Mitreva, M., Tap, J., Zhu, A., Waller, A., Mende, D. R., Kultima, JR., Martin, J., Kota, K., Sunyaev, S. R., Weinstock, G. M. & Bork, P. Genomic variation landscape of the human gut microbiome. *Nature* 493, 45-50 (2013).
44. Peng, L., Tepp, W. H., Johnson, E. A. & Dong, M. botulinum neurotoxin D uses synaptic vesicle protein SV2 and gangliosides as receptors. *PLoS Pathog* 7, e1002008 (2011).

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. An isolated polypeptide, comprising a modified amino acid sequence that is at least 95% identical to the amino acid sequence of any one of SEQ ID NOs: 1-3, and wherein the amino acid sequence of the polypeptide is not 100% identical to the amino acid sequence of any one of SEQ ID NOs: 1-3.

2. The isolated polypeptide of claim 1, comprising a modified amino acid sequence that is at least 98% identical to the amino acid sequence of any one of SEQ ID NOs: 1-3, and wherein the amino acid sequence of the polypeptide is not 100% identical to the amino acid sequence of any one of SEQ ID NOs: 1-3.

3. The isolated polypeptide of claim 1, comprising a modified amino acid sequence that is at least 99% identical to the amino acid sequence of any one of SEQ ID NOs: 1-3, and wherein the amino acid sequence of the polypeptide is not 100% identical to the amino acid sequence of any one of SEQ ID NOs: 1-3.

4. The isolated polypeptide of claim 1, comprising the amino acid sequence of any one of SEQ ID NOs: 5-22.

5. The isolated polypeptide of claim 1, comprising the amino acid sequence of SEQ ID NO: 5.

6. An isolated nucleic acid molecule comprising a polynucleotide encoding the isolated polypeptide of claim 1.

7. An isolated cell comprising an isolated nucleic acid molecule comprising a polynucleotide encoding isolated polypeptide of claim 1.

8. A method of producing an isolated polypeptide, the method comprising culturing the cell of claim 7 under conditions to produce the polypeptide, and isolating the polypeptide from the cell.

9. An isolated polypeptide, comprising a modified amino acid sequence that is at least 95% identical to the amino acid sequence of SEQ ID NO: 4, and wherein the amino acid sequence of the polypeptide is not 100% identical to the amino acid sequence of SEQ ID NO: 4.

10. The isolated polypeptide of claim 9, comprising a modified amino acid sequence that is at least 98% identical to the amino acid sequence of SEQ ID NO: 4, and wherein the amino acid sequence of the polypeptide is not 100% identical to SEQ ID NO: 4.

11. The isolated polypeptide of claim 9, comprising a modified amino acid sequence that is at least 99% identical to the amino acid sequence of SEQ ID NO: 4, and wherein the amino acid sequence of the polypeptide is not 100% identical to SEQ ID NO: 4.

* * * * *

SEQUENCE LISTING

```
<160> NUMBER OF SEQ ID NOS: 88

<210> SEQ ID NO 1
<211> LENGTH: 1279
<212> TYPE: PRT
<213> ORGANISM: Unknown
<220> FEATURE:
<223> OTHER INFORMATION: Enterococcus

<400> SEQUENCE: 1

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
            20                  25                  30

Gln Phe Ile Asn His Asn Val Pro Asp Leu Lys Ala Phe Gln Val Phe
        35                  40                  45

Pro Asn Val Trp Val Val Pro Glu Arg Tyr Thr Phe Tyr Ser Thr Met
    50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
    130                 135                 140

Lys Gly Asn Val Leu Lys His Arg Arg Ala His Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190
```

```
Tyr His Lys Thr Tyr Ser Thr Lys Leu Thr Asn Lys Asn Ser Leu Val
            195                 200                 205

Asp Lys Ser Val Gln Glu Phe Val Pro Asp Pro Ala Val Thr Leu Ile
210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
                260                 265                 270

Phe Gly Gly Glu Asp Val Lys Val Ile Lys Ser Glu Ile Asp Lys Lys
                275                 280                 285

Ile Pro Gly Ile Leu Asn Leu Ile Lys Thr Thr Val Glu Pro Ile Ile
290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
                340                 345                 350

Thr Met Phe Ala Glu Asn Leu Lys Ala Leu Thr Arg Ala Arg Tyr Leu
            355                 360                 365

Val Pro Lys Val Glu Asn Ile Val Gln Val Asp Ile Leu Ser Pro Asn
            370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Pro Asn Pro His Phe Ser Ser Gln
                420                 425                 430

Arg Gly Leu Ser Ser Cys Ile Glu Ile Leu Glu Asp Asp Leu Phe Ile
            435                 440                 445

Met Ser Ser Lys Asp Ser Phe Thr Asp Thr Asp Phe Ser Glu Pro Ser
450                 455                 460

Val Gly Pro Val Ser Tyr Lys Ala Lys Lys Gly Ala Asp Thr Ile Leu
465                 470                 475                 480

Asp Ser Thr Leu Ser Asn Tyr Asp Phe Ser Lys Glu Ile Asn Phe Thr
                485                 490                 495

Ser Thr Val Pro Ile Ile Thr Val Glu Asp Pro Leu Glu Thr Asp Glu
            500                 505                 510

Asp Val Pro Val Ile Ser Glu Asp Arg Thr Val Tyr Val Asp Asp Tyr
            515                 520                 525

Thr Thr Phe His Phe Leu Glu Ala Gln Lys Ile Gly Lys Glu Val Val
            530                 535                 540

Pro Thr Gln Thr Lys Val Val Phe Thr Thr Asn Met Glu Glu Ala Leu
545                 550                 555                 560

Phe Asp Ser Lys Lys Val Tyr Thr Val Phe Glu Asn Thr Ala Ser Arg
                565                 570                 575

Ile Asn Glu Ala Gly Thr Gly Ile Ala Asn Gly Met Met Phe Tyr Gln
                580                 585                 590

Trp Leu Lys Gly Ile Val Gln Asp Phe Thr Glu Glu Ala Thr Gln Lys
            595                 600                 605

Asp Thr Phe Asp Lys Ile Ser Asp Val Thr Met Ile Val Pro Tyr Leu
```

```
            610                 615                 620
Gly Asn Ile Leu Asn Ile Gly Asn Asp Ile Arg Lys Gly Asp Phe Met
625                 630                 635                 640

Gly Ala Val Glu Leu Gly Gly Val Thr Ile Leu Leu Glu Ala Ile Pro
                645                 650                 655

Glu Leu Thr Leu Pro Val Leu Ile Gly Leu Thr Ile Ile Glu Asp Glu
                660                 665                 670

Leu Glu Lys Glu Gln Val Ser Gln Thr Val Tyr Asn Val Leu Asp Lys
                675                 680                 685

Arg Asp Glu Lys Trp Glu Val Tyr Gly Phe Val Lys Gln Gln Trp
690                 695                 700

Trp Trp Met Val His Thr Gln Phe Glu Thr Arg Ile Leu His Ala Tyr
705                 710                 715                 720

Gln Ala Leu Asn His Gln Val Glu Ala Ile Lys Ala Asn Met Thr Tyr
                725                 730                 735

Gln Leu Ala Asn Tyr Arg Gly Asn Gln Glu Asp Lys Glu Leu Leu Glu
                740                 745                 750

Lys Ala Ile Asp Asp Thr Leu Gln Ser Leu Tyr Tyr Ala Val Asp Gln
                755                 760                 765

Ala Met His Asn Ile Lys Arg Phe Leu Ile Gln Ser Ser Lys Ser Tyr
770                 775                 780

Leu Leu Asn Gln Met Leu Pro Lys Thr Lys Glu Gln Leu Leu Ala Phe
785                 790                 795                 800

Asp Gln Gln Thr Leu Arg Asn Val Asn Asp Phe Ile Asn Lys Asn Gln
                805                 810                 815

Gly Val Leu Gly Glu Ser Leu Ala Lys Asp Leu Lys Lys Val Glu
                820                 825                 830

Lys Arg Leu Thr Ser Leu Pro Val Phe Asn Leu Glu Asp Leu Pro Ile
                835                 840                 845

Ser Glu Phe Glu Asp Leu Ile His Ser His Glu Ile Asp Ile Gln Asp
850                 855                 860

Ser Glu Val Leu Asn Ile Gly Val Asn Asn Gly Lys Ile Gln Asp Leu
865                 870                 875                 880

Ser Gly Glu Asn Thr Pro Leu Thr Leu Gly Glu Asn Leu His Ile Val
                885                 890                 895

Asn Gly Arg Asp Asn Gln Ala Val Arg Leu Asn Asn Gln Leu Asp Ser
                900                 905                 910

Lys Leu Glu Ile Gln Ser Arg Pro Asn Ile His Phe Thr Ala Phe Glu
                915                 920                 925

Asp Phe Ser Ile Ser Ile Trp Ile Arg Cys Ser Met Leu Arg Asn Asn
930                 935                 940

Arg Asn Arg Gly Gln Lys Tyr Thr Ile Ile Gln Phe Asn Lys Tyr
945                 950                 955                 960

Gly Trp Gln Leu Ala Ile Gln Asp Ser Val Phe Val Trp Thr Leu His
                965                 970                 975

Asp Thr Phe Asn Asn Gln Ile Gln Leu Thr Ser Gly Ser Ala Leu Thr
                980                 985                 990

Asn Lys Asn Tyr Leu Leu Gln Asn Phe Trp Leu His Ile Thr Val Thr
                995                 1000                1005

Asn Lys Arg Ser Glu Lys Ser Arg Leu Tyr Ile Asn Gly Val Leu
    1010                1015                1020

Gln Asp Gln Lys Asp Ile Ser Val Leu Gly Asn Cys His Pro Lys
    1025                1030                1035
```

-continued

Glu Pro Ile Leu Phe Ser Ile Gln Asp Asn Ser Asp Pro Asn Tyr
    1040                1045                1050

Phe Val Arg Phe Glu Gln Phe Asn Val Tyr Arg Lys Ala Leu Thr
    1055                1060                1065

Asp Ser Glu Val Asn Arg Leu Tyr Trp Lys Tyr Phe Glu Gly Ser
    1070                1075                1080

Tyr Leu Arg Asp Val Trp Gly Glu Arg Leu Thr Tyr Asn Arg Asp
    1085                1090                1095

Tyr Tyr Met Gln Leu Ser Thr Leu Pro Gly Arg Gly Ile Lys Arg
    1100                1105                1110

Glu Tyr Arg Thr Trp Ser Gly Phe Asp Tyr Ile Ile Leu Ser Glu
    1115                1120                1125

Leu Gly Thr Gln Lys Ile Pro Thr His Glu Val Thr Tyr Pro Lys
    1130                1135                1140

Leu Tyr Gln Gly Gln Lys Ile Thr Ile His Ser Asp Gly Lys Asn
    1145                1150                1155

Leu Glu Pro His Val Lys Ser Asn Lys Asn Ile Arg Leu Lys Ile
    1160                1165                1170

Asp Asp Phe Tyr Ile Gly Val Val Asn Pro Phe Lys Leu Pro Glu
    1175                1180                1185

Trp Arg Pro Glu Ser Gly Ala Tyr Val Val Thr Tyr Asn His
    1190                1195                1200

Ala Glu Asp Leu Cys Leu Tyr Phe Arg Thr Arg Ser Ser Ser Gln
    1205                1210                1215

Ser Leu Tyr Tyr Gly Gln Leu Ile Met Asn Asp Gly Arg Asn Lys
    1220                1225                1230

Ser Leu Leu Asn Tyr Thr Leu Lys Gly Ser Thr Tyr Trp Ile Trp
    1235                1240                1245

Ser Ser Ala Trp Tyr Glu Asn Tyr Asn Thr Ser Ser Lys Thr
    1250                1255                1260

Ala Gly Asn Trp Tyr Phe Ile Pro Val Asp Glu Gly Trp Lys Glu
    1265                1270                1275

Asp

<210> SEQ ID NO 2
<211> LENGTH: 433
<212> TYPE: PRT
<213> ORGANISM: Artificial Sequence
<220> FEATURE:
<223> OTHER INFORMATION: Synthetic Polypeptide

<400> SEQUENCE: 2

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

Pro Asn Val Trp Val Pro Glu Arg Tyr Thr Phe Tyr Ser Thr Met
    50                  55                  60

Lys Asn Leu Asp Ala Pro Ala Asn Pro Ser Arg Ser Ser Tyr Tyr Asp
65              70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
    130                 135                 140

Lys Gly Asn Val Leu Lys His Arg Arg Ala His Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
    210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
        275                 280                 285

Ile Pro Gly Ile Leu Asn Leu Ile Lys Thr Thr Val Glu Pro Ile Ile
    290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
        355                 360                 365

Val Pro Lys Val Glu Asn Ile Val Gln Val Asp Ile Leu Ser Pro Asn
370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Pro Asn Pro His Phe Ser Ser Gln
            420                 425                 430

Arg

<210> SEQ ID NO 3
<211> LENGTH: 862
<212> TYPE: PRT
<213> ORGANISM: Artificial Sequence
<220> FEATURE:
<223> OTHER INFORMATION: Synthetic Polypeptide

<400> SEQUENCE: 3

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp

-continued

```
                    20                  25                  30
        Gln Phe Ile Asn His Asn Val Pro Asp Leu Lys Ala Phe Gln Val Phe
                        35                  40                  45
        Pro Asn Val Trp Val Val Pro Glu Arg Tyr Thr Phe Tyr Ser Thr Met
         50                  55                  60
        Lys Asn Leu Asp Ala Pro Ala Asn Pro Ser Arg Ser Ser Tyr Tyr Asp
         65                  70                  75                  80
        Pro Thr Tyr Leu Gln Ser Asp Ala Glu Lys Glu Val Phe Leu Gln Gln
                        85                  90                  95
        Met Ile Leu Leu Phe Lys Arg Ile Asn Ser Thr Gln Glu Gly Gln Gln
                        100                 105                 110
        Phe Leu Asn Leu Leu Ser Arg Ser Ile Pro Val Pro Tyr Glu Ser Asn
                        115                 120                 125
        Gly Asp Val Ala Met Gly Thr Thr Gln Val Ile Lys Gln Met Asp Asp
                        130                 135                 140
        Lys Gly Asn Val Leu Lys His Arg Arg Ala His Ile Ile Ile Tyr Gly
         145                 150                 155                 160
        Pro Gly Pro Asp Leu Met Ala Lys Gly Ser Lys Ala Leu Thr Lys Ser
                        165                 170                 175
        Arg Glu Thr Gly Arg Gly Cys Met Ala Glu Ile Tyr Phe Ser Pro Met
                        180                 185                 190
        Tyr His Lys Thr Tyr Ser Thr Lys Leu Thr Asn Lys Asn Ser Leu Val
                        195                 200                 205
        Asp Lys Ser Val Gln Glu Phe Val Pro Asp Pro Ala Val Thr Leu Ile
                        210                 215                 220
        His Glu Leu Cys His Gly Leu His Ala Leu Tyr Gly Ile Asp Leu Gly
         225                 230                 235                 240
        Asn Val Gly Ser Trp Glu Phe Asn Ser Asn Pro Asn Ser Leu Phe Ser
                        245                 250                 255
        Ser Trp Phe Ser Ser Lys Glu Ala Val Asn Phe Glu Glu Val Met Thr
                        260                 265                 270
        Phe Gly Gly Glu Asp Val Lys Val Ile Lys Ser Glu Ile Asp Lys Lys
                        275                 280                 285
        Ile Pro Gly Ile Leu Asn Leu Ile Lys Thr Thr Val Glu Pro Ile Ile
                        290                 295                 300
        Asn Lys Ile Thr Asp Pro His Asp Glu Met Leu Gln Cys Leu Gln Ser
         305                 310                 315                 320
        Lys Tyr Pro Ser Leu Lys Gly Thr Leu Gly Gln Phe Phe Asp Asp
                        325                 330                 335
        Thr Gln Leu Glu Lys Asp Ile Arg Asp Leu Trp Met Val Met Asn Glu
                        340                 345                 350
        Thr Met Phe Ala Glu Asn Leu Lys Ala Leu Thr Arg Ala Arg Tyr Leu
                        355                 360                 365
        Val Pro Lys Val Glu Asn Ile Val Gln Val Asp Ile Leu Ser Pro Asn
                        370                 375                 380
        Val Tyr Thr Ile Asp Lys Gly Phe Asn His Leu Ser Lys Gly Phe Lys
         385                 390                 395                 400
        Gly Gln Ser Val Ser Gln Ser Tyr Phe Arg Lys Ile Ser Ala Leu Ala
                        405                 410                 415
        Arg Gly Ala Val Val Arg Ala Cys Pro Asn Pro His Phe Ser Ser Gln
                        420                 425                 430
        Arg Gly Leu Ser Ser Cys Ile Glu Ile Leu Glu Asp Asp Leu Phe Ile
                        435                 440                 445
```

```
Met Ser Ser Lys Asp Ser Phe Thr Asp Thr Asp Phe Ser Glu Pro Ser
    450                 455                 460

Val Gly Pro Val Ser Tyr Lys Ala Lys Lys Gly Ala Asp Thr Ile Leu
465                 470                 475                 480

Asp Ser Thr Leu Ser Asn Tyr Asp Phe Ser Lys Glu Ile Asn Phe Thr
                    485                 490                 495

Ser Thr Val Pro Ile Ile Thr Val Glu Asp Pro Leu Glu Thr Asp Glu
                500                 505                 510

Asp Val Pro Val Ile Ser Glu Asp Arg Thr Val Tyr Val Asp Asp Tyr
            515                 520                 525

Thr Thr Phe His Phe Leu Glu Ala Gln Lys Ile Gly Lys Glu Val Val
    530                 535                 540

Pro Thr Gln Thr Lys Val Val Phe Thr Thr Asn Met Glu Glu Ala Leu
545                 550                 555                 560

Phe Asp Ser Lys Lys Val Tyr Thr Val Phe Glu Asn Thr Ala Ser Arg
                565                 570                 575

Ile Asn Glu Ala Gly Thr Gly Ile Ala Asn Gly Met Met Phe Tyr Gln
                580                 585                 590

Trp Leu Lys Gly Ile Val Gln Asp Phe Thr Glu Ala Thr Gln Lys
            595                 600                 605

Asp Thr Phe Asp Lys Ile Ser Asp Val Thr Met Ile Val Pro Tyr Leu
            610                 615                 620

Gly Asn Ile Leu Asn Ile Gly Asn Asp Ile Arg Lys Gly Asp Phe Met
625                 630                 635                 640

Gly Ala Val Glu Leu Gly Gly Val Thr Ile Leu Leu Glu Ala Ile Pro
                645                 650                 655

Glu Leu Thr Leu Pro Val Leu Ile Gly Leu Thr Ile Ile Glu Asp Glu
                660                 665                 670

Leu Glu Lys Glu Gln Val Ser Gln Thr Val Tyr Asn Val Leu Asp Lys
            675                 680                 685

Arg Asp Glu Lys Trp Glu Glu Val Tyr Gly Phe Val Lys Gln Gln Trp
    690                 695                 700

Trp Trp Met Val His Thr Gln Phe Glu Thr Arg Ile Leu His Ala Tyr
705                 710                 715                 720

Gln Ala Leu Asn His Gln Val Glu Ala Ile Lys Ala Asn Met Thr Tyr
                725                 730                 735

Gln Leu Ala Asn Tyr Arg Gly Asn Gln Glu Asp Lys Glu Leu Leu Glu
                740                 745                 750

Lys Ala Ile Asp Asp Thr Leu Gln Ser Leu Tyr Tyr Ala Val Asp Gln
            755                 760                 765

Ala Met His Asn Ile Lys Arg Phe Leu Ile Gln Ser Ser Lys Ser Tyr
    770                 775                 780

Leu Leu Asn Gln Met Leu Pro Lys Thr Lys Glu Gln Leu Leu Ala Phe
785                 790                 795                 800

Asp Gln Gln Thr Leu Arg Asn Val Asn Asp Phe Ile Asn Lys Asn Gln
                805                 810                 815

Gly Val Leu Gly Glu Ser Leu Ala Lys Asp Leu Lys Lys Val Glu
            820                 825                 830

Lys Arg Leu Thr Ser Leu Pro Val Phe Asn Leu Glu Asp Leu Pro Ile
    835                 840                 845

Ser Glu Phe Glu Asp Leu Ile His Ser His Glu Ile Asp Ile
    850                 855                 860
```

```
<210> SEQ ID NO 4
<211> LENGTH: 417
<212> TYPE: PRT
<213> ORGANISM: Artificial Sequence
<220> FEATURE:
<223> OTHER INFORMATION: Synthetic Polypeptide

<400> SEQUENCE: 4

Gln Asp Ser Glu Val Leu Asn Ile Gly Val Asn Asn Gly Lys Ile Gln
1               5                   10                  15

Asp Leu Ser Gly Glu Asn Thr Pro Leu Thr Leu Gly Glu Asn Leu His
            20                  25                  30

Ile Val Asn Gly Arg Asp Asn Gln Ala Val Arg Leu Asn Asn Gln Leu
        35                  40                  45

Asp Ser Lys Leu Glu Ile Gln Ser Arg Pro Asn Ile His Phe Thr Ala
    50                  55                  60

Phe Glu Asp Phe Ser Ile Ser Ile Trp Ile Arg Cys Ser Met Leu Arg
65                  70                  75                  80

Asn Asn Arg Asn Arg Gly Gln Lys Tyr Thr Ile Ile Gln Gln Phe Asn
                85                  90                  95

Lys Tyr Gly Trp Gln Leu Ala Ile Gln Asp Ser Val Phe Val Trp Thr
            100                 105                 110

Leu His Asp Thr Phe Asn Asn Gln Ile Gln Leu Thr Ser Gly Ser Ala
        115                 120                 125

Leu Thr Asn Lys Asn Tyr Leu Leu Gln Asn Phe Trp Leu His Ile Thr
    130                 135                 140

Val Thr Asn Lys Arg Ser Glu Lys Ser Arg Leu Tyr Ile Asn Gly Val
145                 150                 155                 160

Leu Gln Asp Gln Lys Asp Ile Ser Val Leu Gly Asn Cys His Pro Lys
                165                 170                 175

Glu Pro Ile Leu Phe Ser Ile Gln Asp Asn Ser Asp Pro Asn Tyr Phe
            180                 185                 190

Val Arg Phe Glu Gln Phe Asn Val Tyr Arg Lys Ala Leu Thr Asp Ser
        195                 200                 205

Glu Val Asn Arg Leu Tyr Trp Lys Tyr Phe Gly Ser Tyr Leu Arg
    210                 215                 220

Asp Val Trp Gly Glu Arg Leu Thr Tyr Asn Arg Asp Tyr Tyr Met Gln
225                 230                 235                 240

Leu Ser Thr Leu Pro Gly Arg Gly Ile Lys Arg Glu Tyr Arg Thr Trp
                245                 250                 255

Ser Gly Phe Asp Tyr Ile Ile Leu Ser Glu Leu Gly Thr Gln Lys Ile
            260                 265                 270

Pro Thr His Glu Val Thr Tyr Pro Lys Leu Tyr Gln Gly Gln Lys Ile
        275                 280                 285

Thr Ile His Ser Asp Gly Lys Asn Leu Glu Pro His Val Lys Ser Asn
    290                 295                 300

Lys Asn Ile Arg Leu Lys Ile Asp Asp Phe Tyr Ile Gly Val Val Asn
305                 310                 315                 320

Pro Phe Lys Leu Pro Glu Trp Arg Pro Glu Ser Gly Ala Tyr Val Val
                325                 330                 335

Thr Thr Tyr Asn His Ala Glu Asp Leu Cys Leu Tyr Phe Arg Thr Arg
            340                 345                 350

Ser Ser Ser Gln Ser Leu Tyr Tyr Gly Gln Leu Ile Met Asn Asp Gly
        355                 360                 365
```

-continued

```
Arg Asn Lys Ser Leu Leu Asn Tyr Thr Leu Lys Gly Ser Thr Tyr Trp
370                 375                 380

Ile Trp Ser Ser Ala Trp Tyr Tyr Glu Asn Tyr Asn Thr Ser Ser Lys
385                 390                 395                 400

Thr Ala Gly Asn Trp Tyr Phe Ile Pro Val Asp Glu Gly Trp Lys Glu
                405                 410                 415

Asp
```

<210> SEQ ID NO 5
<211> LENGTH: 866
<212> TYPE: PRT
<213> ORGANISM: Artificial Sequence
<220> FEATURE:
<223> OTHER INFORMATION: Synthetic Polypeptide

<400> SEQUENCE: 5

```
Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

Pro Asn Val Trp Val Pro Glu Arg Tyr Thr Phe Tyr Ser Thr Met
50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
        275                 280                 285

Ile Pro Gly Ile Leu Asn Leu Ile Lys Thr Thr Val Glu Pro Ile Ile
290                 295                 300

Asn Lys Ile Thr Asp Pro His Asp Glu Met Leu Gln Cys Leu Gln Ser
```

-continued

```
                305                 310                 315                 320
        Lys Tyr Pro Ser Leu Lys Gly Thr Leu Gly Gln Phe Phe Asp Asp
                            325                 330                 335

Thr Gln Leu Glu Lys Asp Ile Arg Asp Leu Trp Met Val Met Asn Glu
                            340                 345                 350

Thr Met Phe Ala Glu Asn Leu Lys Ala Leu Thr Arg Ala Arg Tyr Leu
                            355                 360                 365

Val Pro Lys Val Glu Asn Ile Val Gln Val Asp Ile Leu Ser Pro Asn
                    370                 375                 380

Val Tyr Thr Ile Asp Lys Gly Phe Asn His Leu Ser Lys Gly Phe Lys
        385                 390                 395                 400

Gly Gln Ser Val Ser Gln Ser Tyr Phe Arg Lys Ile Ser Ala Leu Ala
                            405                 410                 415

Arg Gly Ala Val Arg Ala Cys Pro Asn Pro His Phe Ser Ser Gln
                    420                 425                 430

Leu Val Pro Arg Gly Ser Leu Ser Ser Cys Ile Glu Ile Leu Glu Asp
                    435                 440                 445

Asp Leu Phe Ile Met Ser Ser Lys Asp Ser Phe Thr Asp Thr Asp Phe
                    450                 455                 460

Ser Glu Pro Ser Val Gly Pro Val Ser Tyr Lys Ala Lys Lys Gly Ala
        465                 470                 475                 480

Asp Thr Ile Leu Asp Ser Thr Leu Ser Asn Tyr Asp Phe Ser Lys Glu
                            485                 490                 495

Ile Asn Phe Thr Ser Thr Val Pro Ile Ile Thr Val Glu Asp Pro Leu
                    500                 505                 510

Glu Thr Asp Glu Asp Val Pro Val Ile Ser Glu Asp Arg Thr Val Tyr
                    515                 520                 525

Val Asp Asp Tyr Thr Thr Phe His Phe Leu Glu Ala Gln Lys Ile Gly
                    530                 535                 540

Lys Glu Val Val Pro Thr Gln Thr Lys Val Val Phe Thr Thr Asn Met
        545                 550                 555                 560

Glu Glu Ala Leu Phe Asp Ser Lys Lys Val Tyr Thr Val Phe Glu Asn
                            565                 570                 575

Thr Ala Ser Arg Ile Asn Glu Ala Gly Thr Gly Ile Ala Asn Gly Met
                    580                 585                 590

Met Phe Tyr Gln Trp Leu Lys Gly Ile Val Gln Asp Phe Thr Glu Glu
                    595                 600                 605

Ala Thr Gln Lys Asp Thr Phe Asp Lys Ile Ser Asp Val Thr Met Ile
                    610                 615                 620

Val Pro Tyr Leu Gly Asn Ile Leu Asn Ile Gly Asn Asp Ile Arg Lys
        625                 630                 635                 640

Gly Asp Phe Met Gly Ala Val Glu Leu Gly Val Thr Ile Leu Leu
                            645                 650                 655

Glu Ala Ile Pro Glu Leu Thr Leu Pro Val Leu Ile Gly Leu Thr Ile
                            660                 665                 670

Ile Glu Asp Glu Leu Glu Lys Glu Gln Val Ser Gln Thr Val Tyr Asn
                    675                 680                 685

Val Leu Asp Lys Arg Asp Glu Lys Trp Glu Val Tyr Gly Phe Val
                    690                 695                 700

Lys Gln Gln Trp Trp Met Val His Thr Gln Phe Glu Thr Arg Ile
        705                 710                 715                 720

Leu His Ala Tyr Gln Ala Leu Asn His Gln Val Glu Ala Ile Lys Ala
                            725                 730                 735
```

```
Asn Met Thr Tyr Gln Leu Ala Asn Tyr Arg Gly Asn Gln Glu Asp Lys
            740                 745                 750

Glu Leu Leu Glu Lys Ala Ile Asp Asp Thr Leu Gln Ser Leu Tyr Tyr
            755                 760                 765

Ala Val Asp Gln Ala Met His Asn Ile Lys Arg Phe Leu Ile Gln Ser
770                 775                 780

Ser Lys Ser Tyr Leu Leu Asn Gln Met Leu Pro Lys Thr Lys Glu Gln
785                 790                 795                 800

Leu Leu Ala Phe Asp Gln Gln Thr Leu Arg Asn Val Asn Asp Phe Ile
                805                 810                 815

Asn Lys Asn Gln Gly Val Leu Gly Glu Ser Leu Ala Lys Asp Leu Lys
            820                 825                 830

Lys Lys Val Glu Lys Arg Leu Thr Ser Leu Pro Val Phe Asn Leu Glu
            835                 840                 845

Asp Leu Pro Ile Ser Glu Phe Glu Asp Leu Ile His Ser His Glu Ile
            850                 855                 860

Asp Ile
865

<210> SEQ ID NO 6
<211> LENGTH: 872
<212> TYPE: PRT
<213> ORGANISM: Artificial Sequence
<220> FEATURE:
<223> OTHER INFORMATION: Synthetic Polypeptide

<400> SEQUENCE: 6

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
            20                  25                  30

Gln Phe Ile Asn His Asn Val Pro Asp Leu Lys Ala Phe Gln Val Phe
        35                  40                  45

Pro Asn Val Trp Val Val Pro Glu Arg Tyr Thr Phe Tyr Ser Thr Met
50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
    130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
    210                 215                 220
```

```
His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
        275                 280                 285

Ile Pro Gly Ile Leu Asn Leu Ile Lys Thr Thr Val Glu Pro Ile Ile
    290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
        355                 360                 365

Val Pro Lys Val Glu Asn Ile Val Gln Val Asp Ile Leu Ser Pro Asn
370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Val Arg Gly Ile Ile Thr Ser Lys
            420                 425                 430

Thr Lys Ser Leu Asp Lys Gly Tyr Asn Lys Ala Leu Asn Asp Leu Cys
        435                 440                 445

Ile Glu Ile Leu Glu Asp Asp Leu Phe Ile Met Ser Ser Lys Asp Ser
    450                 455                 460

Phe Thr Asp Thr Asp Phe Ser Glu Pro Ser Val Gly Pro Val Ser Tyr
465                 470                 475                 480

Lys Ala Lys Lys Gly Ala Asp Thr Ile Leu Asp Ser Thr Leu Ser Asn
                485                 490                 495

Tyr Asp Phe Ser Lys Glu Ile Asn Phe Thr Ser Thr Val Pro Ile Ile
            500                 505                 510

Thr Val Glu Asp Pro Leu Glu Thr Asp Glu Asp Val Pro Val Ile Ser
        515                 520                 525

Glu Asp Arg Thr Val Tyr Val Asp Tyr Thr Thr Phe His Phe Leu
530                 535                 540

Glu Ala Gln Lys Ile Gly Lys Glu Val Val Pro Thr Gln Thr Lys Val
545                 550                 555                 560

Val Phe Thr Thr Asn Met Glu Glu Ala Leu Phe Asp Ser Lys Lys Val
                565                 570                 575

Tyr Thr Val Phe Glu Asn Thr Ala Ser Arg Ile Asn Glu Ala Gly Thr
            580                 585                 590

Gly Ile Ala Asn Gly Met Met Phe Tyr Gln Trp Leu Lys Gly Ile Val
        595                 600                 605

Gln Asp Phe Thr Glu Glu Ala Thr Gln Lys Asp Thr Phe Asp Lys Ile
    610                 615                 620

Ser Asp Val Thr Met Ile Val Pro Tyr Leu Gly Asn Ile Leu Asn Ile
625                 630                 635                 640
```

```
Gly Asn Asp Ile Arg Lys Gly Asp Phe Met Gly Ala Val Glu Leu Gly
            645                 650                 655

Gly Val Thr Ile Leu Leu Glu Ala Ile Pro Glu Leu Thr Leu Pro Val
        660                 665                 670

Leu Ile Gly Leu Thr Ile Ile Glu Asp Glu Leu Glu Lys Glu Gln Val
    675                 680                 685

Ser Gln Thr Val Tyr Asn Val Leu Asp Lys Arg Asp Glu Lys Trp Glu
690                 695                 700

Glu Val Tyr Gly Phe Val Lys Gln Gln Trp Trp Met Val His Thr
705                 710                 715                 720

Gln Phe Glu Thr Arg Ile Leu His Ala Tyr Gln Ala Leu Asn His Gln
                725                 730                 735

Val Glu Ala Ile Lys Ala Asn Met Thr Tyr Gln Leu Ala Asn Tyr Arg
            740                 745                 750

Gly Asn Gln Glu Asp Lys Glu Leu Leu Glu Lys Ala Ile Asp Asp Thr
        755                 760                 765

Leu Gln Ser Leu Tyr Tyr Ala Val Asp Gln Ala Met His Asn Ile Lys
    770                 775                 780

Arg Phe Leu Ile Gln Ser Ser Lys Ser Tyr Leu Leu Asn Gln Met Leu
785                 790                 795                 800

Pro Lys Thr Lys Glu Gln Leu Leu Ala Phe Asp Gln Gln Thr Leu Arg
                805                 810                 815

Asn Val Asn Asp Phe Ile Asn Lys Asn Gln Gly Val Leu Gly Glu Ser
            820                 825                 830

Leu Ala Lys Asp Leu Lys Lys Lys Val Glu Lys Arg Leu Thr Ser Leu
        835                 840                 845

Pro Val Phe Asn Leu Glu Asp Leu Pro Ile Ser Glu Phe Glu Asp Leu
    850                 855                 860

Ile His Ser His Glu Ile Asp Ile
865                 870

<210> SEQ ID NO 7
<211> LENGTH: 857
<212> TYPE: PRT
<213> ORGANISM: Artificial Sequence
<220> FEATURE:
<223> OTHER INFORMATION: Synthetic Polypeptide

<400> SEQUENCE: 7

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
            20                  25                  30

Gln Phe Ile Asn His Asn Val Pro Asp Leu Lys Ala Phe Gln Val Phe
        35                  40                  45

Pro Asn Val Trp Val Val Pro Glu Arg Tyr Thr Phe Tyr Ser Thr Met
    50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125
```

```
Gly Asp Val Ala Met Gly Thr Thr Gln Val Ile Lys Gln Met Asp Asp
130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
        275                 280                 285

Ile Pro Gly Ile Leu Asn Leu Ile Lys Thr Thr Val Glu Pro Ile Ile
290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
        355                 360                 365

Val Pro Lys Val Glu Asn Ile Val Gln Val Asp Ile Leu Ser Pro Asn
370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Lys Ser Val Lys Ala Pro Gly Ile
            420                 425                 430

Cys Ile Glu Ile Leu Glu Asp Asp Leu Phe Ile Met Ser Ser Lys Asp
        435                 440                 445

Ser Phe Thr Asp Thr Asp Phe Ser Glu Pro Ser Val Gly Pro Val Ser
450                 455                 460

Tyr Lys Ala Lys Lys Gly Ala Asp Thr Ile Leu Asp Ser Thr Leu Ser
465                 470                 475                 480

Asn Tyr Asp Phe Ser Lys Glu Ile Asn Phe Thr Ser Thr Val Pro Ile
                485                 490                 495

Ile Thr Val Glu Asp Pro Leu Glu Thr Asp Glu Asp Val Pro Val Ile
            500                 505                 510

Ser Glu Asp Arg Thr Val Tyr Val Asp Asp Tyr Thr Thr Phe His Phe
        515                 520                 525

Leu Glu Ala Gln Lys Ile Gly Lys Glu Val Val Pro Thr Gln Thr Lys
530                 535                 540

Val Val Phe Thr Thr Asn Met Glu Glu Ala Leu Phe Asp Ser Lys Lys
```

```
                545                 550                 555                 560
Val Tyr Thr Val Phe Glu Asn Thr Ala Ser Arg Ile Asn Glu Ala Gly
                    565                 570                 575

Thr Gly Ile Ala Asn Gly Met Met Phe Tyr Gln Trp Leu Lys Gly Ile
            580                 585                 590

Val Gln Asp Phe Thr Glu Glu Ala Thr Gln Lys Asp Thr Phe Asp Lys
                595                 600                 605

Ile Ser Asp Val Thr Met Ile Val Pro Tyr Leu Gly Asn Ile Leu Asn
            610                 615                 620

Ile Gly Asn Asp Ile Arg Lys Gly Asp Phe Met Gly Ala Val Glu Leu
625                 630                 635                 640

Gly Gly Val Thr Ile Leu Leu Glu Ala Ile Pro Glu Leu Thr Leu Pro
                645                 650                 655

Val Leu Ile Gly Leu Thr Ile Ile Glu Asp Glu Leu Glu Lys Glu Gln
            660                 665                 670

Val Ser Gln Thr Val Tyr Asn Val Leu Asp Lys Arg Asp Glu Lys Trp
                675                 680                 685

Glu Glu Val Tyr Gly Phe Val Lys Gln Gln Trp Trp Trp Met Val His
            690                 695                 700

Thr Gln Phe Glu Thr Arg Ile Leu His Ala Tyr Gln Ala Leu Asn His
705                 710                 715                 720

Gln Val Glu Ala Ile Lys Ala Asn Met Thr Tyr Gln Leu Ala Asn Tyr
                725                 730                 735

Arg Gly Asn Gln Glu Asp Lys Glu Leu Leu Glu Lys Ala Ile Asp Asp
            740                 745                 750

Thr Leu Gln Ser Leu Tyr Tyr Ala Val Asp Gln Ala Met His Asn Ile
                755                 760                 765

Lys Arg Phe Leu Ile Gln Ser Ser Lys Ser Tyr Leu Leu Asn Gln Met
            770                 775                 780

Leu Pro Lys Thr Lys Glu Gln Leu Leu Ala Phe Asp Gln Gln Thr Leu
785                 790                 795                 800

Arg Asn Val Asn Asp Phe Ile Asn Lys Asn Gln Gly Val Leu Gly Glu
                805                 810                 815

Ser Leu Ala Lys Asp Leu Lys Lys Lys Val Glu Lys Arg Leu Thr Ser
            820                 825                 830

Leu Pro Val Phe Asn Leu Glu Asp Leu Pro Ile Ser Glu Phe Glu Asp
835                 840                 845

Leu Ile His Ser His Glu Ile Asp Ile
    850                 855

<210> SEQ ID NO 8
<211> LENGTH: 864
<212> TYPE: PRT
<213> ORGANISM: Artificial Sequence
<220> FEATURE:
<223> OTHER INFORMATION: Synthetic Polypeptide

<400> SEQUENCE: 8

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                    20                  25                  30

Gln Phe Ile Asn His Asn Val Pro Asp Leu Lys Ala Phe Gln Val Phe
            35                  40                  45

Pro Asn Val Trp Val Val Pro Glu Arg Tyr Thr Phe Tyr Ser Thr Met
```

```
            50                  55                  60
Lys Asn Leu Asp Ala Pro Ala Asn Pro Ser Arg Ser Ser Tyr Tyr Asp
 65                  70                  75                  80

Pro Thr Tyr Leu Gln Ser Asp Ala Glu Lys Glu Val Phe Leu Gln Gln
                     85                  90                  95

Met Ile Leu Leu Phe Lys Arg Ile Asn Ser Thr Gln Glu Gly Gln Gln
                100                 105                 110

Phe Leu Asn Leu Leu Ser Arg Ser Ile Pro Val Pro Tyr Glu Ser Asn
                115                 120                 125

Gly Asp Val Ala Met Gly Thr Thr Gln Val Ile Lys Gln Met Asp Asp
130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
                180                 185                 190

Tyr His Lys Thr Tyr Ser Thr Lys Leu Thr Asn Lys Asn Ser Leu Val
            195                 200                 205

Asp Lys Ser Val Gln Glu Phe Val Pro Asp Pro Ala Val Thr Leu Ile
            210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
                260                 265                 270

Phe Gly Gly Glu Asp Val Lys Val Ile Lys Ser Glu Ile Asp Lys Lys
                275                 280                 285

Ile Pro Gly Ile Leu Asn Leu Ile Lys Thr Thr Val Glu Pro Ile Ile
                290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
                340                 345                 350

Thr Met Phe Ala Glu Asn Leu Lys Ala Leu Thr Arg Ala Arg Tyr Leu
                355                 360                 365

Val Pro Lys Val Glu Asn Ile Val Gln Val Asp Ile Leu Ser Pro Asn
            370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys His Lys Ala Ile Asp Gly Arg Ser
                420                 425                 430

Leu Tyr Asn Lys Thr Leu Asp Cys Ile Glu Ile Leu Glu Asp Asp Leu
                435                 440                 445

Phe Ile Met Ser Ser Lys Asp Ser Phe Thr Asp Thr Asp Phe Ser Glu
                450                 455                 460

Pro Ser Val Gly Pro Val Ser Tyr Lys Ala Lys Lys Gly Ala Asp Thr
465                 470                 475                 480
```

Ile Leu Asp Ser Thr Leu Ser Asn Tyr Asp Phe Ser Lys Glu Ile Asn
            485                 490                 495

Phe Thr Ser Thr Val Pro Ile Ile Thr Val Glu Asp Pro Leu Glu Thr
            500                 505                 510

Asp Glu Asp Val Pro Val Ile Ser Glu Asp Arg Thr Val Tyr Val Asp
            515                 520                 525

Asp Tyr Thr Thr Phe His Phe Leu Glu Ala Gln Lys Ile Gly Lys Glu
            530                 535                 540

Val Val Pro Thr Gln Thr Lys Val Val Phe Thr Thr Asn Met Glu Glu
545                 550                 555                 560

Ala Leu Phe Asp Ser Lys Lys Val Tyr Thr Val Phe Glu Asn Thr Ala
            565                 570                 575

Ser Arg Ile Asn Glu Ala Gly Thr Gly Ile Ala Asn Gly Met Met Phe
            580                 585                 590

Tyr Gln Trp Leu Lys Gly Ile Val Gln Asp Phe Thr Glu Glu Ala Thr
            595                 600                 605

Gln Lys Asp Thr Phe Asp Lys Ile Ser Asp Val Thr Met Ile Val Pro
            610                 615                 620

Tyr Leu Gly Asn Ile Leu Asn Ile Gly Asn Asp Ile Arg Lys Gly Asp
625                 630                 635                 640

Phe Met Gly Ala Val Glu Leu Gly Gly Val Thr Ile Leu Leu Glu Ala
            645                 650                 655

Ile Pro Glu Leu Thr Leu Pro Val Leu Ile Gly Leu Thr Ile Ile Glu
            660                 665                 670

Asp Glu Leu Glu Lys Glu Gln Val Ser Gln Thr Val Tyr Asn Val Leu
            675                 680                 685

Asp Lys Arg Asp Glu Lys Trp Glu Glu Val Tyr Gly Phe Val Lys Gln
            690                 695                 700

Gln Trp Trp Trp Met Val His Thr Gln Phe Glu Thr Arg Ile Leu His
705                 710                 715                 720

Ala Tyr Gln Ala Leu Asn His Gln Val Glu Ala Ile Lys Ala Asn Met
            725                 730                 735

Thr Tyr Gln Leu Ala Asn Tyr Arg Gly Asn Gln Glu Asp Lys Glu Leu
            740                 745                 750

Leu Glu Lys Ala Ile Asp Asp Thr Leu Gln Ser Leu Tyr Tyr Ala Val
            755                 760                 765

Asp Gln Ala Met His Asn Ile Lys Arg Phe Leu Ile Gln Ser Ser Lys
            770                 775                 780

Ser Tyr Leu Leu Asn Gln Met Leu Pro Lys Thr Lys Glu Gln Leu Leu
785                 790                 795                 800

Ala Phe Asp Gln Gln Thr Leu Arg Asn Val Asn Asp Phe Ile Asn Lys
            805                 810                 815

Asn Gln Gly Val Leu Gly Glu Ser Leu Ala Lys Asp Leu Lys Lys Lys
            820                 825                 830

Val Glu Lys Arg Leu Thr Ser Leu Pro Val Phe Asn Leu Glu Asp Leu
            835                 840                 845

Pro Ile Ser Glu Phe Glu Asp Leu Ile His Ser His Glu Ile Asp Ile
            850                 855                 860

<210> SEQ ID NO 9
<211> LENGTH: 861
<212> TYPE: PRT
<213> ORGANISM: Artificial Sequence
<220> FEATURE:

<223> OTHER INFORMATION: Synthetic Polypeptide

<400> SEQUENCE: 9

```
Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
            20                  25                  30

Gln Phe Ile Asn His Asn Val Pro Asp Leu Lys Ala Phe Gln Val Phe
        35                  40                  45

Pro Asn Val Trp Val Val Pro Glu Arg Tyr Thr Phe Tyr Ser Thr Met
    50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
    210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
        275                 280                 285

Ile Pro Gly Ile Leu Asn Leu Ile Lys Thr Thr Val Glu Pro Ile Ile
    290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
        355                 360                 365

Val Pro Lys Val Glu Asn Ile Val Gln Val Asp Ile Leu Ser Pro Asn
    370                 375                 380

Val Tyr Thr Ile Asp Lys Gly Phe Asn His Leu Ser Lys Gly Phe Lys
385                 390                 395                 400
```

```
Gly Gln Ser Val Ser Gln Ser Tyr Phe Arg Lys Ile Ser Ala Leu Ala
                405                 410                 415

Arg Gly Ala Val Val Arg Ala Cys Leu Arg Leu Thr Lys Asn Ser Arg
            420                 425                 430

Asp Asp Ser Thr Cys Ile Glu Ile Leu Glu Asp Asp Leu Phe Ile Met
        435                 440                 445

Ser Ser Lys Asp Ser Phe Thr Asp Thr Asp Phe Ser Glu Pro Ser Val
    450                 455                 460

Gly Pro Val Ser Tyr Lys Ala Lys Lys Gly Asp Thr Ile Leu Asp
465                 470                 475                 480

Ser Thr Leu Ser Asn Tyr Asp Phe Ser Lys Glu Ile Asn Phe Thr Ser
                485                 490                 495

Thr Val Pro Ile Ile Thr Val Glu Asp Pro Leu Glu Thr Asp Glu Asp
            500                 505                 510

Val Pro Val Ile Ser Glu Asp Arg Thr Val Tyr Val Asp Asp Tyr Thr
        515                 520                 525

Thr Phe His Phe Leu Glu Ala Gln Lys Ile Gly Lys Glu Val Val Pro
    530                 535                 540

Thr Gln Thr Lys Val Val Phe Thr Thr Asn Met Glu Glu Ala Leu Phe
545                 550                 555                 560

Asp Ser Lys Lys Val Tyr Thr Val Phe Glu Asn Thr Ala Ser Arg Ile
                565                 570                 575

Asn Glu Ala Gly Thr Gly Ile Ala Asn Gly Met Met Phe Tyr Gln Trp
            580                 585                 590

Leu Lys Gly Ile Val Gln Asp Phe Thr Glu Ala Thr Gln Lys Asp
        595                 600                 605

Thr Phe Asp Lys Ile Ser Asp Val Thr Met Ile Val Pro Tyr Leu Gly
    610                 615                 620

Asn Ile Leu Asn Ile Gly Asn Asp Ile Arg Lys Gly Asp Phe Met Gly
625                 630                 635                 640

Ala Val Glu Leu Gly Gly Val Thr Ile Leu Leu Glu Ala Ile Pro Glu
                645                 650                 655

Leu Thr Leu Pro Val Leu Ile Gly Leu Thr Ile Ile Glu Asp Glu Leu
            660                 665                 670

Glu Lys Glu Gln Val Ser Gln Thr Val Tyr Asn Val Leu Asp Lys Arg
        675                 680                 685

Asp Glu Lys Trp Glu Glu Val Tyr Gly Phe Val Lys Gln Gln Trp Trp
    690                 695                 700

Trp Met Val His Thr Gln Phe Glu Thr Arg Ile Leu His Ala Tyr Gln
705                 710                 715                 720

Ala Leu Asn His Gln Val Glu Ala Ile Lys Ala Asn Met Thr Tyr Gln
                725                 730                 735

Leu Ala Asn Tyr Arg Gly Asn Gln Glu Asp Lys Glu Leu Leu Glu Lys
            740                 745                 750

Ala Ile Asp Asp Thr Leu Gln Ser Leu Tyr Tyr Ala Val Asp Gln Ala
        755                 760                 765

Met His Asn Ile Lys Arg Phe Leu Ile Gln Ser Ser Lys Ser Tyr Leu
    770                 775                 780

Leu Asn Gln Met Leu Pro Lys Thr Lys Glu Gln Leu Leu Ala Phe Asp
785                 790                 795                 800

Gln Gln Thr Leu Arg Asn Val Asn Asp Phe Ile Asn Lys Asn Gln Gly
                805                 810                 815

Val Leu Gly Glu Ser Leu Ala Lys Asp Leu Lys Lys Lys Val Glu Lys
```

```
                    820                 825                 830
Arg Leu Thr Ser Leu Pro Val Phe Asn Leu Glu Asp Leu Pro Ile Ser
                835                 840                 845

Glu Phe Glu Asp Leu Ile His Ser His Glu Ile Asp Ile
            850                 855                 860

<210> SEQ ID NO 10
<211> LENGTH: 862
<212> TYPE: PRT
<213> ORGANISM: Artificial Sequence
<220> FEATURE:
<223> OTHER INFORMATION: Synthetic Polypeptide

<400> SEQUENCE: 10

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

Pro Asn Val Trp Val Pro Glu Arg Tyr Thr Phe Tyr Ser Thr Met
    50                  55                  60

Lys Asn Leu Asp Ala Pro Ala Asn Pro Ser Arg Ser Ser Tyr Tyr Asp
65              70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
    130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
    210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
        275                 280                 285

Ile Pro Gly Ile Leu Asn Leu Ile Lys Thr Thr Val Glu Pro Ile Ile
    290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Phe Asp Asp
```

-continued

```
                325                 330                 335
Thr Gln Leu Glu Lys Asp Ile Arg Asp Leu Trp Met Val Met Asn Glu
                340                 345                 350
Thr Met Phe Ala Glu Asn Leu Lys Ala Leu Thr Arg Ala Arg Tyr Leu
                355                 360                 365
Val Pro Lys Val Glu Asn Ile Val Gln Val Asp Ile Leu Ser Pro Asn
    370                 375                 380
Val Tyr Thr Ile Asp Lys Gly Phe Asn His Leu Ser Lys Gly Phe Lys
385                 390                 395                 400
Gly Gln Ser Val Ser Gln Ser Tyr Phe Arg Lys Ile Ser Ala Leu Ala
                405                 410                 415
Arg Gly Ala Val Val Arg Ala Cys Lys Asn Ile Val Ser Val Lys Gly
                420                 425                 430
Ile Arg Lys Ser Ile Cys Ile Glu Ile Leu Glu Asp Asp Leu Phe Ile
                435                 440                 445
Met Ser Ser Lys Asp Ser Phe Thr Asp Thr Asp Phe Ser Glu Pro Ser
    450                 455                 460
Val Gly Pro Val Ser Tyr Lys Ala Lys Lys Gly Ala Asp Thr Ile Leu
465                 470                 475                 480
Asp Ser Thr Leu Ser Asn Tyr Asp Phe Ser Lys Glu Ile Asn Phe Thr
                485                 490                 495
Ser Thr Val Pro Ile Ile Thr Val Glu Asp Pro Leu Glu Thr Asp Glu
                500                 505                 510
Asp Val Pro Val Ile Ser Glu Asp Arg Thr Val Tyr Val Asp Asp Tyr
                515                 520                 525
Thr Thr Phe His Phe Leu Glu Ala Gln Lys Ile Gly Lys Glu Val Val
    530                 535                 540
Pro Thr Gln Thr Lys Val Val Phe Thr Thr Asn Met Glu Glu Ala Leu
545                 550                 555                 560
Phe Asp Ser Lys Lys Val Tyr Thr Val Phe Glu Asn Thr Ala Ser Arg
                565                 570                 575
Ile Asn Glu Ala Gly Thr Gly Ile Ala Asn Gly Met Met Phe Tyr Gln
                580                 585                 590
Trp Leu Lys Gly Ile Val Gln Asp Phe Thr Glu Glu Ala Thr Gln Lys
                595                 600                 605
Asp Thr Phe Asp Lys Ile Ser Asp Val Thr Met Ile Val Pro Tyr Leu
    610                 615                 620
Gly Asn Ile Leu Asn Ile Gly Asn Asp Ile Arg Lys Gly Asp Phe Met
625                 630                 635                 640
Gly Ala Val Glu Leu Gly Gly Val Thr Ile Leu Leu Glu Ala Ile Pro
                645                 650                 655
Glu Leu Thr Leu Pro Val Leu Ile Gly Leu Thr Ile Ile Glu Asp Glu
                660                 665                 670
Leu Glu Lys Glu Gln Val Ser Gln Thr Val Tyr Asn Val Leu Asp Lys
                675                 680                 685
Arg Asp Glu Lys Trp Glu Glu Val Tyr Gly Phe Val Lys Gln Gln Trp
    690                 695                 700
Trp Trp Met Val His Thr Gln Phe Glu Thr Arg Ile Leu His Ala Tyr
705                 710                 715                 720
Gln Ala Leu Asn His Gln Val Glu Ala Ile Lys Ala Asn Met Thr Tyr
                725                 730                 735
Gln Leu Ala Asn Tyr Arg Gly Asn Gln Glu Asp Lys Glu Leu Leu Glu
                740                 745                 750
```

```
Lys Ala Ile Asp Asp Thr Leu Gln Ser Leu Tyr Tyr Ala Val Asp Gln
                755                 760                 765

Ala Met His Asn Ile Lys Arg Phe Leu Ile Gln Ser Ser Lys Ser Tyr
        770                 775                 780

Leu Leu Asn Gln Met Leu Pro Lys Thr Lys Glu Gln Leu Leu Ala Phe
785                 790                 795                 800

Asp Gln Gln Thr Leu Arg Asn Val Asn Asp Phe Ile Asn Lys Asn Gln
                805                 810                 815

Gly Val Leu Gly Glu Ser Leu Ala Lys Asp Leu Lys Lys Lys Val Glu
                820                 825                 830

Lys Arg Leu Thr Ser Leu Pro Val Phe Asn Leu Glu Asp Leu Pro Ile
                835                 840                 845

Ser Glu Phe Glu Asp Leu Ile His Ser His Glu Ile Asp Ile
                850                 855                 860
```

<210> SEQ ID NO 11
<211> LENGTH: 864
<212> TYPE: PRT
<213> ORGANISM: Artificial Sequence
<220> FEATURE:
<223> OTHER INFORMATION: Synthetic Polypeptide

<400> SEQUENCE: 11

```
Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

Pro Asn Val Trp Val Val Pro Glu Arg Tyr Thr Phe Tyr Ser Thr Met
50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
                100                 105                 110

Phe Leu Asn Leu Leu Ser Arg Ser Ile Pro Val Pro Tyr Glu Ser Asn
            115                 120                 125

Gly Asp Val Ala Met Gly Thr Thr Gln Val Ile Lys Gln Met Asp Asp
130                 135                 140

Lys Gly Asn Val Leu Lys His Arg Arg Ala His Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
                180                 185                 190

Tyr His Lys Thr Tyr Ser Thr Lys Leu Thr Asn Lys Asn Ser Leu Val
            195                 200                 205

Asp Lys Ser Val Gln Glu Phe Val Pro Asp Pro Ala Val Thr Leu Ile
210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255
```

```
Ser Trp Phe Ser Ser Lys Glu Ala Val Asn Phe Glu Val Met Thr
            260                 265                 270

Phe Gly Gly Glu Asp Val Lys Val Ile Lys Ser Glu Ile Asp Lys Lys
        275                 280                 285

Ile Pro Gly Ile Leu Asn Leu Ile Lys Thr Thr Val Glu Pro Ile Ile
290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
            325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
            355                 360                 365

Val Pro Lys Val Glu Asn Ile Val Gln Val Asp Ile Leu Ser Pro Asn
            370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
            405                 410                 415

Arg Gly Ala Val Val Arg Ala Cys Lys Ser Val Ile Pro Arg Lys Gly
            420                 425                 430

Thr Lys Ala Pro Pro Arg Leu Cys Ile Glu Ile Leu Glu Asp Asp Leu
            435                 440                 445

Phe Ile Met Ser Ser Lys Asp Ser Phe Thr Asp Thr Asp Phe Ser Glu
            450                 455                 460

Pro Ser Val Gly Pro Val Ser Tyr Lys Ala Lys Lys Gly Ala Asp Thr
465                 470                 475                 480

Ile Leu Asp Ser Thr Leu Ser Asn Tyr Asp Phe Ser Lys Glu Ile Asn
            485                 490                 495

Phe Thr Ser Thr Val Pro Ile Ile Thr Val Glu Asp Pro Leu Glu Thr
            500                 505                 510

Asp Glu Asp Val Pro Val Ile Ser Glu Asp Arg Thr Val Tyr Val Asp
            515                 520                 525

Asp Tyr Thr Thr Phe His Phe Leu Glu Ala Gln Lys Ile Gly Lys Glu
            530                 535                 540

Val Val Pro Thr Gln Thr Lys Val Val Phe Thr Thr Asn Met Glu Glu
545                 550                 555                 560

Ala Leu Phe Asp Ser Lys Lys Val Tyr Thr Val Phe Glu Asn Thr Ala
                565                 570                 575

Ser Arg Ile Asn Glu Ala Gly Thr Gly Ile Ala Asn Gly Met Met Phe
            580                 585                 590

Tyr Gln Trp Leu Lys Gly Ile Val Gln Asp Phe Thr Glu Glu Ala Thr
            595                 600                 605

Gln Lys Asp Thr Phe Asp Lys Ile Ser Asp Val Thr Met Ile Val Pro
            610                 615                 620

Tyr Leu Gly Asn Ile Leu Asn Ile Gly Asn Asp Ile Arg Lys Gly Asp
625                 630                 635                 640

Phe Met Gly Ala Val Glu Leu Gly Gly Val Thr Ile Leu Leu Glu Ala
                645                 650                 655

Ile Pro Glu Leu Thr Leu Pro Val Leu Ile Gly Leu Thr Ile Ile Glu
            660                 665                 670
```

Asp Glu Leu Glu Lys Glu Gln Val Ser Gln Thr Val Tyr Asn Val Leu
            675                 680                 685

Asp Lys Arg Asp Glu Lys Trp Glu Val Tyr Gly Phe Val Lys Gln
690                 695                 700

Gln Trp Trp Trp Met Val His Thr Gln Phe Glu Thr Arg Ile Leu His
705                 710                 715                 720

Ala Tyr Gln Ala Leu Asn His Gln Val Glu Ala Ile Lys Ala Asn Met
            725                 730                 735

Thr Tyr Gln Leu Ala Asn Tyr Arg Gly Asn Gln Glu Asp Lys Glu Leu
            740                 745                 750

Leu Glu Lys Ala Ile Asp Asp Thr Leu Gln Ser Leu Tyr Tyr Ala Val
            755                 760                 765

Asp Gln Ala Met His Asn Ile Lys Arg Phe Leu Ile Gln Ser Ser Lys
            770                 775                 780

Ser Tyr Leu Leu Asn Gln Met Leu Pro Lys Thr Lys Glu Gln Leu Leu
785                 790                 795                 800

Ala Phe Asp Gln Gln Thr Leu Arg Asn Val Asn Asp Phe Ile Asn Lys
                805                 810                 815

Asn Gln Gly Val Leu Gly Glu Ser Leu Ala Lys Asp Leu Lys Lys Lys
            820                 825                 830

Val Glu Lys Arg Leu Thr Ser Leu Pro Val Phe Asn Leu Glu Asp Leu
            835                 840                 845

Pro Ile Ser Glu Phe Glu Asp Leu Ile His Ser His Glu Ile Asp Ile
            850                 855                 860

<210> SEQ ID NO 12
<211> LENGTH: 862
<212> TYPE: PRT
<213> ORGANISM: Artificial Sequence
<220> FEATURE:
<223> OTHER INFORMATION: Synthetic Polypeptide

<400> SEQUENCE: 12

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
            20                  25                  30

Gln Phe Ile Asn His Asn Val Pro Asp Leu Lys Ala Phe Gln Val Phe
        35                  40                  45

Pro Asn Val Trp Val Pro Glu Arg Tyr Thr Phe Tyr Ser Thr Met
    50                  55                  60

Lys Asn Leu Asp Ala Pro Ala Asn Pro Ser Arg Ser Tyr Tyr Asp
65                  70                  75                  80

Pro Thr Tyr Leu Gln Ser Asp Ala Glu Lys Glu Val Phe Leu Gln Gln
            85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
130                 135                 140

Lys Gly Asn Val Leu Lys His Arg Arg Ala His Ile Ile Tyr Gly
145                 150                 155                 160

Pro Gly Pro Asp Leu Met Ala Lys Gly Ser Lys Ala Leu Thr Lys Ser
            165                 170                 175

-continued

```
Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
    210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
        275                 280                 285

Ile Pro Gly Ile Leu Asn Leu Ile Lys Thr Thr Val Glu Pro Ile Ile
    290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
        355                 360                 365

Val Pro Lys Val Glu Asn Ile Val Gln Val Asp Ile Leu Ser Pro Asn
    370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Lys Pro Val Met Tyr Lys Asn Thr
            420                 425                 430

Gly Lys Ser Glu Gln Cys Ile Glu Ile Leu Glu Asp Asp Leu Phe Ile
        435                 440                 445

Met Ser Ser Lys Asp Ser Phe Thr Asp Thr Asp Phe Ser Glu Pro Ser
    450                 455                 460

Val Gly Pro Val Ser Tyr Lys Ala Lys Lys Gly Ala Asp Thr Ile Leu
465                 470                 475                 480

Asp Ser Thr Leu Ser Asn Tyr Asp Phe Ser Lys Glu Ile Asn Phe Thr
                485                 490                 495

Ser Thr Val Pro Ile Ile Thr Val Glu Asp Pro Leu Glu Thr Asp Glu
            500                 505                 510

Asp Val Pro Val Ile Ser Glu Asp Arg Thr Val Tyr Val Asp Asp Tyr
        515                 520                 525

Thr Thr Phe His Phe Leu Glu Ala Gln Lys Ile Gly Lys Glu Val Val
    530                 535                 540

Pro Thr Gln Thr Lys Val Val Phe Thr Thr Asn Met Glu Glu Ala Leu
545                 550                 555                 560

Phe Asp Ser Lys Lys Val Tyr Thr Val Phe Glu Asn Thr Ala Ser Arg
                565                 570                 575

Ile Asn Glu Ala Gly Thr Gly Ile Ala Asn Gly Met Met Phe Tyr Gln
            580                 585                 590

Trp Leu Lys Gly Ile Val Gln Asp Phe Thr Glu Glu Ala Thr Gln Lys
```

```
                595                 600                 605
Asp Thr Phe Asp Lys Ile Ser Asp Val Thr Met Ile Val Pro Tyr Leu
    610                 615                 620

Gly Asn Ile Leu Asn Ile Gly Asn Asp Ile Arg Lys Gly Asp Phe Met
625                 630                 635                 640

Gly Ala Val Glu Leu Gly Gly Val Thr Ile Leu Glu Ala Ile Pro
            645                 650                 655

Glu Leu Thr Leu Pro Val Leu Ile Gly Leu Thr Ile Ile Glu Asp Glu
                660                 665                 670

Leu Glu Lys Glu Gln Val Ser Gln Thr Val Tyr Asn Val Leu Asp Lys
            675                 680                 685

Arg Asp Glu Lys Trp Glu Val Tyr Gly Phe Val Lys Gln Gln Trp
    690                 695                 700

Trp Trp Met Val His Thr Gln Phe Glu Thr Arg Ile Leu His Ala Tyr
705                 710                 715                 720

Gln Ala Leu Asn His Gln Val Glu Ala Ile Lys Ala Asn Met Thr Tyr
            725                 730                 735

Gln Leu Ala Asn Tyr Arg Gly Asn Gln Glu Asp Lys Glu Leu Leu Glu
                740                 745                 750

Lys Ala Ile Asp Asp Thr Leu Gln Ser Leu Tyr Tyr Ala Val Asp Gln
            755                 760                 765

Ala Met His Asn Ile Lys Arg Phe Leu Ile Gln Ser Ser Lys Ser Tyr
770                 775                 780

Leu Leu Asn Gln Met Leu Pro Lys Thr Lys Glu Gln Leu Leu Ala Phe
785                 790                 795                 800

Asp Gln Gln Thr Leu Arg Asn Val Asn Asp Phe Ile Asn Lys Asn Gln
            805                 810                 815

Gly Val Leu Gly Glu Ser Leu Ala Lys Asp Leu Lys Lys Lys Val Glu
                820                 825                 830

Lys Arg Leu Thr Ser Leu Pro Val Phe Asn Leu Glu Asp Leu Pro Ile
            835                 840                 845

Ser Glu Phe Glu Asp Leu Ile His Ser His Glu Ile Asp Ile
    850                 855                 860

<210> SEQ ID NO 13
<211> LENGTH: 892
<212> TYPE: PRT
<213> ORGANISM: Artificial Sequence
<220> FEATURE:
<223> OTHER INFORMATION: Synthetic Polypeptide

<400> SEQUENCE: 13

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

Pro Asn Val Trp Val Pro Glu Arg Tyr Thr Phe Tyr Ser Thr Met
50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
```

```
             100                 105                 110
Phe Leu Asn Leu Leu Ser Arg Ser Ile Pro Val Pro Tyr Glu Ser Asn
            115                 120                 125
Gly Asp Val Ala Met Gly Thr Thr Gln Val Ile Lys Gln Met Asp Asp
            130                 135                 140
Lys Gly Asn Val Leu Lys His Arg Arg Ala His Ile Ile Ile Tyr Gly
145                 150                 155                 160
Pro Gly Pro Asp Leu Met Ala Lys Gly Ser Lys Ala Leu Thr Lys Ser
                    165                 170                 175
Arg Glu Thr Gly Arg Gly Cys Met Ala Glu Ile Tyr Phe Ser Pro Met
                180                 185                 190
Tyr His Lys Thr Tyr Ser Thr Lys Leu Thr Asn Lys Asn Ser Leu Val
            195                 200                 205
Asp Lys Ser Val Gln Glu Phe Val Pro Asp Pro Ala Val Thr Leu Ile
            210                 215                 220
His Glu Leu Cys His Gly Leu His Ala Leu Tyr Gly Ile Asp Leu Gly
225                 230                 235                 240
Asn Val Gly Ser Trp Glu Phe Asn Ser Asn Pro Asn Ser Leu Phe Ser
                    245                 250                 255
Ser Trp Phe Ser Ser Lys Glu Ala Val Asn Phe Glu Val Met Thr
                260                 265                 270
Phe Gly Gly Glu Asp Val Lys Val Ile Lys Ser Glu Ile Asp Lys Lys
                275                 280                 285
Ile Pro Gly Ile Leu Asn Leu Ile Lys Thr Thr Val Glu Pro Ile Ile
            290                 295                 300
Asn Lys Ile Thr Asp Pro His Asp Glu Met Leu Gln Cys Leu Gln Ser
305                 310                 315                 320
Lys Tyr Pro Ser Leu Lys Gly Thr Leu Gly Gln Phe Phe Asp Asp
                    325                 330                 335
Thr Gln Leu Glu Lys Asp Ile Arg Asp Leu Trp Met Val Met Asn Glu
                340                 345                 350
Thr Met Phe Ala Glu Asn Leu Lys Ala Leu Thr Arg Ala Arg Tyr Leu
                355                 360                 365
Val Pro Lys Val Glu Asn Ile Val Gln Val Asp Ile Leu Ser Pro Asn
370                 375                 380
Val Tyr Thr Ile Asp Lys Gly Phe Asn His Leu Ser Lys Gly Phe Lys
385                 390                 395                 400
Gly Gln Ser Val Ser Gln Ser Tyr Phe Arg Lys Ile Ser Ala Leu Ala
                    405                 410                 415
Arg Gly Ala Val Val Arg Ala Cys Pro Arg Asn Gly Leu Leu Tyr Asn
                420                 425                 430
Ala Ile Tyr Arg Asn Ser Lys Asn Tyr Leu Asn Asn Ile Asp Leu Glu
            435                 440                 445
Asp Lys Lys Thr Thr Ser Lys Thr Asn Val Ser Tyr Pro Cys Ser Leu
            450                 455                 460
Leu Asn Gly Cys Ile Glu Ile Leu Glu Asp Asp Leu Phe Ile Met Ser
465                 470                 475                 480
Ser Lys Asp Ser Phe Thr Asp Thr Asp Phe Ser Glu Pro Ser Val Gly
                    485                 490                 495
Pro Val Ser Tyr Lys Ala Lys Lys Gly Ala Asp Thr Ile Leu Asp Ser
                500                 505                 510
Thr Leu Ser Asn Tyr Asp Phe Ser Lys Glu Ile Asn Phe Thr Ser Thr
            515                 520                 525
```

Val Pro Ile Ile Thr Val Glu Asp Pro Leu Glu Thr Asp Glu Asp Val
            530                 535                 540

Pro Val Ile Ser Glu Asp Arg Thr Val Tyr Val Asp Asp Tyr Thr Thr
545                 550                 555                 560

Phe His Phe Leu Glu Ala Gln Lys Ile Gly Lys Glu Val Val Pro Thr
                565                 570                 575

Gln Thr Lys Val Val Phe Thr Thr Asn Met Glu Glu Ala Leu Phe Asp
            580                 585                 590

Ser Lys Lys Val Tyr Thr Val Phe Glu Asn Thr Ala Ser Arg Ile Asn
            595                 600                 605

Glu Ala Gly Thr Gly Ile Ala Asn Gly Met Met Phe Tyr Gln Trp Leu
            610                 615                 620

Lys Gly Ile Val Gln Asp Phe Thr Glu Ala Thr Gln Lys Asp Thr
625                 630                 635                 640

Phe Asp Lys Ile Ser Asp Val Thr Met Ile Val Pro Tyr Leu Gly Asn
                645                 650                 655

Ile Leu Asn Ile Gly Asn Asp Ile Arg Lys Gly Asp Phe Met Gly Ala
            660                 665                 670

Val Glu Leu Gly Gly Val Thr Ile Leu Leu Glu Ala Ile Pro Glu Leu
            675                 680                 685

Thr Leu Pro Val Leu Ile Gly Leu Thr Ile Ile Glu Asp Glu Leu Glu
            690                 695                 700

Lys Glu Gln Val Ser Gln Thr Val Tyr Asn Val Leu Asp Lys Arg Asp
705                 710                 715                 720

Glu Lys Trp Glu Glu Val Tyr Gly Phe Val Lys Gln Gln Trp Trp Trp
                725                 730                 735

Met Val His Thr Gln Phe Glu Thr Arg Ile Leu His Ala Tyr Gln Ala
            740                 745                 750

Leu Asn His Gln Val Glu Ala Ile Lys Ala Asn Met Thr Tyr Gln Leu
            755                 760                 765

Ala Asn Tyr Arg Gly Asn Gln Glu Asp Lys Glu Leu Leu Glu Lys Ala
            770                 775                 780

Ile Asp Asp Thr Leu Gln Ser Leu Tyr Tyr Ala Val Asp Gln Ala Met
785                 790                 795                 800

His Asn Ile Lys Arg Phe Leu Ile Gln Ser Ser Lys Ser Tyr Leu Leu
                805                 810                 815

Asn Gln Met Leu Pro Lys Thr Lys Glu Gln Leu Leu Ala Phe Asp Gln
            820                 825                 830

Gln Thr Leu Arg Asn Val Asn Asp Phe Ile Asn Lys Asn Gln Gly Val
            835                 840                 845

Leu Gly Glu Ser Leu Ala Lys Asp Leu Lys Lys Val Glu Lys Arg
            850                 855                 860

Leu Thr Ser Leu Pro Val Phe Asn Leu Glu Asp Leu Pro Ile Ser Glu
865                 870                 875                 880

Phe Glu Asp Leu Ile His Ser His Glu Ile Asp Ile
                885                 890

<210> SEQ ID NO 14
<211> LENGTH: 1283
<212> TYPE: PRT
<213> ORGANISM: Artificial Sequence
<220> FEATURE:
<223> OTHER INFORMATION: Synthetic Polypeptide

<400> SEQUENCE: 14

```
Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

Pro Asn Val Trp Val Pro Glu Arg Tyr Thr Phe Tyr Ser Thr Met
50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
                100                 105                 110

Phe Leu Asn Leu Leu Ser Arg Ser Ile Pro Val Pro Tyr Glu Ser Asn
            115                 120                 125

Gly Asp Val Ala Met Gly Thr Thr Gln Val Ile Lys Gln Met Asp Asp
130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
                180                 185                 190

Tyr His Lys Thr Tyr Ser Thr Lys Leu Thr Asn Lys Asn Ser Leu Val
            195                 200                 205

Asp Lys Ser Val Gln Glu Phe Val Pro Asp Pro Ala Val Thr Leu Ile
210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
                260                 265                 270

Phe Gly Gly Glu Asp Val Lys Val Ile Lys Ser Glu Ile Asp Lys Lys
            275                 280                 285

Ile Pro Gly Ile Leu Asn Leu Ile Lys Thr Thr Val Glu Pro Ile Ile
290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
            355                 360                 365

Val Pro Lys Val Glu Asn Ile Val Gln Val Asp Ile Leu Ser Pro Asn
370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415
```

```
Arg Gly Ala Val Val Arg Ala Cys Pro Asn Pro His Phe Ser Ser Gln
            420             425                 430

Leu Val Pro Arg Gly Ser Leu Ser Ser Cys Ile Glu Ile Leu Glu Asp
            435                 440                 445

Asp Leu Phe Ile Met Ser Ser Lys Asp Ser Phe Thr Asp Thr Asp Phe
450                 455                 460

Ser Glu Pro Ser Val Gly Pro Val Ser Tyr Lys Ala Lys Lys Gly Ala
465                 470                 475                 480

Asp Thr Ile Leu Asp Ser Thr Leu Ser Asn Tyr Asp Phe Ser Lys Glu
            485                 490                 495

Ile Asn Phe Thr Ser Thr Val Pro Ile Ile Thr Val Glu Asp Pro Leu
            500                 505                 510

Glu Thr Asp Glu Asp Val Pro Val Ile Ser Glu Asp Arg Thr Val Tyr
            515                 520                 525

Val Asp Asp Tyr Thr Thr Phe His Phe Leu Glu Ala Gln Lys Ile Gly
            530                 535                 540

Lys Glu Val Val Pro Thr Gln Thr Lys Val Val Phe Thr Thr Asn Met
545                 550                 555                 560

Glu Glu Ala Leu Phe Asp Ser Lys Lys Val Tyr Thr Val Phe Glu Asn
            565                 570                 575

Thr Ala Ser Arg Ile Asn Glu Ala Gly Thr Gly Ile Ala Asn Gly Met
            580                 585                 590

Met Phe Tyr Gln Trp Leu Lys Gly Ile Val Gln Asp Phe Thr Glu Glu
            595                 600                 605

Ala Thr Gln Lys Asp Thr Phe Asp Lys Ile Ser Asp Val Thr Met Ile
            610                 615                 620

Val Pro Tyr Leu Gly Asn Ile Leu Asn Ile Gly Asn Asp Ile Arg Lys
625                 630                 635                 640

Gly Asp Phe Met Gly Ala Val Glu Leu Gly Gly Val Thr Ile Leu Leu
            645                 650                 655

Glu Ala Ile Pro Glu Leu Thr Leu Pro Val Leu Ile Gly Leu Thr Ile
            660                 665                 670

Ile Glu Asp Glu Leu Glu Lys Glu Gln Val Ser Gln Thr Val Tyr Asn
            675                 680                 685

Val Leu Asp Lys Arg Asp Glu Lys Trp Glu Glu Val Tyr Gly Phe Val
690                 695                 700

Lys Gln Gln Trp Trp Met Val His Thr Gln Phe Glu Thr Arg Ile
705                 710                 715                 720

Leu His Ala Tyr Gln Ala Leu Asn His Gln Val Glu Ala Ile Lys Ala
            725                 730                 735

Asn Met Thr Tyr Gln Leu Ala Asn Tyr Arg Gly Asn Gln Glu Asp Lys
            740                 745                 750

Glu Leu Leu Glu Lys Ala Ile Asp Asp Thr Leu Gln Ser Leu Tyr Tyr
            755                 760                 765

Ala Val Asp Gln Ala Met His Asn Ile Lys Arg Phe Leu Ile Gln Ser
            770                 775                 780

Ser Lys Ser Tyr Leu Leu Asn Gln Met Leu Pro Lys Thr Lys Glu Gln
785                 790                 795                 800

Leu Leu Ala Phe Asp Gln Gln Thr Leu Arg Asn Val Asn Asp Phe Ile
            805                 810                 815

Asn Lys Asn Gln Gly Val Leu Gly Glu Ser Leu Ala Lys Asp Leu Lys
            820                 825                 830

Lys Lys Val Glu Lys Arg Leu Thr Ser Leu Pro Val Phe Asn Leu Glu
```

-continued

```
                835                 840                 845
Asp Leu Pro Ile Ser Glu Phe Glu Asp Leu Ile His Ser His Glu Ile
            850                 855                 860
Asp Ile Gln Asp Ser Glu Val Leu Asn Ile Gly Val Asn Asn Gly Lys
865                 870                 875                 880
Ile Gln Asp Leu Ser Gly Glu Asn Thr Pro Leu Thr Leu Gly Glu Asn
                885                 890                 895
Leu His Ile Val Asn Gly Arg Asp Asn Gln Ala Val Arg Leu Asn Asn
            900                 905                 910
Gln Leu Asp Ser Lys Leu Glu Ile Gln Ser Arg Pro Asn Ile His Phe
            915                 920                 925
Thr Ala Phe Glu Asp Phe Ser Ile Ser Ile Trp Ile Arg Cys Ser Met
            930                 935                 940
Leu Arg Asn Asn Arg Asn Arg Gly Gln Lys Tyr Thr Ile Ile Gln Gln
945                 950                 955                 960
Phe Asn Lys Tyr Gly Trp Gln Leu Ala Ile Gln Asp Ser Val Phe Val
                965                 970                 975
Trp Thr Leu His Asp Thr Phe Asn Asn Gln Ile Gln Leu Thr Ser Gly
            980                 985                 990
Ser Ala Leu Thr Asn Lys Asn Tyr Leu Leu Gln Asn Phe Trp Leu His
                995                1000                1005
Ile Thr Val Thr Asn Lys Arg Ser Glu Lys Ser Arg Leu Tyr Ile
    1010                1015                1020
Asn Gly Val Leu Gln Asp Gln Lys Asp Ile Ser Val Leu Gly Asn
    1025                1030                1035
Cys His Pro Lys Glu Pro Ile Leu Phe Ser Ile Gln Asp Asn Ser
    1040                1045                1050
Asp Pro Asn Tyr Phe Val Arg Phe Glu Gln Phe Asn Val Tyr Arg
    1055                1060                1065
Lys Ala Leu Thr Asp Ser Glu Val Asn Arg Leu Tyr Trp Lys Tyr
    1070                1075                1080
Phe Glu Gly Ser Tyr Leu Arg Asp Val Trp Gly Glu Arg Leu Thr
    1085                1090                1095
Tyr Asn Arg Asp Tyr Tyr Met Gln Leu Ser Thr Leu Pro Gly Arg
    1100                1105                1110
Gly Ile Lys Arg Glu Tyr Arg Thr Trp Ser Gly Phe Asp Tyr Ile
    1115                1120                1125
Ile Leu Ser Glu Leu Gly Thr Gln Lys Ile Pro Thr His Glu Val
    1130                1135                1140
Thr Tyr Pro Lys Leu Tyr Gln Gly Gln Lys Ile Thr Ile His Ser
    1145                1150                1155
Asp Gly Lys Asn Leu Glu Pro His Val Lys Ser Asn Lys Asn Ile
    1160                1165                1170
Arg Leu Lys Ile Asp Asp Phe Tyr Ile Gly Val Val Asn Pro Phe
    1175                1180                1185
Lys Leu Pro Glu Trp Arg Pro Glu Ser Gly Ala Tyr Val Val Thr
    1190                1195                1200
Thr Tyr Asn His Ala Glu Asp Leu Cys Leu Tyr Phe Arg Thr Arg
    1205                1210                1215
Ser Ser Ser Gln Ser Leu Tyr Tyr Gly Gln Leu Ile Met Asn Asp
    1220                1225                1230
Gly Arg Asn Lys Ser Leu Leu Asn Tyr Thr Leu Lys Gly Ser Thr
    1235                1240                1245
```

```
Tyr Trp Ile Trp Ser Ser Ala Trp Tyr Glu Asn Tyr Asn Thr
    1250                1255                1260

Ser Ser Lys Thr Ala Gly Asn Trp Tyr Phe Ile Pro Val Asp Glu
    1265                1270                1275

Gly Trp Lys Glu Asp
    1280

<210> SEQ ID NO 15
<211> LENGTH: 1289
<212> TYPE: PRT
<213> ORGANISM: Artificial Sequence
<220> FEATURE:
<223> OTHER INFORMATION: Synthetic Polypeptide

<400> SEQUENCE: 15

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
            20                  25                  30

Gln Phe Ile Asn His Asn Val Pro Asp Leu Lys Ala Phe Gln Val Phe
        35                  40                  45

Pro Asn Val Trp Val Val Pro Glu Arg Tyr Thr Phe Tyr Ser Thr Met
    50                  55                  60

Lys Asn Leu Asp Ala Pro Ala Asn Pro Ser Arg Ser Tyr Tyr Asp
65              70                  75                  80

Pro Thr Tyr Leu Gln Ser Asp Ala Glu Lys Glu Val Phe Leu Gln Gln
            85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
            115                 120                 125

Gly Asp Val Ala Met Gly Thr Thr Gln Val Ile Lys Gln Met Asp Asp
        130                 135                 140

Lys Gly Asn Val Leu Lys His Arg Arg Ala His Ile Ile Ile Tyr Gly
145             150                 155                 160

Pro Gly Pro Asp Leu Met Ala Lys Gly Ser Lys Ala Leu Thr Lys Ser
            165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
            195                 200                 205

Asp Lys Ser Val Gln Glu Phe Val Pro Asp Pro Ala Val Thr Leu Ile
        210                 215                 220

His Glu Leu Cys His Gly Leu His Ala Leu Tyr Gly Ile Asp Leu Gly
225             230                 235                 240

Asn Val Gly Ser Trp Glu Phe Asn Ser Asn Pro Asn Ser Leu Phe Ser
            245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
            275                 280                 285

Ile Pro Gly Ile Leu Asn Leu Ile Lys Thr Thr Val Glu Pro Ile Ile
        290                 295                 300

Asn Lys Ile Thr Asp Pro His Asp Glu Met Leu Gln Cys Leu Gln Ser
305             310                 315                 320
```

-continued

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
        355                 360                 365

Val Pro Lys Val Glu Asn Ile Val Gln Val Asp Ile Leu Ser Pro Asn
    370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Val Arg Gly Ile Ile Thr Ser Lys
            420                 425                 430

Thr Lys Ser Leu Asp Lys Gly Tyr Asn Lys Ala Leu Asn Asp Leu Cys
        435                 440                 445

Ile Glu Ile Leu Glu Asp Asp Leu Phe Ile Met Ser Ser Lys Asp Ser
    450                 455                 460

Phe Thr Asp Thr Asp Phe Ser Glu Pro Ser Val Gly Pro Val Ser Tyr
465                 470                 475                 480

Lys Ala Lys Lys Gly Ala Asp Thr Ile Leu Asp Ser Thr Leu Ser Asn
                485                 490                 495

Tyr Asp Phe Ser Lys Glu Ile Asn Phe Thr Ser Thr Val Pro Ile Ile
            500                 505                 510

Thr Val Glu Asp Pro Leu Glu Thr Asp Glu Asp Val Pro Val Ile Ser
        515                 520                 525

Glu Asp Arg Thr Val Tyr Val Asp Asp Tyr Thr Thr Phe His Phe Leu
    530                 535                 540

Glu Ala Gln Lys Ile Gly Lys Glu Val Val Pro Thr Gln Thr Lys Val
545                 550                 555                 560

Val Phe Thr Thr Asn Met Glu Glu Ala Leu Phe Asp Ser Lys Lys Val
                565                 570                 575

Tyr Thr Val Phe Glu Asn Thr Ala Ser Arg Ile Asn Glu Ala Gly Thr
            580                 585                 590

Gly Ile Ala Asn Gly Met Met Phe Tyr Gln Trp Leu Lys Gly Ile Val
        595                 600                 605

Gln Asp Phe Thr Glu Glu Ala Thr Gln Lys Asp Thr Phe Asp Lys Ile
    610                 615                 620

Ser Asp Val Thr Met Ile Val Pro Tyr Leu Gly Asn Ile Leu Asn Ile
625                 630                 635                 640

Gly Asn Asp Ile Arg Lys Gly Asp Phe Met Gly Ala Val Glu Leu Gly
                645                 650                 655

Gly Val Thr Ile Leu Leu Glu Ala Ile Pro Glu Leu Thr Leu Pro Val
            660                 665                 670

Leu Ile Gly Leu Thr Ile Ile Glu Asp Glu Leu Glu Lys Glu Gln Val
        675                 680                 685

Ser Gln Thr Val Tyr Asn Val Leu Asp Lys Arg Asp Glu Lys Trp Glu
    690                 695                 700

Glu Val Tyr Gly Phe Val Lys Gln Gln Trp Trp Trp Met Val His Thr
705                 710                 715                 720

Gln Phe Glu Thr Arg Ile Leu His Ala Tyr Gln Ala Leu Asn His Gln
                725                 730                 735

Val Glu Ala Ile Lys Ala Asn Met Thr Tyr Gln Leu Ala Asn Tyr Arg
                740                 745                 750

Gly Asn Gln Glu Asp Lys Glu Leu Leu Glu Lys Ala Ile Asp Asp Thr
            755                 760                 765

Leu Gln Ser Leu Tyr Tyr Ala Val Asp Gln Ala Met His Asn Ile Lys
        770                 775                 780

Arg Phe Leu Ile Gln Ser Ser Lys Ser Tyr Leu Leu Asn Gln Met Leu
785                 790                 795                 800

Pro Lys Thr Lys Glu Gln Leu Leu Ala Phe Asp Gln Gln Thr Leu Arg
                805                 810                 815

Asn Val Asn Asp Phe Ile Asn Lys Asn Gln Gly Val Leu Gly Glu Ser
            820                 825                 830

Leu Ala Lys Asp Leu Lys Lys Lys Val Glu Lys Arg Leu Thr Ser Leu
        835                 840                 845

Pro Val Phe Asn Leu Glu Asp Leu Pro Ile Ser Glu Phe Glu Asp Leu
    850                 855                 860

Ile His Ser His Glu Ile Asp Ile Gln Asp Ser Glu Val Leu Asn Ile
865                 870                 875                 880

Gly Val Asn Asn Gly Lys Ile Gln Asp Leu Ser Gly Glu Asn Thr Pro
                885                 890                 895

Leu Thr Leu Gly Glu Asn Leu His Ile Val Asn Gly Arg Asp Asn Gln
            900                 905                 910

Ala Val Arg Leu Asn Asn Gln Leu Asp Ser Lys Leu Glu Ile Gln Ser
        915                 920                 925

Arg Pro Asn Ile His Phe Thr Ala Phe Glu Asp Phe Ser Ile Ser Ile
    930                 935                 940

Trp Ile Arg Cys Ser Met Leu Arg Asn Asn Arg Asn Arg Gly Gln Lys
945                 950                 955                 960

Tyr Thr Ile Ile Gln Gln Phe Asn Lys Tyr Gly Trp Gln Leu Ala Ile
                965                 970                 975

Gln Asp Ser Val Phe Val Trp Thr Leu His Asp Thr Phe Asn Asn Gln
            980                 985                 990

Ile Gln Leu Thr Ser Gly Ser Ala Leu Thr Asn Lys Asn Tyr Leu Leu
        995                 1000                1005

Gln Asn Phe Trp Leu His Ile Thr Val Thr Asn Lys Arg Ser Glu
    1010                1015                1020

Lys Ser Arg Leu Tyr Ile Asn Gly Val Leu Gln Asp Gln Lys Asp
    1025                1030                1035

Ile Ser Val Leu Gly Asn Cys His Pro Lys Glu Pro Ile Leu Phe
    1040                1045                1050

Ser Ile Gln Asp Asn Ser Asp Pro Asn Tyr Phe Val Arg Phe Glu
    1055                1060                1065

Gln Phe Asn Val Tyr Arg Lys Ala Leu Thr Asp Ser Glu Val Asn
    1070                1075                1080

Arg Leu Tyr Trp Lys Tyr Phe Glu Gly Ser Tyr Leu Arg Asp Val
    1085                1090                1095

Trp Gly Glu Arg Leu Thr Tyr Asn Arg Asp Tyr Tyr Met Gln Leu
    1100                1105                1110

Ser Thr Leu Pro Gly Arg Gly Ile Lys Arg Glu Tyr Arg Thr Trp
    1115                1120                1125

Ser Gly Phe Asp Tyr Ile Ile Leu Ser Glu Leu Gly Thr Gln Lys
    1130                1135                1140

Ile Pro Thr His Glu Val Thr Tyr Pro Lys Leu Tyr Gln Gly Gln

```
                    1145                1150               1155

Lys Ile Thr Ile His Ser Asp Gly Lys Asn Leu Glu Pro His Val
            1160                1165               1170

Lys Ser Asn Lys Asn Ile Arg Leu Lys Ile Asp Asp Phe Tyr Ile
        1175                1180               1185

Gly Val Val Asn Pro Phe Lys Leu Pro Glu Trp Arg Pro Glu Ser
    1190                1195               1200

Gly Ala Tyr Val Val Thr Thr Tyr Asn His Ala Glu Asp Leu Cys
    1205                1210               1215

Leu Tyr Phe Arg Thr Arg Ser Ser Ser Gln Ser Leu Tyr Tyr Gly
    1220                1225               1230

Gln Leu Ile Met Asn Asp Gly Arg Asn Lys Ser Leu Leu Asn Tyr
        1235                1240               1245

Thr Leu Lys Gly Ser Thr Tyr Trp Ile Trp Ser Ser Ala Trp Tyr
    1250                1255               1260

Tyr Glu Asn Tyr Asn Thr Ser Ser Lys Thr Ala Gly Asn Trp Tyr
    1265                1270               1275

Phe Ile Pro Val Asp Glu Gly Trp Lys Glu Asp
    1280                1285

<210> SEQ ID NO 16
<211> LENGTH: 1274
<212> TYPE: PRT
<213> ORGANISM: Artificial Sequence
<220> FEATURE:
<223> OTHER INFORMATION: Synthetic Polypeptide

<400> SEQUENCE: 16

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

Pro Asn Val Trp Val Val Pro Glu Arg Tyr Thr Phe Tyr Ser Thr Met
        50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
    130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
```

```
            210                 215                 220
His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
                260                 265                 270

Phe Gly Gly Glu Asp Val Lys Val Ile Lys Ser Glu Ile Asp Lys Lys
                275                 280                 285

Ile Pro Gly Ile Leu Asn Leu Ile Lys Thr Thr Val Glu Pro Ile Ile
                290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
                340                 345                 350

Thr Met Phe Ala Glu Asn Leu Lys Ala Leu Thr Arg Ala Arg Tyr Leu
                355                 360                 365

Val Pro Lys Val Glu Asn Ile Val Gln Val Asp Ile Leu Ser Pro Asn
                370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Lys Ser Val Lys Ala Pro Gly Ile
                420                 425                 430

Cys Ile Glu Ile Leu Glu Asp Asp Leu Phe Ile Met Ser Ser Lys Asp
                435                 440                 445

Ser Phe Thr Asp Thr Asp Phe Ser Glu Pro Ser Val Gly Pro Val Ser
                450                 455                 460

Tyr Lys Ala Lys Lys Gly Ala Asp Thr Ile Leu Asp Ser Thr Leu Ser
465                 470                 475                 480

Asn Tyr Asp Phe Ser Lys Glu Ile Asn Phe Thr Ser Thr Val Pro Ile
                485                 490                 495

Ile Thr Val Glu Asp Pro Leu Glu Thr Asp Glu Asp Val Pro Val Ile
                500                 505                 510

Ser Glu Asp Arg Thr Val Tyr Val Asp Tyr Thr Thr Phe His Phe
                515                 520                 525

Leu Glu Ala Gln Lys Ile Gly Lys Glu Val Val Pro Thr Gln Thr Lys
                530                 535                 540

Val Val Phe Thr Thr Asn Met Glu Glu Ala Leu Phe Asp Ser Lys Lys
545                 550                 555                 560

Val Tyr Thr Val Phe Glu Asn Thr Ala Ser Arg Ile Asn Glu Ala Gly
                565                 570                 575

Thr Gly Ile Ala Asn Gly Met Met Phe Tyr Gln Trp Leu Lys Gly Ile
                580                 585                 590

Val Gln Asp Phe Thr Glu Glu Ala Thr Gln Lys Asp Thr Phe Asp Lys
                595                 600                 605

Ile Ser Asp Val Thr Met Ile Val Pro Tyr Leu Gly Asn Ile Leu Asn
                610                 615                 620

Ile Gly Asn Asp Ile Arg Lys Gly Asp Phe Met Gly Ala Val Glu Leu
625                 630                 635                 640
```

```
Gly Gly Val Thr Ile Leu Leu Glu Ala Ile Pro Glu Leu Thr Leu Pro
            645                 650                 655

Val Leu Ile Gly Leu Thr Ile Ile Glu Asp Glu Leu Glu Lys Glu Gln
        660                 665                 670

Val Ser Gln Thr Val Tyr Asn Val Leu Asp Lys Arg Asp Glu Lys Trp
    675                 680                 685

Glu Glu Val Tyr Gly Phe Val Lys Gln Gln Trp Trp Trp Met Val His
690                 695                 700

Thr Gln Phe Glu Thr Arg Ile Leu His Ala Tyr Gln Ala Leu Asn His
705                 710                 715                 720

Gln Val Glu Ala Ile Lys Ala Asn Met Thr Tyr Gln Leu Ala Asn Tyr
                725                 730                 735

Arg Gly Asn Gln Glu Asp Lys Glu Leu Leu Glu Lys Ala Ile Asp Asp
            740                 745                 750

Thr Leu Gln Ser Leu Tyr Tyr Ala Val Asp Gln Ala Met His Asn Ile
        755                 760                 765

Lys Arg Phe Leu Ile Gln Ser Ser Lys Ser Tyr Leu Leu Asn Gln Met
    770                 775                 780

Leu Pro Lys Thr Lys Glu Gln Leu Leu Ala Phe Asp Gln Gln Thr Leu
785                 790                 795                 800

Arg Asn Val Asn Asp Phe Ile Asn Lys Asn Gln Gly Val Leu Gly Glu
                805                 810                 815

Ser Leu Ala Lys Asp Leu Lys Lys Lys Val Glu Lys Arg Leu Thr Ser
            820                 825                 830

Leu Pro Val Phe Asn Leu Glu Asp Leu Pro Ile Ser Glu Phe Glu Asp
        835                 840                 845

Leu Ile His Ser His Glu Ile Asp Ile Gln Asp Ser Glu Val Leu Asn
    850                 855                 860

Ile Gly Val Asn Asn Gly Lys Ile Gln Asp Leu Ser Gly Glu Asn Thr
865                 870                 875                 880

Pro Leu Thr Leu Gly Glu Asn Leu His Ile Val Asn Gly Arg Asp Asn
                885                 890                 895

Gln Ala Val Arg Leu Asn Asn Gln Leu Asp Ser Lys Leu Glu Ile Gln
            900                 905                 910

Ser Arg Pro Asn Ile His Phe Thr Ala Phe Glu Asp Phe Ser Ile Ser
        915                 920                 925

Ile Trp Ile Arg Cys Ser Met Leu Arg Asn Asn Arg Asn Arg Gly Gln
    930                 935                 940

Lys Tyr Thr Ile Ile Gln Gln Phe Asn Lys Tyr Gly Trp Gln Leu Ala
945                 950                 955                 960

Ile Gln Asp Ser Val Phe Val Trp Thr Leu His Asp Thr Phe Asn Asn
                965                 970                 975

Gln Ile Gln Leu Thr Ser Gly Ser Ala Leu Thr Asn Lys Asn Tyr Leu
            980                 985                 990

Leu Gln Asn Phe Trp Leu His Ile Thr Val Thr Asn Lys Arg Ser Glu
        995                 1000                1005

Lys Ser Arg Leu Tyr Ile Asn Gly Val Leu Gln Asp Gln Lys Asp
        1010                1015                1020

Ile Ser Val Leu Gly Asn Cys His Pro Lys Glu Pro Ile Leu Phe
        1025                1030                1035

Ser Ile Gln Asp Asn Ser Asp Pro Asn Tyr Phe Val Arg Phe Glu
        1040                1045                1050
```

-continued

```
Gln Phe Asn Val Tyr Arg Lys Ala Leu Thr Asp Ser Glu Val Asn
    1055                1060                1065

Arg Leu Tyr Trp Lys Tyr Phe Glu Gly Ser Tyr Leu Arg Asp Val
    1070                1075                1080

Trp Gly Glu Arg Leu Thr Tyr Asn Arg Asp Tyr Tyr Met Gln Leu
    1085                1090                1095

Ser Thr Leu Pro Gly Arg Gly Ile Lys Arg Glu Tyr Arg Thr Trp
    1100                1105                1110

Ser Gly Phe Asp Tyr Ile Ile Leu Ser Glu Leu Gly Thr Gln Lys
    1115                1120                1125

Ile Pro Thr His Glu Val Thr Tyr Pro Lys Leu Tyr Gln Gly Gln
    1130                1135                1140

Lys Ile Thr Ile His Ser Asp Gly Lys Asn Leu Glu Pro His Val
    1145                1150                1155

Lys Ser Asn Lys Asn Ile Arg Leu Lys Ile Asp Asp Phe Tyr Ile
    1160                1165                1170

Gly Val Val Asn Pro Phe Lys Leu Pro Glu Trp Arg Pro Glu Ser
    1175                1180                1185

Gly Ala Tyr Val Val Thr Thr Tyr Asn His Ala Glu Asp Leu Cys
    1190                1195                1200

Leu Tyr Phe Arg Thr Arg Ser Ser Ser Gln Ser Leu Tyr Tyr Gly
    1205                1210                1215

Gln Leu Ile Met Asn Asp Gly Arg Asn Lys Ser Leu Leu Asn Tyr
    1220                1225                1230

Thr Leu Lys Gly Ser Thr Tyr Trp Ile Trp Ser Ser Ala Trp Tyr
    1235                1240                1245

Tyr Glu Asn Tyr Asn Thr Ser Ser Lys Thr Ala Gly Asn Trp Tyr
    1250                1255                1260

Phe Ile Pro Val Asp Glu Gly Trp Lys Glu Asp
    1265                1270

<210> SEQ ID NO 17
<211> LENGTH: 1281
<212> TYPE: PRT
<213> ORGANISM: Artificial Sequence
<220> FEATURE:
<223> OTHER INFORMATION: Synthetic Polypeptide

<400> SEQUENCE: 17

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
            20                  25                  30

Gln Phe Ile Asn His Asn Val Pro Asp Leu Lys Ala Phe Gln Val Phe
        35                  40                  45

Pro Asn Val Trp Val Pro Glu Arg Tyr Thr Phe Tyr Ser Thr Met
    50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125
```

-continued

Gly Asp Val Ala Met Gly Thr Thr Gln Val Ile Lys Gln Met Asp Asp
130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
        275                 280                 285

Ile Pro Gly Ile Leu Asn Leu Ile Lys Thr Thr Val Glu Pro Ile Ile
290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Phe Asp Asp
                325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
        355                 360                 365

Val Pro Lys Val Glu Asn Ile Val Gln Val Asp Ile Leu Ser Pro Asn
370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys His Lys Ala Ile Asp Gly Arg Ser
            420                 425                 430

Leu Tyr Asn Lys Thr Leu Asp Cys Ile Glu Ile Leu Glu Asp Asp Leu
        435                 440                 445

Phe Ile Met Ser Ser Lys Asp Ser Phe Thr Asp Thr Asp Phe Ser Glu
450                 455                 460

Pro Ser Val Gly Pro Val Ser Tyr Lys Ala Lys Lys Gly Ala Asp Thr
465                 470                 475                 480

Ile Leu Asp Ser Thr Leu Ser Asn Tyr Asp Phe Ser Lys Glu Ile Asn
                485                 490                 495

Phe Thr Ser Thr Val Pro Ile Ile Thr Val Glu Asp Pro Leu Glu Thr
            500                 505                 510

Asp Glu Asp Val Pro Val Ile Ser Glu Asp Arg Thr Val Tyr Val Asp
        515                 520                 525

Asp Tyr Thr Thr Phe His Phe Leu Glu Ala Gln Lys Ile Gly Lys Glu
530                 535                 540

Val Val Pro Thr Gln Thr Lys Val Val Phe Thr Thr Asn Met Glu Glu

```
               545                  550                  555                  560
          Ala Leu Phe Asp Ser Lys Lys Val Tyr Thr Val Phe Glu Asn Thr Ala
                            565                  570                  575

Ser Arg Ile Asn Glu Ala Gly Thr Gly Ile Ala Asn Gly Met Met Phe
                            580                  585                  590

Tyr Gln Trp Leu Lys Gly Ile Val Gln Asp Phe Thr Glu Ala Thr
                        595                  600                  605

Gln Lys Asp Thr Phe Asp Lys Ile Ser Asp Val Thr Met Ile Val Pro
                        610                  615                  620

Tyr Leu Gly Asn Ile Leu Asn Ile Gly Asn Asp Ile Arg Lys Gly Asp
          625                  630                  635                  640

Phe Met Gly Ala Val Glu Leu Gly Val Thr Ile Leu Leu Glu Ala
                                645                  650                  655

Ile Pro Glu Leu Thr Leu Pro Val Leu Ile Gly Leu Thr Ile Ile Glu
                            660                  665                  670

Asp Glu Leu Glu Lys Glu Gln Val Ser Gln Thr Val Tyr Asn Val Leu
                            675                  680                  685

Asp Lys Arg Asp Glu Lys Trp Glu Glu Val Tyr Gly Phe Val Lys Gln
                            690                  695                  700

Gln Trp Trp Trp Met Val His Thr Gln Phe Glu Thr Arg Ile Leu His
          705                  710                  715                  720

Ala Tyr Gln Ala Leu Asn His Gln Val Glu Ala Ile Lys Ala Asn Met
                            725                  730                  735

Thr Tyr Gln Leu Ala Asn Tyr Arg Gly Asn Gln Glu Asp Lys Glu Leu
                        740                  745                  750

Leu Glu Lys Ala Ile Asp Asp Thr Leu Gln Ser Leu Tyr Tyr Ala Val
                        755                  760                  765

Asp Gln Ala Met His Asn Ile Lys Arg Phe Leu Ile Gln Ser Ser Lys
                        770                  775                  780

Ser Tyr Leu Leu Asn Gln Met Leu Pro Lys Thr Lys Glu Gln Leu Leu
          785                  790                  795                  800

Ala Phe Asp Gln Gln Thr Leu Arg Asn Val Asn Asp Phe Ile Asn Lys
                            805                  810                  815

Asn Gln Gly Val Leu Gly Glu Ser Leu Ala Lys Asp Leu Lys Lys Lys
                            820                  825                  830

Val Glu Lys Arg Leu Thr Ser Leu Pro Val Phe Asn Leu Glu Asp Leu
                            835                  840                  845

Pro Ile Ser Glu Phe Glu Asp Leu Ile His Ser His Glu Ile Asp Ile
          850                  855                  860

Gln Asp Ser Glu Val Leu Asn Ile Gly Val Asn Asn Gly Lys Ile Gln
          865                  870                  875                  880

Asp Leu Ser Gly Glu Asn Thr Pro Leu Thr Leu Gly Glu Asn Leu His
                            885                  890                  895

Ile Val Asn Gly Arg Asp Asn Gln Ala Val Arg Leu Asn Asn Gln Leu
                            900                  905                  910

Asp Ser Lys Leu Glu Ile Gln Ser Arg Pro Asn Ile His Phe Thr Ala
                        915                  920                  925

Phe Glu Asp Phe Ser Ile Ser Ile Trp Ile Arg Cys Ser Met Leu Arg
                        930                  935                  940

Asn Asn Arg Asn Arg Gly Gln Lys Tyr Thr Ile Ile Gln Gln Phe Asn
          945                  950                  955                  960

Lys Tyr Gly Trp Gln Leu Ala Ile Gln Asp Ser Val Phe Val Trp Thr
                        965                  970                  975
```

-continued

```
Leu His Asp Thr Phe Asn Asn Gln Ile Gln Leu Thr Ser Gly Ser Ala
                980                 985                 990

Leu Thr Asn Lys Asn Tyr Leu Leu Gln Asn Phe Trp Leu His Ile Thr
        995                 1000                1005

Val Thr Asn Lys Arg Ser Glu Lys Ser Arg Leu Tyr Ile Asn Gly
    1010                1015                1020

Val Leu Gln Asp Gln Lys Asp Ile Ser Val Leu Gly Asn Cys His
    1025                1030                1035

Pro Lys Glu Pro Ile Leu Phe Ser Ile Gln Asp Asn Ser Asp Pro
    1040                1045                1050

Asn Tyr Phe Val Arg Phe Glu Gln Phe Asn Val Tyr Arg Lys Ala
    1055                1060                1065

Leu Thr Asp Ser Glu Val Asn Arg Leu Tyr Trp Lys Tyr Phe Glu
    1070                1075                1080

Gly Ser Tyr Leu Arg Asp Val Trp Gly Glu Arg Leu Thr Tyr Asn
    1085                1090                1095

Arg Asp Tyr Tyr Met Gln Leu Ser Thr Leu Pro Gly Arg Gly Ile
    1100                1105                1110

Lys Arg Glu Tyr Arg Thr Trp Ser Gly Phe Asp Tyr Ile Ile Leu
    1115                1120                1125

Ser Glu Leu Gly Thr Gln Lys Ile Pro Thr His Glu Val Thr Tyr
    1130                1135                1140

Pro Lys Leu Tyr Gln Gly Gln Lys Ile Thr Ile His Ser Asp Gly
    1145                1150                1155

Lys Asn Leu Glu Pro His Val Lys Ser Asn Lys Asn Ile Arg Leu
    1160                1165                1170

Lys Ile Asp Asp Phe Tyr Ile Gly Val Val Asn Pro Phe Lys Leu
    1175                1180                1185

Pro Glu Trp Arg Pro Glu Ser Gly Ala Tyr Val Val Thr Thr Tyr
    1190                1195                1200

Asn His Ala Glu Asp Leu Cys Leu Tyr Phe Arg Thr Arg Ser Ser
    1205                1210                1215

Ser Gln Ser Leu Tyr Tyr Gly Gln Leu Ile Met Asn Asp Gly Arg
    1220                1225                1230

Asn Lys Ser Leu Leu Asn Tyr Thr Leu Lys Gly Ser Thr Tyr Trp
    1235                1240                1245

Ile Trp Ser Ser Ala Trp Tyr Tyr Glu Asn Tyr Asn Thr Ser Ser
    1250                1255                1260

Lys Thr Ala Gly Asn Trp Tyr Phe Ile Pro Val Asp Glu Gly Trp
    1265                1270                1275

Lys Glu Asp
    1280
```

<210> SEQ ID NO 18
<211> LENGTH: 1278
<212> TYPE: PRT
<213> ORGANISM: Artificial Sequence
<220> FEATURE:
<223> OTHER INFORMATION: Synthetic Polypeptide

<400> SEQUENCE: 18

```
Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
            20                  25                  30
```

```
Gln Phe Ile Asn His Asn Val Pro Asp Leu Lys Ala Phe Gln Val Phe
         35                  40                  45

Pro Asn Val Trp Val Val Pro Glu Arg Tyr Thr Phe Tyr Ser Thr Met
     50                  55                  60

Lys Asn Leu Asp Ala Pro Ala Asn Pro Ser Arg Ser Ser Tyr Tyr Asp
 65                  70                  75                  80

Pro Thr Tyr Leu Gln Ser Asp Ala Glu Lys Glu Val Phe Leu Gln Gln
                 85                  90                  95

Met Ile Leu Leu Phe Lys Arg Ile Asn Ser Thr Gln Glu Gly Gln Gln
                100                 105                 110

Phe Leu Asn Leu Leu Ser Arg Ser Ile Pro Val Pro Tyr Glu Ser Asn
            115                 120                 125

Gly Asp Val Ala Met Gly Thr Thr Gln Val Ile Lys Gln Met Asp Asp
        130                 135                 140

Lys Gly Asn Val Leu Lys His Arg Arg Ala His Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
        275                 280                 285

Ile Pro Gly Ile Leu Asn Leu Ile Lys Thr Thr Val Glu Pro Ile Ile
290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
        355                 360                 365

Val Pro Lys Val Glu Asn Ile Val Gln Val Asp Ile Leu Ser Pro Asn
370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Leu Arg Leu Thr Lys Asn Ser Arg
            420                 425                 430

Asp Asp Ser Thr Cys Ile Glu Ile Leu Glu Asp Asp Leu Phe Ile Met
        435                 440                 445
```

```
Ser Ser Lys Asp Ser Phe Thr Asp Thr Asp Phe Ser Glu Pro Ser Val
    450                 455                 460

Gly Pro Val Ser Tyr Lys Ala Lys Gly Ala Asp Thr Ile Leu Asp
465                 470                 475                 480

Ser Thr Leu Ser Asn Tyr Asp Phe Ser Lys Glu Ile Asn Phe Thr Ser
                485                 490                 495

Thr Val Pro Ile Ile Thr Val Glu Asp Pro Leu Glu Thr Asp Glu Asp
            500                 505                 510

Val Pro Val Ile Ser Glu Asp Arg Thr Val Tyr Val Asp Tyr Thr
                515                 520                 525

Thr Phe His Phe Leu Glu Ala Gln Lys Ile Gly Lys Glu Val Val Pro
    530                 535                 540

Thr Gln Thr Lys Val Val Phe Thr Thr Asn Met Glu Glu Ala Leu Phe
545                 550                 555                 560

Asp Ser Lys Lys Val Tyr Thr Val Phe Glu Asn Thr Ala Ser Arg Ile
                565                 570                 575

Asn Glu Ala Gly Thr Gly Ile Ala Asn Gly Met Met Phe Tyr Gln Trp
            580                 585                 590

Leu Lys Gly Ile Val Gln Asp Phe Thr Glu Ala Thr Gln Lys Asp
            595                 600                 605

Thr Phe Asp Lys Ile Ser Asp Val Thr Met Ile Val Pro Tyr Leu Gly
    610                 615                 620

Asn Ile Leu Asn Ile Gly Asn Asp Ile Arg Lys Gly Asp Phe Met Gly
625                 630                 635                 640

Ala Val Glu Leu Gly Gly Val Thr Ile Leu Leu Glu Ala Ile Pro Glu
                645                 650                 655

Leu Thr Leu Pro Val Leu Ile Gly Leu Thr Ile Ile Glu Asp Glu Leu
            660                 665                 670

Glu Lys Glu Gln Val Ser Gln Thr Val Tyr Asn Val Leu Asp Lys Arg
            675                 680                 685

Asp Glu Lys Trp Glu Glu Val Tyr Gly Phe Val Lys Gln Gln Trp Trp
    690                 695                 700

Trp Met Val His Thr Gln Phe Glu Thr Arg Ile Leu His Ala Tyr Gln
705                 710                 715                 720

Ala Leu Asn His Gln Val Glu Ala Ile Lys Ala Asn Met Thr Tyr Gln
                725                 730                 735

Leu Ala Asn Tyr Arg Gly Asn Gln Glu Asp Lys Glu Leu Leu Glu Lys
            740                 745                 750

Ala Ile Asp Asp Thr Leu Gln Ser Leu Tyr Tyr Ala Val Asp Gln Ala
            755                 760                 765

Met His Asn Ile Lys Arg Phe Leu Ile Gln Ser Ser Lys Ser Tyr Leu
    770                 775                 780

Leu Asn Gln Met Leu Pro Lys Thr Lys Glu Gln Leu Leu Ala Phe Asp
785                 790                 795                 800

Gln Gln Thr Leu Arg Asn Val Asn Asp Phe Ile Asn Lys Asn Gln Gly
                805                 810                 815

Val Leu Gly Glu Ser Leu Ala Lys Asp Leu Lys Lys Val Glu Lys
            820                 825                 830

Arg Leu Thr Ser Leu Pro Val Phe Asn Leu Glu Asp Leu Pro Ile Ser
            835                 840                 845

Glu Phe Glu Asp Leu Ile His Ser His Glu Ile Asp Ile Gln Asp Ser
    850                 855                 860

Glu Val Leu Asn Ile Gly Val Asn Asn Gly Lys Ile Gln Asp Leu Ser
```

-continued

```
                865                 870                 875                 880
Gly Glu Asn Thr Pro Leu Thr Leu Gly Glu Asn Leu His Ile Val Asn
                    885                 890                 895
Gly Arg Asp Asn Gln Ala Val Arg Leu Asn Asn Gln Leu Asp Ser Lys
                    900                 905                 910
Leu Glu Ile Gln Ser Arg Pro Asn Ile His Phe Thr Ala Phe Glu Asp
                    915                 920                 925
Phe Ser Ile Ser Ile Trp Ile Arg Cys Ser Met Leu Arg Asn Asn Arg
                    930                 935                 940
Asn Arg Gly Gln Lys Tyr Thr Ile Ile Gln Gln Phe Asn Lys Tyr Gly
945                 950                 955                 960
Trp Gln Leu Ala Ile Gln Asp Ser Val Phe Val Trp Thr Leu His Asp
                    965                 970                 975
Thr Phe Asn Asn Gln Ile Gln Leu Thr Ser Gly Ser Ala Leu Thr Asn
                    980                 985                 990
Lys Asn Tyr Leu Leu Gln Asn Phe Trp Leu His Ile Thr Val Thr Asn
                    995                 1000                1005
Lys Arg Ser Glu Lys Ser Arg Leu Tyr Ile Asn Gly Val Leu Gln
            1010                1015                1020
Asp Gln Lys Asp Ile Ser Val Leu Gly Asn Cys His Pro Lys Glu
            1025                1030                1035
Pro Ile Leu Phe Ser Ile Gln Asp Asn Ser Asp Pro Asn Tyr Phe
            1040                1045                1050
Val Arg Phe Glu Gln Phe Asn Val Tyr Arg Lys Ala Leu Thr Asp
            1055                1060                1065
Ser Glu Val Asn Arg Leu Tyr Trp Lys Tyr Phe Glu Gly Ser Tyr
            1070                1075                1080
Leu Arg Asp Val Trp Gly Glu Arg Leu Thr Tyr Asn Arg Asp Tyr
            1085                1090                1095
Tyr Met Gln Leu Ser Thr Leu Pro Gly Arg Gly Ile Lys Arg Glu
            1100                1105                1110
Tyr Arg Thr Trp Ser Gly Phe Asp Tyr Ile Ile Leu Ser Glu Leu
            1115                1120                1125
Gly Thr Gln Lys Ile Pro Thr His Glu Val Thr Tyr Pro Lys Leu
            1130                1135                1140
Tyr Gln Gly Gln Lys Ile Thr Ile His Ser Asp Gly Lys Asn Leu
            1145                1150                1155
Glu Pro His Val Lys Ser Asn Lys Asn Ile Arg Leu Lys Ile Asp
            1160                1165                1170
Asp Phe Tyr Ile Gly Val Val Asn Pro Phe Lys Leu Pro Glu Trp
            1175                1180                1185
Arg Pro Glu Ser Gly Ala Tyr Val Val Thr Thr Tyr Asn His Ala
            1190                1195                1200
Glu Asp Leu Cys Leu Tyr Phe Arg Thr Arg Ser Ser Ser Gln Ser
            1205                1210                1215
Leu Tyr Tyr Gly Gln Leu Ile Met Asn Asp Gly Arg Asn Lys Ser
            1220                1225                1230
Leu Leu Asn Tyr Thr Leu Lys Gly Ser Thr Tyr Trp Ile Trp Ser
            1235                1240                1245
Ser Ala Trp Tyr Tyr Glu Asn Tyr Asn Thr Ser Ser Lys Thr Ala
            1250                1255                1260
Gly Asn Trp Tyr Phe Ile Pro Val Asp Glu Gly Trp Lys Glu Asp
            1265                1270                1275
```

```
<210> SEQ ID NO 19
<211> LENGTH: 1279
<212> TYPE: PRT
<213> ORGANISM: Artificial Sequence
<220> FEATURE:
<223> OTHER INFORMATION: Synthetic Polypeptide

<400> SEQUENCE: 19
```

| | | | | | | | | | | | | | | |
|---|---|---|---|---|---|---|---|---|---|---|---|---|---|---|
| Met | Val | Thr | Ile | Asn | Asp | Leu | His | Tyr | Ser | Asp | Pro | Ile | Asp | Glu | Asp |
| 1 | | | | 5 | | | | | 10 | | | | | 15 | |
| Asn | Ile | Ile | Asn | Met | Arg | Ile | Pro | Leu | Tyr | Asp | Leu | Glu | Val | Asp | Asp |
| | | | 20 | | | | | 25 | | | | | 30 | | |
| Gln | Phe | Ile | Asn | His | Asn | Val | Pro | Asp | Leu | Lys | Ala | Phe | Gln | Val | Phe |
| | | | 35 | | | | | 40 | | | | | 45 | | |
| Pro | Asn | Val | Trp | Val | Pro | Glu | Arg | Tyr | Thr | Phe | Tyr | Ser | Thr | Met | |
| | 50 | | | | | 55 | | | | | 60 | | | | |
| Lys | Asn | Leu | Asp | Ala | Pro | Ala | Asn | Pro | Ser | Arg | Ser | Ser | Tyr | Tyr | Asp |
| 65 | | | | | 70 | | | | | 75 | | | | | 80 |
| Pro | Thr | Tyr | Leu | Gln | Ser | Asp | Ala | Glu | Lys | Glu | Val | Phe | Leu | Gln | Gln |
| | | | | 85 | | | | | 90 | | | | | 95 | |
| Met | Ile | Leu | Leu | Phe | Lys | Arg | Ile | Asn | Ser | Thr | Gln | Glu | Gly | Gln | Gln |
| | | | | 100 | | | | | 105 | | | | | 110 | |
| Phe | Leu | Asn | Leu | Leu | Ser | Arg | Ser | Ile | Pro | Val | Pro | Tyr | Glu | Ser | Asn |
| | | | | 115 | | | | | 120 | | | | | 125 | |
| Gly | Asp | Val | Ala | Met | Gly | Thr | Thr | Gln | Val | Ile | Lys | Gln | Met | Asp | Asp |
| | | 130 | | | | | 135 | | | | | 140 | | | |
| Lys | Gly | Asn | Val | Leu | Lys | His | Arg | Arg | Ala | His | Ile | Ile | Ile | Tyr | Gly |
| 145 | | | | | 150 | | | | | 155 | | | | | 160 |
| Pro | Gly | Pro | Asp | Leu | Met | Ala | Lys | Gly | Ser | Lys | Ala | Leu | Thr | Lys | Ser |
| | | | | 165 | | | | | 170 | | | | | 175 | |
| Arg | Glu | Thr | Gly | Arg | Gly | Cys | Met | Ala | Glu | Ile | Tyr | Phe | Ser | Pro | Met |
| | | | 180 | | | | | 185 | | | | | 190 | | |
| Tyr | His | Lys | Thr | Tyr | Ser | Thr | Lys | Leu | Thr | Asn | Lys | Asn | Ser | Leu | Val |
| | | | 195 | | | | | 200 | | | | | 205 | | |
| Asp | Lys | Ser | Val | Gln | Glu | Phe | Val | Pro | Asp | Pro | Ala | Val | Thr | Leu | Ile |
| | | 210 | | | | | 215 | | | | | 220 | | | |
| His | Glu | Leu | Cys | His | Gly | Leu | His | Ala | Leu | Tyr | Gly | Ile | Asp | Leu | Gly |
| 225 | | | | | 230 | | | | | 235 | | | | | 240 |
| Asn | Val | Gly | Ser | Trp | Glu | Phe | Asn | Ser | Asn | Pro | Asn | Ser | Leu | Phe | Ser |
| | | | | 245 | | | | | 250 | | | | | 255 | |
| Ser | Trp | Phe | Ser | Ser | Lys | Glu | Ala | Val | Asn | Phe | Glu | Glu | Val | Met | Thr |
| | | | 260 | | | | | 265 | | | | | 270 | | |
| Phe | Gly | Gly | Glu | Asp | Val | Lys | Val | Ile | Lys | Ser | Glu | Ile | Asp | Lys | Lys |
| | | | 275 | | | | | 280 | | | | | 285 | | |
| Ile | Pro | Gly | Ile | Leu | Asn | Leu | Ile | Lys | Thr | Thr | Val | Glu | Pro | Ile | Ile |
| | | | 290 | | | | | 295 | | | | | 300 | | |
| Asn | Lys | Ile | Thr | Asp | Pro | His | Asp | Glu | Met | Leu | Gln | Cys | Leu | Gln | Ser |
| 305 | | | | | 310 | | | | | 315 | | | | | 320 |
| Lys | Tyr | Pro | Ser | Leu | Lys | Gly | Thr | Leu | Gly | Gln | Phe | Phe | Asp | Asp | |
| | | | | 325 | | | | | 330 | | | | | 335 | |
| Thr | Gln | Leu | Glu | Lys | Asp | Ile | Arg | Asp | Leu | Trp | Met | Val | Met | Asn | Glu |
| | | | | 340 | | | | | 345 | | | | | 350 | |
| Thr | Met | Phe | Ala | Glu | Asn | Leu | Lys | Ala | Leu | Thr | Arg | Ala | Arg | Tyr | Leu |
| | | | 355 | | | | | 360 | | | | | 365 | | |

-continued

Val Pro Lys Val Glu Asn Ile Val Gln Val Asp Ile Leu Ser Pro Asn
    370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Arg Ala Cys Lys Asn Ile Val Ser Val Lys Gly
            420                 425                 430

Ile Arg Lys Ser Ile Cys Ile Glu Ile Leu Glu Asp Leu Phe Ile
        435                 440                 445

Met Ser Ser Lys Asp Ser Phe Thr Asp Thr Asp Phe Ser Glu Pro Ser
    450                 455                 460

Val Gly Pro Val Ser Tyr Lys Ala Lys Lys Gly Ala Asp Thr Ile Leu
465                 470                 475                 480

Asp Ser Thr Leu Ser Asn Tyr Asp Phe Ser Lys Glu Ile Asn Phe Thr
                485                 490                 495

Ser Thr Val Pro Ile Ile Thr Val Glu Asp Pro Leu Glu Thr Asp Glu
            500                 505                 510

Asp Val Pro Val Ile Ser Glu Asp Arg Thr Val Tyr Val Asp Asp Tyr
        515                 520                 525

Thr Thr Phe His Phe Leu Glu Ala Gln Lys Ile Gly Lys Glu Val Val
    530                 535                 540

Pro Thr Gln Thr Lys Val Val Phe Thr Thr Asn Met Glu Glu Ala Leu
545                 550                 555                 560

Phe Asp Ser Lys Lys Val Tyr Thr Val Phe Glu Asn Thr Ala Ser Arg
                565                 570                 575

Ile Asn Glu Ala Gly Thr Gly Ile Ala Asn Gly Met Met Phe Tyr Gln
            580                 585                 590

Trp Leu Lys Gly Ile Val Gln Asp Phe Thr Glu Ala Thr Gln Lys
        595                 600                 605

Asp Thr Phe Asp Lys Ile Ser Asp Val Thr Met Ile Val Pro Tyr Leu
    610                 615                 620

Gly Asn Ile Leu Asn Ile Gly Asn Asp Ile Arg Lys Gly Asp Phe Met
625                 630                 635                 640

Gly Ala Val Glu Leu Gly Gly Val Thr Ile Leu Leu Glu Ala Ile Pro
                645                 650                 655

Glu Leu Thr Leu Pro Val Leu Ile Gly Leu Thr Ile Ile Glu Asp Glu
            660                 665                 670

Leu Glu Lys Glu Gln Val Ser Gln Thr Val Tyr Asn Val Leu Asp Lys
        675                 680                 685

Arg Asp Glu Lys Trp Glu Glu Val Tyr Gly Phe Val Lys Gln Gln Trp
    690                 695                 700

Trp Trp Met Val His Thr Gln Phe Glu Thr Arg Ile Leu His Ala Tyr
705                 710                 715                 720

Gln Ala Leu Asn His Gln Val Glu Ala Ile Lys Ala Asn Met Thr Tyr
                725                 730                 735

Gln Leu Ala Asn Tyr Arg Gly Asn Gln Glu Asp Lys Glu Leu Leu Glu
            740                 745                 750

Lys Ala Ile Asp Asp Thr Leu Gln Ser Leu Tyr Tyr Ala Val Asp Gln
        755                 760                 765

Ala Met His Asn Ile Lys Arg Phe Leu Ile Gln Ser Ser Lys Ser Tyr
    770                 775                 780

```
Leu Leu Asn Gln Met Leu Pro Lys Thr Lys Glu Gln Leu Leu Ala Phe
785                 790                 795                 800

Asp Gln Gln Thr Leu Arg Asn Val Asn Asp Phe Ile Asn Lys Asn Gln
                805                 810                 815

Gly Val Leu Gly Glu Ser Leu Ala Lys Asp Leu Lys Lys Lys Val Glu
                820                 825                 830

Lys Arg Leu Thr Ser Leu Pro Val Phe Asn Leu Glu Asp Leu Pro Ile
                835                 840                 845

Ser Glu Phe Glu Asp Leu Ile His Ser His Glu Ile Asp Ile Gln Asp
850                 855                 860

Ser Glu Val Leu Asn Ile Gly Val Asn Gly Lys Ile Gln Asp Leu
865                 870                 875                 880

Ser Gly Glu Asn Thr Pro Leu Thr Leu Gly Glu Asn Leu His Ile Val
                885                 890                 895

Asn Gly Arg Asp Asn Gln Ala Val Arg Leu Asn Asn Gln Leu Asp Ser
                900                 905                 910

Lys Leu Glu Ile Gln Ser Arg Pro Asn Ile His Phe Thr Ala Phe Glu
                915                 920                 925

Asp Phe Ser Ile Ser Ile Trp Ile Arg Cys Ser Met Leu Arg Asn Asn
930                 935                 940

Arg Asn Arg Gly Gln Lys Tyr Thr Ile Ile Gln Gln Phe Asn Lys Tyr
945                 950                 955                 960

Gly Trp Gln Leu Ala Ile Gln Asp Ser Val Phe Val Trp Thr Leu His
                965                 970                 975

Asp Thr Phe Asn Asn Gln Ile Gln Leu Thr Ser Gly Ser Ala Leu Thr
                980                 985                 990

Asn Lys Asn Tyr Leu Leu Gln Asn Phe Trp Leu His Ile Thr Val Thr
                995                 1000                1005

Asn Lys Arg Ser Glu Lys Ser Arg Leu Tyr Ile Asn Gly Val Leu
        1010            1015            1020

Gln Asp Gln Lys Asp Ile Ser Val Leu Gly Asn Cys His Pro Lys
        1025            1030            1035

Glu Pro Ile Leu Phe Ser Ile Gln Asp Asn Ser Asp Pro Asn Tyr
        1040            1045            1050

Phe Val Arg Phe Glu Gln Phe Asn Val Tyr Arg Lys Ala Leu Thr
        1055            1060            1065

Asp Ser Glu Val Asn Arg Leu Tyr Trp Lys Tyr Phe Glu Gly Ser
        1070            1075            1080

Tyr Leu Arg Asp Val Trp Gly Glu Arg Leu Thr Tyr Asn Arg Asp
        1085            1090            1095

Tyr Tyr Met Gln Leu Ser Thr Leu Pro Gly Arg Gly Ile Lys Arg
        1100            1105            1110

Glu Tyr Arg Thr Trp Ser Gly Phe Asp Tyr Ile Ile Leu Ser Glu
        1115            1120            1125

Leu Gly Thr Gln Lys Ile Pro Thr His Glu Val Thr Tyr Pro Lys
        1130            1135            1140

Leu Tyr Gln Gly Gln Lys Ile Thr Ile His Ser Asp Gly Lys Asn
        1145            1150            1155

Leu Glu Pro His Val Lys Ser Asn Lys Asn Ile Arg Leu Lys Ile
        1160            1165            1170

Asp Asp Phe Tyr Ile Gly Val Val Asn Pro Phe Lys Leu Pro Glu
        1175            1180            1185

Trp Arg Pro Glu Ser Gly Ala Tyr Val Val Thr Thr Tyr Asn His
```

```
                    1190            1195            1200

Ala Glu Asp Leu Cys Leu Tyr Phe Arg Thr Arg Ser Ser Ser Gln
    1205            1210            1215

Ser Leu Tyr Tyr Gly Gln Leu Ile Met Asn Asp Gly Arg Asn Lys
    1220            1225            1230

Ser Leu Leu Asn Tyr Thr Leu Lys Gly Ser Thr Tyr Trp Ile Trp
    1235            1240            1245

Ser Ser Ala Trp Tyr Tyr Glu Asn Tyr Asn Thr Ser Ser Lys Thr
    1250            1255            1260

Ala Gly Asn Trp Tyr Phe Ile Pro Val Asp Glu Gly Trp Lys Glu
    1265            1270            1275

Asp

<210> SEQ ID NO 20
<211> LENGTH: 1281
<212> TYPE: PRT
<213> ORGANISM: Artificial Sequence
<220> FEATURE:
<223> OTHER INFORMATION: Synthetic Polypeptide

<400> SEQUENCE: 20

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

Pro Asn Val Trp Val Pro Glu Arg Tyr Thr Phe Tyr Ser Thr Met
    50                  55                  60

Lys Asn Leu Asp Ala Pro Ala Asn Pro Ser Arg Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
    210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
            260                 265                 270
```

```
Phe Gly Gly Glu Asp Val Lys Val Ile Lys Ser Glu Ile Asp Lys Lys
        275                 280                 285

Ile Pro Gly Ile Leu Asn Leu Ile Lys Thr Thr Val Glu Pro Ile Ile
290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp
                325                 330                 335

Thr Gln Leu Glu Lys Asp Ile Arg Asp Leu Trp Met Val Met Asn Glu
                340                 345                 350

Thr Met Phe Ala Glu Asn Leu Lys Ala Leu Thr Arg Ala Arg Tyr Leu
                355                 360                 365

Val Pro Lys Val Glu Asn Ile Val Gln Val Asp Ile Leu Ser Pro Asn
370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Lys Ser Val Ile Pro Arg Lys Gly
                420                 425                 430

Thr Lys Ala Pro Pro Arg Leu Cys Ile Glu Ile Leu Glu Asp Asp Leu
                435                 440                 445

Phe Ile Met Ser Ser Lys Asp Ser Phe Thr Asp Phe Ser Glu
450                 455                 460

Pro Ser Val Gly Pro Val Ser Tyr Lys Ala Lys Gly Ala Asp Thr
465                 470                 475                 480

Ile Leu Asp Ser Thr Leu Ser Asn Tyr Asp Phe Ser Lys Glu Ile Asn
                485                 490                 495

Phe Thr Ser Thr Val Pro Ile Ile Thr Val Glu Asp Pro Leu Glu Thr
                500                 505                 510

Asp Glu Asp Val Pro Val Ile Ser Glu Asp Arg Thr Val Tyr Val Asp
                515                 520                 525

Asp Tyr Thr Thr Phe His Phe Leu Glu Ala Gln Lys Ile Gly Lys Glu
                530                 535                 540

Val Val Pro Thr Gln Thr Lys Val Val Phe Thr Thr Asn Met Glu Glu
545                 550                 555                 560

Ala Leu Phe Asp Ser Lys Lys Val Tyr Thr Val Phe Glu Asn Thr Ala
                565                 570                 575

Ser Arg Ile Asn Glu Ala Gly Thr Gly Ile Ala Asn Gly Met Met Phe
                580                 585                 590

Tyr Gln Trp Leu Lys Gly Ile Val Gln Asp Phe Thr Glu Glu Ala Thr
                595                 600                 605

Gln Lys Asp Thr Phe Asp Lys Ile Ser Asp Val Thr Met Ile Val Pro
                610                 615                 620

Tyr Leu Gly Asn Ile Leu Asn Ile Gly Asn Asp Ile Arg Lys Gly Asp
625                 630                 635                 640

Phe Met Gly Ala Val Glu Leu Gly Gly Val Thr Ile Leu Leu Glu Ala
                645                 650                 655

Ile Pro Glu Leu Thr Leu Pro Val Leu Ile Gly Leu Thr Ile Ile Glu
                660                 665                 670

Asp Glu Leu Glu Lys Glu Gln Val Ser Gln Thr Val Tyr Asn Val Leu
                675                 680                 685
```

```
Asp Lys Arg Asp Glu Lys Trp Glu Val Tyr Gly Phe Val Lys Gln
    690             695             700

Gln Trp Trp Trp Met Val His Thr Gln Phe Glu Thr Arg Ile Leu His
705             710             715                         720

Ala Tyr Gln Ala Leu Asn His Gln Val Glu Ala Ile Lys Ala Asn Met
            725             730                     735

Thr Tyr Gln Leu Ala Asn Tyr Arg Gly Asn Gln Glu Asp Lys Glu Leu
            740             745             750

Leu Glu Lys Ala Ile Asp Asp Thr Leu Gln Ser Leu Tyr Tyr Ala Val
            755             760             765

Asp Gln Ala Met His Asn Ile Lys Arg Phe Leu Ile Gln Ser Ser Lys
770             775             780

Ser Tyr Leu Leu Asn Gln Met Leu Pro Lys Thr Lys Glu Gln Leu Leu
785             790             795                         800

Ala Phe Asp Gln Gln Thr Leu Arg Asn Val Asn Asp Phe Ile Asn Lys
            805             810             815

Asn Gln Gly Val Leu Gly Glu Ser Leu Ala Lys Asp Leu Lys Lys Lys
            820             825             830

Val Glu Lys Arg Leu Thr Ser Leu Pro Val Phe Asn Leu Glu Asp Leu
            835             840             845

Pro Ile Ser Glu Phe Glu Asp Leu Ile His Ser His Glu Ile Asp Ile
850             855             860

Gln Asp Ser Glu Val Leu Asn Ile Gly Val Asn Asn Gly Lys Ile Gln
865             870             875             880

Asp Leu Ser Gly Glu Asn Thr Pro Leu Thr Leu Gly Glu Asn Leu His
            885             890             895

Ile Val Asn Gly Arg Asp Asn Gln Ala Val Arg Leu Asn Asn Gln Leu
            900             905             910

Asp Ser Lys Leu Glu Ile Gln Ser Arg Pro Asn Ile His Phe Thr Ala
            915             920             925

Phe Glu Asp Phe Ser Ile Ser Ile Trp Ile Arg Cys Ser Met Leu Arg
    930             935             940

Asn Asn Arg Asn Arg Gly Gln Lys Tyr Thr Ile Ile Gln Gln Phe Asn
945             950             955             960

Lys Tyr Gly Trp Gln Leu Ala Ile Gln Asp Ser Val Phe Val Trp Thr
            965             970             975

Leu His Asp Thr Phe Asn Asn Gln Ile Gln Leu Thr Ser Gly Ser Ala
    980             985             990

Leu Thr Asn Lys Asn Tyr Leu Leu Gln Asn Phe Trp Leu His Ile Thr
            995             1000            1005

Val Thr Asn Lys Arg Ser Glu Lys Ser Arg Leu Tyr Ile Asn Gly
    1010            1015            1020

Val Leu Gln Asp Gln Lys Asp Ile Ser Val Leu Gly Asn Cys His
    1025            1030            1035

Pro Lys Glu Pro Ile Leu Phe Ser Ile Gln Asp Asn Ser Asp Pro
    1040            1045            1050

Asn Tyr Phe Val Arg Phe Glu Gln Phe Asn Val Tyr Arg Lys Ala
    1055            1060            1065

Leu Thr Asp Ser Glu Val Asn Arg Leu Tyr Trp Lys Tyr Phe Glu
    1070            1075            1080

Gly Ser Tyr Leu Arg Asp Val Trp Gly Glu Arg Leu Thr Tyr Asn
    1085            1090            1095

Arg Asp Tyr Tyr Met Gln Leu Ser Thr Leu Pro Gly Arg Gly Ile
```

```
                1100                1105                1110
Lys Arg Glu Tyr Arg Thr Trp Ser Gly Phe Asp Tyr Ile Ile Leu
        1115                1120                1125

Ser Glu Leu Gly Thr Gln Lys Ile Pro Thr His Glu Val Thr Tyr
        1130                1135                1140

Pro Lys Leu Tyr Gln Gly Gln Lys Ile Thr Ile His Ser Asp Gly
        1145                1150                1155

Lys Asn Leu Glu Pro His Val Lys Ser Asn Lys Asn Ile Arg Leu
        1160                1165                1170

Lys Ile Asp Asp Phe Tyr Ile Gly Val Val Asn Pro Phe Lys Leu
        1175                1180                1185

Pro Glu Trp Arg Pro Glu Ser Gly Ala Tyr Val Val Thr Thr Tyr
        1190                1195                1200

Asn His Ala Glu Asp Leu Cys Leu Tyr Phe Arg Thr Arg Ser Ser
        1205                1210                1215

Ser Gln Ser Leu Tyr Tyr Gly Gln Leu Ile Met Asn Asp Gly Arg
        1220                1225                1230

Asn Lys Ser Leu Leu Asn Tyr Thr Leu Lys Gly Ser Thr Tyr Trp
        1235                1240                1245

Ile Trp Ser Ser Ala Trp Tyr Tyr Glu Asn Tyr Asn Thr Ser Ser
        1250                1255                1260

Lys Thr Ala Gly Asn Trp Tyr Phe Ile Pro Val Asp Glu Gly Trp
        1265                1270                1275

Lys Glu Asp
        1280

<210> SEQ ID NO 21
<211> LENGTH: 1279
<212> TYPE: PRT
<213> ORGANISM: Artificial Sequence
<220> FEATURE:
<223> OTHER INFORMATION: Synthetic Polypeptide

<400> SEQUENCE: 21

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

Pro Asn Val Trp Val Val Pro Glu Arg Tyr Thr Phe Tyr Ser Thr Met
        50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
    130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
```

-continued

```
                165                 170                 175
Arg Glu Thr Gly Arg Gly Cys Met Ala Glu Ile Tyr Phe Ser Pro Met
                    180                 185                 190

Tyr His Lys Thr Tyr Ser Thr Lys Leu Thr Asn Lys Asn Ser Leu Val
            195                 200                 205

Asp Lys Ser Val Gln Glu Phe Val Pro Asp Pro Ala Val Thr Leu Ile
        210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
                260                 265                 270

Phe Gly Gly Glu Asp Val Lys Val Ile Lys Ser Glu Ile Asp Lys Lys
                275                 280                 285

Ile Pro Gly Ile Leu Asn Leu Ile Lys Thr Thr Val Glu Pro Ile Ile
            290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp
                325                 330                 335

Thr Gln Leu Glu Lys Asp Ile Arg Asp Leu Trp Met Val Met Asn Glu
                340                 345                 350

Thr Met Phe Ala Glu Asn Leu Lys Ala Leu Thr Arg Ala Arg Tyr Leu
                355                 360                 365

Val Pro Lys Val Glu Asn Ile Val Gln Val Asp Ile Leu Ser Pro Asn
            370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Lys Pro Val Met Tyr Lys Asn Thr
                420                 425                 430

Gly Lys Ser Glu Gln Cys Ile Glu Ile Leu Glu Asp Asp Leu Phe Ile
            435                 440                 445

Met Ser Ser Lys Asp Ser Phe Thr Asp Thr Asp Phe Ser Glu Pro Ser
    450                 455                 460

Val Gly Pro Val Ser Tyr Lys Ala Lys Lys Gly Ala Asp Thr Ile Leu
465                 470                 475                 480

Asp Ser Thr Leu Ser Asn Tyr Asp Phe Ser Lys Glu Ile Asn Phe Thr
                485                 490                 495

Ser Thr Val Pro Ile Ile Thr Val Glu Asp Pro Leu Glu Thr Asp Glu
                500                 505                 510

Asp Val Pro Val Ile Ser Glu Asp Arg Thr Val Tyr Val Asp Asp Tyr
            515                 520                 525

Thr Thr Phe His Phe Leu Glu Ala Gln Lys Ile Gly Lys Glu Val Val
        530                 535                 540

Pro Thr Gln Thr Lys Val Phe Thr Thr Asn Met Glu Glu Ala Leu
545                 550                 555                 560

Phe Asp Ser Lys Lys Val Tyr Thr Val Phe Glu Asn Thr Ala Ser Arg
                565                 570                 575

Ile Asn Glu Ala Gly Thr Gly Ile Ala Asn Gly Met Met Phe Tyr Gln
                580                 585                 590
```

-continued

```
Trp Leu Lys Gly Ile Val Gln Asp Phe Thr Glu Ala Thr Gln Lys
            595                 600                 605
Asp Thr Phe Asp Lys Ile Ser Asp Val Thr Met Ile Val Pro Tyr Leu
        610                 615                 620
Gly Asn Ile Leu Asn Ile Gly Asn Asp Ile Arg Lys Gly Asp Phe Met
625                 630                 635                 640
Gly Ala Val Glu Leu Gly Gly Val Thr Ile Leu Glu Ala Ile Pro
                645                 650                 655
Glu Leu Thr Leu Pro Val Leu Ile Gly Leu Thr Ile Ile Glu Asp Glu
            660                 665                 670
Leu Glu Lys Glu Gln Val Ser Gln Thr Val Tyr Asn Val Leu Asp Lys
        675                 680                 685
Arg Asp Glu Lys Trp Glu Val Tyr Gly Phe Val Lys Gln Gln Trp
    690                 695                 700
Trp Trp Met Val His Thr Gln Phe Glu Thr Arg Ile Leu His Ala Tyr
705                 710                 715                 720
Gln Ala Leu Asn His Gln Val Glu Ala Ile Lys Ala Asn Met Thr Tyr
                725                 730                 735
Gln Leu Ala Asn Tyr Arg Gly Asn Gln Glu Asp Lys Glu Leu Leu Glu
            740                 745                 750
Lys Ala Ile Asp Asp Thr Leu Gln Ser Leu Tyr Tyr Ala Val Asp Gln
        755                 760                 765
Ala Met His Asn Ile Lys Arg Phe Leu Ile Gln Ser Ser Lys Ser Tyr
    770                 775                 780
Leu Leu Asn Gln Met Leu Pro Lys Thr Lys Glu Gln Leu Leu Ala Phe
785                 790                 795                 800
Asp Gln Gln Thr Leu Arg Asn Val Asn Asp Phe Ile Asn Lys Asn Gln
                805                 810                 815
Gly Val Leu Gly Glu Ser Leu Ala Lys Asp Leu Lys Lys Val Glu
            820                 825                 830
Lys Arg Leu Thr Ser Leu Pro Val Phe Asn Leu Glu Asp Leu Pro Ile
        835                 840                 845
Ser Glu Phe Glu Asp Leu Ile His Ser His Glu Ile Asp Ile Gln Asp
    850                 855                 860
Ser Glu Val Leu Asn Ile Gly Val Asn Asn Gly Lys Ile Gln Asp Leu
865                 870                 875                 880
Ser Gly Glu Asn Thr Pro Leu Thr Leu Gly Glu Asn Leu His Ile Val
                885                 890                 895
Asn Gly Arg Asp Asn Gln Ala Val Arg Leu Asn Asn Gln Leu Asp Ser
            900                 905                 910
Lys Leu Glu Ile Gln Ser Arg Pro Asn Ile His Phe Thr Ala Phe Glu
        915                 920                 925
Asp Phe Ser Ile Ser Ile Trp Ile Arg Cys Ser Met Leu Arg Asn Asn
    930                 935                 940
Arg Asn Arg Gly Gln Lys Tyr Thr Ile Ile Gln Gln Phe Asn Lys Tyr
945                 950                 955                 960
Gly Trp Gln Leu Ala Ile Gln Asp Ser Val Phe Val Trp Thr Leu His
                965                 970                 975
Asp Thr Phe Asn Asn Gln Ile Gln Leu Thr Ser Gly Ser Ala Leu Thr
            980                 985                 990
Asn Lys Asn Tyr Leu Leu Gln Asn Phe Trp Leu His Ile Thr Val Thr
        995                1000                1005
```

-continued

Asn Lys Arg Ser Glu Lys Ser Arg Leu Tyr Ile Asn Gly Val Leu
    1010                1015                1020

Gln Asp Gln Lys Asp Ile Ser Val Leu Gly Asn Cys His Pro Lys
    1025                1030                1035

Glu Pro Ile Leu Phe Ser Ile Gln Asp Asn Ser Asp Pro Asn Tyr
    1040                1045                1050

Phe Val Arg Phe Glu Gln Phe Asn Val Tyr Arg Lys Ala Leu Thr
    1055                1060                1065

Asp Ser Glu Val Asn Arg Leu Tyr Trp Lys Tyr Phe Glu Gly Ser
    1070                1075                1080

Tyr Leu Arg Asp Val Trp Gly Glu Arg Leu Thr Tyr Asn Arg Asp
    1085                1090                1095

Tyr Tyr Met Gln Leu Ser Thr Leu Pro Gly Arg Gly Ile Lys Arg
    1100                1105                1110

Glu Tyr Arg Thr Trp Ser Gly Phe Asp Tyr Ile Ile Leu Ser Glu
    1115                1120                1125

Leu Gly Thr Gln Lys Ile Pro Thr His Glu Val Thr Tyr Pro Lys
    1130                1135                1140

Leu Tyr Gln Gly Gln Lys Ile Thr Ile His Ser Asp Gly Lys Asn
    1145                1150                1155

Leu Glu Pro His Val Lys Ser Asn Lys Asn Ile Arg Leu Lys Ile
    1160                1165                1170

Asp Asp Phe Tyr Ile Gly Val Val Asn Pro Phe Lys Leu Pro Glu
    1175                1180                1185

Trp Arg Pro Glu Ser Gly Ala Tyr Val Val Thr Tyr Asn His
    1190                1195                1200

Ala Glu Asp Leu Cys Leu Tyr Phe Arg Thr Arg Ser Ser Ser Gln
    1205                1210                1215

Ser Leu Tyr Tyr Gly Gln Leu Ile Met Asn Asp Gly Arg Asn Lys
    1220                1225                1230

Ser Leu Leu Asn Tyr Thr Leu Lys Gly Ser Thr Tyr Trp Ile Trp
    1235                1240                1245

Ser Ser Ala Trp Tyr Tyr Glu Asn Tyr Asn Thr Ser Ser Lys Thr
    1250                1255                1260

Ala Gly Asn Trp Tyr Phe Ile Pro Val Asp Glu Gly Trp Lys Glu
    1265                1270                1275

Asp

<210> SEQ ID NO 22
<211> LENGTH: 1309
<212> TYPE: PRT
<213> ORGANISM: Artificial Sequence
<220> FEATURE:
<223> OTHER INFORMATION: Synthetic Polypeptide

<400> SEQUENCE: 22

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

Pro Asn Val Trp Val Pro Glu Arg Tyr Thr Phe Tyr Ser Thr Met
        50                  55                  60

Lys Asn Leu Asp Ala Pro Ala Asn Pro Ser Arg Ser Ser Tyr Tyr Asp

```
                65                  70                  75                  80
Pro Thr Tyr Leu Gln Ser Asp Ala Glu Lys Glu Val Phe Leu Gln Gln
                    85                  90                  95

Met Ile Leu Leu Phe Lys Arg Ile Asn Ser Thr Glu Gly Gln Gln
                100                 105                 110

Phe Leu Asn Leu Leu Ser Arg Ser Ile Pro Val Pro Tyr Glu Ser Asn
                115                 120                 125

Gly Asp Val Ala Met Gly Thr Thr Gln Val Ile Lys Gln Met Asp Asp
                130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
                180                 185                 190

Tyr His Lys Thr Tyr Ser Thr Lys Leu Thr Asn Lys Asn Ser Leu Val
                195                 200                 205

Asp Lys Ser Val Gln Glu Phe Val Pro Asp Pro Ala Val Thr Leu Ile
                210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
                260                 265                 270

Phe Gly Gly Glu Asp Val Lys Val Ile Lys Ser Glu Ile Asp Lys Lys
                275                 280                 285

Ile Pro Gly Ile Leu Asn Leu Ile Lys Thr Thr Val Glu Pro Ile Ile
                290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
                340                 345                 350

Thr Met Phe Ala Glu Asn Leu Lys Ala Leu Thr Arg Ala Arg Tyr Leu
                355                 360                 365

Val Pro Lys Val Glu Asn Ile Val Gln Val Asp Ile Leu Ser Pro Asn
370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Pro Arg Asn Gly Leu Leu Tyr Asn
                420                 425                 430

Ala Ile Tyr Arg Asn Ser Lys Asn Tyr Leu Asn Asn Ile Asp Leu Glu
                435                 440                 445

Asp Lys Lys Thr Thr Ser Lys Thr Asn Val Ser Tyr Pro Cys Ser Leu
450                 455                 460

Leu Asn Gly Cys Ile Glu Ile Leu Glu Asp Asp Leu Phe Ile Met Ser
465                 470                 475                 480

Ser Lys Asp Ser Phe Thr Asp Thr Asp Phe Ser Glu Pro Ser Val Gly
                485                 490                 495
```

-continued

Pro Val Ser Tyr Lys Ala Lys Gly Ala Asp Thr Ile Leu Asp Ser
              500                 505                 510

Thr Leu Ser Asn Tyr Asp Phe Ser Lys Glu Ile Asn Phe Thr Ser Thr
              515                 520                 525

Val Pro Ile Ile Thr Val Glu Asp Pro Leu Glu Thr Asp Glu Asp Val
              530                 535                 540

Pro Val Ile Ser Glu Asp Arg Thr Val Tyr Val Asp Asp Tyr Thr Thr
545                 550                 555                 560

Phe His Phe Leu Glu Ala Gln Lys Ile Gly Lys Glu Val Val Pro Thr
              565                 570                 575

Gln Thr Lys Val Val Phe Thr Thr Asn Met Glu Glu Ala Leu Phe Asp
              580                 585                 590

Ser Lys Lys Val Tyr Thr Val Phe Glu Asn Thr Ala Ser Arg Ile Asn
              595                 600                 605

Glu Ala Gly Thr Gly Ile Ala Asn Gly Met Met Phe Tyr Gln Trp Leu
              610                 615                 620

Lys Gly Ile Val Gln Asp Phe Thr Glu Glu Ala Thr Gln Lys Asp Thr
625                 630                 635                 640

Phe Asp Lys Ile Ser Asp Val Thr Met Ile Val Pro Tyr Leu Gly Asn
              645                 650                 655

Ile Leu Asn Ile Gly Asn Asp Ile Arg Lys Gly Asp Phe Met Gly Ala
              660                 665                 670

Val Glu Leu Gly Gly Val Thr Ile Leu Leu Glu Ala Ile Pro Glu Leu
              675                 680                 685

Thr Leu Pro Val Leu Ile Gly Leu Thr Ile Ile Glu Asp Glu Leu Glu
              690                 695                 700

Lys Glu Gln Val Ser Gln Thr Val Tyr Asn Val Leu Asp Lys Arg Asp
705                 710                 715                 720

Glu Lys Trp Glu Glu Val Tyr Gly Phe Val Lys Gln Gln Trp Trp Trp
              725                 730                 735

Met Val His Thr Gln Phe Glu Thr Arg Ile Leu His Ala Tyr Gln Ala
              740                 745                 750

Leu Asn His Gln Val Glu Ala Ile Lys Ala Asn Met Thr Tyr Gln Leu
              755                 760                 765

Ala Asn Tyr Arg Gly Asn Gln Glu Asp Lys Glu Leu Leu Glu Lys Ala
              770                 775                 780

Ile Asp Asp Thr Leu Gln Ser Leu Tyr Tyr Ala Val Asp Gln Ala Met
785                 790                 795                 800

His Asn Ile Lys Arg Phe Leu Ile Gln Ser Ser Lys Ser Tyr Leu Leu
              805                 810                 815

Asn Gln Met Leu Pro Lys Thr Lys Glu Gln Leu Leu Ala Phe Asp Gln
              820                 825                 830

Gln Thr Leu Arg Asn Val Asn Asp Phe Ile Asn Lys Asn Gln Gly Val
              835                 840                 845

Leu Gly Glu Ser Leu Ala Lys Asp Leu Lys Lys Val Glu Lys Arg
              850                 855                 860

Leu Thr Ser Leu Pro Val Phe Asn Leu Glu Asp Leu Pro Ile Ser Glu
865                 870                 875                 880

Phe Glu Asp Leu Ile His Ser His Glu Ile Asp Ile Gln Asp Ser Glu
              885                 890                 895

Val Leu Asn Ile Gly Val Asn Asn Gly Lys Ile Gln Asp Leu Ser Gly
              900                 905                 910

```
Glu Asn Thr Pro Leu Thr Leu Gly Glu Asn Leu His Ile Val Asn Gly
            915                 920                 925

Arg Asp Asn Gln Ala Val Arg Leu Asn Gln Leu Asp Ser Lys Leu
        930                 935                 940

Glu Ile Gln Ser Arg Pro Asn Ile His Phe Thr Ala Phe Glu Asp Phe
945                 950                 955                 960

Ser Ile Ser Ile Trp Ile Arg Cys Ser Met Leu Arg Asn Asn Arg Asn
                965                 970                 975

Arg Gly Gln Lys Tyr Thr Ile Ile Gln Gln Phe Asn Lys Tyr Gly Trp
            980                 985                 990

Gln Leu Ala Ile Gln Asp Ser Val Phe Val Trp Thr Leu His Asp Thr
        995                 1000                1005

Phe Asn Asn Gln Ile Gln Leu Thr Ser Gly Ser Ala Leu Thr Asn
    1010                1015                1020

Lys Asn Tyr Leu Leu Gln Asn Phe Trp Leu His Ile Thr Val Thr
    1025                1030                1035

Asn Lys Arg Ser Glu Lys Ser Arg Leu Tyr Ile Asn Gly Val Leu
    1040                1045                1050

Gln Asp Gln Lys Asp Ile Ser Val Leu Gly Asn Cys His Pro Lys
    1055                1060                1065

Glu Pro Ile Leu Phe Ser Ile Gln Asp Asn Ser Asp Pro Asn Tyr
    1070                1075                1080

Phe Val Arg Phe Glu Gln Phe Asn Val Tyr Arg Lys Ala Leu Thr
    1085                1090                1095

Asp Ser Glu Val Asn Arg Leu Tyr Trp Lys Tyr Phe Glu Gly Ser
    1100                1105                1110

Tyr Leu Arg Asp Val Trp Gly Glu Arg Leu Thr Tyr Asn Arg Asp
    1115                1120                1125

Tyr Tyr Met Gln Leu Ser Thr Leu Pro Gly Arg Gly Ile Lys Arg
    1130                1135                1140

Glu Tyr Arg Thr Trp Ser Gly Phe Asp Tyr Ile Ile Leu Ser Glu
    1145                1150                1155

Leu Gly Thr Gln Lys Ile Pro Thr His Glu Val Thr Tyr Pro Lys
    1160                1165                1170

Leu Tyr Gln Gly Gln Lys Ile Thr Ile His Ser Asp Gly Lys Asn
    1175                1180                1185

Leu Glu Pro His Val Lys Ser Asn Lys Asn Ile Arg Leu Lys Ile
    1190                1195                1200

Asp Asp Phe Tyr Ile Gly Val Val Asn Pro Phe Lys Leu Pro Glu
    1205                1210                1215

Trp Arg Pro Glu Ser Gly Ala Tyr Val Val Thr Tyr Asn His
    1220                1225                1230

Ala Glu Asp Leu Cys Leu Tyr Phe Arg Thr Arg Ser Ser Ser Gln
    1235                1240                1245

Ser Leu Tyr Tyr Gly Gln Leu Ile Met Asn Asp Gly Arg Asn Lys
    1250                1255                1260

Ser Leu Leu Asn Tyr Thr Leu Lys Gly Ser Thr Tyr Trp Ile Trp
    1265                1270                1275

Ser Ser Ala Trp Tyr Tyr Glu Asn Tyr Asn Thr Ser Ser Lys Thr
    1280                1285                1290

Ala Gly Asn Trp Tyr Phe Ile Pro Val Asp Glu Gly Trp Lys Glu
    1295                1300                1305

Asp
```

<210> SEQ ID NO 23
<211> LENGTH: 1286
<212> TYPE: PRT
<213> ORGANISM: Artificial Sequence
<220> FEATURE:
<223> OTHER INFORMATION: Synthetic Polypeptide

<400> SEQUENCE: 23

```
Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
            20                  25                  30

Gln Phe Ile Asn His Asn Val Pro Asp Leu Lys Ala Phe Gln Val Phe
        35                  40                  45

Pro Asn Val Trp Val Pro Glu Arg Tyr Thr Phe Tyr Ser Thr Met
    50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
    130                 135                 140

Lys Gly Asn Val Leu Lys His Arg Arg Ala His Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
    210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
        275                 280                 285

Ile Pro Gly Ile Leu Asn Leu Ile Lys Thr Thr Val Glu Pro Ile Ile
    290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
        355                 360                 365
```

```
Val Pro Lys Val Glu Asn Ile Val Gln Val Asp Ile Leu Ser Pro Asn
    370                 375                 380
Val Tyr Thr Ile Asp Lys Gly Phe Asn His Leu Ser Lys Gly Phe Lys
385                 390                 395                 400
Gly Gln Ser Val Ser Gln Ser Tyr Phe Arg Lys Ile Ser Ala Leu Ala
                405                 410                 415
Arg Gly Ala Val Val Arg Ala Cys Pro Asn Pro His Phe Ser Ser Gln
            420                 425                 430
Arg Gly Leu Ser Ser Cys Ile Glu Ile Leu Glu Asp Asp Leu Phe Ile
        435                 440                 445
Met Ser Ser Lys Asp Ser Phe Thr Asp Thr Asp Phe Ser Glu Pro Ser
    450                 455                 460
Val Gly Pro Val Ser Tyr Lys Ala Lys Lys Gly Ala Asp Thr Ile Leu
465                 470                 475                 480
Asp Ser Thr Leu Ser Asn Tyr Asp Phe Ser Lys Glu Ile Asn Phe Thr
                485                 490                 495
Ser Thr Val Pro Ile Ile Thr Val Glu Asp Pro Leu Glu Thr Asp Glu
            500                 505                 510
Asp Val Pro Val Ile Ser Glu Asp Arg Thr Val Tyr Val Asp Asp Tyr
        515                 520                 525
Thr Thr Phe His Phe Leu Glu Ala Gln Lys Ile Gly Lys Glu Val Val
    530                 535                 540
Pro Thr Gln Thr Lys Val Val Phe Thr Thr Asn Met Glu Glu Ala Leu
545                 550                 555                 560
Phe Asp Ser Lys Lys Val Tyr Thr Val Phe Glu Asn Thr Ala Ser Arg
                565                 570                 575
Ile Asn Glu Ala Gly Thr Gly Ile Ala Asn Gly Met Met Phe Tyr Gln
            580                 585                 590
Trp Leu Lys Gly Ile Val Gln Asp Phe Thr Glu Glu Ala Thr Gln Lys
        595                 600                 605
Asp Thr Phe Asp Lys Ile Ser Asp Val Thr Met Ile Val Pro Tyr Leu
    610                 615                 620
Gly Asn Ile Leu Asn Ile Gly Asn Asp Ile Arg Lys Gly Asp Phe Met
625                 630                 635                 640
Gly Ala Val Glu Leu Gly Gly Val Thr Ile Leu Leu Glu Ala Ile Pro
                645                 650                 655
Glu Leu Thr Leu Pro Val Leu Ile Gly Leu Thr Ile Ile Glu Asp Glu
            660                 665                 670
Leu Glu Lys Glu Gln Val Ser Gln Thr Val Tyr Asn Val Leu Asp Lys
        675                 680                 685
Arg Asp Glu Lys Trp Glu Glu Val Tyr Gly Phe Val Lys Gln Gln Trp
    690                 695                 700
Trp Trp Met Val His Thr Gln Phe Glu Thr Arg Ile Leu His Ala Tyr
705                 710                 715                 720
Gln Ala Leu Asn His Gln Val Glu Ala Ile Lys Ala Asn Met Thr Tyr
                725                 730                 735
Gln Leu Ala Asn Tyr Arg Gly Asn Gln Glu Asp Lys Glu Leu Leu Glu
            740                 745                 750
Lys Ala Ile Asp Asp Thr Leu Gln Ser Leu Tyr Tyr Ala Val Asp Gln
        755                 760                 765
Ala Met His Asn Ile Lys Arg Phe Leu Ile Gln Ser Ser Lys Ser Tyr
    770                 775                 780
```

```
Leu Leu Asn Gln Met Leu Pro Lys Thr Lys Glu Gln Leu Leu Ala Phe
785                 790                 795                 800

Asp Gln Gln Thr Leu Arg Asn Val Asn Asp Phe Ile Asn Lys Asn Gln
                805                 810                 815

Gly Val Leu Gly Glu Ser Leu Ala Lys Asp Leu Lys Lys Val Glu
                820                 825                 830

Lys Arg Leu Thr Ser Leu Pro Val Phe Asn Leu Glu Asp Leu Pro Ile
                835                 840                 845

Ser Glu Phe Glu Asp Leu Ile His Ser His Glu Ile Asp Ile Ile Ile
    850                 855                 860

Asn Thr Ser Ile Leu Asn Leu Arg Tyr Glu Ser Asn His Leu Ile Asp
865                 870                 875                 880

Leu Ser Arg Tyr Ala Ser Lys Ile Asn Ile Gly Ser Lys Val Asn Phe
                885                 890                 895

Asp Pro Ile Asp Lys Asn Gln Ile Gln Leu Phe Asn Leu Glu Ser Ser
                900                 905                 910

Lys Ile Glu Val Ile Leu Lys Asn Ala Ile Val Tyr Asn Ser Met Tyr
                915                 920                 925

Glu Asn Phe Ser Thr Ser Phe Trp Ile Arg Ile Pro Lys Tyr Phe Asn
930                 935                 940

Ser Ile Ser Leu Asn Asn Glu Tyr Thr Ile Ile Asn Cys Met Glu Asn
945                 950                 955                 960

Asn Ser Gly Trp Lys Val Ser Leu Asn Tyr Gly Glu Ile Ile Trp Thr
                965                 970                 975

Leu Gln Asp Thr Gln Glu Ile Lys Gln Arg Val Val Phe Lys Tyr Ser
                980                 985                 990

Gln Met Ile Asn Ile Ser Asp Tyr Ile Asn Arg Trp Ile Phe Val Thr
                995                 1000                1005

Ile Thr Asn Asn Arg Leu Asn Asn Ser Lys Ile Tyr Ile Asn Gly
    1010                1015                1020

Arg Leu Ile Asp Gln Lys Pro Ile Ser Asn Leu Gly Asn Ile His
    1025                1030                1035

Ala Ser Asn Asn Ile Met Phe Lys Leu Asp Gly Cys Arg Asp Thr
    1040                1045                1050

His Arg Tyr Ile Trp Ile Lys Tyr Phe Asn Leu Phe Asp Lys Glu
    1055                1060                1065

Leu Asn Glu Lys Glu Ile Lys Asp Leu Tyr Asp Asn Gln Ser Asn
    1070                1075                1080

Ser Gly Ile Leu Lys Asp Phe Trp Gly Asp Tyr Leu Gln Tyr Asp
    1085                1090                1095

Lys Pro Tyr Tyr Met Leu Asn Leu Tyr Asp Pro Asn Lys Tyr Val
    1100                1105                1110

Asp Val Asn Asn Val Gly Ile Arg Gly Tyr Met Tyr Leu Lys Gly
    1115                1120                1125

Pro Arg Gly Ser Val Met Thr Thr Asn Ile Tyr Leu Asn Ser Ser
    1130                1135                1140

Leu Tyr Arg Gly Thr Lys Phe Ile Ile Lys Lys Tyr Ala Ser Gly
    1145                1150                1155

Asn Lys Asp Asn Ile Val Arg Asn Asn Asp Arg Val Tyr Ile Asn
    1160                1165                1170

Val Val Val Lys Asn Lys Glu Tyr Arg Leu Ala Thr Asn Ala Ser
    1175                1180                1185

Gln Ala Gly Val Glu Lys Ile Leu Ser Ala Leu Glu Ile Pro Asp
```

```
            1190              1195              1200
Val Gly Asn Leu Ser Gln Val Val Met Lys Ser Lys Asn Asp
    1205              1210              1215

Gln Gly Ile Thr Asn Lys Cys Lys Met Asn Leu Gln Asp Asn Asn
    1220              1225              1230

Gly Asn Asp Ile Gly Phe Ile Gly Phe His Gln Phe Asn Asn Ile
    1235              1240              1245

Ala Lys Leu Val Ala Ser Asn Trp Tyr Asn Arg Gln Ile Glu Arg
    1250              1255              1260

Ser Ser Arg Thr Leu Gly Cys Ser Trp Glu Phe Ile Pro Val Asp
    1265              1270              1275

Asp Gly Trp Gly Glu Arg Pro Leu
    1280              1285

<210> SEQ ID NO 24
<211> LENGTH: 1294
<212> TYPE: PRT
<213> ORGANISM: Artificial Sequence
<220> FEATURE:
<223> OTHER INFORMATION: Synthetic Polypeptide

<400> SEQUENCE: 24

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
            20                  25                  30

Gln Phe Ile Asn His Asn Val Pro Asp Leu Lys Ala Phe Gln Val Phe
        35                  40                  45

Pro Asn Val Trp Val Val Pro Glu Arg Tyr Thr Phe Tyr Ser Thr Met
    50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
    130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
    210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
```

```
              260             265             270
Phe Gly Gly Glu Asp Val Lys Val Ile Lys Ser Glu Ile Asp Lys Lys
            275             280             285
Ile Pro Gly Ile Leu Asn Leu Ile Lys Thr Thr Val Glu Pro Ile Ile
            290             295             300
Asn Lys Ile Thr Asp Pro His Asp Glu Met Leu Gln Cys Leu Gln Ser
305             310             315             320
Lys Tyr Pro Ser Leu Lys Gly Thr Leu Gly Gln Phe Phe Asp Asp
            325             330             335
Thr Gln Leu Glu Lys Asp Ile Arg Asp Leu Trp Met Val Met Asn Glu
            340             345             350
Thr Met Phe Ala Glu Asn Leu Lys Ala Leu Thr Arg Ala Arg Tyr Leu
            355             360             365
Val Pro Lys Val Glu Asn Ile Val Gln Val Asp Ile Leu Ser Pro Asn
            370             375             380
Val Tyr Thr Ile Asp Lys Gly Phe Asn His Leu Ser Lys Gly Phe Lys
385             390             395             400
Gly Gln Ser Val Ser Gln Ser Tyr Phe Arg Lys Ile Ser Ala Leu Ala
            405             410             415
Arg Gly Ala Val Val Arg Ala Cys Pro Asn Pro His Phe Ser Ser Gln
            420             425             430
Arg Gly Leu Ser Ser Cys Ile Glu Ile Leu Glu Asp Asp Leu Phe Ile
            435             440             445
Met Ser Ser Lys Asp Ser Phe Thr Asp Thr Asp Phe Ser Glu Pro Ser
            450             455             460
Val Gly Pro Val Ser Tyr Lys Ala Lys Lys Gly Ala Asp Thr Ile Leu
465             470             475             480
Asp Ser Thr Leu Ser Asn Tyr Asp Phe Ser Lys Glu Ile Asn Phe Thr
            485             490             495
Ser Thr Val Pro Ile Ile Thr Val Glu Asp Pro Leu Glu Thr Asp Glu
            500             505             510
Asp Val Pro Val Ile Ser Glu Asp Arg Thr Val Tyr Val Asp Asp Tyr
            515             520             525
Thr Thr Phe His Phe Leu Glu Ala Gln Lys Ile Gly Lys Glu Val Val
            530             535             540
Pro Thr Gln Thr Lys Val Val Phe Thr Thr Asn Met Glu Glu Ala Leu
545             550             555             560
Phe Asp Ser Lys Lys Val Tyr Thr Val Phe Glu Asn Thr Ala Ser Arg
            565             570             575
Ile Asn Glu Ala Gly Thr Gly Ile Ala Asn Gly Met Met Phe Tyr Gln
            580             585             590
Trp Leu Lys Gly Ile Val Gln Asp Phe Thr Glu Ala Thr Gln Lys
            595             600             605
Asp Thr Phe Asp Lys Ile Ser Asp Val Thr Met Ile Val Pro Tyr Leu
            610             615             620
Gly Asn Ile Leu Asn Ile Gly Asn Asp Ile Arg Lys Gly Asp Phe Met
625             630             635             640
Gly Ala Val Glu Leu Gly Gly Val Thr Ile Leu Leu Glu Ala Ile Pro
            645             650             655
Glu Leu Thr Leu Pro Val Leu Ile Gly Leu Thr Ile Ile Glu Asp Glu
            660             665             670
Leu Glu Lys Glu Gln Val Ser Gln Thr Val Tyr Asn Val Leu Asp Lys
            675             680             685
```

```
Arg Asp Glu Lys Trp Glu Val Tyr Gly Phe Val Lys Gln Gln Trp
690             695             700

Trp Trp Met Val His Thr Gln Phe Glu Thr Arg Ile Leu His Ala Tyr
705             710             715             720

Gln Ala Leu Asn His Gln Val Glu Ala Ile Lys Ala Asn Met Thr Tyr
                725             730             735

Gln Leu Ala Asn Tyr Arg Gly Asn Gln Glu Asp Lys Glu Leu Leu Glu
            740             745             750

Lys Ala Ile Asp Asp Thr Leu Gln Ser Leu Tyr Tyr Ala Val Asp Gln
        755             760             765

Ala Met His Asn Ile Lys Arg Phe Leu Ile Gln Ser Ser Lys Ser Tyr
770             775             780

Leu Leu Asn Gln Met Leu Pro Lys Thr Lys Glu Gln Leu Leu Ala Phe
785             790             795             800

Asp Gln Gln Thr Leu Arg Asn Val Asn Asp Phe Ile Asn Lys Asn Gln
            805             810             815

Gly Val Leu Gly Glu Ser Leu Ala Lys Asp Leu Lys Lys Val Glu
            820             825             830

Lys Arg Leu Thr Ser Leu Pro Val Phe Asn Leu Glu Asp Leu Pro Ile
        835             840             845

Ser Glu Phe Glu Asp Leu Ile His Ser His Glu Ile Asp Ile Ile Leu
850             855             860

Asn Asn Ile Ile Leu Asn Leu Arg Tyr Lys Asp Asn Asn Leu Ile Asp
865             870             875             880

Leu Ser Gly Tyr Gly Ala Lys Val Glu Val Tyr Asp Gly Val Glu Leu
            885             890             895

Asn Asp Lys Asn Gln Phe Lys Leu Thr Ser Ser Ala Asn Ser Lys Ile
            900             905             910

Arg Val Thr Gln Asn Gln Asn Ile Ile Phe Asn Ser Val Phe Leu Asp
            915             920             925

Phe Ser Val Ser Phe Trp Ile Arg Ile Pro Lys Tyr Lys Asn Asp Gly
930             935             940

Ile Gln Asn Tyr Ile His Asn Glu Tyr Thr Ile Ile Asn Cys Met Lys
945             950             955             960

Asn Asn Ser Gly Trp Lys Ile Ser Ile Arg Gly Asn Arg Ile Ile Trp
            965             970             975

Thr Leu Ile Asp Ile Asn Gly Lys Thr Lys Ser Val Phe Phe Glu Tyr
            980             985             990

Asn Ile Arg Glu Asp Ile Ser Glu Tyr Ile Asn Arg Trp Phe Phe Val
            995             1000            1005

Thr Ile Thr Asn Asn Leu Asn Asn Ala Lys Ile Tyr Ile Asn Gly
        1010            1015            1020

Lys Leu Glu Ser Asn Thr Asp Ile Lys Asp Ile Arg Glu Val Ile
        1025            1030            1035

Ala Asn Gly Glu Ile Ile Phe Lys Leu Asp Gly Asp Ile Asp Arg
        1040            1045            1050

Thr Gln Phe Ile Trp Met Lys Tyr Phe Ser Ile Phe Asn Thr Glu
        1055            1060            1065

Leu Ser Gln Ser Asn Ile Glu Glu Arg Tyr Lys Ile Gln Ser Tyr
        1070            1075            1080

Ser Glu Tyr Leu Lys Asp Phe Trp Gly Asn Pro Leu Met Tyr Asn
        1085            1090            1095
```

```
Lys Glu Tyr Tyr Met Phe Asn Ala Gly Asn Lys Asn Ser Tyr Ile
    1100                1105                1110

Lys Leu Lys Lys Asp Ser Pro Val Gly Glu Ile Leu Thr Arg Ser
    1115                1120                1125

Lys Tyr Asn Gln Asn Ser Lys Tyr Ile Asn Tyr Arg Asp Leu Tyr
    1130                1135                1140

Ile Gly Glu Lys Phe Ile Ile Arg Arg Lys Ser Asn Ser Gln Ser
    1145                1150                1155

Ile Asn Asp Asp Ile Val Arg Lys Glu Asp Tyr Ile Tyr Leu Asp
    1160                1165                1170

Phe Phe Asn Leu Asn Gln Glu Trp Arg Val Tyr Thr Tyr Lys Tyr
    1175                1180                1185

Phe Lys Lys Glu Glu Lys Leu Phe Leu Ala Pro Ile Ser Asp
    1190                1195                1200

Ser Asp Glu Phe Tyr Asn Thr Ile Gln Ile Lys Glu Tyr Asp Glu
    1205                1210                1215

Gln Pro Thr Tyr Ser Cys Gln Leu Leu Phe Lys Lys Asp Glu Glu
    1220                1225                1230

Ser Thr Asp Glu Ile Gly Leu Ile Gly Ile His Arg Phe Tyr Glu
    1235                1240                1245

Ser Gly Ile Val Phe Glu Glu Tyr Lys Asp Tyr Phe Cys Ile Ser
    1250                1255                1260

Lys Trp Tyr Leu Lys Glu Val Lys Arg Lys Pro Tyr Asn Leu Lys
    1265                1270                1275

Leu Gly Cys Asn Trp Gln Phe Ile Pro Lys Asp Glu Gly Trp Thr
    1280                1285                1290

Glu

<210> SEQ ID NO 25
<211> LENGTH: 1286
<212> TYPE: PRT
<213> ORGANISM: Artificial Sequence
<220> FEATURE:
<223> OTHER INFORMATION: Synthetic Polypeptide

<400> SEQUENCE: 25

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

Pro Asn Val Trp Val Val Pro Glu Arg Tyr Thr Phe Tyr Ser Thr Met
        50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
    130                 135                 140

Lys Gly Asn Val Leu Lys His Arg Arg Ala His Ile Ile Ile Tyr Gly
```

```
            145                 150                 155                 160
Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
                180                 185                 190

Tyr His Lys Thr Tyr Ser Thr Lys Leu Thr Asn Lys Asn Ser Leu Val
                195                 200                 205

Asp Lys Ser Val Gln Glu Phe Val Pro Asp Pro Ala Val Thr Leu Ile
            210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
                260                 265                 270

Phe Gly Gly Glu Asp Val Lys Val Ile Lys Ser Glu Ile Asp Lys Lys
                275                 280                 285

Ile Pro Gly Ile Leu Asn Leu Ile Lys Thr Thr Val Glu Pro Ile Ile
            290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
                340                 345                 350

Thr Met Phe Ala Glu Asn Leu Lys Ala Leu Thr Arg Ala Arg Tyr Leu
            355                 360                 365

Val Pro Lys Val Glu Asn Ile Val Gln Val Asp Ile Leu Ser Pro Asn
            370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Pro Asn Pro His Phe Ser Ser Gln
                420                 425                 430

Arg Gly Leu Ser Ser Cys Ile Glu Ile Leu Glu Asp Asp Leu Phe Ile
                435                 440                 445

Met Ser Ser Lys Asp Ser Phe Thr Asp Thr Asp Phe Ser Glu Pro Ser
450                 455                 460

Val Gly Pro Val Ser Tyr Lys Ala Lys Lys Gly Ala Asp Thr Ile Leu
465                 470                 475                 480

Asp Ser Thr Leu Ser Asn Tyr Asp Phe Ser Lys Glu Ile Asn Phe Thr
                485                 490                 495

Ser Thr Val Pro Ile Ile Thr Val Glu Asp Pro Leu Glu Thr Asp Glu
                500                 505                 510

Asp Val Pro Val Ile Ser Glu Asp Arg Thr Val Tyr Val Asp Asp Tyr
            515                 520                 525

Thr Thr Phe His Phe Leu Glu Ala Gln Lys Ile Gly Lys Glu Val Val
            530                 535                 540

Pro Thr Gln Thr Lys Val Val Phe Thr Thr Asn Met Glu Glu Ala Leu
545                 550                 555                 560

Phe Asp Ser Lys Lys Val Tyr Thr Val Phe Glu Asn Thr Ala Ser Arg
                565                 570                 575
```

```
Ile Asn Glu Ala Gly Thr Gly Ile Ala Asn Gly Met Met Phe Tyr Gln
            580                 585                 590

Trp Leu Lys Gly Ile Val Gln Asp Phe Thr Glu Ala Thr Gln Lys
            595                 600                 605

Asp Thr Phe Asp Lys Ile Ser Asp Val Thr Met Ile Val Pro Tyr Leu
            610                 615                 620

Gly Asn Ile Leu Asn Ile Gly Asn Asp Ile Arg Lys Gly Asp Phe Met
625                 630                 635                 640

Gly Ala Val Glu Leu Gly Gly Val Thr Ile Leu Leu Glu Ala Ile Pro
                645                 650                 655

Glu Leu Thr Leu Pro Val Leu Ile Gly Leu Thr Ile Ile Glu Asp Glu
            660                 665                 670

Leu Glu Lys Glu Gln Val Ser Gln Thr Val Tyr Asn Val Leu Asp Lys
            675                 680                 685

Arg Asp Glu Lys Trp Glu Val Tyr Gly Phe Val Lys Gln Gln Trp
            690                 695                 700

Trp Trp Met Val His Thr Gln Phe Glu Thr Arg Ile Leu His Ala Tyr
705                 710                 715                 720

Gln Ala Leu Asn His Gln Val Glu Ala Ile Lys Ala Asn Met Thr Tyr
                725                 730                 735

Gln Leu Ala Asn Tyr Arg Gly Asn Gln Glu Asp Lys Glu Leu Leu Glu
            740                 745                 750

Lys Ala Ile Asp Asp Thr Leu Gln Ser Leu Tyr Tyr Ala Val Asp Gln
            755                 760                 765

Ala Met His Asn Ile Lys Arg Phe Leu Ile Gln Ser Ser Lys Ser Tyr
            770                 775                 780

Leu Leu Asn Gln Met Leu Pro Lys Thr Lys Glu Gln Leu Leu Ala Phe
785                 790                 795                 800

Asp Gln Gln Thr Leu Arg Asn Val Asn Asp Phe Ile Asn Lys Asn Gln
                805                 810                 815

Gly Val Leu Gly Glu Ser Leu Ala Lys Asp Leu Lys Lys Lys Val Glu
            820                 825                 830

Lys Arg Leu Thr Ser Leu Pro Val Phe Asn Leu Glu Asp Leu Pro Ile
            835                 840                 845

Ser Glu Phe Glu Asp Leu Ile His Ser His Glu Ile Asp Ile Ile Asn
            850                 855                 860

Asp Ser Lys Ile Leu Ser Leu Gln Asn Arg Lys Asn Thr Leu Val Asp
865                 870                 875                 880

Thr Ser Gly Tyr Asn Ala Glu Val Ser Glu Glu Gly Asp Val Gln Leu
                885                 890                 895

Asn Pro Ile Phe Pro Phe Asp Phe Lys Leu Gly Ser Ser Gly Glu Asp
            900                 905                 910

Arg Gly Lys Val Ile Val Thr Gln Asn Glu Asn Ile Val Tyr Asn Ser
            915                 920                 925

Met Tyr Glu Ser Phe Ser Ile Ser Phe Trp Ile Arg Ile Asn Lys Trp
            930                 935                 940

Val Ser Asn Leu Pro Gly Tyr Thr Ile Ile Asp Ser Val Lys Asn Asn
945                 950                 955                 960

Ser Gly Trp Ser Ile Gly Ile Ile Ser Asn Phe Leu Val Phe Thr Leu
                965                 970                 975

Lys Gln Asn Glu Asp Ser Glu Gln Ser Ile Asn Phe Ser Tyr Asp Ile
            980                 985                 990
```

Ser Asn Asn Ala Pro Gly Tyr Asn Lys Trp Phe Phe Val Thr Val Thr
        995                 1000                1005

Asn Asn Met Met Gly Asn Met Lys Ile Tyr Ile Asn Gly Lys Leu
    1010                1015                1020

Ile Asp Thr Ile Lys Val Lys Glu Leu Thr Gly Ile Asn Phe Ser
    1025                1030                1035

Lys Thr Ile Thr Phe Glu Ile Asn Lys Ile Pro Asp Thr Gly Leu
    1040                1045                1050

Ile Thr Ser Asp Ser Asp Asn Ile Asn Met Trp Ile Arg Asp Phe
    1055                1060                1065

Tyr Ile Phe Ala Lys Glu Leu Asp Gly Lys Asp Ile Asn Ile Leu
    1070                1075                1080

Phe Asn Ser Leu Gln Tyr Thr Asn Val Val Lys Asp Tyr Trp Gly
    1085                1090                1095

Asn Asp Leu Arg Tyr Asn Lys Glu Tyr Tyr Met Val Asn Ile Asp
    1100                1105                1110

Tyr Leu Asn Arg Tyr Met Tyr Ala Asn Ser Arg Gln Ile Val Phe
    1115                1120                1125

Asn Thr Arg Arg Asn Asn Asn Asp Phe Asn Glu Gly Tyr Lys Ile
    1130                1135                1140

Ile Ile Lys Arg Ile Arg Gly Asn Thr Asn Asp Thr Arg Val Arg
    1145                1150                1155

Gly Gly Asp Ile Leu Tyr Phe Asp Met Thr Ile Asn Asn Lys Ala
    1160                1165                1170

Tyr Asn Leu Phe Met Lys Asn Glu Thr Met Tyr Ala Asp Asn His
    1175                1180                1185

Ser Thr Glu Asp Ile Tyr Ala Ile Gly Leu Arg Glu Gln Thr Lys
    1190                1195                1200

Asp Ile Asn Asp Asn Ile Ile Phe Gln Ile Gln Pro Met Asn Asn
    1205                1210                1215

Thr Tyr Tyr Tyr Ala Ser Gln Ile Phe Lys Ser Asn Phe Asn Gly
    1220                1225                1230

Glu Asn Ile Ser Gly Ile Cys Ser Ile Gly Thr Tyr Arg Phe Arg
    1235                1240                1245

Leu Gly Gly Asp Trp Tyr Arg His Asn Tyr Leu Val Pro Thr Val
    1250                1255                1260

Lys Gln Gly Asn Tyr Ala Ser Leu Leu Glu Ser Thr Ser Thr His
    1265                1270                1275

Trp Gly Phe Val Pro Val Ser Glu
    1280                1285

<210> SEQ ID NO 26
<211> LENGTH: 1276
<212> TYPE: PRT
<213> ORGANISM: Artificial Sequence
<220> FEATURE:
<223> OTHER INFORMATION: Synthetic Polypeptide

<400> SEQUENCE: 26

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

-continued

```
Pro Asn Val Trp Val Pro Glu Arg Tyr Thr Phe Tyr Ser Thr Met
 50                  55                  60

Lys Asn Leu Asp Ala Pro Ala Asn Pro Ser Arg Ser Ser Tyr Tyr Asp
 65                  70                  75                  80

Pro Thr Tyr Leu Gln Ser Asp Ala Glu Lys Glu Val Phe Leu Gln Gln
                 85                  90                  95

Met Ile Leu Leu Phe Lys Arg Ile Asn Ser Thr Gln Glu Gly Gln Gln
                100                 105                 110

Phe Leu Asn Leu Leu Ser Arg Ser Ile Pro Val Pro Tyr Glu Ser Asn
                115                 120                 125

Gly Asp Val Ala Met Gly Thr Thr Gln Val Ile Lys Gln Met Asp Asp
130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
                180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
        210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
                260                 265                 270

Phe Gly Gly Glu Asp Val Lys Val Ile Lys Ser Glu Ile Asp Lys Lys
                275                 280                 285

Ile Pro Gly Ile Leu Asn Leu Ile Lys Thr Thr Val Glu Pro Ile Ile
                290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
                340                 345                 350

Thr Met Phe Ala Glu Asn Leu Lys Ala Leu Thr Arg Ala Arg Tyr Leu
                355                 360                 365

Val Pro Lys Val Glu Asn Ile Val Gln Val Asp Ile Leu Ser Pro Asn
                370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Pro Asn Pro His Phe Ser Ser Gln
                420                 425                 430

Arg Gly Leu Ser Ser Cys Ile Glu Ile Leu Glu Asp Asp Leu Phe Ile
                435                 440                 445

Met Ser Ser Lys Asp Ser Phe Thr Asp Thr Asp Phe Ser Glu Pro Ser
450                 455                 460

Val Gly Pro Val Ser Tyr Lys Ala Lys Lys Gly Ala Asp Thr Ile Leu
```

-continued

```
         465                 470                 475                 480
Asp Ser Thr Leu Ser Asn Tyr Asp Phe Ser Lys Glu Ile Asn Phe Thr
                485                 490                 495

Ser Thr Val Pro Ile Ile Thr Val Glu Asp Pro Leu Glu Thr Asp Glu
                500                 505                 510

Asp Val Pro Val Ile Ser Glu Asp Arg Thr Val Tyr Val Asp Asp Tyr
                515                 520                 525

Thr Thr Phe His Phe Leu Glu Ala Gln Lys Ile Gly Lys Glu Val Val
        530                 535                 540

Pro Thr Gln Thr Lys Val Val Phe Thr Thr Asn Met Glu Glu Ala Leu
545                 550                 555                 560

Phe Asp Ser Lys Lys Val Tyr Thr Val Phe Glu Asn Thr Ala Ser Arg
                565                 570                 575

Ile Asn Glu Ala Gly Thr Gly Ile Ala Asn Gly Met Met Phe Tyr Gln
                580                 585                 590

Trp Leu Lys Gly Ile Val Gln Asp Phe Thr Glu Glu Ala Thr Gln Lys
        595                 600                 605

Asp Thr Phe Asp Lys Ile Ser Asp Val Thr Met Ile Val Pro Tyr Leu
        610                 615                 620

Gly Asn Ile Leu Asn Ile Gly Asn Asp Ile Arg Lys Gly Asp Phe Met
625                 630                 635                 640

Gly Ala Val Glu Leu Gly Gly Val Thr Ile Leu Leu Glu Ala Ile Pro
                645                 650                 655

Glu Leu Thr Leu Pro Val Leu Ile Gly Leu Thr Ile Ile Glu Asp Glu
                660                 665                 670

Leu Glu Lys Glu Gln Val Ser Gln Thr Val Tyr Asn Val Leu Asp Lys
        675                 680                 685

Arg Asp Glu Lys Trp Glu Glu Val Tyr Gly Phe Val Lys Gln Gln Trp
        690                 695                 700

Trp Trp Met Val His Thr Gln Phe Glu Thr Arg Ile Leu His Ala Tyr
705                 710                 715                 720

Gln Ala Leu Asn His Gln Val Glu Ala Ile Lys Ala Asn Met Thr Tyr
                725                 730                 735

Gln Leu Ala Asn Tyr Arg Gly Asn Gln Glu Asp Lys Glu Leu Leu Glu
                740                 745                 750

Lys Ala Ile Asp Asp Thr Leu Gln Ser Leu Tyr Tyr Ala Val Asp Gln
        755                 760                 765

Ala Met His Asn Ile Lys Arg Phe Leu Ile Gln Ser Ser Lys Ser Tyr
770                 775                 780

Leu Leu Asn Gln Met Leu Pro Lys Thr Lys Glu Gln Leu Leu Ala Phe
785                 790                 795                 800

Asp Gln Gln Thr Leu Arg Asn Val Asn Asp Phe Ile Asn Lys Asn Gln
                805                 810                 815

Gly Val Leu Gly Glu Ser Leu Ala Lys Asp Leu Lys Lys Val Glu
                820                 825                 830

Lys Arg Leu Thr Ser Leu Pro Val Phe Asn Leu Glu Asp Leu Pro Ile
        835                 840                 845

Ser Glu Phe Glu Asp Leu Ile His Ser His Ile Asp Ile Glu Asp
        850                 855                 860

Tyr Glu Val Leu Asn Leu Gly Ala Glu Asp Gly Lys Ile Lys Asp Leu
865                 870                 875                 880

Ser Gly Thr Thr Ser Asp Ile Asn Ile Gly Ser Asp Ile Glu Leu Ala
                885                 890                 895
```

```
Asp Gly Arg Glu Asn Lys Ala Ile Lys Ile Lys Gly Ser Glu Asn Ser
                900                 905                 910

Thr Ile Lys Ile Ala Met Asn Lys Tyr Leu Arg Phe Ser Ala Thr Asp
                915                 920                 925

Asn Phe Ser Ile Ser Phe Trp Ile Lys His Pro Lys Pro Thr Asn Leu
                930                 935                 940

Leu Asn Asn Gly Ile Glu Tyr Thr Leu Val Glu Asn Phe Asn Gln Arg
945                 950                 955                 960

Gly Trp Lys Ile Ser Ile Gln Asp Ser Lys Leu Ile Trp Tyr Leu Arg
                965                 970                 975

Asp His Asn Asn Ser Ile Lys Ile Val Thr Pro Asp Tyr Ile Ala Phe
                980                 985                 990

Asn Gly Trp Asn Leu Ile Thr Ile Thr Asn Asn Arg Ser Lys Gly Ser
                995                 1000                1005

Ile Val Tyr Val Asn Gly Ser Lys Ile Glu Glu Lys Asp Ile Ser
    1010                1015                1020

Ser Ile Trp Asn Thr Glu Val Asp Asp Pro Ile Ile Phe Arg Leu
    1025                1030                1035

Lys Asn Asn Arg Asp Thr Gln Ala Phe Thr Leu Leu Asp Gln Phe
    1040                1045                1050

Ser Ile Tyr Arg Lys Glu Leu Asn Gln Asn Glu Val Val Lys Leu
    1055                1060                1065

Tyr Asn Tyr Tyr Phe Asn Ser Asn Tyr Ile Arg Asp Ile Trp Gly
    1070                1075                1080

Asn Pro Leu Gln Tyr Asn Lys Lys Tyr Tyr Leu Gln Thr Gln Asp
    1085                1090                1095

Lys Pro Gly Lys Gly Leu Ile Arg Glu Tyr Trp Ser Ser Phe Gly
    1100                1105                1110

Tyr Asp Tyr Val Ile Leu Ser Asp Ser Lys Thr Ile Thr Phe Pro
    1115                1120                1125

Asn Asn Ile Arg Tyr Gly Ala Leu Tyr Asn Gly Ser Lys Val Leu
    1130                1135                1140

Ile Lys Asn Ser Lys Lys Leu Asp Gly Leu Val Arg Asn Lys Asp
    1145                1150                1155

Phe Ile Gln Leu Glu Ile Asp Gly Tyr Asn Met Gly Ile Ser Ala
    1160                1165                1170

Asp Arg Phe Asn Glu Asp Thr Asn Tyr Ile Gly Thr Thr Tyr Gly
    1175                1180                1185

Thr Thr His Asp Leu Thr Thr Asp Phe Glu Ile Ile Gln Arg Gln
    1190                1195                1200

Glu Lys Tyr Arg Asn Tyr Cys Gln Leu Lys Thr Pro Tyr Asn Ile
    1205                1210                1215

Phe His Lys Ser Gly Leu Met Ser Thr Glu Thr Ser Lys Pro Thr
    1220                1225                1230

Phe His Asp Tyr Arg Asp Trp Val Tyr Ser Ser Ala Trp Tyr Phe
    1235                1240                1245

Gln Asn Tyr Glu Asn Leu Asn Leu Arg Lys His Thr Lys Thr Asn
    1250                1255                1260

Trp Tyr Phe Ile Pro Lys Asp Glu Gly Trp Asp Glu Asp
    1265                1270                1275

<210> SEQ ID NO 27
<211> LENGTH: 1290
```

<212> TYPE: PRT
<213> ORGANISM: Artificial Sequence
<220> FEATURE:
<223> OTHER INFORMATION: Synthetic Polypeptide

<400> SEQUENCE: 27

```
Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
            20                  25                  30

Gln Phe Ile Asn His Asn Val Pro Asp Leu Lys Ala Phe Gln Val Phe
        35                  40                  45

Pro Asn Val Trp Val Pro Glu Arg Tyr Thr Phe Tyr Ser Thr Met
50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
130                 135                 140

Lys Gly Asn Val Leu Lys His Arg Arg Ala His Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
        275                 280                 285

Ile Pro Gly Ile Leu Asn Leu Ile Lys Thr Thr Val Glu Pro Ile Ile
290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
        355                 360                 365

Val Pro Lys Val Glu Asn Ile Val Gln Val Asp Ile Leu Ser Pro Asn
370                 375                 380
```

```
Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
        405                 410                 415

Arg Gly Ala Val Val Arg Ala Cys Pro Asn Pro His Phe Ser Ser Gln
        420                 425                 430

Leu Val Pro Arg Gly Ser Leu Ser Ser Cys Ile Glu Ile Leu Glu Asp
        435                 440                 445

Asp Leu Phe Ile Met Ser Ser Lys Asp Ser Phe Thr Asp Thr Asp Phe
    450                 455                 460

Ser Glu Pro Ser Val Gly Pro Val Ser Tyr Lys Ala Lys Lys Gly Ala
465                 470                 475                 480

Asp Thr Ile Leu Asp Ser Thr Leu Ser Asn Tyr Asp Phe Ser Lys Glu
            485                 490                 495

Ile Asn Phe Thr Ser Thr Val Pro Ile Ile Thr Val Glu Asp Pro Leu
            500                 505                 510

Glu Thr Asp Glu Asp Val Pro Val Ile Ser Glu Asp Arg Thr Val Tyr
        515                 520                 525

Val Asp Asp Tyr Thr Thr Phe His Phe Leu Glu Ala Gln Lys Ile Gly
    530                 535                 540

Lys Glu Val Val Pro Thr Gln Thr Lys Val Val Phe Thr Thr Asn Met
545                 550                 555                 560

Glu Glu Ala Leu Phe Asp Ser Lys Lys Val Tyr Thr Val Phe Glu Asn
                565                 570                 575

Thr Ala Ser Arg Ile Asn Glu Ala Gly Thr Gly Ile Ala Asn Gly Met
            580                 585                 590

Met Phe Tyr Gln Trp Leu Lys Gly Ile Val Gln Asp Phe Thr Glu Glu
        595                 600                 605

Ala Thr Gln Lys Asp Thr Phe Asp Lys Ile Ser Asp Val Thr Met Ile
    610                 615                 620

Val Pro Tyr Leu Gly Asn Ile Leu Asn Ile Gly Asn Asp Ile Arg Lys
625                 630                 635                 640

Gly Asp Phe Met Gly Ala Val Glu Leu Gly Gly Val Thr Ile Leu Leu
                645                 650                 655

Glu Ala Ile Pro Glu Leu Thr Leu Pro Val Leu Ile Gly Leu Thr Ile
                660                 665                 670

Ile Glu Asp Glu Leu Glu Lys Glu Gln Val Ser Gln Thr Val Tyr Asn
        675                 680                 685

Val Leu Asp Lys Arg Asp Glu Lys Trp Glu Val Tyr Gly Phe Val
690                 695                 700

Lys Gln Gln Trp Trp Met Val His Thr Gln Phe Glu Thr Arg Ile
705                 710                 715                 720

Leu His Ala Tyr Gln Ala Leu Asn His Gln Val Glu Ala Ile Lys Ala
                725                 730                 735

Asn Met Thr Tyr Gln Leu Ala Asn Tyr Arg Gly Asn Gln Glu Asp Lys
            740                 745                 750

Glu Leu Leu Glu Lys Ala Ile Asp Asp Thr Leu Gln Ser Leu Tyr Tyr
        755                 760                 765

Ala Val Asp Gln Ala Met His Asn Ile Lys Arg Phe Leu Ile Gln Ser
    770                 775                 780

Ser Lys Ser Tyr Leu Leu Asn Gln Met Leu Pro Lys Thr Lys Glu Gln
785                 790                 795                 800

Leu Leu Ala Phe Asp Gln Gln Thr Leu Arg Asn Val Asn Asp Phe Ile
```

```
                805                 810                 815
Asn Lys Asn Gln Gly Val Leu Gly Glu Ser Leu Ala Lys Asp Leu Lys
            820                 825                 830

Lys Lys Val Glu Lys Arg Leu Thr Ser Leu Pro Val Phe Asn Leu Glu
            835                 840                 845

Asp Leu Pro Ile Ser Glu Phe Glu Asp Leu Ile His Ser His Glu Ile
        850                 855                 860

Asp Ile Ile Ile Asn Thr Ser Ile Leu Asn Leu Arg Tyr Glu Ser Asn
865                 870                 875                 880

His Leu Ile Asp Leu Ser Arg Tyr Ala Ser Lys Ile Asn Ile Gly Ser
                885                 890                 895

Lys Val Asn Phe Asp Pro Ile Asp Lys Asn Gln Ile Gln Leu Phe Asn
            900                 905                 910

Leu Glu Ser Ser Lys Ile Glu Val Ile Leu Lys Asn Ala Ile Val Tyr
        915                 920                 925

Asn Ser Met Tyr Glu Asn Phe Ser Thr Ser Phe Trp Ile Arg Ile Pro
    930                 935                 940

Lys Tyr Phe Asn Ser Ile Ser Leu Asn Asn Glu Tyr Thr Ile Ile Asn
945                 950                 955                 960

Cys Met Glu Asn Asn Ser Gly Trp Lys Val Ser Leu Asn Tyr Gly Glu
                965                 970                 975

Ile Ile Trp Thr Leu Gln Asp Thr Gln Glu Ile Lys Gln Arg Val Val
            980                 985                 990

Phe Lys Tyr Ser Gln Met Ile Asn Ile Ser Asp Tyr Ile Asn Arg Trp
        995                 1000                1005

Ile Phe Val Thr Ile Thr Asn Asn Arg Leu Asn Asn Ser Lys Ile
    1010                1015                1020

Tyr Ile Asn Gly Arg Leu Ile Asp Gln Lys Pro Ile Ser Asn Leu
    1025                1030                1035

Gly Asn Ile His Ala Ser Asn Asn Ile Met Phe Lys Leu Asp Gly
    1040                1045                1050

Cys Arg Asp Thr His Arg Tyr Ile Trp Ile Lys Tyr Phe Asn Leu
    1055                1060                1065

Phe Asp Lys Glu Leu Asn Glu Lys Glu Ile Lys Asp Leu Tyr Asp
    1070                1075                1080

Asn Gln Ser Asn Ser Gly Ile Leu Lys Asp Phe Trp Gly Asp Tyr
    1085                1090                1095

Leu Gln Tyr Asp Lys Pro Tyr Tyr Met Leu Asn Leu Tyr Asp Pro
    1100                1105                1110

Asn Lys Tyr Val Asp Val Asn Asn Val Gly Ile Arg Gly Tyr Met
    1115                1120                1125

Tyr Leu Lys Gly Pro Arg Gly Ser Val Met Thr Thr Asn Ile Tyr
    1130                1135                1140

Leu Asn Ser Ser Leu Tyr Arg Gly Thr Lys Phe Ile Ile Lys Lys
    1145                1150                1155

Tyr Ala Ser Gly Asn Lys Asp Asn Ile Val Arg Asn Asn Asp Arg
    1160                1165                1170

Val Tyr Ile Asn Val Val Val Lys Asn Lys Glu Tyr Arg Leu Ala
    1175                1180                1185

Thr Asn Ala Ser Gln Ala Gly Val Glu Lys Ile Leu Ser Ala Leu
    1190                1195                1200

Glu Ile Pro Asp Val Gly Asn Leu Ser Gln Val Val Val Met Lys
    1205                1210                1215
```

Ser Lys Asn Asp Gln Gly Ile Thr Asn Lys Cys Lys Met Asn Leu
1220                1225                1230

Gln Asp Asn Asn Gly Asn Asp Ile Gly Phe Ile Gly Phe His Gln
1235                1240                1245

Phe Asn Asn Ile Ala Lys Leu Val Ala Ser Asn Trp Tyr Asn Arg
1250                1255                1260

Gln Ile Glu Arg Ser Ser Arg Thr Leu Gly Cys Ser Trp Glu Phe
1265                1270                1275

Ile Pro Val Asp Asp Gly Trp Gly Glu Arg Pro Leu
1280                1285                1290

<210> SEQ ID NO 28
<211> LENGTH: 1298
<212> TYPE: PRT
<213> ORGANISM: Artificial Sequence
<220> FEATURE:
<223> OTHER INFORMATION: Synthetic Polypeptide

<400> SEQUENCE: 28

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

Pro Asn Val Trp Val Pro Glu Arg Tyr Thr Phe Tyr Ser Thr Met
        50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
    210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
        275                 280                 285

```
Ile Pro Gly Ile Leu Asn Leu Ile Lys Thr Thr Val Glu Pro Ile Ile
    290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
        355                 360                 365

Val Pro Lys Val Glu Asn Ile Val Gln Val Asp Ile Leu Ser Pro Asn
    370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Pro Asn Pro His Phe Ser Ser Gln
            420                 425                 430

Leu Val Pro Arg Gly Ser Leu Ser Ser Cys Ile Glu Ile Leu Glu Asp
        435                 440                 445

Asp Leu Phe Ile Met Ser Ser Lys Asp Ser Phe Thr Asp Thr Asp Phe
    450                 455                 460

Ser Glu Pro Ser Val Gly Pro Val Ser Tyr Lys Ala Lys Lys Gly Ala
465                 470                 475                 480

Asp Thr Ile Leu Asp Ser Thr Leu Ser Asn Tyr Asp Phe Ser Lys Glu
                485                 490                 495

Ile Asn Phe Thr Ser Thr Val Pro Ile Ile Thr Val Glu Asp Pro Leu
            500                 505                 510

Glu Thr Asp Glu Asp Val Pro Val Ile Ser Glu Asp Arg Thr Val Tyr
        515                 520                 525

Val Asp Asp Tyr Thr Thr Phe His Phe Leu Glu Ala Gln Lys Ile Gly
    530                 535                 540

Lys Glu Val Val Pro Thr Gln Thr Lys Val Val Phe Thr Thr Asn Met
545                 550                 555                 560

Glu Glu Ala Leu Phe Asp Ser Lys Lys Val Tyr Thr Val Phe Glu Asn
                565                 570                 575

Thr Ala Ser Arg Ile Asn Glu Ala Gly Thr Gly Ile Ala Asn Gly Met
            580                 585                 590

Met Phe Tyr Gln Trp Leu Lys Gly Ile Val Gln Asp Phe Thr Glu Glu
        595                 600                 605

Ala Thr Gln Lys Asp Thr Phe Asp Lys Ile Ser Asp Val Thr Met Ile
    610                 615                 620

Val Pro Tyr Leu Gly Asn Ile Leu Asn Ile Gly Asn Asp Ile Arg Lys
625                 630                 635                 640

Gly Asp Phe Met Gly Ala Val Glu Leu Gly Gly Val Thr Ile Leu Leu
                645                 650                 655

Glu Ala Ile Pro Glu Leu Thr Leu Pro Val Leu Ile Gly Leu Thr Ile
            660                 665                 670

Ile Glu Asp Glu Leu Glu Lys Glu Gln Val Ser Gln Thr Val Tyr Asn
        675                 680                 685

Val Leu Asp Lys Arg Asp Glu Lys Trp Glu Glu Val Tyr Gly Phe Val
    690                 695                 700
```

```
Lys Gln Gln Trp Trp Trp Met Val His Thr Gln Phe Glu Thr Arg Ile
705                 710                 715                 720

Leu His Ala Tyr Gln Ala Leu Asn His Gln Val Glu Ala Ile Lys Ala
            725                 730                 735

Asn Met Thr Tyr Gln Leu Ala Asn Tyr Arg Gly Asn Gln Glu Asp Lys
                740                 745                 750

Glu Leu Leu Glu Lys Ala Ile Asp Asp Thr Leu Gln Ser Leu Tyr Tyr
        755                 760                 765

Ala Val Asp Gln Ala Met His Asn Ile Lys Arg Phe Leu Ile Gln Ser
        770                 775                 780

Ser Lys Ser Tyr Leu Leu Asn Gln Met Leu Pro Lys Thr Lys Glu Gln
785                 790                 795                 800

Leu Leu Ala Phe Asp Gln Gln Thr Leu Arg Asn Val Asn Asp Phe Ile
                805                 810                 815

Asn Lys Asn Gln Gly Val Leu Gly Glu Ser Leu Ala Lys Asp Leu Lys
                820                 825                 830

Lys Lys Val Glu Lys Arg Leu Thr Ser Leu Pro Val Phe Asn Leu Glu
                835                 840                 845

Asp Leu Pro Ile Ser Glu Phe Glu Asp Leu Ile His Ser His Glu Ile
        850                 855                 860

Asp Ile Ile Leu Asn Asn Ile Ile Leu Asn Leu Arg Tyr Lys Asp Asn
865                 870                 875                 880

Asn Leu Ile Asp Leu Ser Gly Tyr Gly Ala Lys Val Glu Val Tyr Asp
                    885                 890                 895

Gly Val Glu Leu Asn Asp Lys Asn Gln Phe Lys Leu Thr Ser Ser Ala
            900                 905                 910

Asn Ser Lys Ile Arg Val Thr Gln Asn Gln Asn Ile Ile Phe Asn Ser
            915                 920                 925

Val Phe Leu Asp Phe Ser Val Ser Phe Trp Ile Arg Ile Pro Lys Tyr
        930                 935                 940

Lys Asn Asp Gly Ile Gln Asn Tyr Ile His Asn Glu Tyr Thr Ile Ile
945                 950                 955                 960

Asn Cys Met Lys Asn Asn Ser Gly Trp Lys Ile Ser Ile Arg Gly Asn
            965                 970                 975

Arg Ile Ile Trp Thr Leu Ile Asp Ile Asn Gly Lys Thr Lys Ser Val
            980                 985                 990

Phe Phe Glu Tyr Asn Ile Arg Glu Asp Ile Ser Glu Tyr Ile Asn Arg
        995                 1000                1005

Trp Phe Phe Val Thr Ile Thr Asn Asn Leu Asn Asn Ala Lys Ile
    1010                1015                1020

Tyr Ile Asn Gly Lys Leu Glu Ser Asn Thr Asp Ile Lys Asp Ile
    1025                1030                1035

Arg Glu Val Ile Ala Asn Gly Glu Ile Ile Phe Lys Leu Asp Gly
    1040                1045                1050

Asp Ile Asp Arg Thr Gln Phe Ile Trp Met Lys Tyr Phe Ser Ile
    1055                1060                1065

Phe Asn Thr Glu Leu Ser Gln Ser Asn Ile Glu Glu Arg Tyr Lys
    1070                1075                1080

Ile Gln Ser Tyr Ser Glu Tyr Leu Lys Asp Phe Trp Gly Asn Pro
    1085                1090                1095

Leu Met Tyr Asn Lys Glu Tyr Tyr Met Phe Asn Ala Gly Asn Lys
    1100                1105                1110

Asn Ser Tyr Ile Lys Leu Lys Lys Asp Ser Pro Val Gly Glu Ile
```

```
                1115                1120                1125
Leu Thr Arg Ser Lys Tyr Asn Gln Asn Ser Lys Tyr Ile Asn Tyr
    1130                1135                1140

Arg Asp Leu Tyr Ile Gly Glu Lys Phe Ile Ile Arg Arg Lys Ser
    1145                1150                1155

Asn Ser Gln Ser Ile Asn Asp Asp Ile Val Arg Lys Glu Asp Tyr
    1160                1165                1170

Ile Tyr Leu Asp Phe Phe Asn Leu Asn Gln Glu Trp Arg Val Tyr
    1175                1180                1185

Thr Tyr Lys Tyr Phe Lys Lys Glu Glu Glu Lys Leu Phe Leu Ala
    1190                1195                1200

Pro Ile Ser Asp Ser Asp Glu Phe Tyr Asn Thr Ile Gln Ile Lys
    1205                1210                1215

Glu Tyr Asp Glu Gln Pro Thr Tyr Ser Cys Gln Leu Leu Phe Lys
    1220                1225                1230

Lys Asp Glu Glu Ser Thr Asp Glu Ile Gly Leu Ile Gly Ile His
    1235                1240                1245

Arg Phe Tyr Glu Ser Gly Ile Val Phe Glu Glu Tyr Lys Asp Tyr
    1250                1255                1260

Phe Cys Ile Ser Lys Trp Tyr Leu Lys Glu Val Lys Arg Lys Pro
    1265                1270                1275

Tyr Asn Leu Lys Leu Gly Cys Asn Trp Gln Phe Ile Pro Lys Asp
    1280                1285                1290

Glu Gly Trp Thr Glu
    1295

<210> SEQ ID NO 29
<211> LENGTH: 1290
<212> TYPE: PRT
<213> ORGANISM: Artificial Sequence
<220> FEATURE:
<223> OTHER INFORMATION: Synthetic Polypeptide

<400> SEQUENCE: 29

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

Pro Asn Val Trp Val Val Pro Glu Arg Tyr Thr Phe Tyr Ser Thr Met
        50                  55                  60

Lys Asn Leu Asp Ala Pro Ala Asn Pro Ser Arg Ser Ser Tyr Tyr Asp
65                  70                  75                  80

Pro Thr Tyr Leu Gln Ser Asp Ala Glu Lys Glu Val Phe Leu Gln Gln
                85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
        115                 120                 125

Gly Asp Val Ala Met Gly Thr Thr Gln Val Ile Lys Gln Met Asp Asp
    130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
```

```
            165                 170                 175
Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
            195                 200                 205

Asp Lys Ser Val Gln Glu Phe Val Pro Asp Pro Ala Val Thr Leu Ile
            210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
            245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
            275                 280                 285

Ile Pro Gly Ile Leu Asn Leu Ile Lys Thr Thr Val Glu Pro Ile Ile
            290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Phe Asp Asp
            325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
            355                 360                 365

Val Pro Lys Val Glu Asn Ile Val Gln Val Asp Ile Leu Ser Pro Asn
            370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
            405                 410                 415

Arg Gly Ala Val Val Arg Ala Cys Pro Asn Pro His Phe Ser Ser Gln
            420                 425                 430

Leu Val Pro Arg Gly Ser Leu Ser Ser Cys Ile Glu Ile Leu Glu Asp
            435                 440                 445

Asp Leu Phe Ile Met Ser Ser Lys Asp Ser Phe Thr Asp Thr Asp Phe
            450                 455                 460

Ser Glu Pro Ser Val Gly Pro Val Ser Tyr Lys Ala Lys Lys Gly Ala
465                 470                 475                 480

Asp Thr Ile Leu Asp Ser Thr Leu Ser Asn Tyr Asp Phe Ser Lys Glu
            485                 490                 495

Ile Asn Phe Thr Ser Thr Val Pro Ile Ile Thr Val Glu Asp Pro Leu
            500                 505                 510

Glu Thr Asp Glu Asp Val Pro Val Ile Ser Glu Asp Arg Thr Val Tyr
            515                 520                 525

Val Asp Asp Tyr Thr Thr Phe His Phe Leu Glu Ala Gln Lys Ile Gly
            530                 535                 540

Lys Glu Val Val Pro Thr Gln Thr Lys Val Val Phe Thr Thr Asn Met
545                 550                 555                 560

Glu Glu Ala Leu Phe Asp Ser Lys Lys Val Tyr Thr Val Phe Glu Asn
            565                 570                 575

Thr Ala Ser Arg Ile Asn Glu Ala Gly Thr Gly Ile Ala Asn Gly Met
            580                 585                 590
```

```
Met Phe Tyr Gln Trp Leu Lys Gly Ile Val Gln Asp Phe Thr Glu
            595                 600                 605
Ala Thr Gln Lys Asp Thr Phe Asp Lys Ile Ser Asp Val Thr Met Ile
    610                 615                 620
Val Pro Tyr Leu Gly Asn Ile Leu Asn Ile Gly Asn Asp Ile Arg Lys
625                 630                 635                 640
Gly Asp Phe Met Gly Ala Val Glu Leu Gly Gly Val Thr Ile Leu Leu
                645                 650                 655
Glu Ala Ile Pro Glu Leu Thr Leu Pro Val Leu Ile Gly Leu Thr Ile
                660                 665                 670
Ile Glu Asp Glu Leu Gly Lys Glu Gln Val Ser Gln Thr Val Tyr Asn
            675                 680                 685
Val Leu Asp Lys Arg Asp Glu Lys Trp Glu Val Tyr Gly Phe Val
690                 695                 700
Lys Gln Gln Trp Trp Met Val His Thr Gln Phe Glu Thr Arg Ile
705             710                 715                 720
Leu His Ala Tyr Gln Ala Leu Asn His Gln Val Glu Ala Ile Lys Ala
                725                 730                 735
Asn Met Thr Tyr Gln Leu Ala Asn Tyr Arg Gly Asn Glu Asp Lys
                740                 745                 750
Glu Leu Leu Glu Lys Ala Ile Asp Asp Thr Leu Gln Ser Leu Tyr Tyr
            755                 760                 765
Ala Val Asp Gln Ala Met His Asn Ile Lys Arg Phe Leu Ile Gln Ser
770                 775                 780
Ser Lys Ser Tyr Leu Leu Asn Gln Met Leu Pro Lys Thr Lys Glu Gln
785                 790                 795                 800
Leu Leu Ala Phe Asp Gln Gln Thr Leu Arg Asn Val Asn Asp Phe Ile
                805                 810                 815
Asn Lys Asn Gln Gly Val Leu Gly Glu Ser Leu Ala Lys Asp Leu Lys
                820                 825                 830
Lys Lys Val Glu Lys Arg Leu Thr Ser Leu Pro Val Phe Asn Leu Glu
            835                 840                 845
Asp Leu Pro Ile Ser Glu Phe Glu Asp Leu Ile His Ser His Glu Ile
    850                 855                 860
Asp Ile Ile Asn Asp Ser Lys Ile Leu Ser Leu Gln Asn Arg Lys Asn
865                 870                 875                 880
Thr Leu Val Asp Thr Ser Gly Tyr Asn Ala Glu Val Ser Glu Glu Gly
                885                 890                 895
Asp Val Gln Leu Asn Pro Ile Phe Pro Phe Asp Phe Lys Leu Gly Ser
                900                 905                 910
Ser Gly Glu Asp Arg Gly Lys Val Ile Val Thr Gln Asn Glu Asn Ile
            915                 920                 925
Val Tyr Asn Ser Met Tyr Glu Ser Phe Ser Ile Ser Phe Trp Ile Arg
930                 935                 940
Ile Asn Lys Trp Val Ser Asn Leu Pro Gly Tyr Thr Ile Ile Asp Ser
945                 950                 955                 960
Val Lys Asn Asn Ser Gly Trp Ser Ile Gly Ile Ile Ser Asn Phe Leu
                965                 970                 975
Val Phe Thr Leu Lys Gln Asn Glu Asp Ser Glu Gln Ser Ile Asn Phe
            980                 985                 990
Ser Tyr Asp Ile Ser Asn Asn Ala Pro Gly Tyr Asn Lys Trp Phe Phe
            995                 1000                1005
```

Val Thr Val Thr Asn Asn Met Met Gly Asn Met Lys Ile Tyr Ile
1010                1015                1020

Asn Gly Lys Leu Ile Asp Thr Ile Lys Val Lys Glu Leu Thr Gly
    1025                1030                1035

Ile Asn Phe Ser Lys Thr Ile Thr Phe Glu Ile Asn Lys Ile Pro
    1040                1045                1050

Asp Thr Gly Leu Ile Thr Ser Asp Ser Asp Asn Ile Asn Met Trp
    1055                1060                1065

Ile Arg Asp Phe Tyr Ile Phe Ala Lys Glu Leu Asp Gly Lys Asp
    1070                1075                1080

Ile Asn Ile Leu Phe Asn Ser Leu Gln Tyr Thr Asn Val Val Lys
    1085                1090                1095

Asp Tyr Trp Gly Asn Asp Leu Arg Tyr Asn Lys Glu Tyr Tyr Met
    1100                1105                1110

Val Asn Ile Asp Tyr Leu Asn Arg Tyr Met Tyr Ala Asn Ser Arg
    1115                1120                1125

Gln Ile Val Phe Asn Thr Arg Arg Asn Asn Asn Asp Phe Asn Glu
    1130                1135                1140

Gly Tyr Lys Ile Ile Ile Lys Arg Ile Arg Gly Asn Thr Asn Asp
    1145                1150                1155

Thr Arg Val Arg Gly Gly Asp Ile Leu Tyr Phe Asp Met Thr Ile
    1160                1165                1170

Asn Asn Lys Ala Tyr Asn Leu Phe Met Lys Asn Glu Thr Met Tyr
    1175                1180                1185

Ala Asp Asn His Ser Thr Glu Asp Ile Tyr Ala Ile Gly Leu Arg
    1190                1195                1200

Glu Gln Thr Lys Asp Ile Asn Asp Asn Ile Ile Phe Gln Ile Gln
    1205                1210                1215

Pro Met Asn Asn Thr Tyr Tyr Tyr Ala Ser Gln Ile Phe Lys Ser
    1220                1225                1230

Asn Phe Asn Gly Glu Asn Ile Ser Gly Ile Cys Ser Ile Gly Thr
    1235                1240                1245

Tyr Arg Phe Arg Leu Gly Gly Asp Trp Tyr Arg His Asn Tyr Leu
    1250                1255                1260

Val Pro Thr Val Lys Gln Gly Asn Tyr Ala Ser Leu Leu Glu Ser
    1265                1270                1275

Thr Ser Thr His Trp Gly Phe Val Pro Val Ser Glu
    1280                1285                1290

<210> SEQ ID NO 30
<211> LENGTH: 1280
<212> TYPE: PRT
<213> ORGANISM: Artificial Sequence
<220> FEATURE:
<223> OTHER INFORMATION: Synthetic Polypeptide

<400> SEQUENCE: 30

Met Val Thr Ile Asn Asp Leu His Tyr Ser Asp Pro Ile Asp Glu Asp
1               5                   10                  15

Asn Ile Ile Asn Met Arg Ile Pro Leu Tyr Asp Leu Glu Val Asp Asp
                20                  25                  30

Gln Phe Ile Asn His Asn Val Pro Asp Leu Lys Ala Phe Gln Val Phe
            35                  40                  45

Pro Asn Val Trp Val Val Pro Glu Arg Tyr Thr Phe Tyr Ser Thr Met
        50                  55                  60

```
Lys Asn Leu Asp Ala Pro Ala Asn Pro Ser Arg Ser Ser Tyr Tyr Asp
 65                  70                  75                  80

Pro Thr Tyr Leu Gln Ser Asp Ala Glu Lys Glu Val Phe Leu Gln Gln
                 85                  90                  95

Met Ile Leu Leu Phe Lys Arg Ile Asn Ser Thr Gln Glu Gly Gln Gln
            100                 105                 110

Phe Leu Asn Leu Leu Ser Arg Ser Ile Pro Val Pro Tyr Glu Ser Asn
            115                 120                 125

Gly Asp Val Ala Met Gly Thr Thr Gln Val Ile Lys Gln Met Asp Asp
        130                 135                 140

Lys Gly Asn Val Leu Lys His Arg Arg Ala His Ile Ile Ile Tyr Gly
145                 150                 155                 160

Pro Gly Pro Asp Leu Met Ala Lys Gly Ser Lys Ala Leu Thr Lys Ser
                165                 170                 175

Arg Glu Thr Gly Arg Gly Cys Met Ala Glu Ile Tyr Phe Ser Pro Met
            180                 185                 190

Tyr His Lys Thr Tyr Ser Thr Lys Leu Thr Asn Lys Asn Ser Leu Val
        195                 200                 205

Asp Lys Ser Val Gln Glu Phe Val Pro Asp Pro Ala Val Thr Leu Ile
210                 215                 220

His Glu Leu Cys His Gly Leu His Ala Leu Tyr Gly Ile Asp Leu Gly
225                 230                 235                 240

Asn Val Gly Ser Trp Glu Phe Asn Ser Asn Pro Asn Ser Leu Phe Ser
                245                 250                 255

Ser Trp Phe Ser Ser Lys Glu Ala Val Asn Phe Glu Glu Val Met Thr
            260                 265                 270

Phe Gly Gly Glu Asp Val Lys Val Ile Lys Ser Glu Ile Asp Lys Lys
        275                 280                 285

Ile Pro Gly Ile Leu Asn Leu Ile Lys Thr Thr Val Glu Pro Ile Ile
290                 295                 300

Asn Lys Ile Thr Asp Pro His Asp Glu Met Leu Gln Cys Leu Gln Ser
305                 310                 315                 320

Lys Tyr Pro Ser Leu Lys Gly Thr Leu Gly Gln Phe Phe Asp Asp
                325                 330                 335

Thr Gln Leu Glu Lys Asp Ile Arg Asp Leu Trp Met Val Met Asn Glu
            340                 345                 350

Thr Met Phe Ala Glu Asn Leu Lys Ala Leu Thr Arg Ala Arg Tyr Leu
        355                 360                 365

Val Pro Lys Val Glu Asn Ile Val Gln Val Asp Ile Leu Ser Pro Asn
370                 375                 380

Val Tyr Thr Ile Asp Lys Gly Phe Asn His Leu Ser Lys Gly Phe Lys
385                 390                 395                 400

Gly Gln Ser Val Ser Gln Ser Tyr Phe Arg Lys Ile Ser Ala Leu Ala
                405                 410                 415

Arg Gly Ala Val Val Arg Ala Cys Pro Asn Pro His Phe Ser Ser Gln
            420                 425                 430

Leu Val Pro Arg Gly Ser Leu Ser Ser Cys Ile Glu Ile Leu Glu Asp
        435                 440                 445

Asp Leu Phe Ile Met Ser Ser Lys Asp Ser Phe Thr Asp Thr Asp Phe
        450                 455                 460

Ser Glu Pro Ser Val Gly Pro Val Ser Tyr Lys Ala Lys Lys Gly Ala
465                 470                 475                 480

Asp Thr Ile Leu Asp Ser Thr Leu Ser Asn Tyr Asp Phe Ser Lys Glu
```

```
                485                 490                 495
Ile Asn Phe Thr Ser Thr Val Pro Ile Ile Thr Val Glu Asp Pro Leu
                500                 505                 510

Glu Thr Asp Glu Asp Val Pro Val Ile Ser Glu Asp Arg Thr Val Tyr
            515                 520                 525

Val Asp Asp Tyr Thr Thr Phe His Phe Leu Glu Ala Gln Lys Ile Gly
        530                 535                 540

Lys Glu Val Val Pro Thr Gln Thr Lys Val Val Phe Thr Thr Asn Met
545                 550                 555                 560

Glu Glu Ala Leu Phe Asp Ser Lys Lys Val Tyr Thr Val Phe Glu Asn
                565                 570                 575

Thr Ala Ser Arg Ile Asn Glu Ala Gly Thr Gly Ile Ala Asn Gly Met
            580                 585                 590

Met Phe Tyr Gln Trp Leu Lys Gly Ile Val Gln Asp Phe Thr Glu Glu
        595                 600                 605

Ala Thr Gln Lys Asp Thr Phe Asp Lys Ile Ser Asp Val Thr Met Ile
    610                 615                 620

Val Pro Tyr Leu Gly Asn Ile Leu Asn Ile Gly Asn Asp Ile Arg Lys
625                 630                 635                 640

Gly Asp Phe Met Gly Ala Val Glu Leu Gly Gly Val Thr Ile Leu Leu
                645                 650                 655

Glu Ala Ile Pro Glu Leu Thr Leu Pro Val Leu Ile Gly Leu Thr Ile
            660                 665                 670

Ile Glu Asp Glu Leu Glu Lys Glu Gln Val Ser Gln Thr Val Tyr Asn
        675                 680                 685

Val Leu Asp Lys Arg Asp Glu Lys Trp Glu Glu Val Tyr Gly Phe Val
    690                 695                 700

Lys Gln Gln Trp Trp Met Val His Thr Gln Phe Glu Thr Arg Ile
705                 710                 715                 720

Leu His Ala Tyr Gln Ala Leu Asn His Gln Val Glu Ala Ile Lys Ala
                725                 730                 735

Asn Met Thr Tyr Gln Leu Ala Asn Tyr Arg Gly Asn Gln Glu Asp Lys
            740                 745                 750

Glu Leu Leu Glu Lys Ala Ile Asp Asp Thr Leu Gln Ser Leu Tyr Tyr
        755                 760                 765

Ala Val Asp Gln Ala Met His Asn Ile Lys Arg Phe Leu Ile Gln Ser
    770                 775                 780

Ser Lys Ser Tyr Leu Leu Asn Gln Met Leu Pro Lys Thr Lys Glu Gln
785                 790                 795                 800

Leu Leu Ala Phe Asp Gln Gln Thr Leu Arg Asn Val Asn Asp Phe Ile
                805                 810                 815

Asn Lys Asn Gln Gly Val Leu Gly Glu Ser Leu Ala Lys Asp Leu Lys
            820                 825                 830

Lys Lys Val Glu Lys Arg Leu Thr Ser Leu Pro Val Phe Asn Leu Glu
        835                 840                 845

Asp Leu Pro Ile Ser Glu Phe Glu Asp Leu Ile His Ser His Glu Ile
    850                 855                 860

Asp Ile Glu Asp Tyr Glu Val Leu Asn Leu Gly Ala Glu Asp Gly Lys
865                 870                 875                 880

Ile Lys Asp Leu Ser Gly Thr Thr Ser Asp Ile Asn Ile Gly Ser Asp
                885                 890                 895

Ile Glu Leu Ala Asp Gly Arg Glu Asn Lys Ala Ile Lys Ile Lys Gly
            900                 905                 910
```

Ser Glu Asn Ser Thr Ile Lys Ile Ala Met Asn Lys Tyr Leu Arg Phe
            915                 920                 925

Ser Ala Thr Asp Asn Phe Ser Ile Ser Phe Trp Ile Lys His Pro Lys
        930                 935                 940

Pro Thr Asn Leu Leu Asn Asn Gly Ile Glu Tyr Thr Leu Val Glu Asn
945                 950                 955                 960

Phe Asn Gln Arg Gly Trp Lys Ile Ser Ile Gln Asp Ser Lys Leu Ile
                965                 970                 975

Trp Tyr Leu Arg Asp His Asn Asn Ser Ile Lys Ile Val Thr Pro Asp
            980                 985                 990

Tyr Ile Ala Phe Asn Gly Trp Asn Leu Ile Thr Ile Thr Asn Asn Arg
        995                 1000                1005

Ser Lys Gly Ser Ile Val Tyr Val Asn Gly Ser Lys Ile Glu Glu
    1010                1015                1020

Lys Asp Ile Ser Ser Ile Trp Asn Thr Glu Val Asp Asp Pro Ile
    1025                1030                1035

Ile Phe Arg Leu Lys Asn Asn Arg Asp Thr Gln Ala Phe Thr Leu
    1040                1045                1050

Leu Asp Gln Phe Ser Ile Tyr Arg Lys Glu Leu Asn Gln Asn Glu
    1055                1060                1065

Val Val Lys Leu Tyr Asn Tyr Phe Asn Ser Asn Tyr Ile Arg
    1070                1075                1080

Asp Ile Trp Gly Asn Pro Leu Gln Tyr Asn Lys Lys Tyr Tyr Leu
    1085                1090                1095

Gln Thr Gln Asp Lys Pro Gly Lys Gly Leu Ile Arg Glu Tyr Trp
    1100                1105                1110

Ser Ser Phe Gly Tyr Asp Tyr Val Ile Leu Ser Asp Ser Lys Thr
    1115                1120                1125

Ile Thr Phe Pro Asn Asn Ile Arg Tyr Gly Ala Leu Tyr Asn Gly
    1130                1135                1140

Ser Lys Val Leu Ile Lys Asn Ser Lys Lys Leu Asp Gly Leu Val
    1145                1150                1155

Arg Asn Lys Asp Phe Ile Gln Leu Glu Ile Asp Gly Tyr Asn Met
    1160                1165                1170

Gly Ile Ser Ala Asp Arg Phe Asn Glu Asp Thr Asn Tyr Ile Gly
    1175                1180                1185

Thr Thr Tyr Gly Thr Thr His Asp Leu Thr Thr Asp Phe Glu Ile
    1190                1195                1200

Ile Gln Arg Gln Glu Lys Tyr Arg Asn Tyr Cys Gln Leu Lys Thr
    1205                1210                1215

Pro Tyr Asn Ile Phe His Lys Ser Gly Leu Met Ser Thr Glu Thr
    1220                1225                1230

Ser Lys Pro Thr Phe His Asp Tyr Arg Asp Trp Val Tyr Ser Ser
    1235                1240                1245

Ala Trp Tyr Phe Gln Asn Tyr Glu Asn Leu Asn Leu Arg Lys His
    1250                1255                1260

Thr Lys Thr Asn Trp Tyr Phe Ile Pro Lys Asp Glu Gly Trp Asp
    1265                1270                1275

Glu Asp
    1280

<210> SEQ ID NO 31
<211> LENGTH: 116

-continued

```
<212> TYPE: PRT
<213> ORGANISM: Homo sapiens

<400> SEQUENCE: 31

Met Ser Ala Pro Ala Gln Pro Pro Ala Glu Gly Thr Glu Gly Thr Ala
1               5                   10                  15

Pro Gly Gly Gly Pro Pro Gly Pro Pro Asn Met Thr Ser Asn Arg
            20                  25                  30

Arg Leu Gln Gln Thr Gln Ala Gln Val Glu Glu Val Val Asp Ile Ile
        35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Arg Arg Asp
            115

<210> SEQ ID NO 32
<211> LENGTH: 116
<212> TYPE: PRT
<213> ORGANISM: Homo sapiens

<400> SEQUENCE: 32

Met Ser Ala Thr Ala Ala Thr Ala Pro Pro Ala Pro Ala Gly Glu
1               5                   10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Ser
            115

<210> SEQ ID NO 33
<211> LENGTH: 100
<212> TYPE: PRT
<213> ORGANISM: Homo sapiens

<400> SEQUENCE: 33

Met Ser Thr Gly Pro Thr Ala Ala Thr Gly Ser Asn Arg Arg Leu Gln
1               5                   10                  15

Gln Thr Gln Asn Gln Val Asp Glu Val Val Asp Ile Met Arg Val Asn
            20                  25                  30

Val Asp Lys Val Leu Glu Arg Asp Gln Lys Leu Ser Glu Leu Asp Asp
        35                  40                  45

Arg Ala Asp Ala Leu Gln Ala Gly Ala Ser Gln Phe Glu Thr Ser Ala
```

```
            50                  55                  60
Ala Lys Leu Lys Arg Lys Tyr Trp Trp Lys Asn Cys Lys Met Trp Ala
 65                  70                  75                  80

Ile Gly Ile Thr Val Leu Val Ile Phe Ile Ile Ile Ile Val Trp
                 85                  90                  95

Val Val Ser Ser
            100

<210> SEQ ID NO 34
<211> LENGTH: 211
<212> TYPE: PRT
<213> ORGANISM: Homo sapiens

<400> SEQUENCE: 34

Met Asp Asn Leu Ser Ser Glu Glu Ile Gln Gln Arg Ala His Gln Ile
  1               5                  10                  15

Thr Asp Glu Ser Leu Glu Ser Thr Arg Arg Ile Leu Gly Leu Ala Ile
                 20                  25                  30

Glu Ser Gln Asp Ala Gly Ile Lys Thr Ile Thr Met Leu Asp Glu Gln
             35                  40                  45

Lys Glu Gln Leu Asn Arg Ile Glu Glu Gly Leu Asp Gln Ile Asn Lys
 50                  55                  60

Asp Met Arg Glu Thr Glu Lys Thr Leu Thr Glu Leu Asn Lys Cys Cys
 65                  70                  75                  80

Gly Leu Cys Val Cys Pro Cys Asn Arg Thr Lys Asn Phe Glu Ser Gly
                 85                  90                  95

Lys Ala Tyr Lys Thr Thr Trp Gly Asp Gly Gly Glu Asn Ser Pro Cys
            100                 105                 110

Asn Val Val Ser Lys Gln Pro Gly Pro Val Thr Asn Gly Gln Leu Gln
            115                 120                 125

Gln Pro Thr Thr Gly Ala Val Ser Gly Gly Tyr Ile Lys Arg Ile Thr
        130                 135                 140

Asn Asp Ala Arg Glu Asp Glu Met Glu Glu Asn Leu Thr Gln Val Gly
145                 150                 155                 160

Ser Ile Leu Gly Asn Leu Lys Asp Met Ala Leu Asn Ile Gly Asn Glu
                165                 170                 175

Ile Asp Ala Gln Asn Pro Gln Ile Lys Arg Ile Thr Asp Lys Ala Asp
            180                 185                 190

Thr Asn Arg Asp Arg Ile Asp Ile Ala Asn Ala Arg Ala Lys Lys Leu
            195                 200                 205

Ile Asp Ser
        210

<210> SEQ ID NO 35
<211> LENGTH: 206
<212> TYPE: PRT
<213> ORGANISM: Homo sapiens

<400> SEQUENCE: 35

Met Ala Glu Asp Ala Asp Met Arg Asn Glu Leu Glu Glu Met Gln Arg
  1               5                  10                  15

Arg Ala Asp Gln Leu Ala Asp Glu Ser Leu Glu Ser Thr Arg Arg Met
                 20                  25                  30

Leu Gln Leu Val Glu Glu Ser Lys Asp Ala Gly Ile Arg Thr Leu Val
             35                  40                  45

Met Leu Asp Glu Gln Gly Glu Gln Leu Asp Arg Val Glu Glu Gly Met
```

```
                    50                  55                  60

Asn His Ile Asn Gln Asp Met Lys Glu Ala Glu Lys Asn Leu Lys Asp
 65                  70                  75                  80

Leu Gly Lys Cys Cys Gly Leu Phe Ile Cys Pro Cys Asn Lys Leu Lys
                 85                  90                  95

Ser Ser Asp Ala Tyr Lys Lys Ala Trp Gly Asn Asn Gln Asp Gly Val
                100                 105                 110

Val Ala Ser Gln Pro Ala Arg Val Asp Glu Arg Glu Gln Met Ala
                115                 120                 125

Ile Ser Gly Gly Phe Ile Arg Arg Val Thr Asn Asp Ala Arg Glu Asn
                130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
                180                 185                 190

Asp Glu Ala Asn Gln Arg Ala Thr Lys Met Leu Gly Ser Gly
                195                 200                 205

<210> SEQ ID NO 36
<211> LENGTH: 259
<212> TYPE: PRT
<213> ORGANISM: Homo sapiens

<400> SEQUENCE: 36

Met Asp Glu Phe Phe Glu Gln Val Glu Glu Ile Arg Gly Phe Ile Asp
 1               5                  10                  15

Lys Ile Ala Glu Asn Val Glu Glu Val Lys Arg Lys His Ser Ala Ile
                20                  25                  30

Leu Ala Ser Pro Asn Pro Asp Glu Lys Thr Lys Glu Glu Leu Glu Glu
                35                  40                  45

Leu Met Ser Asp Ile Lys Lys Thr Ala Asn Lys Val Arg Ser Lys Leu
 50                  55                  60

Lys Ser Ile Glu Gln Ser Ile Glu Gln Glu Glu Gly Leu Asn Arg Ser
 65                  70                  75                  80

Ser Ala Asp Leu Arg Ile Arg Lys Thr Gln His Ser Thr Leu Ser Arg
                 85                  90                  95

Lys Phe Val Glu Val Met Ser Glu Tyr Asn Ala Thr Gln Ser Asp Tyr
                100                 105                 110

Arg Glu Arg Cys Lys Gly Arg Ile Gln Arg Gln Leu Glu Ile Thr Gly
                115                 120                 125

Arg Thr Thr Thr Ser Glu Glu Leu Glu Asp Met Leu Glu Ser Gly Asn
                130                 135                 140

Pro Ala Ile Phe Ala Ser Gly Ile Ile Met Asp Ser Ser Ile Ser Lys
145                 150                 155                 160

Gln Ala Leu Ser Glu Ile Glu Thr Arg His Ser Glu Ile Ile Lys Leu
                165                 170                 175

Glu Asn Ser Ile Arg Glu Leu His Asp Met Phe Met Asp Met Ala Met
                180                 185                 190

Leu Val Glu Ser Gln Gly Glu Met Ile Asp Arg Ile Glu Tyr Asn Val
                195                 200                 205

Glu His Ala Val Asp Tyr Val Glu Arg Ala Val Ser Asp Thr Lys Lys
                210                 215                 220
```

```
Ala Val Lys Tyr Gln Ser Lys Ala Arg Arg Lys Ile Met Ile Ile
225                 230                 235                 240

Ile Cys Cys Val Ile Leu Gly Ile Val Ile Ala Ser Thr Val Gly Gly
                245                 250                 255

Ile Phe Ala
```

<210> SEQ ID NO 37
<211> LENGTH: 288
<212> TYPE: PRT
<213> ORGANISM: Homo sapiens

<400> SEQUENCE: 37

```
Met Lys Asp Arg Thr Gln Val Leu Arg Thr Arg Arg Asn Ser Asp Asp
1               5                   10                  15

Lys Glu Glu Val Val His Val Asp Arg Asp His Phe Met Asp Glu Phe
                20                  25                  30

Phe Glu Gln Glu Glu Glu Ile Arg Gly Cys Ile Glu Lys Leu Ser Glu
            35                  40                  45

Asp Val Glu Gln Val Lys Lys Gln His Ser Ala Ile Leu Ala Ala Pro
        50                  55                  60

Asn Pro Asp Glu Arg Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Ser Thr Ala Pro Arg Pro Ile Leu
                100                 105                 110

Arg Ile Arg Lys Thr Gln His Ser Thr Leu Ser Arg Lys Phe Val Glu
            115                 120                 125

Val Met Thr Glu Tyr Asn Ala Thr Gln Ser Lys Tyr Arg Asp Arg Cys
        130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Pro Ile Phe
                165                 170                 175

Thr Asp Asp Ile Lys Met Asp Ser Gln Met Thr Lys Gln Ala Leu Asn
                180                 185                 190

Glu Ile Glu Thr Arg His Asn Glu Ile Ile Lys Leu Glu Thr Ser Ile
            195                 200                 205

Arg Glu Leu His Asp Met Phe Val Asp Met Ala Met Leu Val Glu Ser
        210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Ile Ile Ile Cys Cys Val
                260                 265                 270

Val Leu Gly Val Val Leu Ala Ser Ser Ile Gly Cys Thr Leu Gly Leu
            275                 280                 285
```

<210> SEQ ID NO 38
<211> LENGTH: 297
<212> TYPE: PRT
<213> ORGANISM: Drosophila melanogaster

<400> SEQUENCE: 38

```
Met Arg Asp Arg Thr His Glu Leu Arg Gln Gly Asp Asp Ser Ser Asp
```

```
                1               5                   10                  15
            Glu Glu Asp Lys Glu Arg Val Ala Leu Val Val His Pro Gly Thr Ala
                            20                  25                  30

Arg Leu Gly Ser Pro Asp Glu Glu Phe Phe His Lys Val Arg Thr Ile
                            35                  40                  45

Arg Gln Thr Ile Val Lys Leu Gly Asn Lys Val Gln Glu Leu Glu Lys
                            50                  55                  60

Gln Gln Val Thr Ile Leu Ala Thr Pro Leu Pro Glu Glu Ser Met Lys
            65                  70                  75                  80

Gln Glu Leu Gln Asn Leu Arg Asp Glu Ile Lys Gln Leu Gly Arg Glu
                            85                  90                  95

Ile Arg Leu Gln Leu Lys Ala Ile Glu Pro Gln Lys Glu Glu Ala Asp
                            100                 105                 110

Glu Asn Tyr Asn Ser Val Asn Thr Arg Met Arg Lys Thr Gln His Gly
                            115                 120                 125

Val Leu Ser Gln Gln Phe Val Glu Leu Ile Asn Lys Cys Asn Ser Met
                            130                 135                 140

Gln Ser Glu Tyr Arg Glu Lys Asn Val Glu Arg Ile Arg Arg Gln Leu
            145                 150                 155                 160

Lys Ile Thr Asn Ala Gly Met Val Ser Asp Glu Leu Glu Gln Met
                            165                 170                 175

Leu Asp Ser Gly Gln Ser Glu Val Phe Val Ser Asn Ile Leu Lys Asp
                            180                 185                 190

Thr Gln Val Thr Arg Gln Ala Leu Asn Glu Ile Ser Ala Arg His Ser
                            195                 200                 205

Glu Ile Gln Gln Leu Glu Arg Ser Ile Arg Glu Leu His Asp Ile Phe
                            210                 215                 220

Thr Phe Leu Ala Thr Glu Val Glu Met Gln Gly Glu Met Ile Asn Arg
            225                 230                 235                 240

Ile Glu Lys Asn Ile Leu Ser Ser Ala Asp Tyr Val Glu Arg Gly Gln
                            245                 250                 255

Glu His Val Lys Thr Ala Leu Glu Asn Gln Lys Lys Ala Arg Lys Lys
                            260                 265                 270

Lys Val Leu Ile Ala Ile Cys Val Ser Ile Thr Val Val Leu Leu Ala
                            275                 280                 285

Val Ile Ile Gly Val Thr Val Val Gly
                            290                 295

<210> SEQ ID NO 39
            <211> LENGTH: 135
            <212> TYPE: PRT
            <213> ORGANISM: Drosophila melanogaster

<400> SEQUENCE: 39

Met Gly Lys Lys Asp Lys Asn Lys Glu Gln Ala Asp Ala Ala Pro Ala
            1               5                   10                  15

Gly Asp Ala Pro Pro Asn Ala Gly Pro Ala Gly Glu Gly Gly Asp
                            20                  25                  30

Gly Glu Ile Val Gly Gly Pro His Asn Pro Gln Gln Ile Ala Ala Gln
                            35                  40                  45

Lys Arg Leu Gln Gln Thr Gln Ala Gln Val Asp Glu Val Val Asp Ile
                            50                  55                  60

Met Arg Thr Asn Val Glu Lys Val Leu Glu Arg Asp Ser Lys Leu Ser
            65                  70                  75                  80
```

```
Glu Leu Asp Asp Arg Ala Asp Ala Leu Gln Gln Gly Ala Ser Gln Phe
                85                  90                  95

Glu Gln Gln Ala Gly Lys Leu Lys Arg Lys Phe Trp Leu Gln Asn Leu
            100                 105                 110

Lys Met Met Ile Ile Met Gly Val Ile Gly Leu Val Val Val Gly Ile
        115                 120                 125

Ile Ala Lys Lys Asp Glu Glu
        130             135

<210> SEQ ID NO 40
<211> LENGTH: 212
<212> TYPE: PRT
<213> ORGANISM: Artificial Sequence
<220> FEATURE:
<223> OTHER INFORMATION: Synthetic Polypeptide

<400> SEQUENCE: 40

Met Pro Ala Asp Pro Ser Glu Glu Val Ala Pro Gln Val Pro Lys Thr
1               5                   10                  15

Glu Leu Glu Glu Leu Gln Ile Asn Ala Gln Gly Val Ala Asp Glu Ser
            20                  25                  30

Leu Glu Ser Thr Arg Arg Met Leu Ala Leu Cys Glu Glu Ser Lys Glu
        35                  40                  45

Ala Gly Ile Arg Thr Leu Val Ala Leu Asp Asp Gln Gly Glu Gln Leu
    50                  55                  60

Asp Arg Ile Glu Glu Gly Met Asp Gln Ile Asn Ala Asp Met Arg Glu
65                  70                  75                  80

Ala Glu Lys Asn Leu Ser Gly Met Glu Lys Cys Cys Gly Ile Cys Val
                85                  90                  95

Leu Pro Cys Asn Lys Ser Gln Ser Phe Lys Glu Asp Asp Gly Thr Trp
            100                 105                 110

Lys Gly Asn Asp Asp Gly Lys Val Val Asn Asn Gln Pro Gln Arg Val
        115                 120                 125

Met Asp Asp Arg Asn Gly Met Met Ala Gln Ala Gly Tyr Ile Gly Arg
    130                 135                 140

Ile Thr Asn Asp Ala Arg Glu Asp Glu Met Glu Glu Asn Met Gly Gln
145                 150                 155                 160

Val Asn Thr Met Ile Gly Asn Leu Arg Asn Met Ala Leu Asp Met Gly
                165                 170                 175

Ser Glu Leu Glu Asn Gln Asn Arg Gln Ile Asp Arg Ile Asn Arg Lys
            180                 185                 190

Gly Glu Ser Asn Glu Ala Arg Ile Ala Val Ala Asn Gln Arg Ala His
        195                 200                 205

Gln Leu Leu Lys
    210

<210> SEQ ID NO 41
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 41

Leu Val Pro Arg Gly Ser
1               5

<210> SEQ ID NO 42
```

```
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 42

Glu Asn Leu Tyr Phe Gln Gly
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 43

Leu Glu Val Leu Phe Gln Gly Pro
1               5

<210> SEQ ID NO 44
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 44

Ile Glu Gly Arg
1

<210> SEQ ID NO 45
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 45

Ile Asp Gly Arg
1

<210> SEQ ID NO 46
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 46

Asp Asp Asp Asp Lys
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 47

Ala His Arg Glu Gln Ile Gly Gly
1               5

<210> SEQ ID NO 48
<211> LENGTH: 25
```

<212> TYPE: PRT
<213> ORGANISM: Artificial Sequence
<220> FEATURE:
<223> OTHER INFORMATION: Synthetic Polypeptide

<400> SEQUENCE: 48

Cys Val Arg Gly Ile Ile Thr Ser Lys Thr Lys Ser Leu Asp Lys Gly
1               5                   10                  15

Tyr Asn Lys Ala Leu Asn Asp Leu Cys
            20                  25

<210> SEQ ID NO 49
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 49

Cys Lys Ser Val Lys Ala Pro Gly Ile Cys
1               5                   10

<210> SEQ ID NO 50
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 50

Cys His Lys Ala Ile Asp Gly Arg Ser Leu Tyr Asn Lys Thr Leu Asp
1               5                   10                  15

Cys

<210> SEQ ID NO 51
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 51

Cys Leu Arg Leu Thr Lys Asn Ser Arg Asp Asp Ser Thr Cys
1               5                   10

<210> SEQ ID NO 52
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 52

Cys Lys Asn Ile Val Ser Val Lys Gly Ile Arg Lys Ser Ile Cys
1               5                   10                  15

<210> SEQ ID NO 53
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 53

Cys Lys Ser Val Ile Pro Arg Lys Gly Thr Lys Ala Pro Pro Arg Leu
1               5                   10                  15

Cys

<210> SEQ ID NO 54
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 54

Cys Lys Pro Val Met Tyr Lys Asn Thr Gly Lys Ser Glu Gln Cys
1               5                   10                  15

<210> SEQ ID NO 55
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 55

Cys Pro Arg Asn Gly Leu Leu Tyr Asn Ala Ile Tyr Arg Asn Ser Lys
1               5                   10                  15

Asn Tyr Leu Asn Asn Ile Asp Leu Glu Asp Lys Lys Thr Thr Ser Lys
            20                  25                  30

Thr Asn Val Ser Tyr Pro Cys Ser Leu Leu Asn Gly Cys
        35                  40                  45

<210> SEQ ID NO 56
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 56

Cys Pro Asn Pro His Phe Ser Ser Gln Arg Gly Leu Ser Ser Cys
1               5                   10                  15

<210> SEQ ID NO 57
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 57

Leu Pro Xaa Thr Gly Gly
1               5

<210> SEQ ID NO 58
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 58

Pro Asn Pro His Phe Ser Ser Gln Arg Gly Leu Ser Ser
1               5                   10

```
<210> SEQ ID NO 59
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 59

Leu Pro Glu Thr Gly Gly
1               5

<210> SEQ ID NO 60
<211> LENGTH: 102
<212> TYPE: PRT
<213> ORGANISM: Artificial Sequence
<220> FEATURE:
<223> OTHER INFORMATION: Synthetic Polypeptide

<400> SEQUENCE: 60

Met Gly Gly Ser His His His His Gly Met Ala Ser Met Thr Gly
1               5                   10                  15

Gly Gln Gln Met Gly Arg Asp Leu Tyr Asp Asp Asp Lys Asp Arg
                20                  25                  30

Trp Gly Ser Met Ser Ala Thr Ala Ala Thr Val Pro Pro Ala Ala Pro
            35                  40                  45

Ala Gly Glu Gly Gly Pro Pro Ala Pro Pro Pro Asn Leu Thr Ser Asn
        50                  55                  60

Arg Arg Leu Gln Gln Thr Gln Ala Gln Val Asp Glu Val Val Asp Ile
65                  70                  75                  80

Met Arg Val Asn Val Asp Lys Val Leu Glu Arg Asp Gln Lys Leu Ser
                85                  90                  95

Glu Leu Asp Asp Arg Ala
            100

<210> SEQ ID NO 61
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 61

Asp Ala Leu Gln Ala Gly Ala Ser Gln Phe Glu Thr Ser Ala Ala Lys
1               5                   10                  15

Leu Lys Arg Lys Tyr Trp Trp Lys Asn Leu
                20                  25

<210> SEQ ID NO 62
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 62

Gln Val Asp Glu Val Val Asp Ile Met Arg Val Asn Val Asp Lys Val
1               5                   10                  15

Leu Glu Arg Asp Gln Lys Leu Ser Glu Leu Asp Asp Arg Ala Asp Ala
                20                  25                  30

Leu Gln Ala Gly Ala Ser Gln Phe Glu Thr Ser Ala Ala Lys Leu Lys
            35                  40                  45

Arg
```

<210> SEQ ID NO 63
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 63

Gln Val Glu Glu Val Val Asp Ile Met Arg Val Asn Val Asp Lys Val
1               5                   10                  15

Leu Glu Arg Asp Gln Lys Leu Ser Glu Leu Asp Asp Arg Ala Asp Ala
            20                  25                  30

Leu Gln Ala Gly Ala Ser Gln Phe Glu Ser Ser Ala Ala Lys Leu Lys
        35                  40                  45

Arg

<210> SEQ ID NO 64
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 64

Gln Val Asp Glu Val Ile Asp Val Met Gln Glu Asn Ile Thr Lys Val
1               5                   10                  15

Ile Glu Arg Gly Glu Arg Leu Asp Glu Leu Gln Asp Lys Ser Glu Ser
            20                  25                  30

Leu Ser Asp Asn Ala Thr Ala Phe Ser Asn Arg Ser Lys Gln Leu Arg
        35                  40                  45

Arg

<210> SEQ ID NO 65
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 65

Gln Ala Asn Glu Val Thr Glu Ile Met Arg Asn Asn Phe Gly Lys Val
1               5                   10                  15

Leu Glu Arg Gly Val Lys Leu Ala Glu Leu Gln Gln Arg Ser Asp Gln
            20                  25                  30

Leu Leu Asp Met Ser Ser Thr Phe Asn Lys Thr Thr Gln Asn Leu Ala
        35                  40                  45

Gln

<210> SEQ ID NO 66
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 66

Gln Val Asp Glu Leu Lys Gly Ile Met Val Arg Asn Ile Asp Leu Val
1               5                   10                  15

Ala Gln Arg Gly Glu Arg Leu Glu Leu Leu Ile Asp Lys Thr Glu Asn
            20                  25                  30

```
Leu Val Asp Ser Ser Val Thr Phe Lys Thr Thr Ser Arg Asn Leu Ala
        35                  40                  45
Arg
```

<210> SEQ ID NO 67
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 67

```
Glu Val Glu Gly Val Lys Asn Ile Met Thr Gln Asn Val Glu Arg Ile
1               5                   10                  15

Leu Ala Arg Gly Glu Asn Leu Asp His Leu Arg Asn Lys Thr Glu Asp
            20                  25                  30

Leu Glu Ala Thr Ser Glu His Phe Lys Thr Thr Ser Gln Lys Val Ala
        35                  40                  45

Arg
```

<210> SEQ ID NO 68
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 68

```
Glu Leu Gln Asp Val Gln Arg Ile Met Val Ala Asn Ile Glu Glu Val
1               5                   10                  15

Leu Gln Arg Gly Glu Ala Leu Ser Ala Leu Asp Ser Lys Ala Asn Asn
            20                  25                  30

Leu Ser Ser Leu Ser Lys Lys Tyr Arg Gln Asp Ala Lys Tyr Leu Asn
        35                  40                  45

Met
```

<210> SEQ ID NO 69
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 69

```
Glu Leu Asp Glu Thr Lys Ile Ile Leu His Asn Thr Met Glu Ser Leu
1               5                   10                  15

Leu Glu Arg Gly Glu Lys Leu Asp Asp Leu Val Ser Lys Ser Glu Val
            20                  25                  30

Leu Gly Thr Gln Ser Lys Ala Phe Tyr Lys Thr Ala Arg
        35                  40                  45
```

<210> SEQ ID NO 70
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 70

```
Cys Pro Asn Pro His Phe Ser Ser Gln Leu Val Pro Arg Gly Ser Leu
1               5                   10                  15
```

Ser Ser Cys

<210> SEQ ID NO 71
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 71

Gly Ser Thr Leu Val Pro Arg Gly Ser
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 72

Leu Pro Glu Thr Gly Ser
1               5

<210> SEQ ID NO 73
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 73

Ser Glu Val Phe Val Ser Asn Ile Leu Lys Asp Thr Gln Val Thr Arg
1               5                   10                  15

Gln Ala Leu Asn Glu Ile His Val Lys Ile Ala Leu Glu Asn Gln Lys
            20                  25                  30

Lys Ala Arg Lys Lys Lys
        35

<210> SEQ ID NO 74
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 74

Asp Ala Leu Gln Ala Gly Ala Ser Gln Phe Glu Thr Ser Ala Ala Lys
1               5                   10                  15

Leu Lys Arg

<210> SEQ ID NO 75
<211> LENGTH: 260
<212> TYPE: PRT
<213> ORGANISM: Artificial Sequence
<220> FEATURE:
<223> OTHER INFORMATION: Synthetic Polypeptide

<400> SEQUENCE: 75

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Pro Gln Ile Asp Lys Tyr Leu
            180                 185                 190

Lys Ser Ser Lys Tyr Ile Ala Trp Pro Leu Gln Gly Trp Gln Ala Thr
            195                 200                 205

Phe Gly Gly Asp His Pro Pro Lys Ser Asp Leu Val Pro Arg Gly
    210                 215                 220

Ser Gln Gln Thr Gln Ala Gln Val Asp Glu Val Val Asp Ile Met Arg
225                 230                 235                 240

Val Asn Val Asp Lys Val Leu Glu Arg Asp Gln Lys Leu Ser Glu Leu
                245                 250                 255

Asp Asp Arg Ala
            260

<210> SEQ ID NO 76
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 76

Leu Ala Ile Phe Thr Asp Asp Ile Lys Met Asp Ser Gln Met Thr Lys
1               5                   10                  15

<210> SEQ ID NO 77
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 77

Leu Ala Ile Phe Thr Asp Asp Ile Lys Met
1               5                   10

<210> SEQ ID NO 78
<211> LENGTH: 15
<212> TYPE: PRT
<213> ORGANISM: Artificial Sequence
<220> FEATURE:
<223> OTHER INFORMATION: Synthetic Polypeptide

```
<400> SEQUENCE: 78

Val Ser Asn Ile Leu Lys Asp Thr Gln Val Thr Arg Gln Ala Leu
1               5                   10                  15

<210> SEQ ID NO 79
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 79

Val Ser Asn Ile Leu Lys
1               5

<210> SEQ ID NO 80
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 80

Pro Ala Ile Phe Ala Ser Gly Ile Ile Met Asp Ser Ser Ile Ser Lys
1               5                   10                  15

Gln Ala Leu Ser Glu Ile Asp Thr Lys Lys Ala Val Lys Tyr Gln Ser
            20                  25                  30

Lys Ala Arg Arg Lys Lys
                35

<210> SEQ ID NO 81
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 81

Leu Ala Ile Phe Thr Asp Asp Ile Lys Met Asp Ser Gln Met Thr Lys
1               5                   10                  15

Gln Ala Leu Asn Glu Ile Asp Thr Lys Lys Ala Val Lys Tyr Gln Ser
            20                  25                  30

Lys Ala Arg Arg Lys Lys
                35

<210> SEQ ID NO 82
<211> LENGTH: 49
<212> TYPE: PRT
<213> ORGANISM: Artificial Sequence
<220> FEATURE:
<223> OTHER INFORMATION: Synthetic

<400> SEQUENCE: 82

Gln Val Asp Glu Val Val Asp Ile Met Arg Val Asn Val Asp Lys Val
1               5                   10                  15

Leu Glu Arg Asp Gln Lys Leu Ser Glu Leu Asp Asp Arg Ala Asp Ala
            20                  25                  30

Leu Gln Ala Gly Ala Ser Gln Phe Glu Thr Ser Ala Ala Lys Leu Lys
            35                  40                  45

Arg

<210> SEQ ID NO 83
```

```
<211> LENGTH: 22
<212> TYPE: PRT
<213> ORGANISM: Artificial Sequence
<220> FEATURE:
<223> OTHER INFORMATION: Synthetic

<400> SEQUENCE: 83

Pro Ala Ile Phe Ala Ser Gly Ile Ile Met Asp Ser Ser Ile Ser Lys
1               5                   10                  15

Gln Ala Leu Ser Glu Ile
            20

<210> SEQ ID NO 84
<211> LENGTH: 16
<212> TYPE: PRT
<213> ORGANISM: Artificial Sequence
<220> FEATURE:
<223> OTHER INFORMATION: Synthetic

<400> SEQUENCE: 84

Asp Thr Lys Lys Ala Val Lys Tyr Gln Ser Lys Ala Arg Arg Lys Lys
1               5                   10                  15

<210> SEQ ID NO 85
<211> LENGTH: 22
<212> TYPE: PRT
<213> ORGANISM: Artificial Sequence
<220> FEATURE:
<223> OTHER INFORMATION: Synthetic

<400> SEQUENCE: 85

Leu Ala Ile Phe Thr Asp Asp Ile Lys Met Asp Ser Gln Met Thr Lys
1               5                   10                  15

Gln Ala Leu Asn Glu Ile
            20

<210> SEQ ID NO 86
<211> LENGTH: 16
<212> TYPE: PRT
<213> ORGANISM: Artificial Sequence
<220> FEATURE:
<223> OTHER INFORMATION: Synthetic

<400> SEQUENCE: 86

Asp Thr Lys Lys Ala Val Lys Tyr Gln Ser Lys Ala Arg Arg Lys Lys
1               5                   10                  15

<210> SEQ ID NO 87
<211> LENGTH: 22
<212> TYPE: PRT
<213> ORGANISM: Artificial Sequence
<220> FEATURE:
<223> OTHER INFORMATION: Synthetic

<400> SEQUENCE: 87

Ser Glu Val Phe Val Ser Asn Ile Leu Lys Asp Thr Gln Val Thr Arg
1               5                   10                  15

Gln Ala Leu Asn Glu Ile
            20

<210> SEQ ID NO 88
<211> LENGTH: 16
<212> TYPE: PRT
<213> ORGANISM: Artificial Sequence
<220> FEATURE:
<223> OTHER INFORMATION: Synthetic
```

```
<400> SEQUENCE: 88

His Val Lys Ile Ala Leu Glu Asn Gln Lys Lys Ala Arg Lys Lys Lys
1               5                   10                  15
```

UNITED STATES PATENT AND TRADEMARK OFFICE
CERTIFICATE OF CORRECTION

| | | |
|---|---|---|
| PATENT NO. | : 12,098,169 B2 | |
| APPLICATION NO. | : 16/651720 | |
| DATED | : September 24, 2024 | |
| INVENTOR(S) | : Min Dong et al. | |

It is certified that error appears in the above-identified patent and that said Letters Patent is hereby corrected as shown below:

In the Specification

Column 1, Line 15, replace the paragraph titled "GOVERNMENT SUPPORT" with the following paragraph:
FEDERALLY SPONSORED RESEARCH
This invention was made with government support under Grant Numbers NS080833 and AI132387, awarded by the National Institutes of Health. The Government has certain rights in the invention.

Signed and Sealed this
Third Day of December, 2024

Katherine Kelly Vidal
*Director of the United States Patent and Trademark Office*